US011322690B2

(12) United States Patent
Falber

(10) Patent No.: US 11,322,690 B2
(45) Date of Patent: May 3, 2022

(54) LIGHT HARVESTING ARRAY

(71) Applicant: FLUROSOL INDUSTRIES PTY LTD., Prahran (AU)

(72) Inventor: Alexander Falber, Bellevue Hill (AU)

(73) Assignee: Flurosol Industries Pty Ltd, Prahan (AU)

( * ) Notice: Subject to any disclaimer, the term of this patent is extended or adjusted under 35 U.S.C. 154(b) by 0 days.

(21) Appl. No.: 14/913,518

(22) PCT Filed: Aug. 22, 2014

(86) PCT No.: PCT/AU2014/000834
§ 371 (c)(1),
(2) Date: Feb. 22, 2016

(87) PCT Pub. No.: WO2015/024064
PCT Pub. Date: Feb. 26, 2015

(65) Prior Publication Data
US 2016/0211453 A1    Jul. 21, 2016

(30) Foreign Application Priority Data

Aug. 23, 2013    (AU) ................................ 2013903205

(51) Int. Cl.
| | | |
|---|---|---|
| H01L 51/00 | (2006.01) | |
| C07D 491/06 | (2006.01) | |
| C09B 5/62 | (2006.01) | |
| C09B 3/14 | (2006.01) | |
| C07D 471/06 | (2006.01) | |
| C09B 69/10 | (2006.01) | |
| C07C 69/76 | (2006.01) | |
| C07D 221/18 | (2006.01) | |
| C07D 311/78 | (2006.01) | |
| C07D 519/00 | (2006.01) | |
| H01G 9/20 | (2006.01) | |

(52) U.S. Cl.
CPC .......... *H01L 51/0053* (2013.01); *C07C 69/76* (2013.01); *C07D 221/18* (2013.01); *C07D 311/78* (2013.01); *C07D 471/06* (2013.01); *C07D 491/06* (2013.01); *C07D 519/00* (2013.01); *C09B 3/14* (2013.01); *C09B 5/62* (2013.01); *C09B 69/103* (2013.01); *H01G 9/2059* (2013.01); *H01L 51/0051* (2013.01); *C07C 2603/52* (2017.05); *Y02E 10/549* (2013.01)

(58) Field of Classification Search
CPC .. H01L 51/0053; C07D 221/18; C07D 311/78
See application file for complete search history.

(56) References Cited

U.S. PATENT DOCUMENTS

| 5,645,965 A | 7/1997 | Duff et al. |
| 2008/0287678 A1 | 11/2008 | Konemann |

FOREIGN PATENT DOCUMENTS

| EP | 0990951 | 4/2000 |
| EP | 2031322 A2 | 3/2009 |
| WO | WO2000-023446 | 6/2000 |
| WO | WO2007-059297 A2 | 5/2007 |
| WO | WO2009-153887 A1 | 12/2009 |
| WO | WO2011-005575 A2 | 1/2011 |
| WO | WO2011-154916 A2 | 12/2011 |
| WO | WO2012-053779 A2 | 4/2012 |
| WO | WO 2016/026863 A1 | 2/2016 |

OTHER PUBLICATIONS

Qi, G., et al. "Linear perylenetetracarboxylic monoanhydried derivatives for the sensitization of dye-sensitized solar cells." Journal of Photochemistry and Photobiology. (2012), vol. 239, pp. 28-36.*
Bahng, H.W., et al. "Ensemble and Single-Molecule Spectroscopic Study on Excitation Energy Transfer Processes in 1,3-Phenylene-Linked Perylenebisimide Oligomers." J. Phys. Chem. (c) Dec. 23, 2011. pp. 1244-1255.*
Shahar, C., et al. "Self-Assembly of Light-Harvesting Crystalline Nanosheets in Aqueous Media." ACS Nano. (2013), vol. 7, No. 4, pp. 3547-3556.*
Fron, E., et al. "Energy Transfer Pathways in a Rylene-Based Triad." ChemPhysChem (2011), vol. 12, pp. 595-608. (Year: 2011).*
Kang, H., et al. "Construction of well-defined butadiynylene-linked perylene bisimide arrays via cross-coupling." Dyes and Pigments. (2013), vol. 97, pp. 244-249. (Year: 2013).*
Du, Yanan et al., "Perylenetetracarboxylic Diimide Derivatives Linked with Spirobifluorene," Organic Letters 2012 vol. 14, No. 12, 3052-3055.
Petrella, Andrea et al., "Charge Transfer Processes in Conjugated Triarylamine-Oligothiophene-Perylenemonoimide Dendrimers," J. Phys. Chem. A 2005, 11687-11695.
Schweitzer, Gerd et al., "Intramolecular Directional Energy Transfer Processes in Dendrimers Containing Perylene and Terrylene Chromophores," J. Phys. Chem. A 2003, 107, 3199-3207.

(Continued)

*Primary Examiner* — D Margaret M Seaman
(74) *Attorney, Agent, or Firm* — Finnegan, Henderson, Farabow, Garrett & Dunner, LLP

(57) ABSTRACT

The invention relates to a light harvesting array or dye comprising an acceptor linked to a donor, wherein at least one of the acceptor or the donor is an oligomeric unit comprising a first optionally substituted rylene linked via a linker group to a second optionally substituted rylene, the first optionally substituted rylene is linked to the acceptor or the donor and the second optionally substituted rylene is capable of energy transfer to at least one of the first optionally substituted rylene, the acceptor or the donor. The invention also relates to compounds which may be used as light harvesting arrays, methods for their manufacture, and devices and materials comprising the light harvesting array or dye, for example, chromophoric materials, light guides, photobioreactors, photoluminescent algae systems, photodetectors, photovoltaic devices and luminescent/fluorescent solar concentrators.

13 Claims, 4 Drawing Sheets

(56) References Cited

OTHER PUBLICATIONS

Weil, Tanja et al., "The Rylene Colorant Family—Tailored Nanoemitters for Phototonics Research and Applications," Angewandte Chemie International Edition, vol. 49, No. 48, Oct. 25, 2010, 9068-9093.
Supplementary European Search Report for EP Application No. 14838236.9 dated Aug. 18, 2016.
Ahrens et al "Self-assembly of supramolecular light-harvesting arrays from covalent multi-chromophore perylene-3,4:9,10-bis(dicarboximide) building blocks", Journal of the American Chemical Society. 2004, vol. 126 (26), pp. 8284-8294.
Ambrosek et al "Quantum chemical parametrization and spectroscopic characterization of the Frenkel exciton Hamiltonian for a J-aggregate forming perylene bisimide dye" J Phys Chem A 2012, vol. 116, pp. 11451-11458 (abstract only).
An et al "Nano-biohybrid light-harvesting systems for solar energy applications" MRS Online Proc. Libr. 2012, vol. 1445, ISSN 1946-4274 (abstract only).
Avlasevich et al "Synthesis and applications of core-enlarged perylene dyes" Journal of Materials Chemistry 2010, vol. 20, pp. 3814-3826.
Bahng, et al "Ensemble and signle-molecule spectroscopic strudy on excitation energy transfer processes in 1,3-Phenylene-linked perylenebisimide oligomers" Journal of Physical Chemistry B, 2012. vol. 116 (4), pp. 1244-1255.
Basham et al "Forster Resonance Energy Transfer in Dye-Sensitized Solar Cells" ACS Nano 2010, vol. 4, pp. 1253-1258 (with abstract).
Botta et al "Organic nanostructured host-guest materials for luminescent solar concentrators" J. Mater. Chem. A 2013, vol. 1, pp. 510-514 (with abstract).
Calzaferri "Nanochannels: Hosts for the Supramolecular Organization of Molecules and Complexes" Langmuir 2012, vol. 28, pp. 6216-6231 (abstract only).
Chapman et al "A triad study of sediment quality associated with a major, relatively untreated marine sewage discharge" Mar. Pollut. Bull. 1996, vol. 32, pp. 47-64 (abstract only).
Chen et al "Optical bandgaps and fluorescence resonance energy transfer studies of a series of poly(phenyleneethynylene) derivatives" React. Funct. Polym. 2011, vol. 71, pp. 1008-1015 (abstract only).
Cheon et al "Enhanced light-harvesting efficiency by Forster resonance energy transfer in quasi-solid state DSSC using organic blue dye" Electrochim. Acta 2012, vol. 68, pp. 240-245 (abstract only).
Cotlet et al "Intramolecular directional forster resonance energy transfer at the single-molecule level in a dendritic system" J Am Chem Soc, 2003, vol. 125, pp. 13609-13617 (with abstract).
Cotlet et al "Probing Intramolecular Forster resonance energy transfer in a naphthelenelmide-peryleneimide-terrylenediimide-based dendrimer by ensemble and single-molecule fluorescence spectroscopy" J Am Chem Soc 2005, vol. 127, pp. 9760-9768 (with abstract).
Dossel et al "Synthesis and controlled self-assembly of covalently linked hexa-peri-hexabenzocoronene/perylene diimide dyads as models to study fundamental energy and electron transfer processes" J Am Chem Soc 2012, vol. 134, pp. 5876-5886 (abstract only).
Eichberger et al "Charge separation dynamics at inorganic/organic nanostructured hybrid photovoltaic interfaces" J. Photonics Energy 2012, vol. 2, pp. 021003 (abstract only).
Fron et al "Energy transfer pathways in a rylene-based triad" ChemPhysChem 2011, vol. 12, pp. 595-608.
Glaimo et al "Excited singlet states of covalently bound, cofacial dimers and trimers of perylene-3,4:9,10-bis(dicarboximide)s", Journal of Physical Chemistry A, 2008, vol. 112 (11), pp. 2322-2330.
Grimes (Conference Proceedings) "Photovoltaics and photofuels: application of self-assembled 1-D TiO2 nanoarchitectures" Published by American Chemical Society 2010 (abstract only).
Grimes (Conference Proceedings) "Self-assembled 1-D TiO2 nanoarchitectures: Application to photovoltaics and photofuels" Published by American Chemical Society 2011 (abstract only).
Hipplus et al "Sequential FRET processes in Calix[4]arene-linked orange-red-green Perylene Bisimide dye zigzag arrays". Journal of Physical Chemistry C, 2008, vol. 112(7), p. 2476-2486.
Hoke et al "Modeling the efficiency of Forster resonant energy transfer from energy relay dyes in dye-sensitized solar cells" Opt. Express 2010, vol. 18, pp. 3893-3904.
Honda et al "Improvement of photocurrent in polymer/fullerene bulk heterojunction solar cells utilizing the dye sensitization" Polym. Prepr. (Am. Chem. Soc., Div. Polym. Chem.) 2009, vol. 50 (abstract only).
Humphry-Baker et al "Time-Evolution of Poly(3-Hexylthiophene) as an Energy Relay Dye in Dye-Sensitized Solar Cells" Nano Lett. 2012, vol. 12, pp. 634-639 (abstract only).
Ikeda et al "A doubly 2,6-pyridylene-bridged porphyrin-perylene-perphyrin triad" Chem. Commun. (Cambridge, U. K.) 2012, vol. 48, pp. 4317-4319 (abstract only).
Itzhakov "Design principles of FRET-based dye-sensitized solar cells with buried quantum dot donors" Adv. Energy Mater. 2011, vol. 1, pp. 626-633 (abstract only).
Jordens et al "Energy transfer within perylene-terrylene dendrimers evidenced by polychromatic transient absorption measurements" Photochem. Photobiol. Sci. 2003, vol. 2, pp. 177-186 (with abstract).
Kirmaier et al "Excited-State Photodynamics of Perylene-Porphyrin Dyads. 5. Tuning Light-Harvesting Characteristics via Perylene Substituents, Connection Motif, and Three-Dimensional Architecture" J. Phys. Chem. B 2010, vol. 114, pp. 14249-14264 (abstract only).
Klok et al "Star-shapped fluorecent polypeptides" Max-Planck-Institute for Polymer Research 2001, pp. 1572-1583.
Kong et al "A Mesogenic Triphenylene-Perylene-Triphenylene Triad" Org. Lett. 2011. vol. 13, pp. 764-767 (abstract only).
Langhals et al "A versatile standard for bathochromic fluorescence based on intramolecular FRET" Phys. Chem. Chem. Phys. 2011, vol. 13, pp. 1055-1059 (abstract only).
Langhals et al "Angular benzoperylenetetracarboxylic bisimides" Chemistry 2012, vol. 18, pp. 13188-13194 (abstract only).
Langhals et al "Benzothiadiazoloperylenes and benzoxadiazoloperylenes: amorphous functional materials" Synthesis 2012, vol. 44, pp. 3465-3477 (abstract only).
Langhals et al "Foerster Resonant Energy Transfer in Orthogonally Arranged Chromophores" J. Am. Chem. Soc. 2010, vol. 132, pp. 16777-16782 (abstract only).
Langhals et al "FRET in orthogonally arranged chromophores" Eur. J. Org. Chem. 2008, pp. 4559-4562 (with abstract).
Lee et al "Structural effects of alight emitting copolymer having perylene moieties in the side chain on the electroluminescent characteristis" Materials Science and Engineering 2004, pp. 87-90.
Li et al "Photonic logic gates based on control of FRET by a solvatochormic perylene bisimide" J. Org. Chem. 2007, vol. 72, pp. 2878-2885.
McGehee et al "Light harvesting in dye sensitized solar cells" American Chemical Society 2012 (abstract only).
Melnikov et al "Origin of simultaneous donor-acceptor emission in single moledules of peryleneimide-terrylenediimide labeled polyphenylene dendrimers" J Phys Chem B 2007, vol. 111, pp. 703-719 (with abstract).
Meng "Ultrafast energy transfer in blended polyphenothiazine/polyphenylene vinylene film" Chem. Phys. Lett. 2011, vol. 515, pp. 155-158 (abstract only).
Nalbach et al "Noise-Induced Foerster resonant energy transfer between orthogonal dipoles in photoexcited molecules" Phys. Rev. Lett. 2012, vol. 108, pp. 218302/1-218302/5 (abstract only).
Narayanan et al "Foerster resonance energy transfer and carbon dots enhance light harvesting in a solid-state quantum dot solar cell" J. Mater. Chem. A 2013, vol. 1, pp. 3907-3918 (abstract only).
Oesterling et al "Muitichromophoric polyphenylene dendrimers: Toward brilliant light emitters with an increased number of fluorophores", Journal of the American Chemical Society, 2007, vol. 129(15), pp. 4595-4605.
Peralta "Ordered polyelectrolyte multilayers: unidirectional FRET cascade in nanocompartmentalized polyelectrolyte multilayers" Chemophyschem 2009, vol. 10, pp. 137-143 (abstract only).

(56) References Cited

OTHER PUBLICATIONS

Qi, G et al "Efficient collection of excitation energy from a linear-shaped weakly interacted perylenetetracarboxylic diimides array" Physical Chemistry Chemical Physics, 2013, vol. 15 (40), pp. 17342-17353.

Qi, G et al "Linear perylenetetracarboxylic rnonoanhydried derivates for the sensitization of dye-sensitized solar cells", Journal of Photochemistry and Photobiology, A: Chemistry, 2012, vol. 239, pp. 28-36.

Qu et al "Synthesis and optical properties of polyphenylene dendrimers based on perylenes" J Org Chem 2003, vol. 68, pp. 9802-9808 (with abstract).

Russell et al "Efficient light harvesting in a photovoltaic diode composed of a semiconductor conjugated copolymer blend" Appl. Phys. Lett. 2002, vol, 80, pp. 2204-2200 (abstract only).

Salih et al "Cellular organization and spectral diversity of GFP-like proteins in live coral cells studied by single and multiphoton imaging and microspectroscopy" Proc. SPIE—Int. Soc. Opt. Eng. 2003, vol. 4963, pp. 194-200 (abstract only).

Sato et al "Design and characterization of peptide molecules containing the two functional polyarornatic fluorescence probes" Pept. Sci. 2002, vol. 38th, pp. 407-408 (abstract only).

Schlichting et al "A bichromophore based on perylene and terylene for energy transfer studies at the single-moiecule level" Chem.— Eur. J. 1999, vol. 5, pp. 2388-2395 (abstract only).

Schlosser et al "Excitation energy migration in covalently linked perylene bisimide macrocycles" Chem. Sci. 2012, vol. 3, pp. 2778-2785 (with abstract).

Shahar, C. et al "Seif-assembly of light-harvesting crystalline nanosheets in aqueous media" ACS Nano, 2013, vol. 7 (4), pp. 3547-3556.

Shankar et al "Enhancement of photovoltaic device performance in close-packed nanowire excitonic solar cells by Forster resonance energy transfer (FRET)" Mater. Res. Soc. Symp. Proc. 2010, vol. 1208E (abstract only).

Siegers et al "Overcoming kinetic limitations of electron injection in the dye solar cell via coadsorption and FRET" ChemPhysChem 2008, vol. 9, pp. 793-798 (abstract only).

Sivamurugan et al (Conference Proceedings) "Interaction of carbazole substituted unsymmetrical coronene oligomers with perylene bisimide molecules" 2008, Published by American Chemical Society (abstract only).

Sun et al "Mutation of Tyr138 Disrupts the Structural Coupling between the Opposing Domains in Vertebrate Calmodulin" Biochemistry 2001, vol. 40, pp. 9605-9617 (abstract only).

Sun et al "Thin films of poryphyrin-perylene molecular array fabricated by electrophoresis methodology" Chin. Sci. Bull, 2005, vol. 50, pp. 2157-2160 (abstract only).

Takahashi et al "Construction of light-harvesting reverse micelles in nanoscopic dimensions" J. Photochem. Photobiol., A 2009, vol. 203, pp. 55-63 (abstract only).

Tokita "Diels-Alder reaction of dialkyl diazenedicarboxylates with perylenes; a new synthesis of polycyclic aromatic pyridazines" Synthesis 1982, Issue: 2013 American Chemical Society, pp. 229-231 (abstract only).

Tomizaki et al "Synthesis and photophysical Properties of Light-Harvesting Arrays comprised of a porphyrin bearing multiple perylerne-monoimide accessory pigments" JOC 2002 (abstract only).

Trang et al "Enhanced light harvesting from Forst-type resonance energy transfer into" J. Nanosci. Nanotechnol. 2012, vol. 12, pp. 3301-3304 (abstract only).

Viault et al "The first "ready-to-use" benzene-based heterotrifunctional cross-linker for multiple bioconjugation" Org. Biomol. Chem. 2013, vol. 11, pp. 2693-2705 (with abstract).

Vosch et al "Synthesis, ensemble, and single molecule characterization of a diphenyl-acetylene linked perylenediimide trimer", Jounral of Physical Chemistry C, 2009, vol. 113 (27), pp. 11773-11782.

Wagh et al "Polymeric Nanoparticles with Sequential and Multiple FRET Cascade Mechanisms for Multicolor and Multiplexed Imaging" U.S. National Library of Medicine 2013 (abstract only).

Weil et al "Shape-persistent, flurosecent polyphenylene dyads and a triad for efficient vectorial transduction of excitation energy" Agnew. Chem. Int. Ed. 2002, voll. 41, No. 11, pp. 1900-1904.

Weil et al "Synthesis and characterisation of dendritic multichromophores based on rylene dyes for vectorial transduction of excitation enery" Chem. Eur. J. 2004, vol. 10, pp. 1398-1414.

\* cited by examiner

LIGHT HARVESTING ARRAY

CROSS-REFERENCE TO RELATED APPLICATIONS

This application is a national phase application of International Application No PCT/AU2014/000834, filed Aug. 22, 2014, and claims the priority of Australian Application No. 2013903205, filed Aug. 23, 2013, the content of both of which is incorporated herein by reference.

FIELD

The invention relates to light harvesting arrays or dyes, methods for their manufacture, and devices and materials comprising the light harvesting array or dye, for example, chromophoric materials, light guides, photobioreactors, photoluminescent algae systems, photodetectors, photovoltaic devices and luminescent/fluorescent solar concentrators.

BACKGROUND

Light energy has become an important source of renewable energy for a variety of applications, such as, in photobioreactors where biomass may be grown as a biofuel feedstock and luminescent/fluorescent solar concentrators that are fixed with photovoltaic materials for electricity production. For example, the sun emits radiation in the form of light that reaches the earth across the ultraviolet, visible and infrared regions of the light spectrum, i.e. from about 100 nm to about 1 mm. Generally, only a small portion of the available light is harvested for use.

Various systems have been devised to harvest light and convert it into a more desired energy form. For example, photosynthesis in chlorophyll-containing organisms, e.g. plants, phytoplankton and algae, converts solar light energy into biologically meaningful energy, for example by catalysing the conversion of adenosine diphosphate (ADP) to adenosine triphosphate (ATP). For each chlorophyll-containing organism, the photosynthetic process is more efficient for certain wavelengths of light (see FIG. 1). Consequently, for certain applications it may be desirable to expose such organisms to increased levels of the optimal wavelengths of light.

Fluorescence is a process useful for light harvesting as it generally involves the absorption of light at one wavelength by a fluorophore, i.e. a chromophore that is capable of fluorescence, and emitting light at another wavelength, generally of a lower energy. This shift towards lower energy is called the Stokes shift, and the magnitude of the Stokes shift will depend on the properties of the fluorophore. This process has been rationalised as involving the excitation of an electron from a ground state to an excited state, and then internal relaxation of the excited electron by emission of a photon of decreased energy relative to the absorbed photon.

Often absorption and fluorescent emission maxima of a substance overlap, despite the Stokes shift, leading to reduction of efficiency of harvesting the fluorescence from a solid state device or solution due to reabsorption losses as the fluorescence travels through a media to an exit point where it can be utilised or measured. Even a slight overlap of absorption and emission bands can lead to significant reabsorption losses as the fluorescence is conducted through a significantly long path length towards an exit point. Reducing reabsorption losses is generally achieved by lowering the concentration of the fluorophore in the system which also leads to a proportional reduction in the amount of light harvested. One physical phenomenon that has been used to circumvent this is Förster Resonance Energy Transfer (FRET). This term describes the process between two or more different fluorophores that are brought within close proximity to each other (typically, less than $10^{-9}$ meters) to allow a radiationless (non-photonic and non-electronic) transfer of energy. This transfer flows from a fluorophore with higher energy absorption and emission bands, called the 'donor', to a chromophore with a lower energy absorption band, called the 'acceptor', where the acceptor has an absorption band that lies within the region of the donor emission energy level. The acceptor may also be a fluorophore such that the transferred energy, via FRET, from the donor is expressed as fluorescence emitted by the acceptor in addition to the fluorescence already being emitted by the acceptor by its own absorption. The wavelength of acceptor fluorescence contributed by FRET will generally be the same as fluorescence normally emitted by the acceptor. Thus, the total light harvested and total fluorescence achieved are increased by the energy transferred via FRET from the donor, and the reabsorption losses may not be increased because the total acceptor concentration in the system has remained the same.

Another process for transfer of energy is triplet-triplet annihilation, known as up-conversion, where energy is transferred from a low energy 'donor' to a high energy 'acceptor' when they are within close proximity. In such a process, two photons generate two triplet states in two donor molecules that are both transferred to an acceptor where they combine (annihilation of the triplet states) to form one high energy singlet state in the acceptor. The acceptor in this high energy excited state undergoes relaxation back to the ground state allowing the emission of a photon of higher energy than the photons originally absorbed by the donor.

Yet another process for energy transfer is by charge transfer. Energy absorbed by a donor may cause a positive charge, known as an "electron hole", a negative charge, or an electron to be transferred across a short path (typically >10 nm) to an acceptor. The acceptor may transfer yet another charge of lower electronic potential or emit a photon via luminescence depending on the nature of the acceptor molecule. One such example of charge transfer among closely arranged chromophores is Dexter electron transfer. This type of transfer is possible when the wave function of two chromophores overlap sufficiently to allow electron transfer from one to the other, typically when the distance between the chromophores is less than 2 nm.

SUMMARY

The invention relates to a light harvesting array that absorbs light energy from multiple spectral regions and converts the absorbed light energy for emission in a desired form, e.g. into a fluorescent emission with a narrow range of wavelengths of a lower energy relative to the absorbed light energy. The invention also relates to oligomeric units useful as subunits for the light harvesting array and that may also function as light harvesting systems on their own. The invention further relates to methods for the production of the light harvesting arrays and oligomeric units. The invention still further relates to a chromophoric material comprising the light harvesting array and to devices comprising such a light harvesting material. In one embodiment, the light harvesting arrays demonstrate high quantum yield and high photo-stability relative to existing commercially available monomeric dyes. For example, the light harvesting arrays may demonstrate quantum yields of over 90%. Further, the light harvesting arrays may retain at least 60% of their initial fluorescence after exposure to direct sunlight over a period of 5 years.

In a first aspect, there is provided a light harvesting array comprising an acceptor linked to a donor, wherein at least one of the acceptor or the donor is an oligomeric unit comprising a first optionally substituted rylene linked (i.e. chemically bonded) via a linker group to a second optionally substituted rylene, the first optionally substituted rylene is linked to the acceptor or the donor and the second optionally substituted rylene is capable of energy transfer to at least one of the first optionally substituted rylene, the acceptor or the donor.

In a second aspect, there is provided a compound of Formula X:

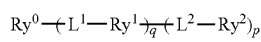

Formula X wherein
$Ry^0$ is an optionally substituted acceptor rylene or an optionally substituted donor rylene;
$Ry^1$ is a first optionally substituted rylene;
$Ry^2$ is a second optionally substituted rylene capable of transfering energy to $Ry^0$, $Ry^1$ or both;
$L^1$ is absent or a linker group;
$L^2$ is a linker group;
q is an integer of 1 to 10; and
p is an integer of 1 to 20.

In a third aspect, there is provided a light harvesting array comprising an acceptor linked (i.e. chemically bonded) to one or more donors, wherein the acceptor is an oligomeric unit comprising an optionally substituted rylene core linked via a linker group to one or more optionally substituted peripheral rylenes. Preferably, the one or more optionally substituted peripheral rylenes are capable of energy transfer to the optionally substituted rylene core.

In a fourth aspect, there is provided a light harvesting array comprising an acceptor linked (i.e. chemically bonded) to one or more donors, wherein at least one donor is an oligomeric unit comprising an optionally substituted donor rylene core linked via a linker group to one or more optionally substituted peripheral donor rylenes.

In a fifth aspect, there is provided a compound of formula I:

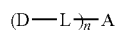

Formula I wherein:
A is an acceptor;
n is an integer of 1 to 10;
D is an oligomeric unit comprising an optionally substituted donor rylene core and one or more
optionally substituted peripheral donor rylenes; and
L is absent or a linker group.

In a sixth aspect, there is provided an oligomeric unit comprising an optionally substituted perylene core linked via a linker group to two or more optionally substituted peripheral donor perylenes. The oligomeric unit may be a donor, an acceptor or both.

In an embodiment, the oligomeric unit may be a compound of formula II:

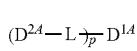

Formula II wherein:
$D^{1A}$ is an optionally substituted perylene core;
$D^{2A}$ is an optionally substituted peripheral donor perylene;
L is a linker group; and
p is an integer of 2 to 10.

In a seventh aspect, there is provided a method for preparing a light harvesting array, comprising coupling an acceptor with one or more donors.

In an eighth aspect, there is provided a method for preparing an oligomeric unit, comprising coupling an optionally substituted perylene core with two or more optionally substituted peripheral donor perylenes.

In a ninth aspect, there is provided a chromophoric material comprising the light harvesting array of the first aspect or compound of the second or fifth aspects.

In a tenth aspect, there is provided a device comprising the chromophoric material described above. The device may be selected from the group consisting of a light guide, a photobioreactor, a photoluminescent algae system, a luminescent/fluorescent solar concentrator, a photodetector and a photovoltaic device.

In an eleventh aspect, there is provided use of the light harvesting array of the first aspect or compound of the second or fifth aspects as a chromophoric dye.

BRIEF DESCRIPTION OF DRAWINGS

The drawings illustrate aspects of some embodiments or illustrate principles of their operation. The drawings are included by way of example and are not intended to limit the scope of the embodiments described below.

DESCRIPTION OF EMBODIMENTS

Figure 1:
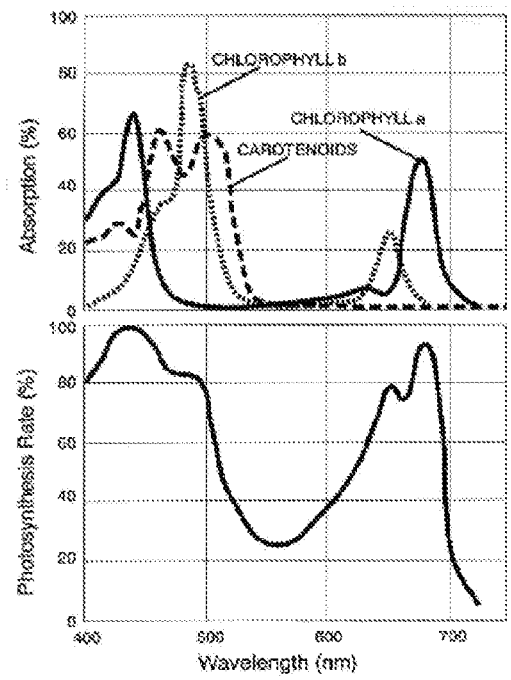
FIG. 1 is the absorbance spectra of chlorophyll a, chlorophyll b, and carotenoids (top) and the related photosynthetic action spectrum (bottom).

In one aspect, the light harvesting array comprises an acceptor linked to a donor. At least one of the acceptor or the donor is an oligomeric unit. The oligomeric unit comprises a first optionally substituted rylene linked via a linker group to a second optionally substituted rylene. The first optionally substituted rylene of the oligomeric unit is linked, optionally via a linker group, to the acceptor or the donor. The second optionally substituted rylene is capable of energy transfer to at least one of the first optionally substituted rylene, the acceptor or the donor.

In one embodiment, the acceptor is the oligomeric unit. Preferably, the oligomeric unit comprises an optionally substituted rylene core linked via a linker group to one or more optionally substituted peripheral rylenes.

In one embodiment, at least one of the one or more donors is the oligomeric unit. Preferably, the oligomeric unit comprises an optionally substituted donor rylene core linked via a linker group to one or more optionally substituted peripheral donor rylenes.

In one embodiment, the acceptor is an oligomeric unit and the donor is a further oligomeric unit. That is to say, in this embodiment, the acceptor and the donor are each an oligomeric unit.

In one aspect, the light harvesting array comprises an acceptor linked to one or more donors. The acceptor is an oligomeric unit. The oligomeric unit comprises an optionally substituted rylene core linked via a linker group to one or more optionally substituted peripheral rylenes.

Preferably, in this aspect, the one or more optionally substituted peripheral rylenes are capable of transferring energy to the optionally substituted rylene core. Preferably, the donor is any donor described herein. In one embodiment, the donor is an oligomeric unit comprising an optionally substituted donor rylene core linked via a linker group to one or more optionally substituted peripheral donor rylenes.

In one aspect, the light harvesting array comprises an acceptor linked to one or more donors. At least one of these donors is an oligomeric unit. The oligomeric unit comprises an optionally substituted donor rylene core linked via a linker group to one or more optionally substituted peripheral donor rylenes. In other words, the oligomeric unit comprises a first optionally substituted rylene linked via a linker group to a second optionally substituted rylene.

In one embodiment, the first optionally substituted rylene has different spectroscopic properties than the second optionally substituted rylene. For example, the first optionally substituted rylene may provide a first absorption maxima when measured by UV-visible (UV-vis) spectroscopy and the second optionally substituted rylene may provide a second absorption maxima when measured by UV-visible spectroscopy, wherein the first and second absorption maxima are at different wavelengths. Generally, the first and second optionally substituted rylenes will have different structures.

In one embodiment, the light harvesting array comprises an acceptor linked to one or more donors, wherein at least one of the donors is an oligomeric unit comprising a first optionally substituted rylene linked via a linker group to a second optionally substituted rylene, wherein the first optionally substituted rylene is capable of donating absorbed energy to the acceptor and the second optionally substituted rylene is capable of transferring absorbed energy to the first optionally substituted rylene, the acceptor or both.

Rylenes, such as perylenes, are advantageously employed due to their favourable photophysical properties. For example, perylenes possess a high quantum yield, are extremely photostable and have a wide range of absorptions and emissions. Further, the photophysical properties of a substituted rylene are influenced by the nature, type and kind of substituent bound to the rylene. For example, inclusion of a para-tert-butylphenoxy substituent at the 1, 6, 7 and/or 12 positions on an optionally substituted perylene, known as the "bay position", typically shifts the absorption maxima to a lower energy for that perylene relative to the corresponding equivalent perylene lacking the para-tert-butylphenoxy substituent. Conversely, inclusion of a phenyl substituent at a bay position of an optionally substituted perylene typically shifts the absorption maxima to a higher energy for that perylene relative to the corresponding equivalent perylene lacking the phenyl substituent.

In one embodiment, the donor is capable of transferring absorbed energy to the acceptor and the acceptor is capable of emitting the transferred energy as light. In another embodiment, each optionally substituted peripheral rylene is capable of transferring energy to the acceptor, the optionally substituted rylene core or both.

In one embodiment, the donor transfers absorbed energy to the acceptor via Förster Resonance Energy Transfer (FRET). The oligomeric unit may comprise an optionally substituted donor rylene core and one or more optionally substituted peripheral donor rylenes that have absorption maxima of a higher energy, i.e. shorter wavelength, than the absorption maxima of the acceptor. In one embodiment, the fluorescence emission maxima of the donor overlaps the absorbance maxima of the acceptor. In this embodiment, the peripheral and core donor rylenes may transfer absorbed energy to the acceptor via FRET.

Figure 2:
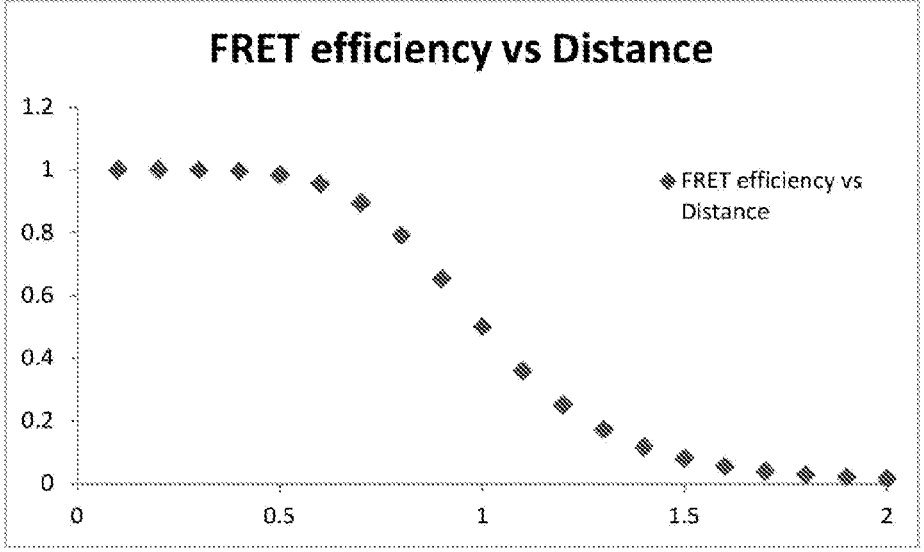
FIG. 2 is a graph showing the efficiency of energy transfer from the overlap region of the fluorescence spectrum of the donor and the absorbance of the acceptor.

The efficiency of the FRET process may be approximated mathematically for a donor and acceptor pair (or FRET pair). For a FRET pair of substituted perylenes, this approximation provides that the FRET efficiency is inversely proportional to the sixth power of the distance between the donor and acceptor pair (FIG. 2). As shown in FIG. 2, a FRET pair separated by 60% of the Förster radius corresponds to an energy transfer efficiency of 95%. Increasing that distance to 70% only decreases the FRET efficiency to 89%. However, beyond this distance there is a rapid decrease in FRET efficiency. Therefore, the spatial orientation of the donor and acceptor within the light harvesting array contributes to its overall efficiency.

In order to increase the number of donor rylenes oriented within the Förster radius of the acceptor, at least one of the donors is an oligomeric unit, for example, an oligomeric unit comprising an optionally substituted donor rylene core linked via a linker group to one or more optionally substituted peripheral donor rylenes.

Figure 4:
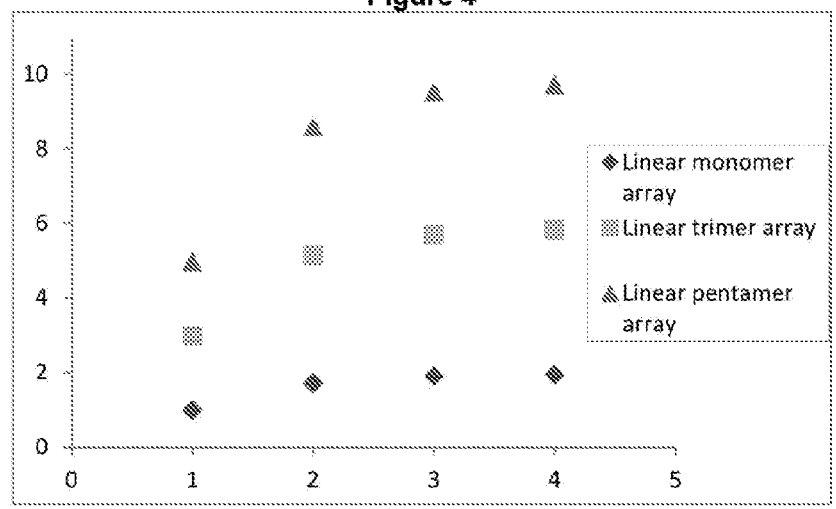
FIG. 4 is a graph of the efficiency of energy transfer falling off with each additional oligomeric unit in a similar manner for various arrays.
Figure 5:
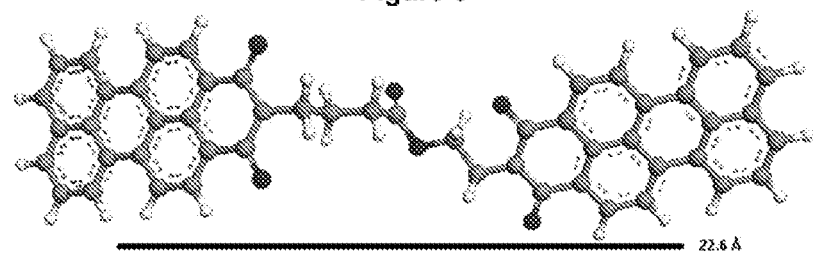
FIG. 5 is a representation of basic level modelling (UFF) of two linked optionally substituted perylenes.

The inventors conducted basic level modelling (UFF) of linear perylene arrays (Example 1). This modelling revealed that increasing the number of fluorophores arranged within the Förster radius of an acceptor increased the predicted efficiency of the linear array. This modelling also revealed that the FRET efficiency drops off with additional generations of oligomeric units. This modelling suggests that the gain in efficiency of a first generation array comprising a monomeric rylene donor compared to a first generation array comprising an oligomeric donor is greater than the corresponding gain in efficiency between, for example, the second and third generations of an array comprising monomeric donors (FIG. 4). The third generation monomeric array comprises an equivalent number of donors as the first generation oligomeric array. Further, this efficiency drop off suggests that increasing the local density of donors (or fluorophores) within the Förster radius of the acceptor will result in additional efficiency increases.

In addition, preferably a substantial majority of the FRET donor fluorescence emission maxima overlap with at least one of the absorption maxima of the FRET acceptor; the better the overlap, the more efficient the FRET. In addition, preferably the FRET occurs on a faster timescale than other energy relaxation pathways that the donor, in its excited state, may undergo, e.g. singlet to triplet relaxation to produce heat or phosphorescence. Additionally, to maximise the fluorescence produced by a FRET pair (donor and acceptor), the acceptor may have a high quantum yield of fluorescence photons relative to absorbed photons when measured as part of a light harvesting array or when measured when a monomer (i.e. when it is not linked to the one or more donors). Poorly overlapping absorption and emission maxima result in partial FRET typically resulting in some energy absorbed by the donor being emitted as donor fluorescence and a light harvesting array comprising such poor FRET acceptor and donor pairs may then be subject to large reabsorption losses. This process is sometimes referred to as "leaky" FRET. Further, non-FRET processes which act as photon "leaks" for the FRET system are also preferably minimised. The ability to "tune" the absorbance/emission profile of the donor and/or the acceptor may increase the overlap of the donor emission maxima with the acceptor absorption maxima which may increase the FRET efficiency. Advantageously, as described above the absorption/emission profile of an optionally substituted rylene may be "tuned" in order to match the absorption/emission profiles of a FRET pair to increase FRET efficiency. In some embodiments, the transfer of energy is at least 80% efficient. The transfer of energy from the one or more optionally substituted peripheral donor rylenes is at least 60%, 65%, 70%, 75%, 80%, 85%, 90%, 95%, 98%, 99%, 99.5%, 99.8%, 99.9% or 99.98% efficient. Further, the transfer of energy from an optionally substituted donor rylene core is at least 60%, 65%, 70%, 75%, 80%, 85%, 90%, 95%, 98%, 99%, 99.5%, 99.8%, 99.9% or 99.98% efficient. Preferably, the transfer of energy overall from the oligomeric unit to the acceptor is at least 60%, 65%, 70%, 75%, 80%, 85%, 90%, 95%, 98%, 99%, 99.5%, 99.8%, 99.9% or 99.98% efficient. This efficiency may be described as "acceptor quantum efficiency" (AQE) measuring the total number of photons produced by the acceptor compared to the total number of photons absorbed by the array. AQE is distinguished from the overall quantum efficiency, or "quantum efficiency" (QE) of a molecule where fluorescence directly produced by "leaking" donor chromophores and the acceptor are both counted relative to the number of photons absorbed by the array. These are also distinguished from the "external quantum efficiency" (EQE) which is a measure of the total acceptor fluorescence relative to the total number of photons available to a solution or dispersion of the light harvesting array, in solution or solid state media, from the light source (usually the sun). In a "leaky" array, where there is poor overlap of absorption/emission maxima, the AQE will be low even if the QE is high. In a tuned system, there is more complete transfer of absorbed energy to the acceptor leading to a relatively higher AQE. In a tuned system with a large number of types of donors, having an overall absorption spectra that overlaps well with the spectral output of the light source, the EQE will be high.

When the FRET acceptor is a fluorophore, the fluorescent emission via FRET is typically the same wavelength normally emitted by the acceptor after direct light absorption, and is generally lower in energy than the absorbance maxima for the FRET donor. Consequently, the emitted light is in effect "decoupled" from the absorption bands of the donor(s). For light harvesting arrays, as described above, the difference in wavelength between the photons absorbed by the donor(s) and the wavelengths of the photons emitted by the acceptor is greater than that typically achievable for monomeric-type systems. Advantageously, the decoupling of the absorbance and fluorescence may result in relatively decreased reabsorption losses and an increase in efficiency of light harvesting.

Acceptor

The acceptor is capable of accepting energy from the one or more donors. This energy transfer may be by any suitable process, including, for example, FRET, up-conversion via triplet-triplet annihilation, and charge transfer such as Dexter charge transfer. The acceptor must also be capable of achieving an excited state as a result of accepting the transferred energy which may then return to the ground state via relaxation by luminescence, charge transfer or any other mechanism where the energy may be utilised.

In one embodiment, the acceptor is selected from the group consisting of an optionally substituted rylene, an optionally substituted porphyrin, an optionally substituted benzocoronene and an oligomeric unit comprising two or more optionally substituted rylenes.

It will be appreciated that the type of acceptor will dictate the form of energy emitted by the light harvesting array. For example, when the acceptor is an optionally substituted porphyrin the light harvesting array may emit the harvested light energy in the form of a charge, e.g. by redox cycling of a metal complexed within the porphyrin, or redox cycling of the porphyrin ring itself, using a redox mediator such as triodide.

For embodiments where the acceptor is an optionally substituted rylene or an oligomeric unit comprising two or more optionally substituted rylenes, the harvested light energy will be emitted as photons. These photons may be of a wavelength within the ultraviolet (UV), visible or near infrared (IR) region of the light spectrum.

The optionally substituted rylene may be selected from the group consisting of an optionally substituted perylene, an optionally substituted terrylene and an optionally substituted quarterrylene. The photophysical properties of the rylene moiety vary according to its size, i.e. the number of constituent naphthylene units. For example, a terrylene generally has an absorption maximum of lower energy (longer wavelength) than that of a perylene, for correspondingly functionalised terrylenes and perylenes. It will also be appreciated that to facilitate FRET, the selected acceptor rylene should possess an absorption maxima at least in part overlapping with a fluorescence emission maxima of one or more of the donors.

In one embodiment, the acceptor emits photons of a wavelength of about 550 nm to about 800 nm, preferably of about 550 nm to about 700 nm, about 575 nm to about 675 nm, or about 700 nm to about 800 nm.

In another embodiment, the acceptor emits photons of a wavelength in the UV spectral region. In some embodiments, the acceptor emits photons of a wavelength of less than about 450 nm. Such embodiments are advantageous as the emitted light is not within the visible range.

In another embodiment, the acceptor emits photons of a wavelength in the near infrared (NIR) spectral region. In some embodiments, the acceptor emits photons of a wavelength of greater than about 700 nm, preferably about 700 nm to about 1200 nm, more preferably about 750 nm to about 850 nm or about 850 nm to about 1200 nm. Such embodiments are advantageous as the emitted light is not within the visible range. Preferably, the acceptor emits photons of a wavelength matching the energy band gap of a material used in a photovoltaic cell, for example, Si, Ga, In or P.

Advantageously, embodiments of the light harvesting array that emit light outside the visible range may be invisible when in solution or incorporated into a material, e.g. a chromophic material as described below.

In one embodiment, the acceptor is an oligomeric unit comprising two or more optionally substituted rylenes. Only one of the two or more optionally substituted rylenes may be an acceptor rylene, the other optionally substituted rylene may be a donor for the acceptor rylene. Preferably, the oligomeric unit comprises an optionally substituted acceptor rylene core and one or more optionally substituted peripheral rylenes. Each optionally substituted peripheral rylene may be an optionally substituted donor perylene. The optionally substituted acceptor rylene core may be an optionally substituted acceptor perylene.

In one embodiment, the acceptor is an optionally substituted perylene or an oligomeric unit comprising two or more optionally substituted perylenes. As described above, perylenes are photostable, possess high quantum yields and provide access to a variety of absorption and emission profiles. Furthermore, compared to other rylenes, perylenes are relatively air and heat stable which may assist in ease of preparation and handling, as well as longevity and robustness of perylene containing materials and devices. For example, perylene is air and heat stable at temperatures of greater than 200° C. The optionally substituted acceptor perylene may comprise one or more bay substituents which shift its absorption maxima to a lower energy.

In one embodiment, the acceptor is an optionally substituted terrylene. Optionally substituted terrylenes advantageously emit light at a wavelength of about 650 nm to about 750 nm depending upon substitution. Furthermore, the increased molecular size of terrylene relative to perylene provides increased opportunity to link a greater number of donors within the Førster radius, thus increasing light harvesting efficiency.

Donor

The light harvesting array comprises an acceptor linked to one or more donors. The donor is any moiety or molecule that is capable of absorbing light energy and donating at least a portion of that energy to the acceptor. Suitable donors include optionally substituted rylenes (such as optionally substituted perylene), optionally substituted naphthylene (such as optionally substituted naphthyleneimide), optionally substituted tetra pyrroles (such as optionally substituted porphyrins, optionally substituted porphyrazines and optionally substituted phthalocyanines), optionally substituted benzopyrones (such as optionally substituted coumairins), optionally substituted xanthene derivatives (such as optionally substituted fluorescein and optionally substituted rhodamine), optionally substituted cyanine derivatives (such as optionally substituted cyanine, optionally substituted indocarbocyanine), optionally substituted oxadiazole derivatives (such as optionally substituted pyridyloxazole, optionally substituted nitrobenzoxadiazole and optionally substituted benzoxadiazole), optionally substituted pyrenes and derivatives thereof, optionally substituted oxazine derivatives (such as Nile red, Nile blue and cresyl violet), optionally substituted acridine derivatives (such as optionally substituted proflavin, optionally substituted acridine orange and optionally substituted acridine yellow), optionally substituted aromatic hydrocarbons (such as optionally substituted terphenyl and optionally substituted quaterphenyl), optionally substituted thiophenes and optionally substituted polyhtiophenes (such as optionally substituted benzothiophene and optionally substituted dibenzothiophene), or combinations thereof. Preferably, the donor transfers absorbed light energy to the acceptor via FRET. This FRET transfer may be either direct or by first undergoing FRET with another donor having lower energy absorption bands that may act as an intermediate acceptor (which in turn acts as a donor to the acceptor described above). Such intermediate acceptors may then act as FRET donors to the final acceptor. Any donor may act as an intermediate acceptor as long as it possesses an absorption band with lower energy than another donor within its Førster radius.

At least one of the donors of the light harvesting array is an oligomeric unit. For example, an oligomeric unit comprising an optionally substituted rylene core and one or more optionally substituted peripheral donor rylenes. In other words, an oligomeric unit comprising an optionally substituted intermediate acceptor rylene and at least one optionally substituted donor rylene. Preferably, the optionally substituted donor rylene is capable of transferring absorbed energy to the optionally substituted intermediate acceptor rylene, the acceptor or both. As described above, the oligomeric unit increases the density of donor rylenes within the Førster radius of the acceptor, increasing the FRET efficiency. By including an optionally substituted intermediate acceptor rylene in the array within the Forster radius of the acceptor, the energy absorbed by the one or more optionally substituted donor rylenes may be transferred to the acceptor with greater FRET efficiency. Furthermore, as the optionally substituted core and peripheral donor rylenes have different absorption profiles a greater bandwidth of light is collected and hence a greater amount of energy is harvested and available for transfer to the acceptor.

As described above, the photophysical properties of rylenes enable their use as donors. The selection of different donor rylenes, i.e. from rylenes of different sizes and/or optional substitution, may provide access to incorporation into a light harvesting array of donors and/or acceptors with various absorption profiles. The ability to select rylenes of various absorption profiles enables "tuning" of the array. For example, an optionally substituted donor rylene core may be selected having a fluorescence emission maxima overlapping with the absorbance maxima of the acceptor, and a peripheral donor rylene may be selected with a fluorescence emission maxima overlapping the absorption maxima of the core donor perylene. In this example, the absorption maxima for the peripheral donor rylene will be higher energy than the absorption maxima of the core donor rylene, which in turn is higher energy than the absorption maxima of the acceptor. In this way, the spectral bandwidth harvested by the oligomeric unit may be increased as light is absorbed in different spectral regions by each of the peripheral donor rylene, the core donor rylene and the acceptor. Furthermore, the decoupling of wavelength of the fluorescence emission from the absorbance may reduce reabsorption losses.

Substitution around the rylene core influences the absorption and emission profile for that rylene. Substituents may affect the absorption/emission profile through steric or electronic effects. For example, without wishing to be limited by theory, substitution of a sterically bulky substituent at a bay position of a rylene core may produce a twist in the rylene core resulting in changes to the energy levels of its orbitals and therefore changes to the available transitions allowed for the absorption/emission of photons. In addition, and also without wishing to be limited by theory, substitution at the end positions of a rylene core, e.g. an imide end group, may also affect the absorption/emission profile for an optionally substituted rylene, for example, the absorption/emission profile for a perylene di-imide (i.e. a perylene substituted with cyclic imide groups at all four rylene end positions) is different to the absorption/emission profile of a perylene tetra-ethylester (i.e. a perylene substituted with ethyl ester groups at each of the rylene end positions).

In one embodiment, the acceptor comprises an optionally substituted acceptor rylene with four substituents at its bay positions, the optionally substituted donor rylene core comprises two substituents at its bay positions, and each optionally substituted peripheral donor rylene comprises no bay substituents. Preferably, the optionally substituted acceptor rylene, optionally substituted donor rylene core and optionally substituted peripheral donor rylene are optionally substituted perylenes. Preferably, the bay substituents are selected from the group consisting of optionally substituted aryloxy, optionally substituted heterocyclyloxy, optionally substituted arylamino, optionally substituted heterocyclylamino, optionally substituted arylthio, optionally substituted $C_{1-6}$alkyl, optionally substituted $C_{2-6}$alkenyl, optionally substituted $C_{2-6}$alkynyl, optionally substituted $C_{3-8}$cycloalkyl, optionally substituted aryl, optionally substituted $C_{1-6}$alkoxy, optionally substituted $C_{2-6}$alkenyloxy, optionally substituted $C_{2-6}$alkynyloxy, optionally substituted $C_{3-8}$cycloalkyloxy, optionally substituted $C_{1-6}$alkylamino, optionally substituted $C_{2-6}$alkenylamino, optionally substituted $C_{2-6}$alkynylamino, optionally substituted $C_{3-8}$cycloalkylamino, optionally substituted $C_{1-6}$alkylthio, optionally substituted $C_{2-6}$alkenylthio, optionally substituted $C_{2-6}$alkynylthio, optionally substituted $C_{3-8}$cycloalkylthio, optionally substituted heterocyclylthio, optionally substituted nitroaryloxy, optionally substituted aminoaryloxy, optionally substituted carboxylaryloxy, optionally substituted $C_{1-6}$alkoxyaryloxy, optionally substituted amidoaryloxy, optionally substituted nitroheterocyclyloxy, optionally substituted aminoheterocyclyloxy, optionally substituted carboxylheterocyclyloxy, optionally substituted $C_{1-6}$alkoxyheterocyclyloxy and optionally substituted amidoheterocyclyloxy. In one embodiment, the bay substituents are selected from the group consisting of optionally substituted aryloxy, optionally substituted heteroaryloxy, optionally substituted $C_{1-6}$alkoxy, optionally substituted $C_{2-6}$alkenyloxy, optionally substituted $C_{2-6}$alkynyloxy and optionally substituted $C_{3-8}$cycloalkyloxy. In another embodiment, the bay substituents are selected from the group consisting of optionally substituted $C_{1-6}$alkyl, optionally substituted $C_{2-6}$alkenyl, optionally substituted $C_{2-6}$alkynyl, optionally substituted $C_{3-8}$cycloalkyl, optionally substituted heterocyclyl, optionally substituted aryl, optionally substituted nitroaryloxy, optionally substituted aminoaryloxy, optionally substituted carboxylaryloxy, optionally substituted $C_{1-6}$alkoxyaryloxy, optionally substituted amidoaryloxy, optionally substituted nitroheteroaryloxy, optionally substituted aminoheteroaryloxy, optionally substituted carboxylheteroaryloxy, optionally substituted $C_{1-6}$alkoxyheteroaryloxy and optionally substituted amidoheteroaryloxy.

In one embodiment, the acceptor comprises an optionally substituted acceptor rylene with imide substitution at all four end positions (preferably two optionally substituted cyclic imides spanning neighbouring rylene end positions, e.g. the 3 and 4 positions of a perylene core), and the oligomeric unit comprises an optionally substituted donor rylene core also comprising imide substitution at all four end positions (preferably an optionally substituted cyclic imide spanning neighbouring rylene end positions), and each optionally substituted peripheral donor rylene comprising an imide substitution at one set of end positions (preferably an optionally substituted cyclic imide) and di-ester substitution at the other two end positions. In another embodiment, the acceptor comprises an optionally substituted acceptor rylene with imide substitution at all four end positions (preferably an optionally substituted cyclic imide spanning neighbouring end positions), and the oligomeric unit comprises an optionally substituted donor rylene core comprising imide substitution at one pair of end positions (preferably an optionally substituted cyclic imide) and di-ester substitution at the other two end positions, and each optionally substituted peripheral donor rylene comprising an imide substitution at one set of end positions (preferably an optionally substituted cyclic imide) and di-ester substitution at the other two end positions. Preferably, the optionally substituted acceptor rylene, optionally substituted donor rylene core and optionally substituted peripheral donor rylene are optionally substituted perylenes. Preferably, the end position substituents are selected from the group consisting of an optionally substituted ester, an optionally substituted amide, an optionally substituted $C_{1-20}$alkyl, optionally substituted $C_{2-20}$alkenyl, optionally substituted $C_{2-20}$alkynyl, an optionally substituted imide, optionally substituted aryl, optionally substituted heterocyclyl, optionally substituted $C_{3-8}$cycloalkyl, optionally substituted ketone, halo, oxo, optionally substituted $C_{1-20}$alkoxy and optionally substituted sulphonamide, or two neighboring rylene end groups (e.g. the 3 and 4 positions of a perylene core) may together form an optionally substituted cyclic imide, an optionally substituted aryl, an optionally substituted heterocyclyl, an optionally substituted $C_{3-8}$cycloalkyl or a cyclic anhydride.

In one embodiment, the light harvesting array comprises two or more donors, wherein at least two of the donors are oligomeric units. In another embodiment, at least three, four, five, six, seven, eight, nine, ten or more donors are oligomeric units each comprising, for example, an optionally substituted rylene core and at least one optionally substituted peripheral donor rylene.

In another embodiment, each oligomeric unit comprises an optionally substituted donor rylene core linked via a linker group to two or more optionally substituted peripheral donor rylenes. The higher the number of peripheral rylenes the greater their density around the acceptor. Therefore, it is advantageous to provide three, four, five, six or more peripheral donor rylenes within the oligomeric unit. Due to the relatively high threshold of photobleaching of rylenes, a large number of optionally substituted peripheral donor rylenes may transfer energy to a single FRET partner, e.g. an optionally substituted rylene core or an optionally substituted rylene acceptor, without significant photobleaching. Therefore, in some embodiments, the maximum number of peripheral donor rylenes included in each oligomeric unit is limited only by steric constraints.

The inclusion of at least one oligomeric unit into the light harvesting array increases the local density of donors surrounding the acceptor compared with a corresponding array including only monomeric donors. It will be appreciated that for a light harvesting array comprising an acceptor and one oligomeric unit comprising an optionally substituted donor rylene core and an optionally substituted peripheral donor rylene that the ratio of optionally substituted donor rylenes to the acceptor will be 2:1. In other embodiments, the ratio of optionally substituted donor rylenes to the acceptor may be 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, or higher.

As used herein the terms "core" and "peripheral" are relative to the oligomeric unit and each other. That is to say that the optionally substituted donor rylene core and the optionally substituted peripheral donor rylene are contained within the oligomeric unit; the core donor rylene may not be spatially at the centre of the oligomeric unit. For example, for an oligomeric unit comprising one optionally substituted donor rylene core and one optionally substituted peripheral donor rylene, the optionally substituted donor rylene core will not be located at the centre of the oligomeric unit. However, when an oligomeric unit comprises more than one optionally substituted peripheral donor rylene all of these will be linked to the optionally substituted donor rylene core. It will be appreciated that the absorbance and emission profiles of the optionally substituted donor rylene core and each optionally substituted peripheral donor rylene will not be identical. Accordingly, the oligomeric unit typically comprises two or more optionally substituted rylenes with different absorption/emission profiles when measured by UV-visible spectroscopy in isolation from the oligomeric unit. Preferably, the emission band of at least one of the two or more rylenes overlaps with the absorption band of another of the two or more rylenes. In some embodiments, there may be more than one type of optionally substituted peripheral donor rylene in each oligomeric unit. It will also be appreciated that other donors, including other donor perylenes, may also be incorporated into an oligomeric unit in addition to the optionally substituted donor rylene core and the one or more optionally substituted peripheral donor rylenes.

Either of the optionally substituted donor rylene core or the optionally substituted peripheral donor rylene may be linked to the acceptor. Consequently, in one embodiment the optionally substituted rylene core is linked to the acceptor. In another embodiment, an optionally substituted peripheral donor rylene is linked to the acceptor. In embodiments where the array comprises two or more oligomeric units, the optionally substituted donor rylene core may be linked to the acceptor for one of the oligomeric units, whereas the optionally substituted peripheral donor rylene of another oligomeric unit may be linked to the acceptor.

In one embodiment, all the dipoles of the optionally substituted rylene donor cores are spatially oriented at an angle to the acceptor to enable FRET. Preferably, all the dipoles of the optionally substituted peripheral donor rylenes are spatially oriented to at least one other donor of lower energy absorbance or to the acceptor to enable FRET. In another embodiment, orthogonal optionally substituted donor rylene cores exhibit coupling to the acceptor that does not require co-planar arrangement of dipoles, such as quadrupolar coupling, that allows FRET to occur typically at very short chromophoric distances, e.g., less than 2 nm.

The optionally substituted donor rylenes may be optionally substituted perylenes. As described above, perylenes possess a high quantum yield, are extremely photostable and have a wide range of absorptions and emissions. In one embodiment, the optionally substituted donor rylene core is an optionally substituted donor perylene core. In another embodiment, each optionally substituted peripheral donor rylene is an optionally substituted peripheral donor perylene.

Linker

A linker group is a tethering moiety extending between linked species, e.g. the acceptor and a donor or a peripheral perylene donor and the perylene core of the oligomeric unit. The link between species may be any type of chemical bonding, e.g. covalent, electrostatic, H-bonding, metal-metal, metal-ligand and so on. Preferably, the species are linked by a covalent bond.

It will be appreciated that in, e.g. the compounds of formulas IB-IH, X, X', XI and XII, and the oligomeric units of Formulas IIA-T, the linker group may link a chromophore and another species, e.g. a hydrogen atom (H).

The optionally substituted donor rylene core is linked via a linker group to the one or more optionally substituted peripheral donor rylenes. The rylene core includes the conjugated system that acts as the chromophoric portion of the rylene, or "chromophore", that undergoes light absorpotion, emission, FRET or other energy transfers distinguished from substituents which may affect the physical properties of the rylene, but are not responsible for actual light absorption, e.g. ester alkyl chains, imide alkyl chains and phenoxy groups. This linker group links two chromophores together and, where dipole orientation is a significant factor in FRET efficiency, preferably orients the chromophores to enable energy transfer. This linker group extends between the chromophore π-system of the optionally substituted donor rylene core and the chromophore π-system of the one or more optionally substituted peripheral donor rylenes.

In one embodiment, the acceptor is linked to each donor via a linker group, which may be the same or different than the linker group linking the optionally substituted donor rylene core with one or more optionally substituted peripheral donor rylenes. In another embodiment, the oligomeric unit is linked to the acceptor via the linker group that links the optionally substituted donor rylene core to an optionally substituted peripheral donor rylene.

The linker group may be attached to an optionally substituted rylene at any position. Preferably, the linker extends from a bay position, an imide position or the 3 or 4 position or equivalent (e.g. the 9 and 10 position of perylene or the 11 and 12 positions of terrylene) of the optionally substituted rylene.

The linker group ensures that the linked subunits are held or oriented in close proximity, e.g. within their respective Førster radii. That is to say that the linker group linking the acceptor to the at least one donor orients the acceptor and the at least one donor within the Førster radius for that FRET pair. Similarly, the linker group between the optionally substituted donor rylene core and the at least one optionally substituted peripheral donor rylene orients the donor rylenes within the Førster radius for that FRET pair. Therefore, the length of the linker group should be selected to match the Førster radius of the FRET pair being linked together.

In one embodiment, the linker group separates the FRET pair by a distance of about 0.5 nanometres to about 10 nanometres, preferably, about 2 nanometres to about 5 nanometres, most preferably about 0.5 to about 2 nanometres.

The distance that separates the FRET pair as used herein is the net spatial distance between the FRET pair.

In one embodiment, the linker group has a chain length of 1 to 20 atoms, preferably, of 3 to 15 atoms, most preferably of 5 to 12 atoms. In another embodiment, the linker group has a chain length of up to 30, 29, 28, 27, 26, 25, 24, 23, 22, 21, 20, 19, 18, 17, 16, 15, 14, 13, 12, 11, 10, 9, 8, 7, 6, 5, 4, 3, 2 or 1 atoms.

The term "chain length" as used herein is the number of atoms in sequence between (and including) the atom through which the FRET pair is attached following the shortest path between the FRET pair. For example, a perylene moiety linked via a 4-para-ethyl-phenoxy moiety from a bay position of a perylene moiety to an imide position of a perylene diimide moiety will have a chain length of 7 atoms, i.e. 1 atom for the O of the oxy group, 4 atoms for the phenyl ring, and 2 atoms for the para-ethyl moiety. The 2 atoms for the N and the carbonyl carbon of the imide moiety of the perylene diimide are included in the chromophore of the perylene diimide moiety and therefore are not part of the linker group. In another example, the same two perylene moieties linked via a 3-meta-ethyl-phenoxy moiety will have a chain length of 6 atoms.

In one embodiment, the linker group is an optionally substituted $C_{1-20}$alkyl group which may be optionally interrupted by one or more of the groups selected from oxy, ester, amide, sulphonamide, thio, sulphoxy, sulphonyl, sulphinyl, optionally substituted aryl, optionally substituted heterocyclyl (e.g. optionally substituted triazolyl), $C_2$alkenyl, $C_2$alkynyl and $C_{3-8}$cycloalkyl. In one embodiment, the optionally substituted $C_{1-20}$alkyl group is interrupted by 0, 1, 2, 3, 4, 5, 6, 7, 8, 9 or 10 of these groups, preferably 0 to 3 groups.

Furthermore, as described above, the substitution of an optionally substituted rylene affects the photophysical properties of the rylene moiety. Consequently, the linker group may be bifunctional, that is, it may link the FRET pair together within their Førster radius and moderate the photophysical properties of either or both members of the FRET pair to facilitate efficient FRET. In some embodiments, the linker group modulates the absorbance profile of the linked optionally substituted rylene. The linker group may be covalently bound to a bay position of the linked optionally substituted rylene. Preferably, the linker group comprises an aryloxy or heteroaryloxy moiety linked via the oxygen atom of the oxy moiety to the bay position of the linked optionally substituted rylene. For example, the linker may comprise a para-$C_{1-6}$alkylaryloxy moiety that may be covalently linked to a bay position of, for example, a core donor rylene at the "oxy" terminus and at the "alkyl" terminus is covalently linked to an imide position of an optionally substituted peripheral donor rylene. The bay substituted core donor rylene will generally exhibit a red shifted absorption profile, that is the absorption maxima is shifted to a lower energy relative to an equivalent rylene without the corresponding bay substitution. Advantageously, the red-shift of the absorbance maxima for this bay substituted optionally substituted donor rylene core results in an overlap with the fluorescence emission maxima of the peripheral rylene. In some embodiments, the linked optionally substituted rylene is an optionally substituted perylene.

The linker group may be selected from the group consisting of: optionally substituted $C_{1-20}$alkyl, optionally substituted $C_{2-20}$alkenyl, optionally substituted $C_{2-20}$alkynyl, optionally substituted $C_{3-8}$cycloalkyl, optionally substituted aryl, optionally substituted heterocyclyl, optionally substituted $C_{1-20}$alkoxy, optionally substituted $C_{2-20}$alkenyloxy, optionally substituted $C_{2-20}$alkynyloxy, optionally substituted $C_{3-8}$cycloalkoxy, optionally substituted aryloxy, optionally substituted heterocyclyloxy, optionally substituted ester, optionally substituted $C_{1-20}$alkylester, optionally substituted $C_{2-20}$alkenylester, optionally substituted $C_{2-20}$alkynylester, optionally substituted $C_{3-8}$cycloalkylester, optionally substituted arylester, optionally substituted heterocyclylester, optionally substituted amino, optionally substituted $C_{1-20}$alkylamino, optionally substituted $C_{2-20}$alkenylamino, optionally substituted $C_{2-20}$alkynylamino, optionally substituted $C_{3-8}$cycloalkylamino, optionally substituted arylamino, optionally substituted heterocyclylamino, optionally substituted amido, optionally substituted $C_{1-20}$alkylamido, optionally substituted $C_{2-20}$alkenylamido, optionally substituted $C_{2-20}$alkynylamido, optionally substituted $C_{3-8}$cycloalkylamido, optionally substituted arylamido, optionally substituted heterocyclylamido, optionally substituted ketone, optionally substituted $C_{1-20}$alkylketone, optionally substituted $C_{2-20}$alkenylketone, optionally substituted $C_{2-20}$alkynylketone, optionally substituted $C_{3-8}$cycloalkylketone, optionally substituted arylketone, optionally substituted heterocyclylketone, optionally substituted thio, optionally substituted $C_{1-20}$alkylthio, optionally substituted $C_{2-20}$alkenylthio, optionally substituted $C_{2-20}$alkynylthio, optionally substituted $C_{3-8}$cycloalkylthio, optionally substituted arylthio, optionally substituted heterocyclylthio, optionally substituted $C_{1-20}$alkylsulfinyl, optionally substituted $C_{2-20}$alkenylsulfinyl, optionally substituted $C_{2-20}$alkynylsulfinyl, optionally substituted $C_{3-8}$cycloalkylsulfinyl, optionally substituted arylsulfinyl, optionally substituted heterocyclylsulfinyl, optionally substituted $C_{1-20}$alkylsulfonyl, optionally substituted $C_{2-20}$alkenylsulfonyl, optionally substituted $C_{2-20}$alkynylsulfonyl, optionally substituted $C_{3-8}$cycloalkylsulfonyl, optionally substituted arylsulfonyl, optionally substituted heterocyclylsulfonyl, optionally substituted $C_{1-20}$alkylsulfonate, optionally substituted $C_{2-20}$alkenylsulfonate, optionally substituted $C_{2-20}$alkynylsulfonate, optionally substituted $C_{3-8}$cycloalkylsulfonate, optionally substituted arylsulfonate, optionally substituted heterocyclylsulfonate, optionally substituted nitroaryloxy, optionally substituted aminoaryloxy, optionally substituted carboxylaryloxy, optionally substituted $C_{1-6}$alkoxyaryloxy, optionally substituted amidoaryloxy, optionally substituted nitroheterocyclyloxy, optionally substituted aminoheterocyclyloxy, optionally substituted carboxylheterocyclyloxy, optionally substituted $C_{1-6}$alkoxyheterocyclyloxy and optionally substituted amidoheterocyclyloxy.

In one embodiment, the linker group may be attached to the bay position of an optionally substituted rylene. This linker group may be selected from the group consisting of an optionally substituted $C_{1-20}$alkoxy, an optionally substituted $C_{2-20}$alkenyloxy, an optionally substituted $C_{2-20}$alkynyloxy, an optionally substituted $C_{1-20}$alkyl, an optionally substituted $C_{2-20}$alkenyl, an optionally substituted $C_{2-20}$alkynyl, an optionally substituted heterocyclyl, an optionally substituted heterocyclyloxy, an optionally substituted aryl, an optionally substituted aryloxy, an optionally substituted arylthio, an optionally substituted arylamino, an optionally substituted heterocyclyloxy, an optionally substituted heterocyclylthio, an optionally substituted heterocyclylamino, an optionally substituted $C_{2-20}$alkenyloxy, an optionally substituted $C_{2-20}$alkynyloxy, an optionally substituted $C_{2-20}$alkenylamino, an optionally substituted $C_{2-20}$alkynylamino, an optionally substituted $C_{2-20}$alkenylthio, an optionally substituted $C_{2-20}$alkynylthio, an optionally substituted $C_{1-20}$alkylamino, an optionally substituted $C_{1-20}$alkylthio, an optionally substituted $C_{3-8}$cycloalkyl, an optionally substituted $C_{3-8}$cycloalkyloxy, an optionally substituted $C_{3-8}$cycloalkylamino, an optionally substituted $C_{3-8}$cycloalkylthio, optionally substituted nitroaryloxy, optionally substituted aminoaryloxy, optionally substituted carboxylaryloxy, optionally substituted $C_{1-6}$alkoxyaryloxy, optionally substituted amidoaryloxy, optionally substituted nitroheterocyclyloxy, optionally substituted aminoheterocyclyloxy, optionally substituted carboxylheterocyclyloxy, optionally substituted $C_{1-6}$alkoxyheterocyclyloxy and optionally substituted amidoheterocyclyloxy.

In another embodiment, the linker group may be attached to the imide position of an optionally substituted rylene. This linker group may be selected from the group consisting of optionally substituted ester, optionally substituted $C_{1-20}$alkylester, optionally substituted $C_{2-20}$alkenylester, optionally substituted $C_{2-20}$alkynylester, optionally substituted $C_{3-8}$cycloalkylester, optionally substituted arylester, optionally substituted heterocyclylester, optionally substituted amido, optionally substituted $C_{1-20}$alkylamido, optionally substituted C$_{2-20}$alkenylamido, optionally substituted C$_{2-20}$alkynylamido, optionally substituted arylamido, optionally substituted heterocyclylamido, optionally substituted amino, optionally substituted C$_{1-20}$alkylamino, optionally substituted C$_{2-20}$alkenylamino, optionally substituted C$_{2-20}$alkynylamino, optionally substituted arylamino, optionally substituted heterocyclylamino, optionally substituted heterocyclyl, optionally substituted C$_{1-20}$alkylheterocyclyl, optionally substituted C$_{2-20}$alkenylheterocyclyl and optionally substituted C$_{2-20}$alkynylheterocyclyl.

It will be appreciated that where the linker group is an optionally substituted moiety, for example an optionally substituted heterocyclyl, the linker group may be attached directly to that moiety, e.g. heterocyclyl, or via one or more of the optional substituents when present. Further, where the linker group links two or more optionally substituted rylenes between a bay position and an imide position, the linker group may include one or more of the preferred linker groups as defined above.

The linker group linking the acceptor to the one or more donors may be any of the linker groups described above. In one embodiment, the linker group linking the acceptor to the one or more donors is selected from the group consisting of optionally substituted C$_{1-20}$alkoxy, an optionally substituted C$_{2-20}$alkenyloxy, an optionally substituted C$_{2-20}$alkynyloxy, an optionally substituted C$_{1-20}$alkyl, an optionally substituted C$_{2-20}$alkenyl, an optionally substituted C$_{2-20}$alkynyl, an optionally substituted heterocyclyl, an optionally substituted heterocyclyloxy, an optionally substituted aryl, an optionally substituted aryloxy, an optionally substituted arylthio, an optionally substituted arylamino, an optionally substituted heterocyclyloxy, an optionally substituted heterocyclylthio, optionally substituted nitroaryloxy, optionally substituted aminoaryloxy, optionally substituted carboxylaryloxy, optionally substituted C$_{1-6}$alkoxyaryloxy, optionally substituted amidoaryloxy, optionally substituted nitroheterocyclyloxy, optionally substituted aminoheterocyclyloxy, optionally substituted carboxylheterocyclyloxy, optionally substituted C$_{1-6}$alkoxyheterocyclyloxy, optionally substituted amidoheterocyclyloxy, an optionally substituted heterocyclylamino, an optionally substituted C$_{2-20}$alkenyloxy, an optionally substituted C$_{2-20}$alkynyloxy, an optionally substituted C$_{2-20}$alkenylamino, an optionally substituted C$_{2-20}$alkynylamino, an optionally substituted C$_{2-20}$alkenylthio, an optionally substituted C$_{2-20}$alkynylthio, an optionally substituted C$_{1-20}$alkylamino, an optionally substituted C$_{1-20}$alkylthio, an optionally substituted C$_{3-8}$cycloalkyl, an optionally substituted C$_{3-8}$cycloalkyloxy, an optionally substituted C$_{3-8}$cycloalkylamino, an optionally substituted C$_{3-8}$cycloalkylthio, optionally substituted ester, optionally substituted C$_{1-20}$alkylester, optionally substituted C$_{2-20}$alkenylester, optionally substituted C$_{2-20}$alkynylester, optionally substituted C$_{3-8}$cycloalkylester, optionally substituted arylester, optionally substituted heterocyclylester, optionally substituted amido, optionally substituted C$_{1-20}$alkylamido, optionally substituted C$_{2-20}$alkenylamido, optionally substituted C$_{2-20}$alkynylamido, optionally substituted arylamido, optionally substituted heterocyclylamido, optionally substituted amino, optionally substituted C$_{1-20}$alkylheterocyclyl, optionally substituted C$_{2-20}$alkenylheterocyclyl and optionally substituted C$_{2-20}$alkynylheterocyclyl.

The linker group linking the optionally substituted donor rylene core and the optionally substituted peripheral donor rylene may be any of the linker groups described above. In one embodiment, the linker group linking the optionally substituted donor rylene core and the optionally substituted peripheral donor rylene may be selected from the group consisting of optionally substituted C$_{1-20}$alkoxy, an optionally substituted C$_{2-20}$alkenyloxy, an optionally substituted C$_{2-20}$alkynyloxy, an optionally substituted C$_{1-20}$alkyl, an optionally substituted C$_{2-20}$alkenyl, an optionally substituted C$_{2-20}$alkynyl, an optionally substituted heterocyclyl, an optionally substituted heterocyclyloxy, an optionally substituted aryl, an optionally substituted aryloxy, an optionally substituted arylthio, an optionally substituted arylamino, an optionally substituted heterocyclyloxy, an optionally substituted heterocyclylthio, an optionally substituted heterocyclylamino, optionally substituted nitroaryloxy, optionally substituted aminoaryloxy, optionally substituted carboxylaryloxy, optionally substituted C$_{1-6}$alkoxyaryloxy, optionally substituted amidoaryloxy, optionally substituted nitroheterocyclyloxy, optionally substituted aminoheterocyclyloxy, optionally substituted carboxylheterocyclyloxy, optionally substituted C$_{1-6}$alkoxyheterocyclyloxy, optionally substituted amidoheterocyclyloxy, an optionally substituted C$_{2-20}$alkenyloxy, an optionally substituted C$_{2-20}$alkynyloxy, an optionally substituted C$_{2-20}$alkenylamino, an optionally substituted C$_{2-20}$alkynylamino, an optionally substituted C$_{2-20}$alkenylthio, an optionally substituted C$_{2-20}$alkynylthio, an optionally substituted C$_{1-20}$alkylamino, an optionally substituted C$_{1-20}$alkylthio, an optionally substituted C$_{3-8}$cycloalkyl, an optionally substituted C$_{3-8}$cycloalkyloxy, an optionally substituted C$_{3-8}$cycloalkylamino, an optionally substituted C$_{3-8}$cycloalkylthio, optionally substituted ester, optionally substituted C$_{1-20}$alkylester, optionally substituted C$_{2-20}$alkenylester, optionally substituted C$_{2-20}$alkynylester, optionally substituted C$_{3-8}$cycloalkylester, optionally substituted arylester, optionally substituted heterocyclylester, optionally substituted amido, optionally substituted C$_{1-20}$alkylamido, optionally substituted C$_{2-20}$alkenylamido, optionally substituted C$_{2-20}$alkynylamido, optionally substituted arylamido, optionally substituted heterocyclylamido, optionally substituted amino, optionally substituted C$_{1-20}$alkylheterocyclyl, optionally substituted C$_{2-20}$alkenylheterocyclyl and optionally substituted C$_{2-20}$alkynylheterocyclyl. Preferably, oxy, thio or amino moiety of these linker groups is bound to a bay position of the optionally substituted donor rylene core.

In one embodiment, the linker group is an optionally substituted tyramine linker group. The optionally substituted tyramine linker group may have the following structure:

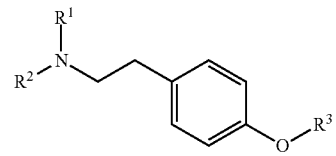

wherein:
R$^1$ and R$^2$ are independently selected from the group consisting of an optionally substituted donor rylene core, an optionally substituted peripheral donor rylene or R$^4$; or
R$^1$ and R$^2$ together with the nitrogen atom to which they are attached form the optionally substituted donor rylene core or the optionally substituted peripheral donor rylene;
R$^3$ is selected from an optionally substituted donor rylene core or an optionally substituted peripheral donor rylene;
R$^4$ is selected from the group consisting of H, optionally substituted C$_{1-6}$alkyl, optionally substituted C$_{2-6}$alkenyl, optionally substituted C$_{2-6}$alkynyl, optionally substituted $C_{3-8}$cycloalkyl, hydroxyl, optionally substituted $C_{1-6}$alkoxy, optionally substituted aryloxy, optionally substituted $C_{1-6}$alkoxyaryl, optionally substituted $C_{1-6}$alkylhalo, optionally substituted $C_{1-6}$alkoxyhalo, carboxyl, optionally substituted esters, optionally substituted ketones, optionally substituted amides, optionally substituted aminoketones, thiol, optionally substituted alkylthio, optionally substituted sulfates, optionally substituted sulfonates, optionally substituted sulfinyl, optionally substituted sulfonyl, substituted sulfonyl, optionally substituted aryl, optionally substituted aryl$C_{1-6}$alkyl, and optionally substituted heterocyclyl;

wherein at least one of $R^1$ and $R^2$ is an optionally substituted donor rylene core or an optionally substituted peripheral donor rylene, or $R^1$ and $R^2$ together with the nitrogen atom to which they are attached form the optionally substituted peripheral donor rylene; and when $R^3$ is the optionally substituted donor rylene core, at least one of $R^1$ and $R^2$ is the optionally substituted peripheral donor rylene; and when $R^3$ is the optionally substituted peripheral donor rylene at least one of $R^1$ and $R^2$ is the optionally substituted donor rylene core, or $R^1$ and $R^2$ together with the nitrogen atom to which they are attached form the optionally substituted donor rylene core. Preferably, $R^3$ is the optionally substituted donor rylene core.

In one embodiment, the linker group comprises an optionally substituted aryl. Preferably, the optionally substituted aryl is an optionally substituted 6 to 10 membered carbocyclic aromatic mono- or bi-cyclic ring system. More preferably, the optionally substituted aryl is an optionally substituted 6 or 10 membered carbocyclic aromatic ring system, such as phenyl or naphthyl, most preferably the optionally substituted aryl is an optionally substituted 6 membered carbocyclic aromatic ring system, such as phenyl.

In one embodiment, the linker group comprises an optionally substituted heterocyclyl. Typically, the optionally substituted heterocyclyl may be an aromatic or non-aromatic, 3 to 10 membered, mono- or bi-cyclic ring system of which 1, 2, 3 or 4 atoms are ring heteroatoms, each ring heteroatom being independently selected from O, S and N. In one embodiment, the optionally substituted heterocyclyl may be an aromatic or non-aromatic, 5 or 6 membered, mono-cyclic ring system of which 1, 2 or 3 atoms are ring heteroatoms, each ring heteroatom being independently selected from O, S and N, preferably N. In another embodiment, the optionally substituted heterocyclyl may be an aromatic, 5 or 6 membered, mono-cyclic ring system of which 1, 2 or 3 atoms are ring heteroatoms, each ring heteroatom being independently selected from O, S and N, preferably N. In yet another embodiment, the optionally substituted heterocyclyl may be an aromatic, 5 or 6 membered, mono-cyclic ring system of which 1, 2 or 3 atoms are ring heteroatoms, each ring heteroatom being N, for example an optionally substituted triazolyl.

Array Embodiments

In an embodiment, the light harvesting array is a compound of formula I described above.

A may be selected from the acceptors described above.

In some embodiments, n is an integer selected from the group consisting of 1, 2, 3, 4, 5, 6, 7, 8, 9 or 10. Preferably, n is selected from the group consisting of 2, 4, 6 and 8, most preferably 4 or 8.

D may be selected from the oligomeric units described above.

L may be selected from the linker groups described above.

In one embodiment, the compound of formula I is a compound of formula IA:

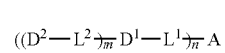

Formula IA wherein:

A is the acceptor;

n is an integer of 1 to 10;

$L^1$ is absent or a linker group;

$L^2$ is absent or a linker group;

$D^1$ is an optionally substituted donor rylene core;

$D^2$ is an optionally substituted peripheral donor rylene; and m is an integer of 1 to 10.

A may be selected from the acceptors described above.

In some embodiments, n is an integer selected from the group consisting of 1, 2, 3, 4, 5, 6, 7, 8, 9 or 10. Preferably, n is selected from the group consisting of 2, 4, 6 and 8, most preferably 4 or 8.

$D^1$ and $D^2$ may be independently selected from an optionally substituted donor rylene described above.

In one embodiment, $D^1$ and $D^2$ are independently an optionally substituted donor perylene. In another embodiment, $D^1$ and $D^2$ are both optionally substituted donor perylenes.

In one embodiment, $D^1$ is an optionally substituted donor perylene comprising one or more bay substituents selected from an optionally substituted aryloxy, an optionally substituted heteroaryloxy, an optionally substituted $C_{1-6}$alkoxy, an optionally substituted arylthio, an optionally substituted heteroarylthio, an optionally substituted arylamino and an optionally substituted heteroarylamino. In another embodiment, $D^1$ is an optionally substituted donor perylene diimide, i.e. an optionally substituted donor perylene comprising two imido groups at the 3, 4 and the 9,10 positions of the perylene.

In one embodiment, $D^2$ is an optionally substituted donor perylene comprising one or more bay substituents selected from an optionally substituted aryl, an optionally substituted $C_{1-6}$alkyl, an optionally substituted heterocyclyl, an optionally substituted $C_{3-8}$cycloalkyl, an optionally substituted $C_{1-6}$alkenyl and an optionally substituted $C_{2-6}$alkynyl. In another embodiment, $D^2$ is an optionally substituted donor perylene comprising one or more substituents at one or more of the 3, 4, 9 or 10 positions selected from an optionally substituted $C_{1-6}$alkylester, an optionally substituted $C_{2-6}$alkenylester, an optionally substituted $C_{1-6}$alkynylester, an optionally substituted $C_{1-6}$alkylamide, an optionally substituted $C_{2-6}$alkenylamide, an optionally substituted $C_{2-6}$alkynylamide and an optionally substituted heterocyclyl. In another embodiment, $D^2$ is an optionally substituted donor perylene monoimide, i.e. an optionally substituted donor perylene comprising a single imido group at the 3,4 or the 9,10 positions of the perylene.

$L^1$ and $L^2$ may be independently selected from the linker groups described above.

In one embodiment, $L^1$ and $L^2$ are independently selected from the group consisting of optionally substituted $C_{1-20}$alkoxy, an optionally substituted $C_{2-20}$alkenyloxy, an optionally substituted $C_{2-20}$alkynyloxy, an optionally substituted $C_{1-20}$alkyl, an optionally substituted $C_{2-20}$alkenyl, an optionally substituted $C_{2-20}$alkynyl, an optionally substituted heterocyclyl, an optionally substituted heterocyclyloxy, an optionally substituted aryl, an optionally substituted aryloxy, an optionally substituted arylthio, an optionally substituted arylamino, an optionally substituted heterocyclyloxy, an optionally substituted heterocyclylthio, an optionally substituted heterocyclylamino, optionally substituted nitroaryloxy, optionally substituted aminoaryloxy, optionally substituted carboxylaryloxy, optionally substituted $C_{1-6}$alkoxyaryloxy, optionally substituted amidoaryloxy, optionally substituted nitroheterocyclyloxy, optionally substituted aminoheterocyclyloxy, optionally substituted carboxylheterocyclyloxy, optionally substituted $C_{1-6}$alkoxyheterocyclyloxy, optionally substituted amidoheterocyclyloxy, an optionally substituted $C_{2-20}$alkenyloxy, an optionally substituted $C_{2-20}$alkynyloxy, an optionally substituted $C_{2-20}$alkenylamino, an optionally substituted $C_{2-20}$alkynylamino, an optionally substituted $C_{2-20}$alkenylthio, an optionally substituted $C_{2-20}$alkynylthio, an optionally substituted $C_{1-20}$alkylamino, an optionally substituted $C_{1-20}$alkylthio, an optionally substituted $C_{3-8}$cycloalkyl, an optionally substituted $C_{3-8}$cycloalkyloxy, an optionally substituted $C_{3-8}$cycloalkylamino, an optionally substituted $C_{3-8}$cycloalkylthio, optionally substituted ester, optionally substituted $C_{1-20}$alkylester, optionally substituted $C_{2-20}$alkenylester, optionally substituted $C_{2-20}$alkynylester, optionally substituted $C_{3-8}$cycloalkylester, optionally substituted arylester, optionally substituted heterocyclylester, optionally substituted amido, optionally substituted $C_{1-20}$alkylamido, optionally substituted $C_{2-20}$alkenylamido, optionally substituted $C_{2-20}$alkynylamido, optionally substituted arylamido, optionally substituted heterocyclylamido, optionally substituted amino, optionally substituted $C_{1-20}$alkylheterocyclyl, optionally substituted $C_{2-20}$alkenylheterocyclyl and optionally substituted $C_{2-20}$alkynylheterocyclyl.

In some embodiments, m is an integer selected from the group consisting of 1, 2, 3, 4, 5, 6, 7, 8, 9 or 10.

In one embodiment, the compound of formula I is a compound of formula IB:

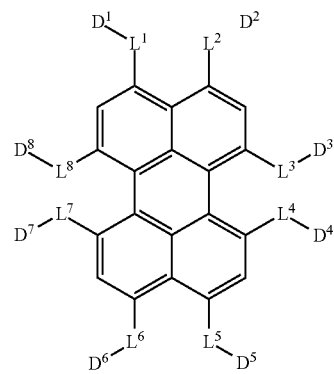

Formula IB wherein:
$L^1$, $L^2$, $L^3$, $L^4$, $L^5$, $L^6$, $L^7$ and $L^8$ are independently absent or a linker group; or
$L^1$ and $L^2$, $L^3$ and $L^4$, $L^5$ and $L^6$, and $L^7$ and $L^8$ together with the perylene scaffold to which they are attached form an optionally substituted $C_{5-8}$cycloalkyl, an optionally substituted heterocyclyl or an optionally substituted aryl group; and
$D^1$, $D^2$, $D^3$, $D^4$, $D^5$, $D^6$, $D^7$ and $D^8$ are independently H or a donor,
wherein at least one of $D^1$, $D^2$, $D^3$, $D^4$, $D^5$, $D^6$, $D^7$ and $D^8$ is an oligomeric unit comprising an optionally substituted donor rylene core and one or more optionally substituted peripheral donor rylenes.

$L^1$, $L^2$, $L^3$, $L^4$, $L^5$, $L^6$, $L^7$ and $L^8$ may be independently selected from the linker groups described above. It will be appreciated that when any one of $D^1$, $D^2$, $D^3$, $D^4$, $D^5$, $D^6$, $D^7$ and $D^8$ is H, the corresponding $L^1$, $L^2$, $L^3$, $L^4$, $L^5$, $L^6$, $L^7$ and $L^8$ may be a linker group linking this hydrogen atom to the perylene scaffold.

When $L^1$ and $L^2$, $L^3$ and $L^4$, $L^5$ and $L^6$, or $L^7$ and $L^8$ together with the perylene scaffold to which they are attached form an optionally substituted $C_{5-8}$cycloalkyl, an optionally substituted heterocyclyl or an optionally substituted aryl group, each of $D^2$, $D^4$, $D^6$ and $D^8$ may independently be H.

In one embodiment, $L^1$ and $L^2$ together with the perylene scaffold to which they are attached form an optionally substituted naphthylene moiety such that the perylene scaffold of the compound of formula IB is extended to a terrylene scaffold.

$D^1$, $D^2$, $D^3$, $D^4$, $D^5$, $D^6$, $D^7$ and $D^8$ may be independently selected from the oligomeric units described above.

In one embodiment, the optionally substituted donor rylene core is an optionally substituted donor perylene. This optionally substituted donor perylene core may comprise one or more bay substituents selected from the group consisting of an optionally substituted $C_{1-20}$alkoxy, an optionally substituted $C_{2-20}$alkenyloxy, an optionally substituted $C_{2-20}$alkynyloxy, an optionally substituted $C_{1-20}$alkyl, an optionally substituted $C_{2-20}$alkenyl, an optionally substituted $C_{2-20}$alkynyl, an optionally substituted heterocyclyl, an optionally substituted heterocyclyloxy, an optionally substituted aryl, an optionally substituted aryloxy, an optionally substituted arylthio, an optionally substituted arylamino, an optionally substituted heterocyclyloxy, an optionally substituted heterocyclylthio, an optionally substituted heterocyclylamino, an optionally substituted $C_{2-20}$alkenyloxy, an optionally substituted $C_{2-20}$alkynyloxy, an optionally substituted $C_{2-20}$alkenylamino, an optionally substituted $C_{2-20}$alkynylamino, an optionally substituted $C_{2-20}$alkenylthio, an optionally substituted $C_{2-20}$alkynylthio, an optionally substituted $C_{1-20}$alkylamino, an optionally substituted $C_{1-20}$alkylthio, an optionally substituted $C_{3-8}$cycloalkyl, an optionally substituted $C_{3-8}$cycloalkyloxy, an optionally substituted $C_{3-8}$cycloalkylamino, an optionally substituted $C_{3-8}$cycloalkylthio, optionally substituted nitroaryloxy, optionally substituted aminoaryloxy, optionally substituted carboxylaryloxy, optionally substituted $C_{1-6}$alkoxyaryloxy, optionally substituted amidoaryloxy, optionally substituted nitroheterocyclyloxy, optionally substituted aminoheterocyclyloxy, optionally substituted carboxylheterocyclyloxy, optionally substituted $C_{1-6}$alkoxyheterocyclyloxy and optionally substituted amidoheterocyclyloxy. Preferably, the optionally substituted donor perylene core may comprise one or more bay substituents selected from the group consisting of an optionally substituted aryloxy and an optionally substituted heteroaryloxy.

The one or more optionally substituted peripheral donor rylenes may be an optionally substituted donor perylene.

In one embodiment, the compound of formula I is a compound of formula IC:

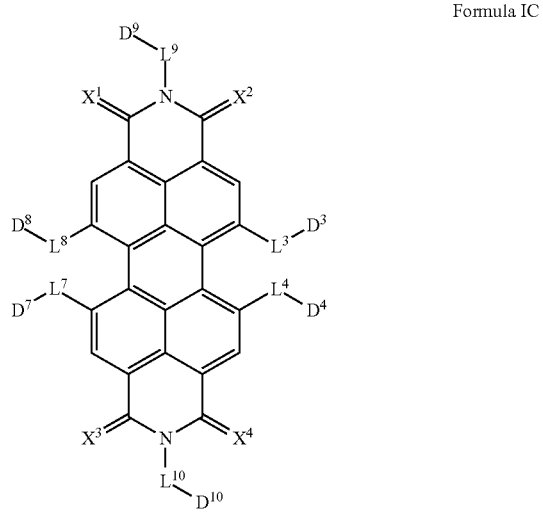

Formula IC wherein:
$X^1$, $X^2$, $X^3$ and $X^4$ are independently selected from O, S, $NR^1$ and $CR^1R^2$;
$R^1$ and $R^2$ are each independently selected from H, optionally substituted $C_{1-6}$alkyl, optionally substituted $C_{2-6}$alkenyl, optionally substituted $C_{2-6}$alkynyl, optionally substituted $C_{3-8}$cycloalkyl, hydroxyl, optionally substituted $C_{1-6}$alkoxy, optionally substituted aryloxy, optionally substituted $C_{1-6}$alkoxyaryl, optionally substituted $C_{1-6}$alkylhalo, optionally substituted $C_{1-6}$alkoxyhalo, carboxyl, optionally substituted esters, optionally substituted ketones, optionally substituted amides, optionally substituted aminoketones, thiol, optionally substituted alkylthio, optionally substituted sulfates, optionally substituted sulfonates, optionally substituted sulfinyl, optionally substituted sulfonyl, substituted sulfonyl, optionally substituted aryl, optionally substituted aryl$C_{1-6}$alkyl, and optionally substituted heterocyclyl;
$L^3$, $L^4$, $L^7$, $L^8$, $L^9$ and $L^{10}$ are independently absent or a linker group, preferably selected from the linker groups described above; or
$L^3$ and $L^4$ and $L^7$ and $L^8$ may together with the perylene scaffold to which they are attached form an optionally substituted $C_{5-8}$cycloalkyl, an optionally substituted heterocyclyl or an optionally substituted aryl group; and
$L^9$ and $X^1$ or $X^2$ may together with the heterocyclic scaffold to which they are attached form an optionally substituted heterocyclyl group; and
$L^{10}$ and $X^3$ or $X^4$ may together with the heterocyclic scaffold to which they are attached form an optionally substituted heterocyclyl group; and
$D^3$, $D^4$, $D^7$, $D^8$, $D^9$ and $D^{10}$ are each independently H or a donor, wherein at least one of $D^3$, $D^4$, $D^7$, $D^8$, $D^9$ and $D^{10}$ is an oligomeric unit comprising an optionally substituted donor rylene core and one or more optionally substituted peripheral donor rylenes.

The oligomeric unit may be as described above.

In one embodiment, $L^3$ and $L^4$, and $L^7$ and $L^8$, form aryl rings together with the perylene scaffold to which they are attached such that the perylene scaffold is ring extended to form a benzocoronene scaffold.

In another embodiment, two or more of $L^3$, $L^4$, $L^7$ and $L^8$ are independently selected from an optionally substituted $C_{1-20}$alkoxy, an optionally substituted $C_{2-20}$alkenyloxy, an optionally substituted $C_{2-20}$alkynyloxy, an optionally substituted $C_{1-20}$alkyl, an optionally substituted $C_{2-20}$alkenyl, an optionally substituted $C_{2-20}$alkynyl, an optionally substituted heterocyclyl, an optionally substituted heterocyclyloxy, an optionally substituted aryl, an optionally substituted aryloxy, an optionally substituted arylthio, an optionally substituted arylamino, an optionally substituted heterocyclyloxy, an optionally substituted heterocyclylthio, an optionally substituted heterocyclylamino, an optionally substituted $C_{2-20}$alkenyloxy, an optionally substituted $C_{2-20}$alkynyloxy, an optionally substituted $C_{2-20}$alkenylamino, an optionally substituted $C_{2-20}$alkynylamino, an optionally substituted $C_{2-20}$alkenylthio, an optionally substituted $C_{2-20}$alkynylthio, an optionally substituted $C_{1-20}$alkylamino, an optionally substituted $C_{1-20}$alkylthio, an optionally substituted $C_{3-8}$cycloalkyl, an optionally substituted $C_{3-8}$cycloalkyloxy, an optionally substituted $C_{3-8}$cycloalkylamino, an optionally substituted $C_{3-8}$cycloalkylthio, optionally substituted nitroaryloxy, optionally substituted aminoaryloxy, optionally substituted carboxylaryloxy, optionally substituted $C_{1-6}$alkoxyaryloxy, optionally substituted amidoaryloxy, optionally substituted nitroheterocyclyloxy, optionally substituted aminoheterocyclyloxy, optionally substituted carboxylheterocyclyloxy, optionally substituted $C_{1-6}$alkoxyheterocyclyloxy and optionally substituted amidoheterocyclyloxy.

In one embodiment, $D^3$, $D^4$, $D^7$ and $D^8$ are H, and $L^3$, $L^4$, $L^7$ and $L^8$ are absent or independently selected from an optionally substituted $C_{1-20}$alkoxy, an optionally substituted $C_{2-20}$alkenyloxy, an optionally substituted $C_{2-20}$alkynyloxy, an optionally substituted $C_{1-20}$alkyl, an optionally substituted $C_{2-20}$alkenyl, an optionally substituted $C_{2-20}$alkynyl, an optionally substituted heterocyclyl, an optionally substituted heterocyclyloxy, an optionally substituted aryl, an optionally substituted aryloxy, an optionally substituted arylthio, an optionally substituted arylamino, an optionally substituted heterocyclyloxy, an optionally substituted heterocyclylthio, an optionally substituted heterocyclylamino, an optionally substituted $C_{2-20}$alkenyloxy, an optionally substituted $C_{2-20}$alkynyloxy, an optionally substituted $C_{2-20}$alkenylamino, an optionally substituted $C_{2-20}$alkynylamino, an optionally substituted $C_{2-20}$alkenylthio, an optionally substituted $C_{2-20}$alkynylthio, an optionally substituted $C_{1-20}$alkylamino, an optionally substituted $C_{1-20}$alkylthio, an optionally substituted $C_{3-8}$cycloalkyl, an optionally substituted $C_{3-8}$cycloalkyloxy, an optionally substituted $C_{3-8}$cycloalkylamino, an optionally substituted $C_{3-8}$cycloalkylthio, optionally substituted nitroaryloxy, optionally substituted aminoaryloxy, optionally substituted carboxyaryloxy, optionally substituted $C_{1-6}$alkoxyaryloxy, optionally substituted amidoaryloxy, optionally substituted nitroheterocyclyloxy, optionally substituted aminoheterocyclyloxy, optionally substituted carboxylheterocyclyloxy, optionally substituted $C_{1-6}$alkoxyheterocyclyloxy and optionally substituted amidoheterocyclyloxy.

In one embodiment, the compound of formula I is a compound of formula ID:

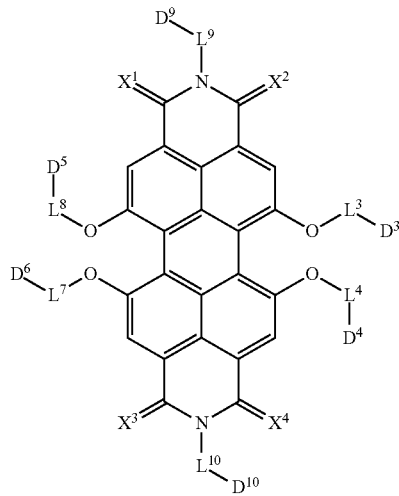

Formula ID wherein:
$X^1$, $X^2$, $X^3$ and $X^4$ are independently selected from O, S, $NR^1$ and $CR^1R^2$;
$R^1$ and $R^2$ are independently selected from H, optionally substituted $C_{1-6}$alkyl, optionally substituted $C_{2-6}$alkenyl, optionally substituted $C_{2-6}$alkynyl, optionally substituted $C_{3-8}$cycloalkyl, hydroxyl, optionally substituted $C_{1-6}$alkoxy, optionally substituted aryloxy, optionally substituted $C_{1-6}$alkoxyaryl, optionally substituted $C_{1-6}$alkylhalo, optionally substituted $C_{1-6}$alkoxyhalo, carboxyl, optionally substituted esters, optionally substituted ketones, optionally substituted amides, optionally substituted aminoketones, thiol, optionally substituted alkylthio, optionally substituted sulfates, optionally substituted sulfonates, optionally substituted sulfinyl, optionally substituted sulfonyl, substituted sulfonyl, optionally substituted aryl, optionally substituted aryl$C_{1-6}$alkyl, and optionally substituted heterocyclyl;

$L^3$, $L^4$, $L^7$, $L^8$, $L^9$ and $L^{10}$ are independently absent or a linker group, preferably selected from the linker groups described above; or $L^3$ and $L^4$ and $L^7$ and $L^8$ together with the perylene scaffold to which they are attached form an optionally substituted $C_{5-8}$cycloalkyl, an optionally substituted heterocyclyl or an optionally substituted aryl group; and $L^9$ and $X^1$ or $X^2$ together with the heterocyclic scaffold to which they are attached form an optionally substituted heterocyclyl group; and $L^{10}$ and $X^3$ or $X^4$ together with the heterocyclic scaffold to which they are attached form an optionally substituted heterocyclyl group; and $D^3$, $D^4$, $D^5$, $D^6$, $D^9$ and $D^{10}$ are independently H or a donor, wherein at least one of $D^3$, $D^4$, $D^5$, $D^6$, $D^9$ and $D^{10}$ is an oligomeric unit comprising an optionally substituted donor rylene core and one or more optionally substituted peripheral donor rylenes.

The oligomeric unit may be as described above.

In one embodiment, the compound of formula I is a compound of formula IE:

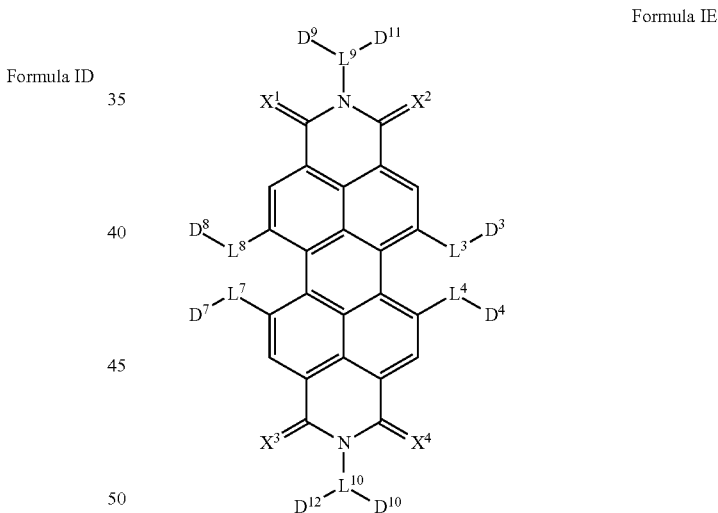

Formula IE wherein:
$X^1$, $X^2$, $X^3$ and $X^4$ are independently selected from O, S, $NR^1$ and $CR^1R^2$;
$R^1$ and $R^2$ are each independently selected from H, optionally substituted $C_{1-6}$alkyl, optionally substituted $C_{2-6}$alkenyl, optionally substituted $C_{2-6}$alkynyl, optionally substituted $C_{3-8}$cycloalkyl, hydroxyl, optionally substituted $C_{1-6}$alkoxy, optionally substituted aryloxy, optionally substituted $C_{1-6}$alkoxyaryl, optionally substituted $C_{1-6}$alkylhalo, optionally substituted $C_{1-6}$alkoxyhalo, carboxyl, optionally substituted esters, optionally substituted ketones, optionally substituted amides, optionally substituted aminoketones, thiol, optionally substituted alkylthio, optionally substituted sulfates, optionally substituted sulfonates, optionally substituted sulfinyl, optionally substituted sulfonyl, substituted sulfonyl, optionally substituted aryl, optionally substituted arylC$_{1-6}$alkyl, and optionally substituted heterocyclyl;

L$^3$, L$^4$, L$^7$, L$^8$, L$^9$ and L$^{10}$ are independently absent or a linker group, preferably selected from the linker groups described above; or L$^3$ and L$^4$ and L$^7$ and L$^8$ may together with the perylene scaffold to which they are attached form an optionally substituted C$_{5-8}$cycloalkyl, an optionally substituted heterocyclyl or an optionally substituted aryl group; and L$^9$ and X$^1$ or X$^2$ may together with the heterocyclic scaffold to which they are attached form an optionally substituted heterocyclyl group; and L$^{10}$ and X$^3$ or X$^4$ may together with the heterocyclic scaffold to which they are attached form an optionally substituted heterocyclyl group; and D$^3$, D$^4$, D$^7$, D$^8$, D$^9$, D$^{10}$, D$^{11}$ and D$^{12}$ are each independently H or a donor, wherein at least one of D$^3$, D$^4$, D$^7$, D$^8$, D$^9$, D$^{10}$, D$^{11}$ and D$^{12}$ is an oligomeric unit comprising an optionally substituted donor rylene core and one or more optionally substituted peripheral donor rylenes.

In one embodiment, the compound of formula I is a compound of formula IF:

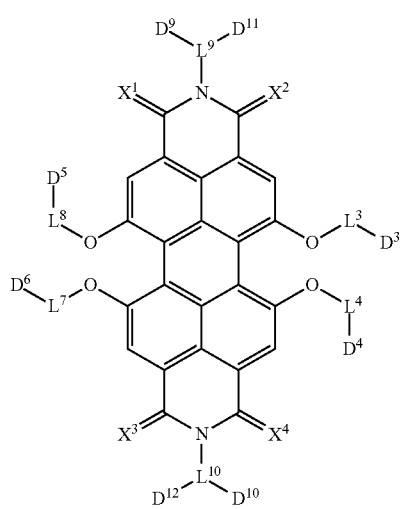

Formula IF wherein:

X$^1$, X$^2$, X$^3$ and X$^4$ are independently selected from O, S, NR$^1$ and CR$^1$R$^2$;

R$^1$ and R$^2$ are independently selected from H, optionally substituted C$_{1-6}$alkyl, optionally substituted C$_{2-6}$alkenyl, optionally substituted C$_{2-6}$alkynyl, optionally substituted C$_{3-8}$cycloalkyl, hydroxyl, optionally substituted C$_{1-6}$alkoxy, optionally substituted aryloxy, optionally substituted C$_{1-6}$alkoxyaryl, optionally substituted C$_{1-6}$alkylhalo, optionally substituted C$_{1-6}$alkoxyhalo, carboxyl, optionally substituted esters, optionally substituted ketones, optionally substituted amides, optionally substituted aminoketones, thiol, optionally substituted alkylthio, optionally substituted sulfates, optionally substituted sulfonates, optionally substituted sulfinyl, optionally substituted sulfonyl, substituted sulfonyl, optionally substituted aryl, optionally substituted arylC$_{1-6}$alkyl, and optionally substituted heterocyclyl;

L$^3$, L$^4$, L$^7$, L$^8$, L$^9$ and L$^{10}$ are independently absent or a linker group, preferably selected from the linker groups described above; or L$^3$ and L$^4$ and L$^7$ and L$^8$ together with the perylene scaffold to which they are attached form an optionally substituted C$_{5-8}$cycloalkyl, an optionally substituted heterocyclyl or an optionally substituted aryl group; and L$^9$ and X$^1$ or X$^2$ together with the heterocyclic scaffold to which they are attached form an optionally substituted heterocyclyl group; and L$^{10}$ and X$^3$ or X$^4$ together with the heterocyclic scaffold to which they are attached form an optionally substituted heterocyclyl group; and D$^3$, D$^4$, D$^7$, D$^8$, D$^9$, D$^{10}$, D$^{11}$ and D$^{12}$ are independently H or a donor, wherein at least one of D$^3$, D$^4$, D$^7$, D$^8$, D$^9$, D$^{10}$, D$^{11}$ and D$^{12}$ is an oligomeric unit comprising an optionally substituted donor rylene core and one or more optionally substituted peripheral donor rylenes.

In one embodiment, the compound of formula I is a compound of formula IG:

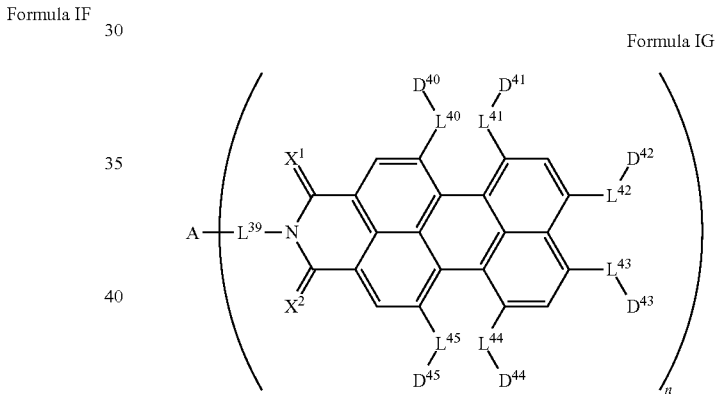

Formula IG wherein:

A is an acceptor;

n is an integer of 1 to 10, preferably 1 to 6, more preferably 1 or 2;

X$^1$ and X$^2$ are independently selected from O, S, NR$^1$ and CR$^1$R$^2$;

R$^1$ and R$^2$ are independently selected from H, optionally substituted C$_{1-6}$alkyl, optionally substituted C$_{2-6}$alkenyl, optionally substituted C$_{2-6}$alkynyl, optionally substituted C$_{3-8}$cycloalkyl, hydroxyl, optionally substituted C$_{1-6}$alkoxy, optionally substituted aryloxy, optionally substituted C$_{1-6}$alkoxyaryl, optionally substituted C$_{1-6}$alkylhalo, optionally substituted C$_{1-6}$alkoxyhalo, carboxyl, optionally substituted esters, optionally substituted ketones, optionally substituted amides, optionally substituted aminoketones, thiol, optionally substituted alkylthio, optionally substituted sulfates, optionally substituted sulfonates, optionally substituted sulfinyl, optionally substituted sulfonyl, substituted sulfonyl, optionally substituted aryl, optionally substituted arylC$_{1-6}$alkyl, and optionally substituted heterocyclyl;

D$^{40}$, D$^{41}$, D$^{42}$, D$^{43}$, D$^{44}$ and D$^{45}$ are independently H or an optionally substituted peripheral donor perylene;

L$^{39}$ is a linker group described above;

L$^{40}$, L$^{41}$, L$^{42}$, L$^{43}$, L$^{44}$ and L$^{45}$ are independently absent or a linker group, preferably independently selected from a linker group as described above; or L$^{40}$ and L$^{41}$, L$^{42}$ and L$^{43}$ and L$^{44}$ and L$^{45}$ together with the perylene scaffold to which they are attached form an optionally substituted C$_{5-8}$cycloalkyl, an optionally substituted heterocyclyl or an optionally substituted aryl group, preferably L$^{44}$ and L$^{45}$ together with the perylene scaffold to which they are attached form an optionally substituted heterocyclyl;

wherein at least one of D$^{40}$, D$^{41}$, D$^{42}$, D$^{43}$, D$^{44}$ and D$^{45}$ is an optionally substituted peripheral donor perylene, preferably at least two of D$^{40}$, D$^{41}$, D$^{42}$, D$^{43}$, D$^{44}$ and D$^{45}$ are optionally substituted peripheral donor perylenes.

In one embodiment, the compound of formula I is a compound of formula IH:

d$^1$, d$^2$, d$^3$, d$^4$ and d$^5$ are independently H or a donor, preferably H or an oligomeric unit;

L$^{46}$ is a linker group described above;

L$^{47}$, L$^{48}$, L$^{49}$, L$^{50}$, L$^{51}$, L$^{52}$, L$^{53}$, L$^{54}$, L$^{55}$, L$^{56}$ and L$^{57}$ are independently absent or a linker group, preferably independently selected from a linker group as described above; or L$^{47}$ and L$^{48}$, L$^{49}$ and L$^{50}$, L$^{51}$ and L$^{52}$, L$^{57}$ and L$^{53}$, L$^{55}$ and L$^{56}$ together with the perylene scaffold to which they are attached form an optionally substituted C$_{5-8}$cycloalkyl, an optionally substituted heterocyclyl or an optionally substituted aryl group, preferably L$^{49}$ and L$^{50}$ together with the perylene scaffold to which they are attached form an optionally substituted heterocyclyl;

wherein at least one of D$^{47}$, D$^{48}$, D$^{49}$, D$^{50}$, D$^{51}$ and D$^{52}$ is an optionally substituted peripheral donor perylene, preferably at least two of D$^{40}$, D$^{41}$, D$^{42}$, D$^{43}$, D$^{44}$ and D$^{45}$ are optionally substituted peripheral donor perylenes.

In one embodiment, D$^{49}$ and D$^{50}$ are H. In this embodiment, L$^{49}$ and L$^{50}$ may be a linker described above, preferably an optionally substituted C$_{1-20}$alkyl group which may

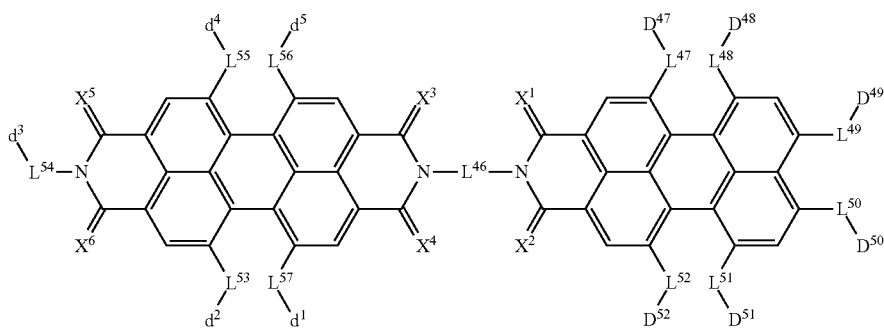

Formula IH wherein:

X$^1$, X$^2$, X$^3$, X$^4$, X$^5$ and X$^6$ are independently selected from O, S, NR$^1$ and CR$^1$R$^2$, preferably X$^1$, X$^2$, X$^3$, X$^4$, X$^5$ and X$^6$ are O;

R$^1$ and R$^2$ are independently selected from H, optionally substituted C$_{1-6}$alkyl, optionally substituted C$_{2-6}$alkenyl, optionally substituted C$_{2-6}$alkynyl, optionally substituted C$_{3-8}$cycloalkyl, hydroxyl, optionally substituted C$_{1-6}$alkoxy, optionally substituted aryloxy, optionally substituted C$_{1-6}$alkoxyaryl, optionally substituted C$_{1-6}$alkylhalo, optionally substituted C$_{1-6}$alkoxyhalo, carboxyl, optionally substituted esters, optionally substituted ketones, optionally substituted amides, optionally substituted aminoketones, thiol, optionally substituted alkylthio, optionally substituted sulfates, optionally substituted sulfonates, optionally substituted sulfinyl, optionally substituted sulfonyl, substituted sulfonyl, optionally substituted aryl, optionally substituted arylC$_{1-6}$alkyl, and optionally substituted heterocyclyl;

D$^{47}$, D$^{48}$, D$^{49}$, D$^{50}$, D$^{51}$ and D$^{52}$ are independently H or an optionally substituted peripheral donor perylene;

be optionally interrupted by one or more of the groups selected from oxy, ester, amide, sulphonamide, thio, sulphoxy, sulphonyl, sulphinyl, optionally substituted aryl, optionally substituted heterocyclyl (e.g. optionally substituted triazolyl), C$_2$alkenyl, C$_2$alkynyl and C$_{3-8}$cycloalkyl.

In one embodiment, d$^1$, d$^2$, d$^4$ and d$^5$ are H. In this embodiment, L$^{57}$, L$^{53}$, L$^{55}$ and L$^{56}$ may be a linker described above, preferably an optionally substituted aryloxy, an optionally substituted hetercyclyloxy, an optionally substituted C$_{3-8}$cycloalkyloxy or an optionally substituted C$_{1-6}$alkoxy.

In one embodiment, d$^3$ is an oligomeric unit described herein.

Accordingly, in one aspect, there is provided a compound of Formula (I) as described above. The compound of Formula (I) may be a compound of any one of Formulas IA, IB, IC, ID, IE, IF, IG and IH as described above.

In one embodiment, the compound of Formula I is selected from any one of compound nos. I-1, I-2 and I-3 shown in Table 1.

TABLE 1
| Compound No. | Structure* |
|---|---|
| I-1 | 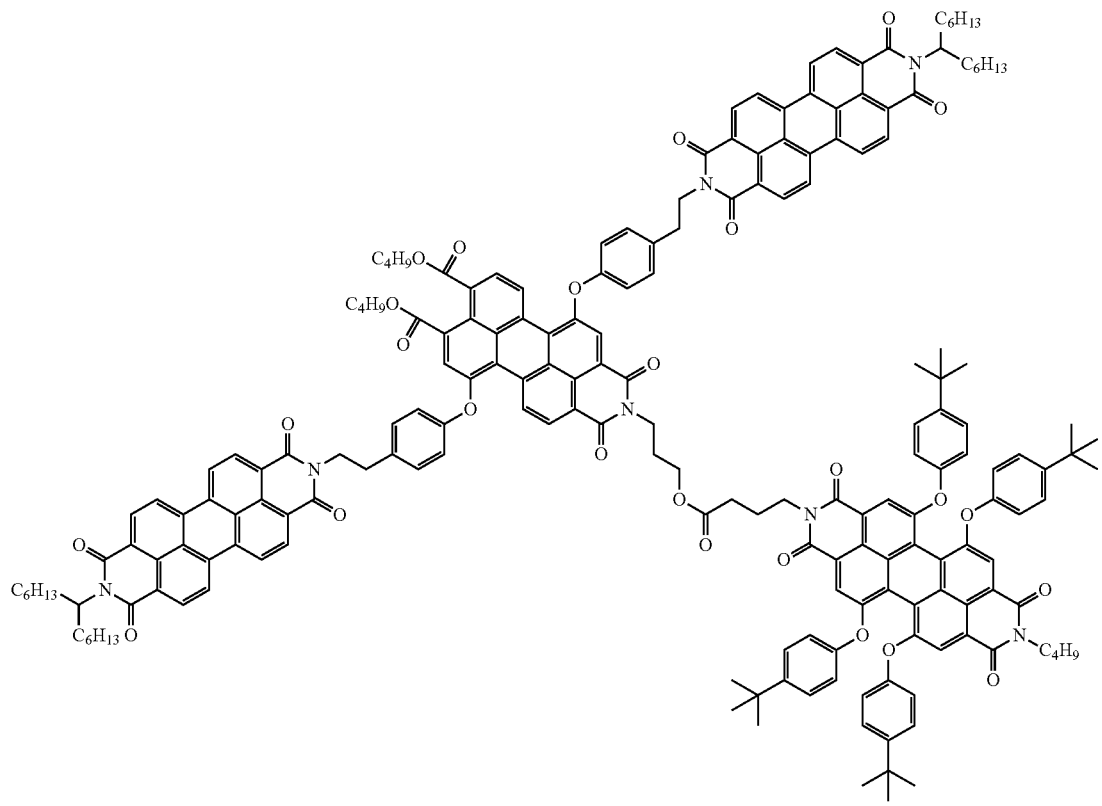 |
| I-2 | 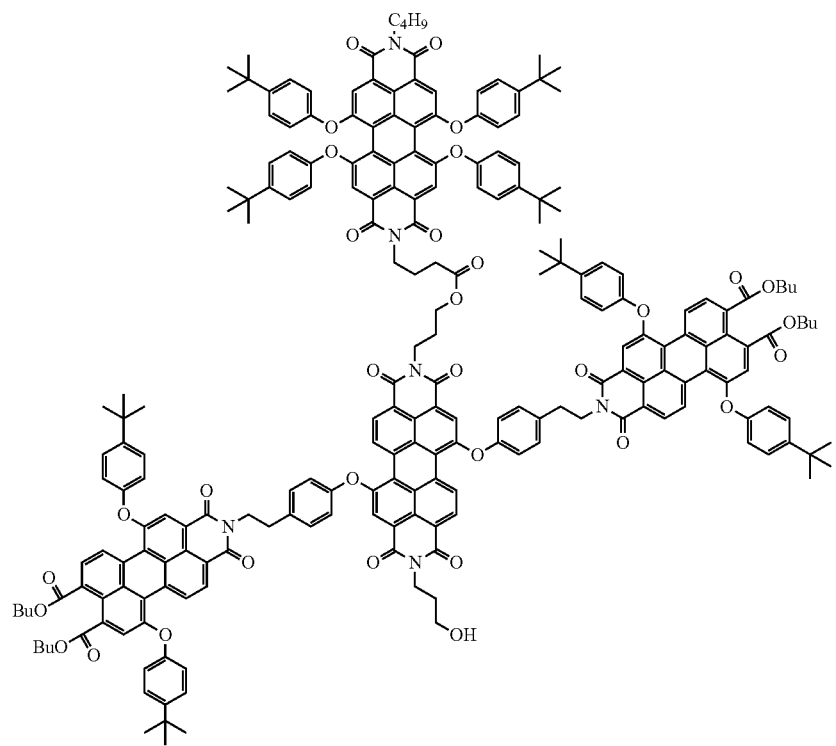 |

TABLE 1-continued

| Compound No. | Structure* |
|---|---|
| I-3 | 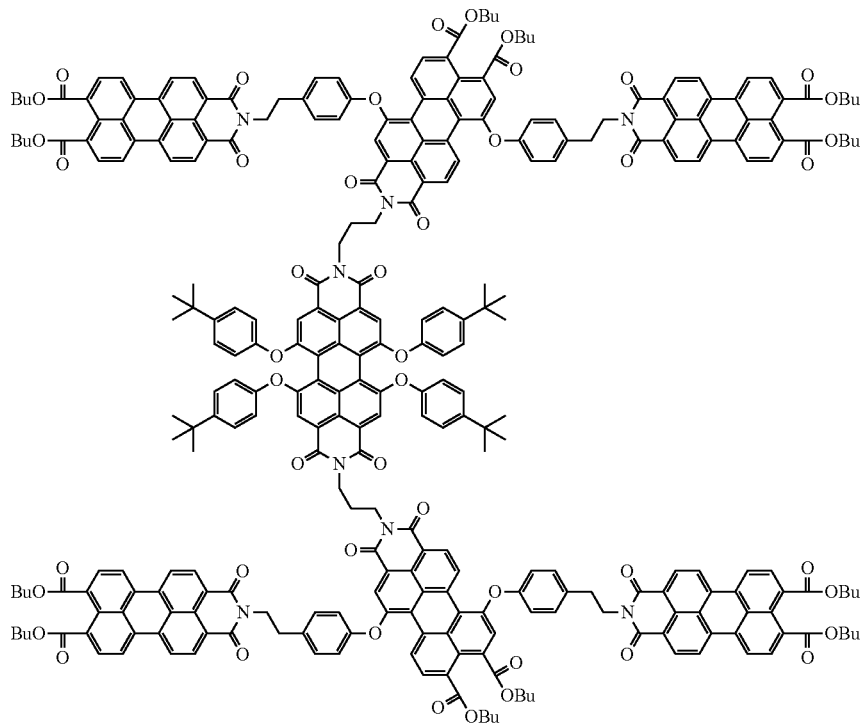 |

Notes:
*Compounds I-1, I-2 and I-3 were isolated as regioisomeric mixtures - the predominant regioisomer is drawn.

In one aspect, there is provided a compound of Formula X as described above.

In one embodiment, $Ry^0$ is an optionally substituted acceptor perylene or an optionally substituted donor perylene. As described above, the substitution of a rylene influences its properties, including its spectral properties. Thus, with appropriate substitution, a rylene having desired spectral properties may be selected.

In one embodiment, $Ry^1$ is an optionally substituted perylene.

In one embodiment, $Ry^1$ is an optionally substituted acceptor rylene, preferably an optionally substituted acceptor perylene. The optionally substituted acceptor rylene may be the acceptor, or when $Ry^1$ is an optionally substituted acceptor rylene, $Ry^1$ together with $L^2$ and $Ry^e$ may be the acceptor which is an oligomeric unit.

In one embodiment, $Ry^1$ is an optionally substituted donor rylene, preferably an optionally substituted donor perylene.

Typically, $Ry^1$ is an optionally substituted rylene capable of transfering energy to $Ry^0$, $Ry^2$ or both. When $Ry^1$ is an optionally substituted rylene capable of transfering energy to $Ry^0$, preferably it is also capable of receiving energy from $Ry^2$, for example via FRET. When $Ry^1$ is an optionally substituted rylene capable of transfering energy to $Ry^2$, preferably it is also capable of receiving energy from $Ry^0$, for example via FRET. Preferably, $Ry^1$ is a substituted perylene capable of transfering energy to $Ry^0$ and receiving energy from $Ry^2$. This substituted perylene may comprise substituents at one or more bay positions (preferably, 1, 2, 3 or 4 bay substituents) or at one or more end positions (preferably all four end positions). The bay position substitutents may be any bay substituent described above. In one embodiment, the one or more bay position substituents are independently selected from optionally substituted aryloxy, optionally substituted heterocyclyloxy, optionally substituted $C_{1-6}$alkoxy, optionally substituted $C_{3-8}$cycloalkoxy, optionally substituted $C_{1-6}$alkenyloxy and optionally substituted $C_{1-6}$alkynyloxy, preferably optionally substituted aryloxy. The end position substituents may be any end group substituent described above. In one embodiment, the one or more end group substituents are independently selected from optionally substituted ester, optionally substituted imide, optionally substituted alkylester or two neighbouring end positions, i.e. the 3 and 4 positions and/or the 9 and 10 positions of the perylene skeleton, form an optionally substituted cyclic imide.

In one embodiment, $Ry^2$ is an optionally substituted perylene.

In one embodiment, $Ry^2$ is an optionally substituted acceptor rylene, preferably an optionally substituted acceptor perylene. In another embodiment, $Ry^2$ is an optionally substituted donor rylene, preferably an optionally substituted donor perylene.

In one embodiment, $L^1$ and $L^2$ are selected from the linker groups described above.

In one embodiment, q is an integer of 1 to 6, preferably 1 or 2.

In one embodiment, p is an integer of 1 to 10, preferably 1 to 5, more preferably 2, 3 or 4.

In one embodiment, the compound of Formula X is a compound of Formula X':

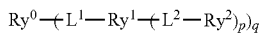

Formula X′ wherein
$Ry^0$, $Ry^1$, $Ry^2$, $L^1$, $L^2$, q and p are as defined above.

In one embodiment, the compound of Formula X is a compound of Formula XI:

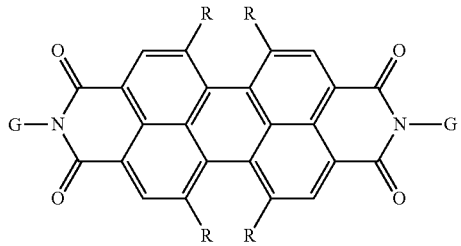

Formula XI wherein:
each R is independently selected from optionally substituted aryloxy, optionally substituted heterocyclyloxy, optionally substituted $C_{1-6}$alkoxy, optionally substituted $C_{3-8}$cycloalkoxy, optionally substituted $C_{1-6}$alkenyloxy and optionally substituted $C_{1-6}$alkynyloxy, preferably optionally substituted aryloxy; and
each G is independently selected from optionally substituted $C_{1-20}$alkyl, optionally substituted $C_{3-8}$cycloalkyl, optionally substituted aryl, optionally substituted heterocyclyl and a moiety of the formula XI′:

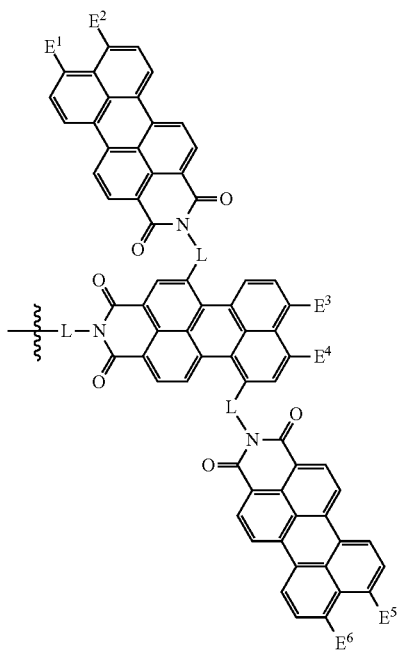

Formula XI′ wherein:
$E^1$, $E^2$, $E^3$, $E^4$, $E^5$ and $E^6$ are independently selected from H, optionally substituted ester, optionally substituted imide and optionally substituted $C_{1-20}$alkylester; or $E^1$ and $E^2$, $E^3$ and $E^4$, or $E^5$ and $E^6$ may together with the perylene scaffold to which they are attached form an optionally substituted heterocyclyl, preferably an optionally substituted 6-membered cyclic imide; and
each L is independently selected from a linker group described herein, preferably selected from an optionally substituted $C_{1-20}$alkyl group which may be optionally interrupted by one or more of the groups selected from oxy, ester, amide, sulphonamide, thio, sulphoxy, sulphonyl, sulphinyl, optionally substituted aryl, optionally substituted heterocyclyl (e.g. optionally substituted triazolyl), $C_2$alkenyl, $C_2$alkynyl and $C_{3-8}$cycloalkyl and an O-linked optionally substituted aryloxy linker group;
wherein at least one G is a moiety of the formula XI′.

In one embodiment, the compound of Formula X is a compound of Formula XII:

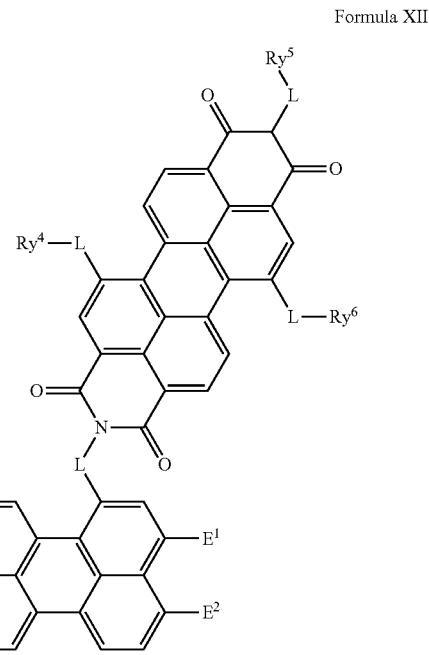

Formula XII wherein:
each L is independently absent or a linker group described herein, preferably a linker group described herein, more preferably a linker group selected from an optionally substituted $C_{1-20}$alkyl group which may be optionally interrupted by one or more of the groups selected from oxy, ester, amide, sulphonamide, thio, sulphoxy, sulphonyl, sulphinyl, optionally substituted aryl, optionally substituted heterocyclyl (e.g. optionally substituted triazolyl), $C_2$alkenyl, $C_2$alkynyl and $C_{3-8}$cycloalkyl and an O-linked optionally substituted aryloxy linker group;
$Ry^4$, $Ry^5$ and $Ry^6$ are independently selected from H or an optionally substituted rylene;
$E^1$, $E^2$, $E^3$ and $E^4$ are independently selected from H, optionally substituted ester, optionally substituted imide and optionally substituted $C_{1-20}$alkylester; or
$E^1$ and $E^2$ and $E^3$ and $E^4$ may together with the perylene scaffold to which they are attached form an optionally substituted heterocyclyl,
wherein at least one of $Ry^4$, $Ry^5$ and $Ry^6$ is an optionally substituted rylene.

In one embodiment, $Ry^4$ and $Ry^6$ are each an optionally substituted rylene, preferably the same optionally substituted rylene. In one embodiment, $Ry^5$ is H.

In one embodiment, the compound of Formula X is selected from any one of compound nos. I-1, I-2 and I-3 shown in Table 1 above, or any one of compounds X-1 to X-4 shown in Table X below.
TABLE X
| Compound No. | Structure* |
|---|---|ит
| X-1 | 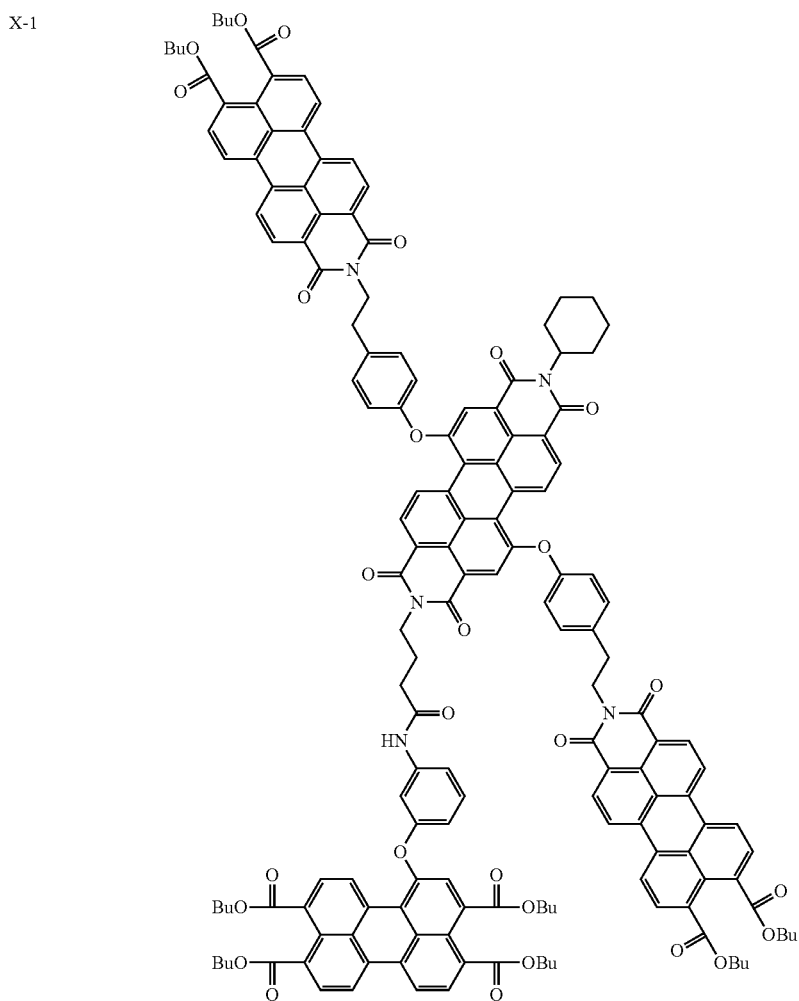 |

TABLE X-continued
| Compound No. | Structure* |
|---|---|
| X-2 | 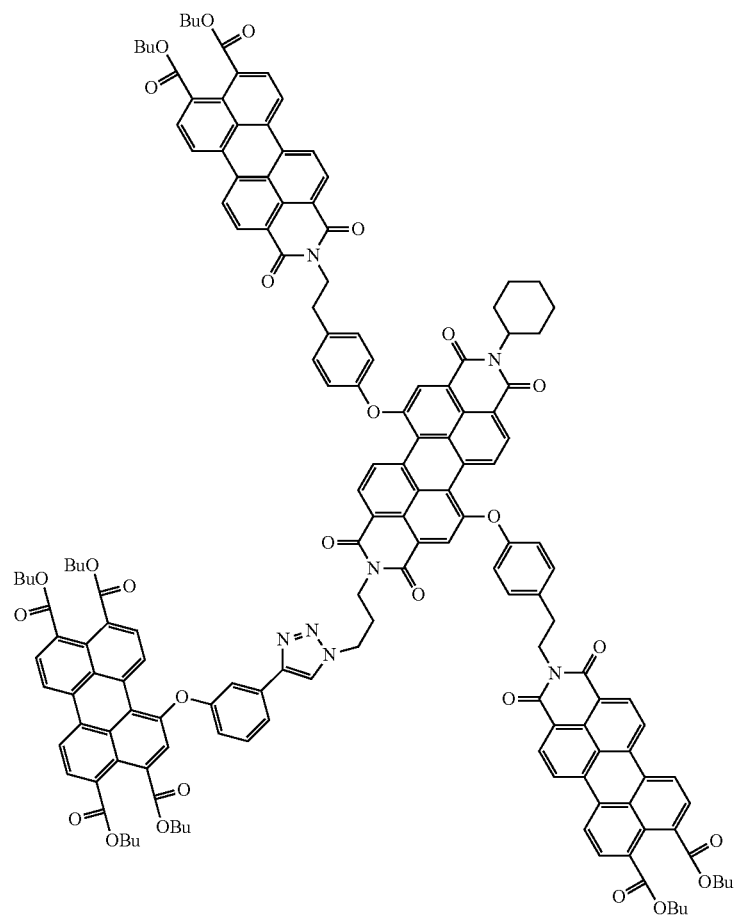 |

TABLE X-continued
| Compound No. | Structure* |
|---|---|
| X-3 | 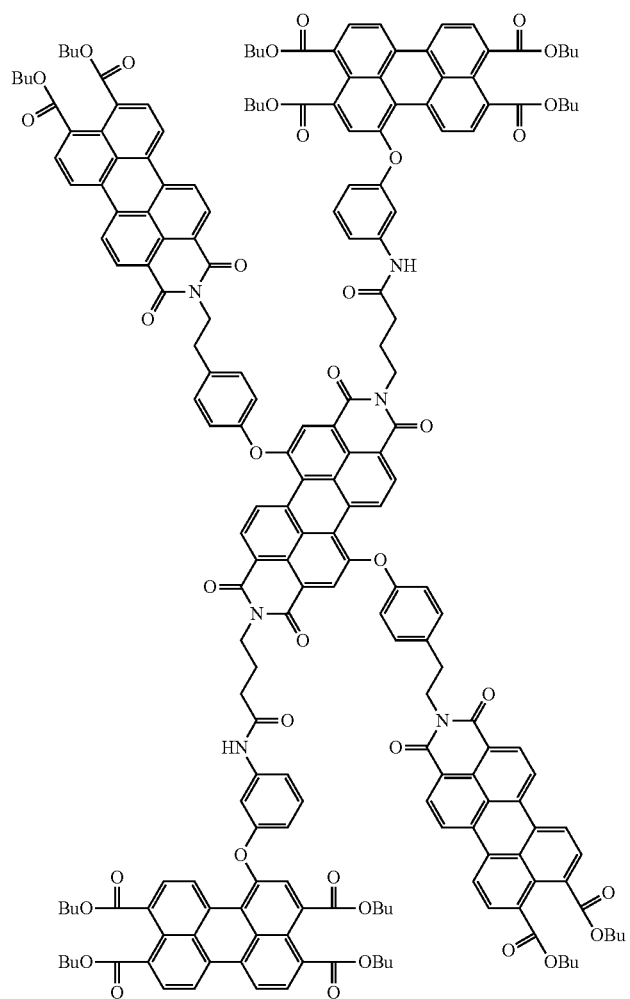 |

TABLE X-continued

| Compound No. | Structure* |
|---|---|
| X-4 | 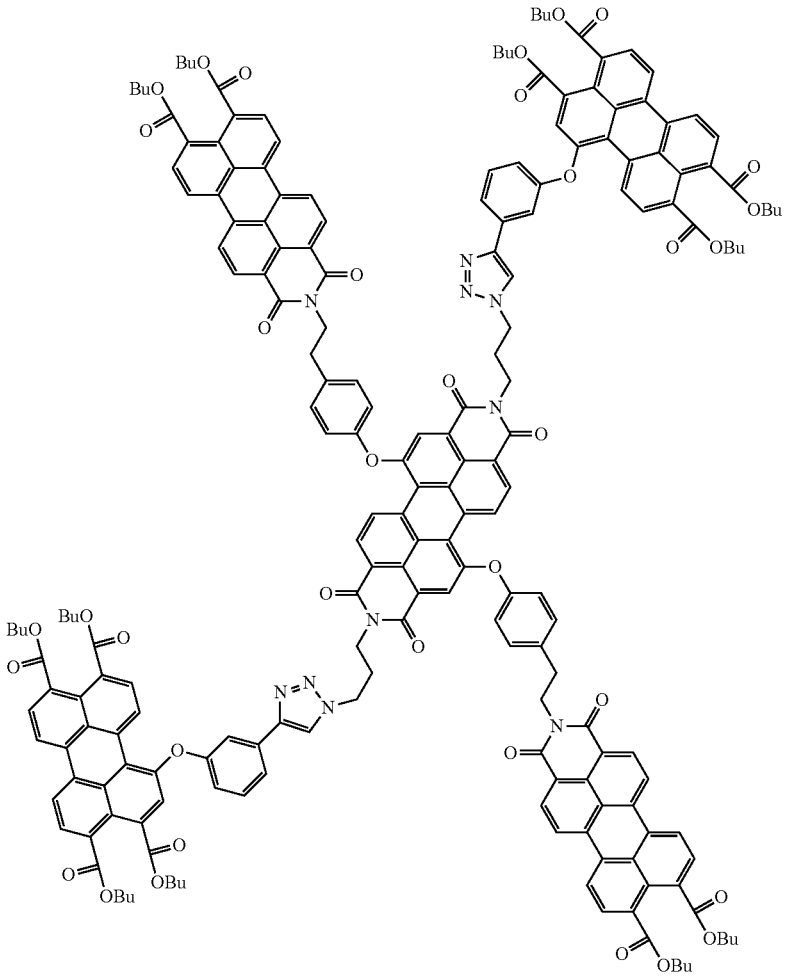 |

Notes:
*These structures show the preferred regioisomer of a regioisomeric mixture.

Compounds of Formula X, including the compounds of Formula X-1 to X-4, may be made by methods similar to the compounds of Formula I and from similar starting materials.

Oligomeric Units

In one aspect, the oligomeric unit comprises an optionally substituted perylene core linked via a linker group to two or more optionally substituted peripheral donor perylenes. In other words, the oligomeric unit comprises a first optionally substituted perylene linked via a linker group to two or more second optionally substituted donor perylenes.

This oligomeric unit may be incorporated into the light harvesting array described above as the acceptor, the donor, or both. In one embodiment, the acceptor and the one or more donors of the light harvesting array described above are oligomeric units.

The oligomeric unit, i.e. either the optionally substituted perylene core or at least one of the optionally substituted peripheral donor perylenes, may be functionalised to couple with the acceptor as described above or with another oligomeric unit.

In one embodiment, when the oligomeric unit is to be incorporated into the light harvesting array as the acceptor, the optionally substituted perylene core should be capable of accepting energy from the one or more donors and emitting the accepted energy. Therefore, the oligomeric unit may be a donor, an acceptor or both.

In another embodiment, when the oligomeric unit is to be incorporated into the light harvesting array as a donor, the oligomeric unit must be capable of absorbing energy and transferring the absorbed energy to the acceptor. In this embodiment, either the optionally substituted perylene core or one or more of the optionally substituted peripheral donor perylenes may be capable of directly transferring energy to the acceptor, for example, via FRET. In one embodiment, both the optionally substituted perylene core and the optionally substituted peripheral donor perylenes are capable of transferring energy directly to the acceptor. In another embodiment, the optionally substituted peripheral donor perylenes are able to transfer energy to the acceptor via a relay with the optionally substituted perylene core, that is to say that the fluorescence emission maxima of the optionally substituted peripheral donor perylene overlaps with the absorbance maxima of the optionally substituted perylene core and not the absorbance maxima of the acceptor.

In addition to use as a "building block" for the light harvesting array, each oligomeric unit may also behave as a light harvesting system.

In one embodiment, the oligomeric unit comprises an optionally substituted perylene core linked to two optionally substituted peripheral donor perylenes forming a perylene trimer or triad. In another embodiment, the oligomeric unit may comprise 3, 4, or 5 peripheral perylenes forming a tetramer or tetrad, pentamer or pentad, or hexamer or hexad, respectively. In a further embodiment, the oligomeric unit may comprise 6, 7, 8, 9, 10 or more optionally substituted peripheral perylenes. Each optionally substituted peripheral perylene may be the same or different, and preferably comprises an optionally substituted perylene with a different energy level of its excited state(s) to allow energy transfer to another optionally substituted perylene in the oligomeric unit. As described above, the two or more optionally substituted peripheral donor perylenes may be able to donate absorbed energy to the optionally substituted perylene core. The optionally substituted peripheral perylenes may exhibit absorbance maxima at higher or lower energy relative to the optionally substituted perylene core. In one embodiment, the optionally substituted peripheral donor perylenes donate absorbed energy to the optionally substituted perylene core via FRET. In another embodiment, one or more of the peripheral donor rylenes accept energy from the optionally substituted perylene core via FRET.

It will be appreciated that any of the linker groups described above may be suitable for incorporation into the oligomeric unit.

In an embodiment, the oligomeric unit is a compound of formula II:

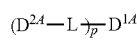

Formula II wherein:
$D^{1A}$ is an optionally substituted perylene core;
$D^{2A}$ is an optionally substituted peripheral donor perylene;
L is a linker group, preferably selected from the linker groups described above; and
p is an integer of 2 to 10.

In one embodiment, the compound of formula II is a compound of formula IIA:

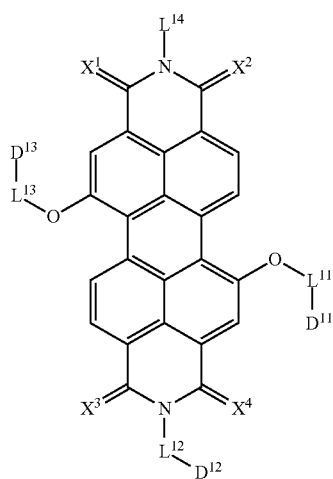

Formula IIA wherein:
$X^1$, $X^2$, $X^3$ and $X^4$ are independently selected from O, S, $NR^1$ and $CR^1R^2$;
$R^1$ and $R^2$ are independently selected from H, optionally substituted $C_{1-6}$alkyl, optionally substituted $C_{2-6}$alkenyl, optionally substituted $C_{2-6}$alkynyl, optionally substituted $C_{3-8}$cycloalkyl, hydroxyl, optionally substituted $C_{1-6}$alkoxy, optionally substituted aryloxy, optionally substituted $C_{1-6}$alkoxyaryl, optionally substituted $C_{1-6}$alkylhalo, optionally substituted $C_{1-6}$alkoxyhalo, carboxyl, optionally substituted esters, optionally substituted ketones, optionally substituted amides, optionally substituted aminoketones, thiol, optionally substituted alkylthio, optionally substituted sulfates, optionally substituted sulfonates, optionally substituted sulfinyl, optionally substituted sulfonyl, substituted sulfonyl, optionally substituted aryl, optionally substituted aryl$C_{1-6}$alkyl, and optionally substituted heterocyclyl;
$D^{11}$, $D^{12}$ and $D^{13}$ are independently H or an optionally substituted peripheral donor perylene;
$L^{11}$, $L^{12}$ and $L^{13}$ are independently absent or a linker group, preferably independently selected from a linker group as described above; or
$L^{12}$ and $X^3$ or $X^4$ together with the heterocyclic scaffold to which they are attached form an optionally substituted heterocyclyl group; and
$L^{14}$ is H or a group capable of linking the compound of formula IIA with an acceptor or a donor; or
$L^{14}$ and $X^1$ or $X^2$ together with the heterocyclic scaffold to which they are attached form an optionally substituted heterocyclyl group.

In one embodiment, the compound of formula II is a compound of formula IIB:

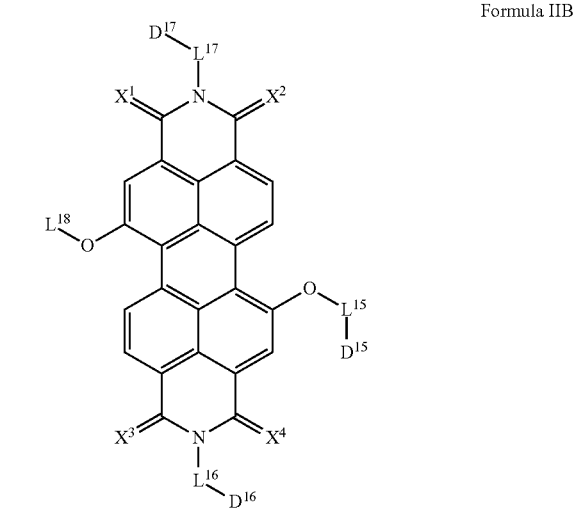

Formula IIB wherein:
$X^1$, $X^2$, $X^3$ and $X^4$ are independently selected from O, S, $NR^1$ and $CR^1R^2$;
$R^1$ and $R^2$ are independently selected from H, optionally substituted $C_{1-6}$alkyl, optionally substituted $C_{2-6}$alkenyl, optionally substituted $C_{2-6}$alkynyl, optionally substituted $C_{3-8}$cycloalkyl, hydroxyl, optionally substituted $C_{1-6}$alkoxy, optionally substituted aryloxy, optionally substituted $C_{1-6}$alkoxyaryl, optionally substituted $C_{1-6}$alkylhalo, optionally substituted $C_{1-6}$alkoxyhalo, carboxyl, optionally substituted esters, optionally substituted ketones, optionally substituted amides, optionally substituted aminoketones, thiol, optionally substituted alkylthio, optionally substituted sulfates, optionally substituted sulfonates, optionally substituted sulfinyl, optionally substituted sulfonyl, substituted sulfonyl, optionally substituted aryl, optionally substituted arylC$_{1-6}$alkyl, and optionally substituted heterocyclyl;

D$^{15}$, D$^{16}$ and D$^{17}$ are independently H or an optionally substituted peripheral donor perylene;

L$^{15}$, L$^{18}$ and L$^{17}$ are independently absent or a linker group, preferably selected from the linker groups described above; or L$^{17}$ and X$^1$ or X$^2$ together with the heterocyclic scaffold to which they are attached form an optionally substituted heterocyclyl group; and L$^{16}$ and X$^3$ or X$^4$ together with the heterocyclic scaffold to which they are attached form an optionally substituted heterocyclyl group; and L$^{18}$ is H or a group capable of linking the compound of formula IIB with an acceptor or a donor.

In one embodiment, the compound of formula II is a compound of formula IIC:

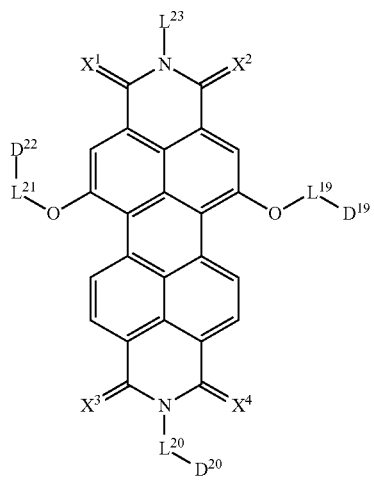

Formula IIC wherein:

X$^1$, X$^2$, X$^3$ and X$^4$ are independently selected from O, S, NR$^1$ and CR$^1$R$^2$;

R$^1$ and R$^2$ are independently selected from H, optionally substituted C$_{1-6}$alkyl, optionally substituted C$_{2-6}$alkenyl, optionally substituted C$_{2-6}$alkynyl, optionally substituted C$_{3-8}$cycloalkyl, hydroxyl, optionally substituted C$_{1-6}$alkoxy, optionally substituted aryloxy, optionally substituted C$_{1-6}$alkoxyaryl, optionally substituted C$_{1-6}$alkylhalo, optionally substituted C$_{1-6}$alkoxyhalo, carboxyl, optionally substituted esters, optionally substituted ketones, optionally substituted amides, optionally substituted aminoketones, thiol, optionally substituted alkylthio, optionally substituted sulfates, optionally substituted sulfonates, optionally substituted sulfinyl, optionally substituted sulfonyl, substituted sulfonyl, optionally substituted aryl, optionally substituted arylC$_{1-6}$alkyl, and optionally substituted heterocyclyl;

D$^{19}$, D$^{20}$ and D$^{22}$ are independently H or an optionally substituted peripheral donor perylene;

L$^{19}$, L$^{20}$ and L$^{22}$ are independently absent or a linker group, preferably selected from the linker groups described above; or L$^{20}$ and X$^3$ or X$^4$ together with the heterocyclic scaffold to which they are attached form an optionally substituted heterocyclyl group; and L$^{14}$ is H or a group capable of linking the compound of formula IIC with an acceptor or a donor; and L$^{23}$ and X$^1$ or X$^2$ together with the heterocyclic scaffold to which they are attached form an optionally substituted heterocyclyl group.

In one embodiment, the compound of formula II is a compound of formula IID:

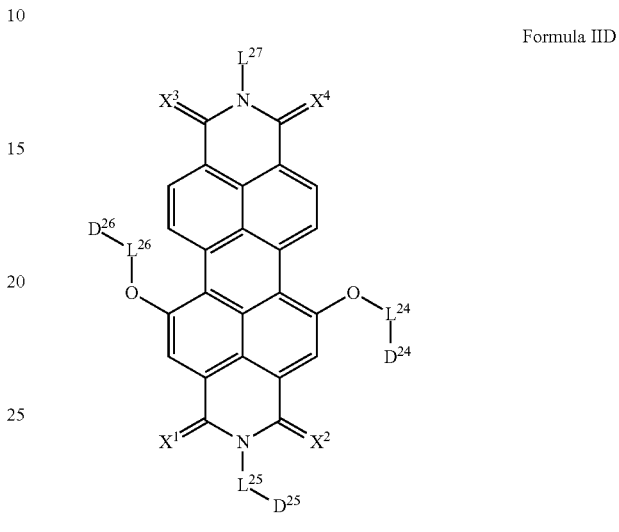

Formula IID wherein:

X$^1$, X$^2$, X$^3$ and X$^4$ are independently selected from O, S, NR$^1$ and CR$^1$R$^2$;

R$^1$ and R$^2$ are independently selected from H, optionally substituted C$_{1-6}$alkyl, optionally substituted C$_{2-6}$alkenyl, optionally substituted C$_{2-6}$alkynyl, optionally substituted C$_{3-8}$cycloalkyl, hydroxyl, optionally substituted C$_{1-6}$alkoxy, optionally substituted aryloxy, optionally substituted C$_{1-6}$alkoxyaryl, optionally substituted C$_{1-6}$alkylhalo, optionally substituted C$_{1-6}$alkoxyhalo, carboxyl, optionally substituted esters, optionally substituted ketones, optionally substituted amides, optionally substituted aminoketones, thiol, optionally substituted alkylthio, optionally substituted sulfates, optionally substituted sulfonates, optionally substituted sulfinyl, optionally substituted sulfonyl, substituted sulfonyl, optionally substituted aryl, optionally substituted arylC$_{1-6}$alkyl, and optionally substituted heterocyclyl;

D$^{24}$, D$^{25}$ and D$^{26}$ are independently H or an optionally substituted peripheral donor perylene;

L$^{24}$, L$^{25}$ and L$^{26}$ are independently absent or a linker group, preferably selected from a linker group as described above; or L$^{25}$ and X$^3$ or X$^4$ together with the heterocyclic scaffold to which they are attached form an optionally substituted heterocyclyl group; and L$^{27}$ is H or a group capable of linking the compound of formula IIA with an acceptor or a donor; and L$^{27}$ and X$^1$ or X$^2$ together with the heterocyclic scaffold to which they are attached form an optionally substituted heterocyclyl group.

In one embodiment, the compound of formula II is a compound of any one of formulas IIE, IIF, IIG, IIH, IIJ, IIK, IIL, IIM, IIN and IIO:

Formula IIE
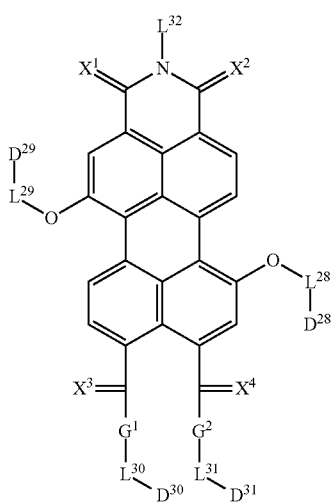
Formula IIH
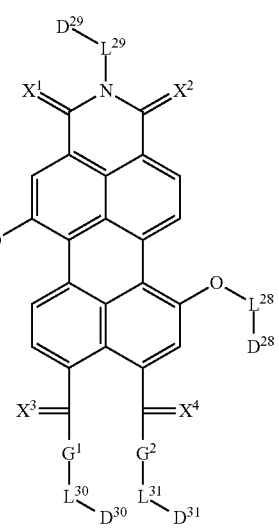
Formula IIF
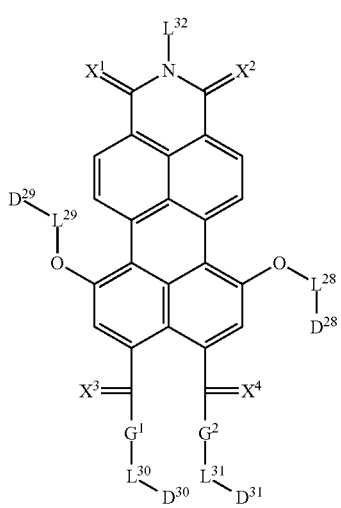
Formula IIJ
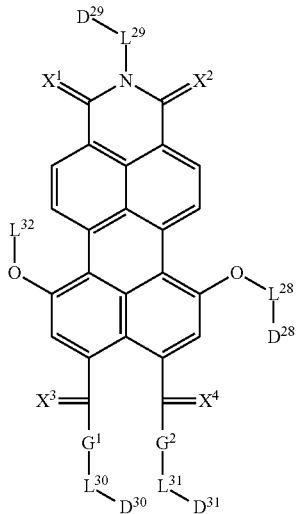
Formula IIG
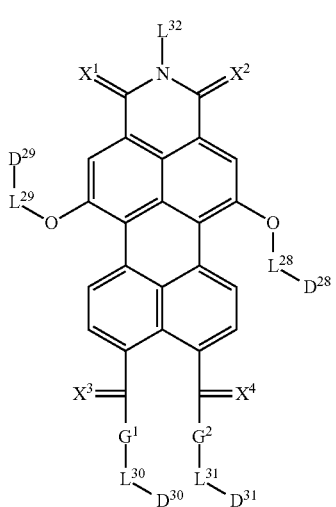
Formula IIK
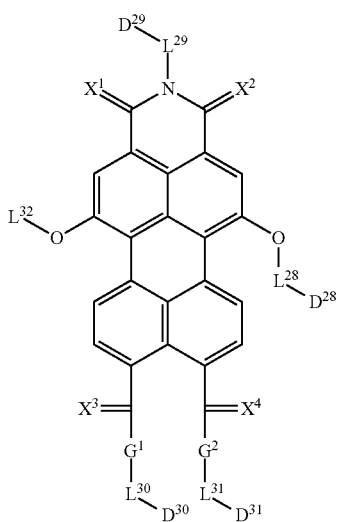

Formula IIL

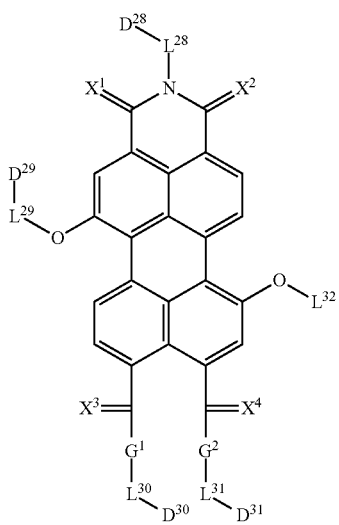

Formula IIM

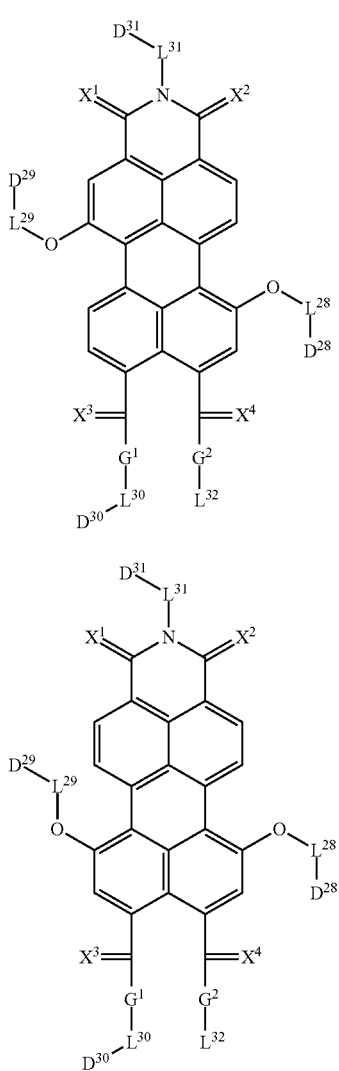

Formula IIN

Formula IIO

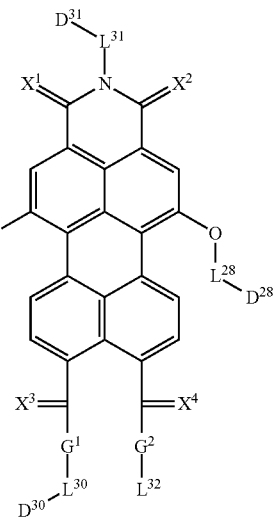

wherein:

$X^1$, $X^2$, $X^3$ and $X^4$ are independently selected from O, S, $NR^1$ and $CR^1R^2$, preferably O;

$R^1$ and $R^2$ are independently selected from H, optionally substituted $C_{1-6}$alkyl, optionally substituted $C_{2-6}$alkenyl, optionally substituted $C_{2-6}$alkynyl, optionally substituted $C_{3-8}$cycloalkyl, hydroxyl, optionally substituted $C_{1-6}$alkoxy, optionally substituted aryloxy, optionally substituted $C_{1-6}$alkoxyaryl, optionally substituted $C_{1-6}$alkylhalo, optionally substituted $C_{1-6}$alkoxyhalo, carboxyl, optionally substituted esters, optionally substituted ketones, optionally substituted amides, optionally substituted aminoketones, thiol, optionally substituted alkylthio, optionally substituted sulfates, optionally substituted sulfonates, optionally substituted sulfinyl, optionally substituted sulfonyl, substituted sulfonyl, optionally substituted aryl, optionally substituted aryl$C_{1-6}$alkyl, and optionally substituted heterocyclyl;

$G^1$ and $G^2$ are independently selected from O, S, sulfinyl, sulphonyl, $NR^1$ and $CR^1R^2$, preferably O;

$D^{28}$, $D^{29}$, $D^{30}$ and $D^{31}$ are independently H or an optionally substituted peripheral donor perylene;

$L^{28}$, $L^{29}$, $L^{30}$ and $L^{31}$ are independently absent or a linker group; and $L^{32}$ is H or a group capable of linking the compound of any one of formulas IIE, IIF, IIG, IIH, IIJ, IIK, IIL, IIM, IIN and IIO with an acceptor or a donor.

In one embodiment, the compound of formula II is a compound of any one of formulas IIP, IIQ, IIR, IIS and IIT:

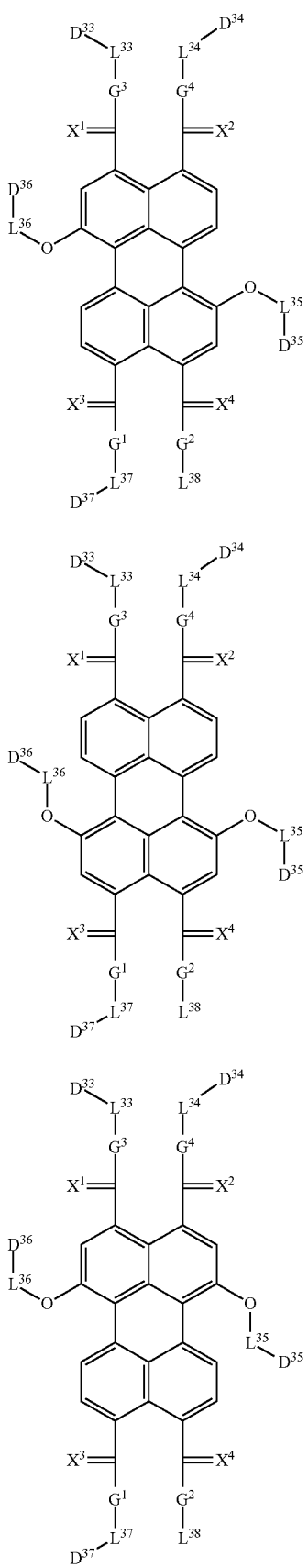

Formula IIP

Formula IIQ

Formula IIR

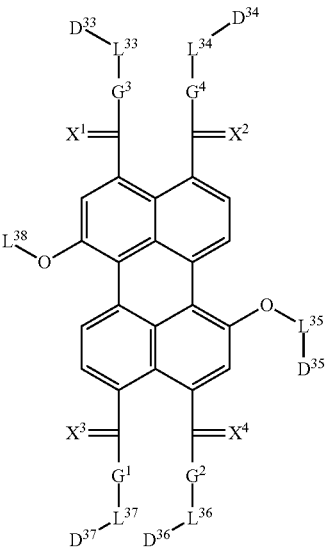

Formula IIS

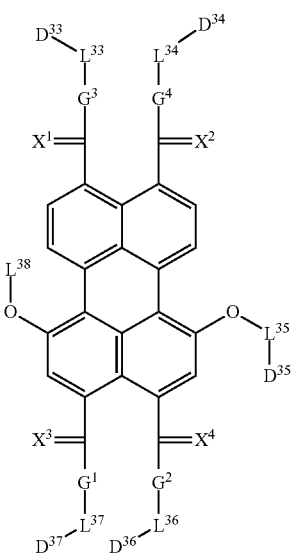

Formula IIT wherein:

$X^1$, $X^2$, $X^3$ and $X^4$ are independently selected from O, S, $NR^1$ and $CR^1R^2$, preferably O;

$R^1$ and $R^2$ are independently selected from H, optionally substituted $C_{1-6}$alkyl, optionally substituted $C_{2-6}$alkenyl, optionally substituted $C_{2-6}$alkynyl, optionally substituted $C_{3-8}$cycloalkyl, hydroxyl, optionally substituted $C_{1-6}$alkoxy, optionally substituted aryloxy, optionally substituted $C_{1-6}$alkoxyaryl, optionally substituted $C_{1-6}$alkylhalo, optionally substituted $C_{1-6}$alkoxyhalo, carboxyl, optionally substituted esters, optionally substituted ketones, optionally substituted amides, optionally substituted aminoketones, thiol, optionally substituted alkylthio, optionally substituted sulfates, optionally substituted sulfonates, optionally substituted sulfinyl, optionally substituted sulfonyl, substituted sulfonyl, optionally substituted aryl, optionally substituted aryl$C_{1-6}$alkyl, and optionally substituted heterocyclyl;

$G^1$, $G^2$, $G^3$ and $G^4$ are independently selected from O, S, sulfinyl, sulphonyl, $NR^1$ and $CR^1R^2$, preferably O;

$D^{33}$, $D^{34}$, $D^{35}$, $D^{36}$ and $D^{37}$ are independently H or an optionally substituted peripheral donor perylene;

$L^{33}$, $L^{34}$, $L^{35}$, $L^{36}$ and $L^{37}$ are independently absent or a linker group;

$L^{38}$ is H or a group capable of linking the compound of any one of formulas IIP, IIQ, IIR, IIS and IIT with an acceptor or a donor.

In the compound of any one of formulas IIA to IIT described above, when $L^{14}$, $L^{18}$, $L^{23}$, $L^{27}$, $L^{32}$ or $L^{38}$ is a group capable of linking the compound with an acceptor or a donor, at least a portion of that group may form part of a linker group as described above. In one embodiment, $L^{14}$, $L^{18}$, $L^{23}$, $L^{27}$, $L^{32}$ or $L^{38}$ comprise a leaving group, such as halo, anhydride, alkylsulphonyl or arylsulphonyl which upon coupling with an acceptor or a donor would not form part of a linker group, in this embodiment the remainder of $L^{14}$, $L^{18}$, $L^{23}$, $L^{27}$, $L^{32}$ or $L^{38}$ does form part of the linker group, e.g. a linker group described above. In another embodiment, $L^{14}$, $L^{18}$, $L^{23}$, $L^{27}$, $L^{32}$ or $L^{38}$ comprise a nucleophilic group, such as hydroxyl or thio, which may form part of a linker group described above.

In another aspect, there is provided a light harvesting array comprising two or more linked oligomeric units as described above.

The following compounds II-1 to II-20 shown in Table 2 are representative examples of oligomeric units.

TABLE 2

| Compound No. | Structure |
|---|---|
| II-1* | 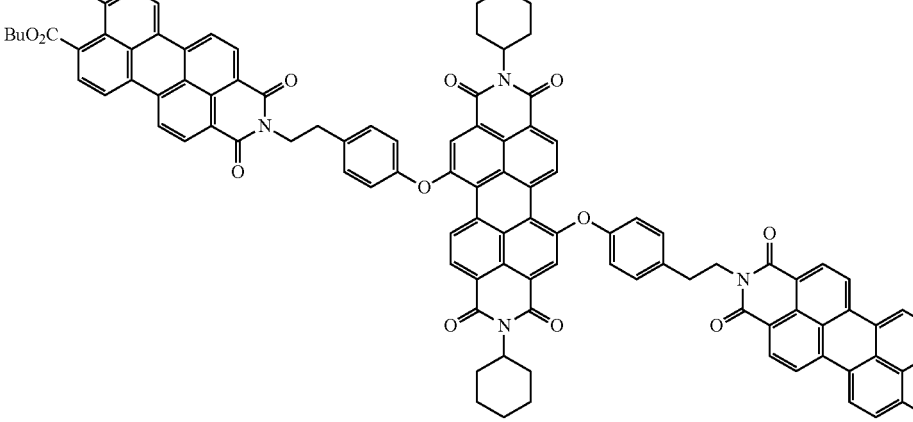 |
| II-2 | 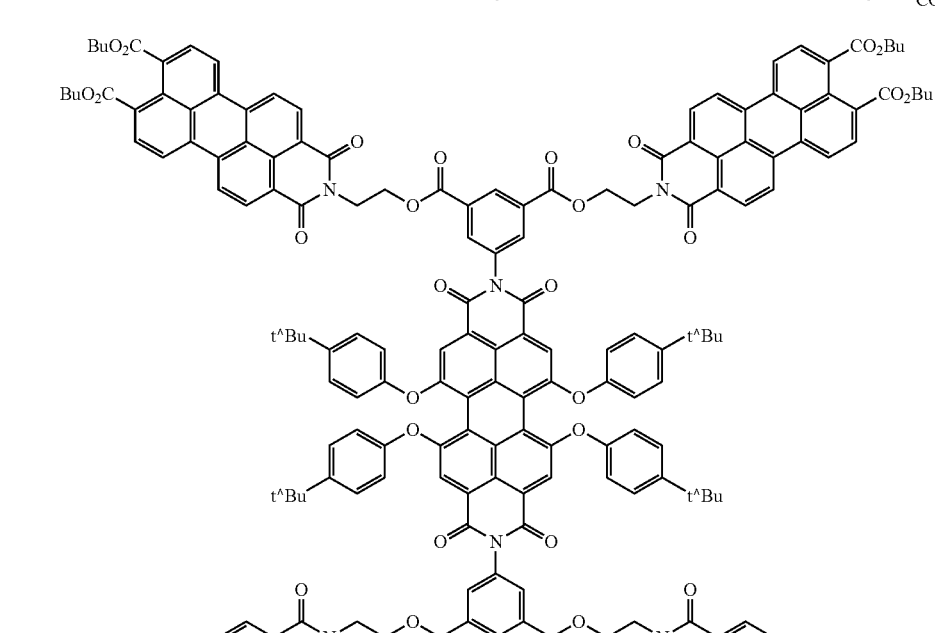 |

TABLE 2-continued
| Compound No. | Structure |
|---|---|
| II-3 | 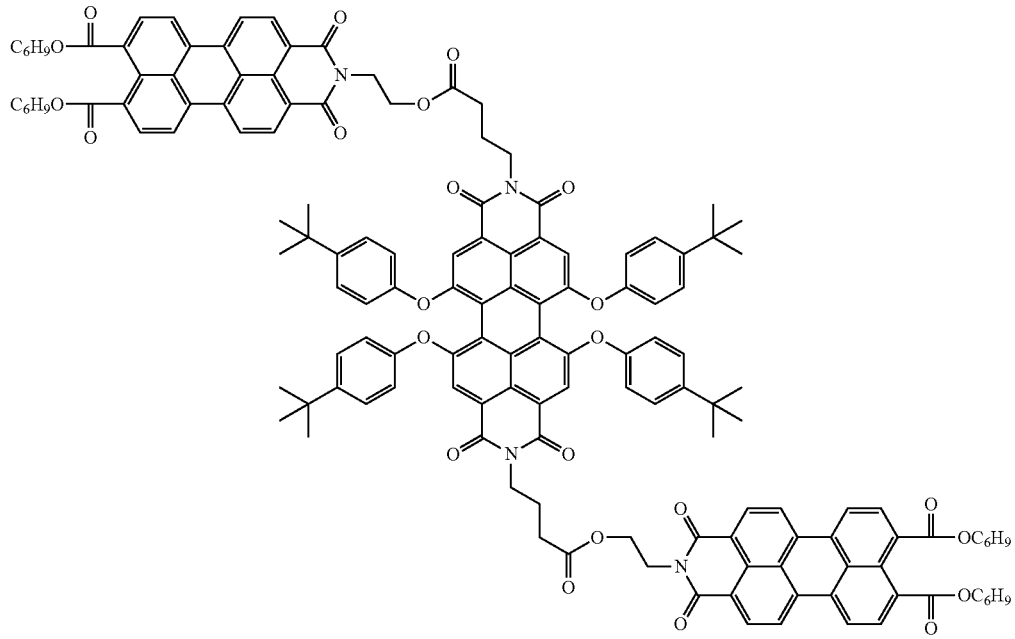 |
| II-4* | 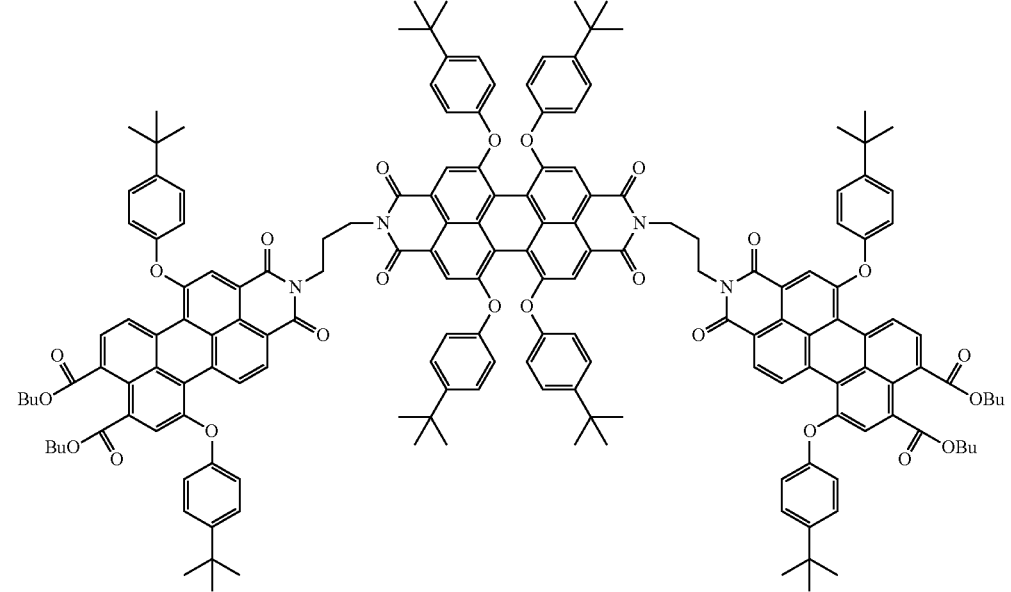 |

US 11,322,690 B2
59                                                           60
TABLE 2-continued
| Compound No. | Structure |
|---|---|
| II-5* | 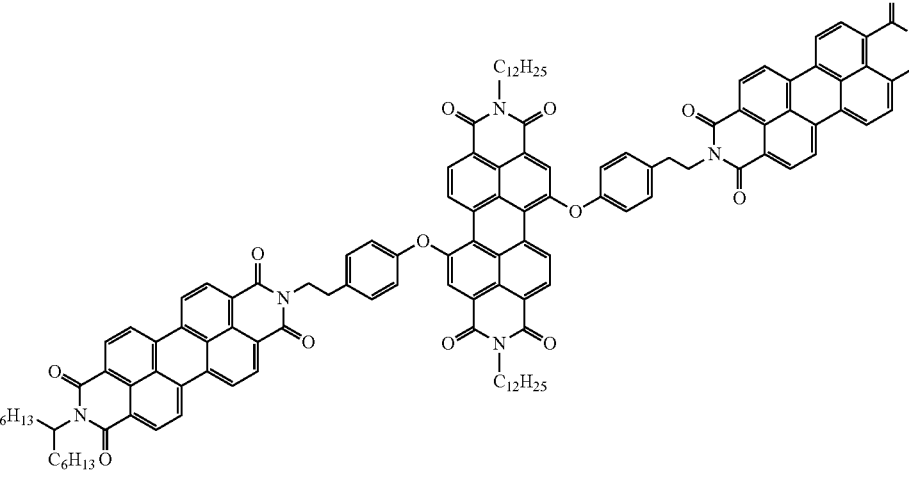 |
| II-6* | 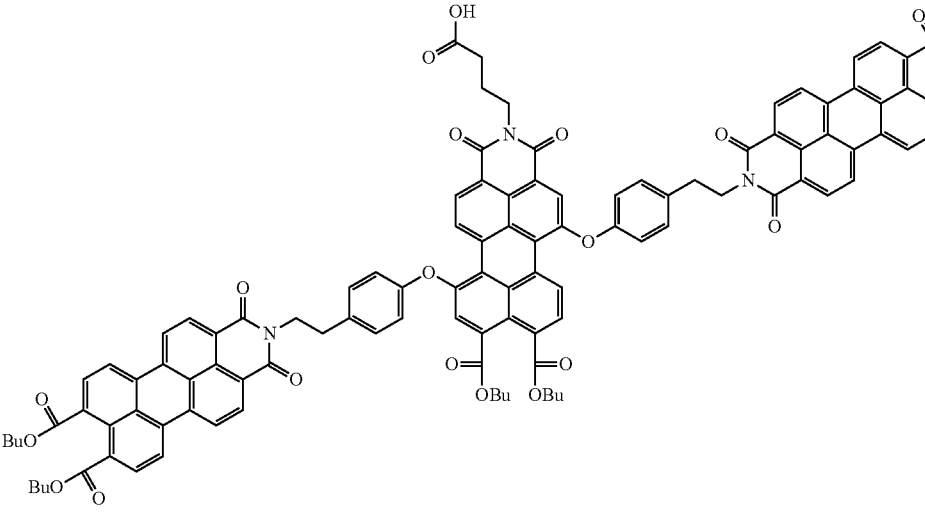 |
| II-7* | 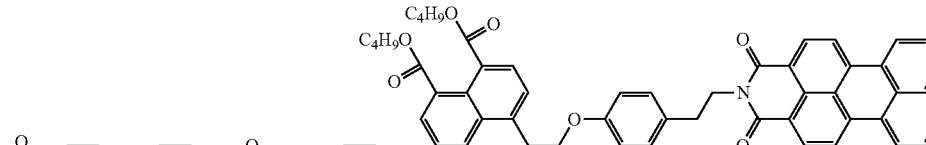 |

TABLE 2-continued
| Compound No. | Structure |
|---|---|
| II-8* | 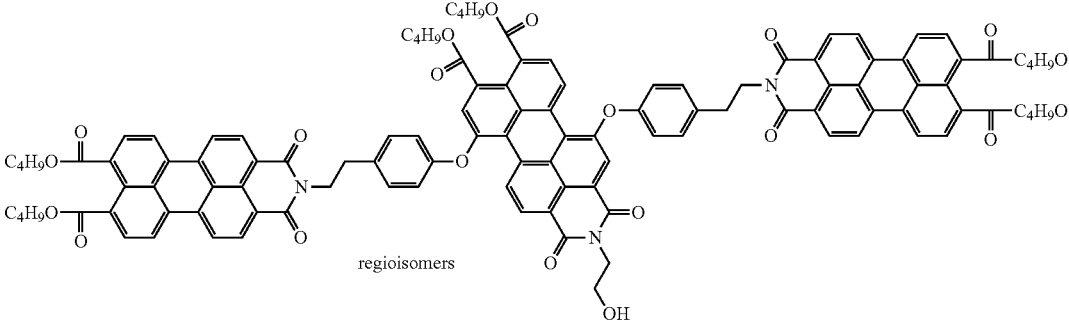 regioisomers |
| II-9* | 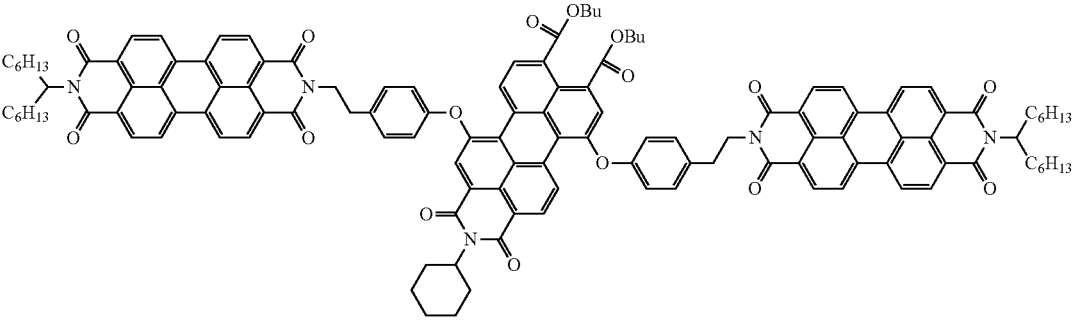 |
| II-10* | 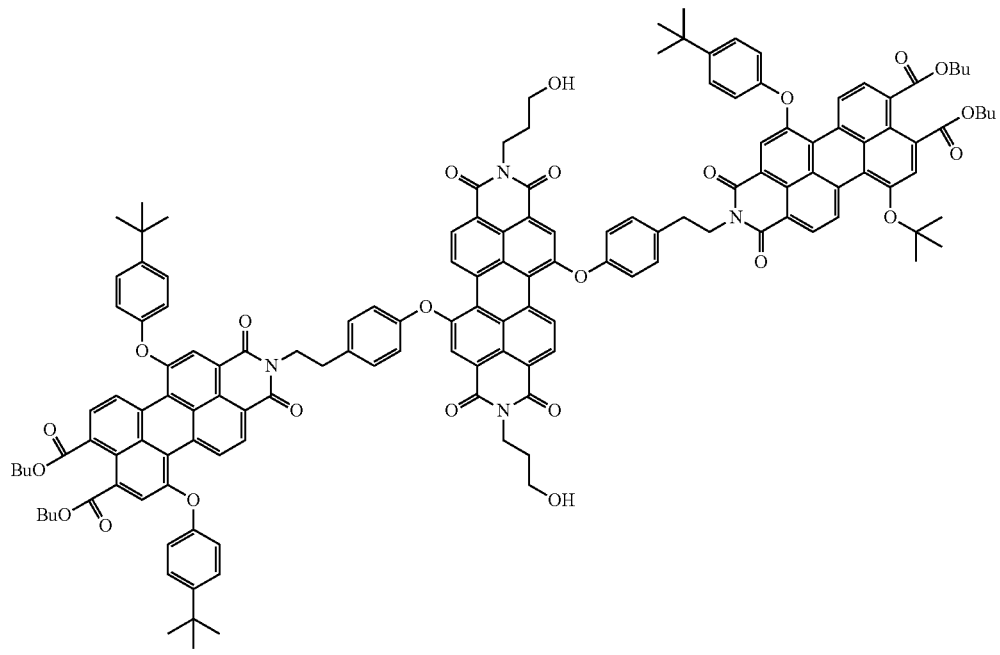 |

TABLE 2-continued
| Compound No. | Structure |
|---|---|
| II-11* | 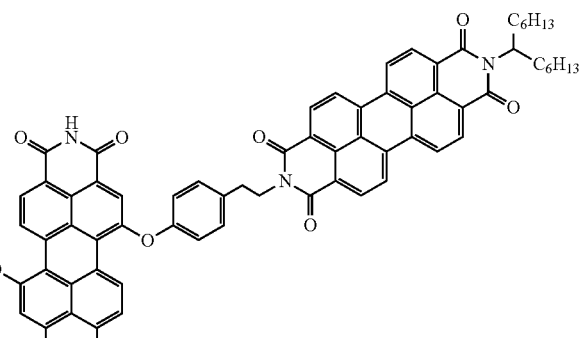 |
| II-12* | 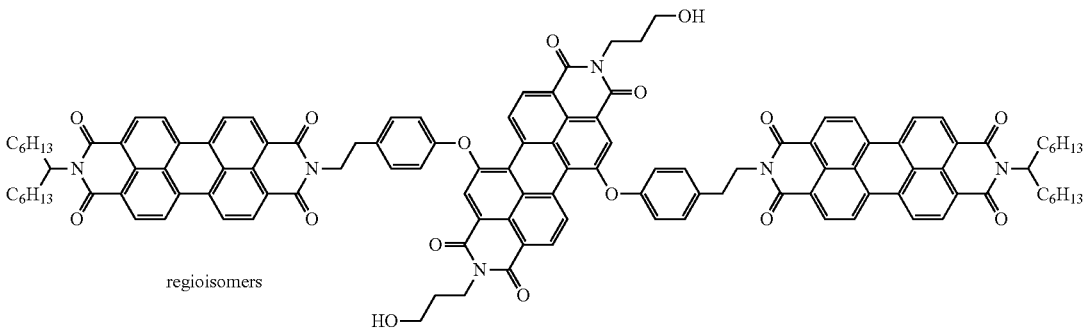 regioisomers |
| II-13 | 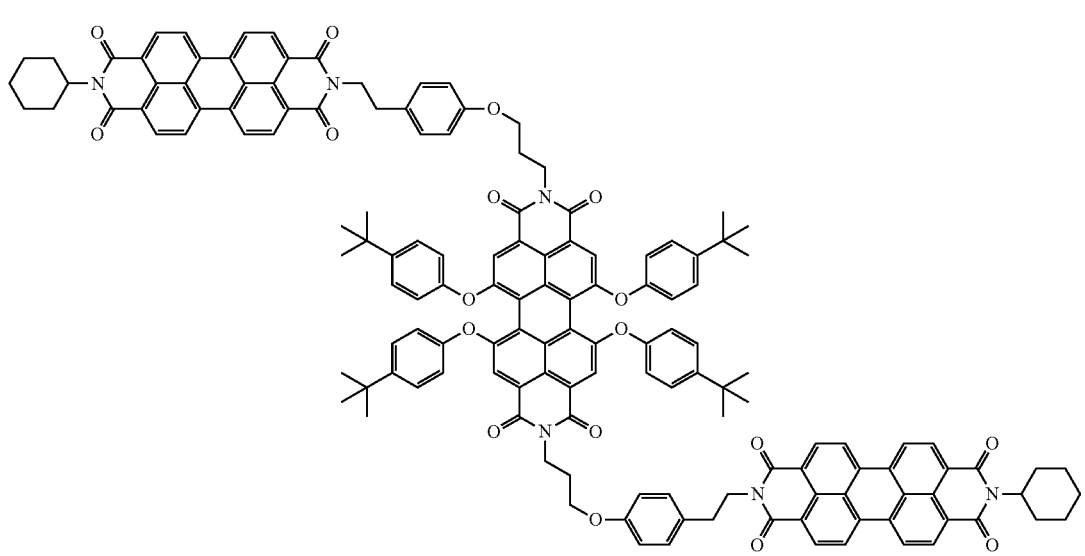 [SMILES: CC(C)(C)c1ccc(Oc2cc3c4c(cc(Oc5ccc(C(C)(C)C)cc5)c5c6c(Oc7ccc(C(C)(C)C)cc7)cc7c8c(cc(Oc9ccc(C(C)(C)C)cc9)c(c2c45)c86)C(=O)N(CCCOc2ccc(CCN4C(=O)c5ccc6c8ccc9c%10c(ccc(c%11ccc(c5c6%11)C4=O)c%108)C(=O)N(C4CCCCC4)C9=O)cc2)C7=O)C(=O)N(CCCOc2ccc(CCN4C(=O)c5ccc6c7ccc8c9c(ccc(c%10ccc(c5c6%10)C4=O)c97)C(=O)N(C4CCCCC4)C8=O)cc2)C3=O)cc1] |

TABLE 2-continued

| Compound No. | Structure |
|---|---|
| II-14* | (structure image) |
| II-15* | (structure image) regioisomers |
| II-16* | (structure image) regioisomers |
| II-17* | (structure image) regioisomers |

TABLE 2-continued

| Compound No. | Structure |
|---|---|
| II-18* | 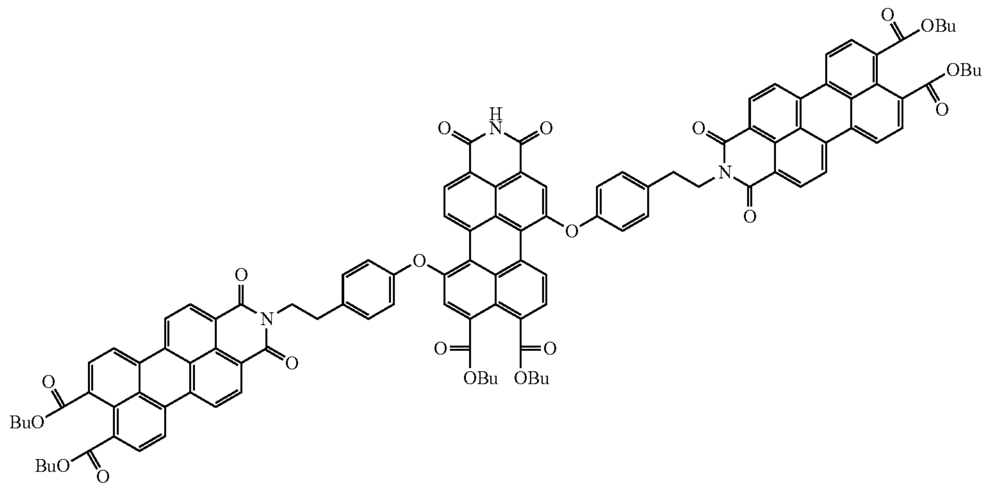 |
| II-19* | regioisomers |
| II-20* | 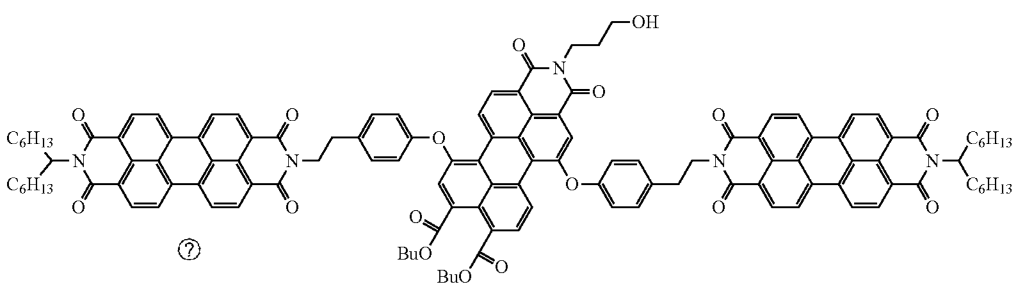 |

Notes:
*Compounds isolated as a mixture of regioisomers - predominant regioisomer shown.

Definitions

Unless otherwise herein defined, the following terms will be understood to have the general meanings which follow.

The term "rylene" refers to a polyaromatic hydrocarbon molecule consisting of two or more naphthylene units linked together at their "peri" positions. As used herein, the term "rylene" includes perylene (2 naphthylene units), terrylene (3 naphthylene units), quarterrylene (4 naphthylene units), quinterrylene (5 naphthylene units), and so on. Furthermore, it will be appreciated that perylene is the smallest example of a rylene moiety, that is to say that naphthylene and functionalised naphthylene moieties are not within the meaning of the term "rylene" as used herein.

The term "substituted rylene" refers to a rylene as defined above where one or more of the hydrogen atoms is replaced with a substituent, for example a $C_{1-6}$alkyl (e.g. $C_{1-6}$alkylperylene), aryloxy (e.g. aryloxyperylene) and so on.

The term "bay position" in the context of a rylene substituent refers to the carbon atoms ortho to the "peri" position linkage between naphthylene subunits. For example, the bay positions of perylene are the carbon atoms numbered 1, 6, 7 and 12 in the following perylene structure, and the bay position of terrylene are the carbon atoms numbered 1, 6, 7, 8, 9, 14, 15, and 16 in the following terrylene structure. The term "end position" in the context of rylene substituents refers to the carbon atoms para to the "peri" position linkage between naphthylene subunits. For example, the end groups of perylene are the carbon atoms numbered 3, 4, 9 and 10 in the following perylene structure, and the end groups of terylene are the carbon atoms numbered 3, 4, 11 and 12 in the following terylene structure.

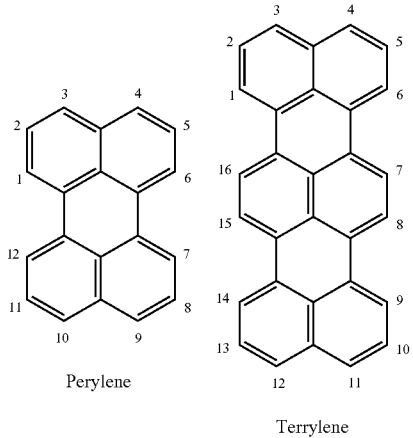

Perylene

Terrylene

The term "imide position" in the context of a substituted rylene refers to the nitrogen atom of an imide substituent of that rylene, for example, the imide position of perylene-3, 4,9,10-tetracarboxylic diimide (sometimes referred to as perylene diimide) is either of the imide nitrogen atoms.

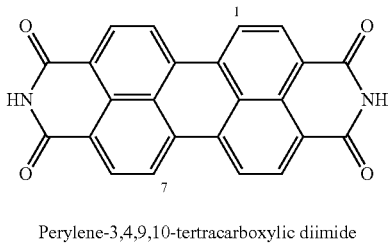

Perylene-3,4,9,10-tertracarboxylic diimide

The term "donor rylene" refers to a rylene as defined above that is capable of absorbing energy and transferring the absorbed energy to an acceptor.

The term "acceptor rylene" refers to a rylene as defined above that is capable of accepting energy from a donor, for example a donor rylene.

The term "$C_{1-20}$alkyl" refers to optionally substituted straight chain or branched chain hydrocarbon groups having from 1 to 20 carbon atoms. Examples include methyl (Me), ethyl (Et), propyl (Pr), isopropyl (i-Pr), butyl (Bu), isobutyl (i-Bu), sec-butyl (s-Bu), tert-butyl (t-Bu), pentyl, neopentyl, hexyl and the like. Unless the context requires otherwise, the term "$C_{1-20}$alkyl" also encompasses alkyl groups containing one less hydrogen atom such that the group is attached via two positions i.e. divalent. "$C_{1-8}$alkyl" and "$C_{1-4}$alkyl" including methyl, ethyl, propyl, isopropyl, n-butyl, iso-butyl, sec-butyl, tert-butyl, pentyl, n-hexyl and octyl are preferred with methyl being particularly preferred.

The term "$C_{2-20}$alkenyl" refers to optionally substituted straight chain or branched chain hydrocarbon groups having at least one double bond of either E or Z stereochemistry where applicable and 2 to 20 carbon atoms. Examples include vinyl, 1-propenyl, 1- and 2-butenyl and 2-methyl-2-propenyl. Unless the context requires otherwise, the term "$C_{2-20}$alkenyl" also encompasses alkenyl groups containing one less hydrogen atom such that the group is attached via two positions i.e. divalent. "$C_{2-6}$alkenyl", "$C_{2-4}$alkenyl" and "$C_{2-3}$alkenyl" including ethenyl, propenyl and butenyl are preferred with ethenyl being particularly preferred.

The term "$C_{2-20}$alkynyl" refers to optionally substituted straight chain or branched chain hydrocarbon groups having at least one triple bond and 2 to 6 carbon atoms. Examples include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl and the like. Unless the context indicates otherwise, the term "$C_{2-20}$alkynyl" also encompasses alkynyl groups containing one less hydrogen atom such that the group is attached via two positions i.e. divalent. $C_{2-6}$alkynyl is preferred.

The term "$C_{3-8}$cycloalkyl" refers to non-aromatic cyclic groups having from 3 to 8 carbon atoms, including cyclopropyl, cyclobutyl, cyclopentyl, cyclohexyl, cycloheptyl and cyclooctyl. It will be understood that cycloalkyl groups may be saturated such as cyclohexyl or unsaturated such as cyclohexenyl. $C_{3-6}$cycloalkyl such as cyclopropyl, cyclobutyl, cyclopentyl and cyclohexyl are preferred.

The terms "hydroxy" and "hydroxyl" refer to the group —OH.

The term "oxo" refers to the group =O.

The term "oxy" refers to the group —O—.

The term "substituted oxy" refers to an oxy group substituted with one or more substituents selected from the optional substituents described herein, for example "$C_{1-6}$alkoxy" and "aryloxy". The term "$C_{1-6}$alkoxy" refers to an alkyl group as defined above covalently bound via an oxy group as defined above containing 1 to 6 carbon atoms, such as methoxy, ethoxy, propoxy, isoproxy, butoxy, tert-butoxy and pentoxy. "$C_{1-4}$alkoxy" and "$C_{1-3}$alkoxy" including methoxy, ethoxy, propoxy and butoxy are preferred with methoxy being particularly preferred. The term "aryloxy" refers to an aryl group as defined herein covalently bound via an oxy group as defined herein, such as 1-phenoxy, 4-ethylamino-1-phenoxy and so on.

The term "carboxylate" or "carboxyl" refers to the group —COO— or —COOH.

The term "ester" refers to a carboxyl group substituted with, for example a $C_{1-6}$alkyl group ("carboxyl$C_{1-6}$alkyl" or "alkylester"), an aryl or aralkyl group ("arylester" or "aralkylester") and so on. $CO_2C_{1-6}$alkyl groups are preferred, such as for example, methylester ($CO_2Me$), ethylester ($CO_2Et$), propylester ($CO_2Pr$) and butylester ($CO_2Bu$) (e.g. n-butylester, i-butylester and t-butylester) and includes reverse esters thereof (e.g. —OCOMe, —OCOEt, —OCOPr, —OCOBu). It will be appreciated that groups such as "optionally substituted arylester" include the mono and di-ester substituents, which may optionally be substituted either on the aryl moiety or the ester moiety. Examples of diesters include —O$_2$CPhCO$_2$—, —CO$_2$PhO$_2$C—, —O$_2$CCH$_2$CO$_2$— and so on. In one embodiment, the term "ester" includes a group selected from optionally substituted $C_{1-6}$alkylester and optionally substituted arylester.

The term "cyano" refers to the group —CN.

The term "nitro" refers to the group —NO$_2$.

The term "amino" refers to the group —NH$_2$.

The term "substituted amino" or "secondary amino" refers to an amino group having a hydrogen replaced with, for example a $C_{1-6}$alkyl group ("$C_{1-6}$alkylamino"), an aryl or aralkyl group ("arylamino", "aralkylamino") and so on. $C_{1-3}$alkylamino groups are preferred, such as for example, methylamino (NHMe), ethylamino (NHEt) and propylamino (NHPr).

The term "disubstituted amino" or "tertiary amino" refers to an amino group having the two hydrogens replaced with, for example a $C_{1-6}$alkyl group, which may be the same or different ("dialkylamino"), an aryl and alkyl group ("aryl (alkyl)amino") and so on. Di($C_{1-3}$alkyl)amino groups are preferred, such as for example, dimethylamino ($NMe_2$), diethylamino ($NEt_2$), dipropylamino ($NPr_2$) and variations thereof (e.g. N(Me)(Et) and so on).

The term "aldehyde" refers to the group —C(=O)H.

The term "ketone" or "carbonyl" refers to >C=O.

The term "substituted ketone" refers to a ketone group as defined herein substituted with, for example a $C_{1-6}$alkyl group ("alkylketone" or "ketoalkyl"), an aryl group ("arylketone"), an aralkyl group ("aralkylketone) and so on.

The term "amido" or "amide" refers to the group —C(O)NH$_2$.

The term "imido" refers to the group —C(O)NHC(O)—.

The term "substituted imido" refers to an imido group as defined herein with the H replaced with a substituent, for example $C_{1-6}$alkylimido refers to the group —C(O)NC$_{1-6}$alkylC(O)—.

The term "formamido" or "aminoaldehyde" refers to the group —NHC(O)H.

The term "substituted amido" or "substituted amide" refers to an amido group having at least one hydrogen replaced with, for example a $C_{1-6}$alkyl group ("$C_{1-6}$alkylamido" or "$C_{1-6}$alkylamide"), an aryl ("arylamido"), aralkyl group ("aralkylamido") and so on. $C_{1-3}$alkylamide groups are preferred, such as for example, methylamide (—C(O)NHMe), ethylamide (—C(O)NHEt) and propylamide (—C(O)NHPr) and includes reverse amides thereof (e.g. —NHMeC(O)—, —NHEtC(O)— and —NHPrC(O)—). It may also refer to an amido group having the two hydrogens replaced with, for example a $C_{1-6}$alkyl group ("di($C_{1-6}$alkyl)amido" or "di($C_{1-6}$alkyl)amide"), an aralkyl and alkyl group ("alkyl(aralkyl)amido") and so on. Di($C_{1-3}$alkyl)amide groups are preferred, such as for example, dimethylamide (—C(O)NMe$_2$), diethylamide (—C(O)NEt$_2$) and dipropylamide ((—C(O)NPr$_2$) and variations thereof (e.g. —C(O)N(Me)Et and so on) and includes reverse amides thereof.

The term "thiol" refers to the group —SH.

The term "$C_{1-20}$alkylthio" refers to a thiol group having the hydrogen replaced with a $C_{1-6}$alkyl group. $C_{1-3}$alkylthio groups are preferred, such as for example, thiolmethyl, thiolethyl and thiolpropyl.

The term "thio" refers to the group —S—.

The term "thioxo" refers to the group =S.

The term "thiocarbonyl" refers to the group >C=S.

The term "sulfinyl" refers to the group —S(=O)H.

The term "substituted sulfinyl" or "sulfoxide" refers to a sulfinyl group having the hydrogen replaced with, for example a $C_{1-6}$alkyl group ("$C_{1-6}$alkylsulfinyl" or "$C_{1-6}$alkylsulfoxide"), an aryl ("arylsulfinyl"), an aralkyl ("aralkyl sulfinyl") and so on. $C_{1-3}$alkylsulfinyl groups are preferred, such as for example, —SOmethyl, —SOethyl and —SOpropyl.

The term "sulfonyl" refers to the group —SO$_2$H.

The term "substituted sulfonyl" refers to a sulfonyl group having the hydrogen replaced with, for example a $C_{1-6}$alkyl group ("sulfonyl$C_{1-6}$alkyl"), an aryl ("arylsulfonyl"), an aralkyl ("aralkylsulfonyl") and so on. Sulfonyl$C_{1-3}$alkyl groups are preferred, such as for example, —SO$_2$Me, —SO$_2$Et and —SO$_2$Pr.

The term "sulfonylamido" or "sulfonamide" refers to the group —SO$_2$NH$_2$.

The term "substituted sulfonamido" or "substituted sulfonamide" refers to a sulfonylamido group having a hydrogen replaced with, for example a $C_{1-6}$alkyl group ("sulfonylamidoC$_{1-6}$alkyl"), an aryl ("arylsulfonamide"), aralkyl ("aralkylsulfonamide") and so on. SulfonylamidoC$_{1-3}$alkyl groups are preferred, such as for example, —SO$_2$NHMe, —SO$_2$NHEt and —SO$_2$NHPr and includes reverse sulfonamides thereof (e.g. —NHSO$_2$Me, —NHSO$_2$Et and —NHSO$_2$Pr).

The term "disubstituted sufonamido" or "disubstituted sulfonamide" refers to a sulfonylamido group having the two hydrogens replaced with, for example a $C_{1-6}$alkyl group, which may be the same or different ("sulfonylamidodi($C_{1-6}$alkyl)"), an aralkyl and alkyl group ("sulfonamido(aralkyl)alkyl") and so on. Sulfonylamidodi($C_{1-3}$alkyl) groups are preferred, such as for example, —SO$_2$NMe$_2$, —SO$_2$NEt$_2$ and —SO$_2$NPr$_2$ and variations thereof (e.g. —SO$_2$N(Me)Et and so on) and includes reserve sulfonamides thereof.

The term "sulfate" refers to the group OS(O)$_2$OH and includes groups having the hydrogen replaced with, for example a $C_{1-6}$alkyl group ("alkylsulfates"), an aryl ("arylsulfate"), an aralkyl ("aralkylsulfate") and so on. $C_{1-3}$sulfates are preferred, such as for example, OS(O)$_2$OMe, OS(O)$_2$OEt and OS(O)$_2$OPr.

The term "sulfonate" refers to the group SO$_3$H and includes groups having the hydrogen replaced with, for example a $C_{1-6}$alkyl group ("alkylsulfonate"), an aryl ("arylsulfonate"), an aralkyl ("aralkylsulfonate") and so on. $C_{1-3}$sulfonates are preferred, such as for example, SO$_3$Me, SO$_3$Et and SO$_3$Pr.

The term "aryl" refers to a carbocyclic (non-heterocyclic) aromatic ring or mono-, bi- or tri-cyclic ring system. The aromatic ring or ring system is generally composed of 6 to 20 or 6 to 14 carbon atoms. Examples of aryl groups include but are not limited to phenyl, biphenyl, naphthyl, tetrahydronaphthyl, phenanthrenyl and anthracenyl. In one embodiment, "aryl" includes a 6-membered aryl, such as phenyl, a 10-membered aryl, such as naphthyl, and a 14-membered aryl, such as phenanthrenyl and anthracenyl. The aryl group may be substituted with 0 to 6 optional substituents, preferably 0 to 3 optional substituents. The term "alkylaryl" refers to $C_{1-6}$alkylaryl such as benzyl.

The term "alkoxyaryl" refers to $C_{1-6}$alkyloxyaryl such as benzyloxy.

The term "heterocyclyl" refers to a moiety obtained by removing a hydrogen atom from a ring atom of a heterocyclic compound which moiety has from 3 to 10 ring atoms (unless otherwise specified), of which 1, 2, 3 or 4 are ring heteroatoms each heteroatom being independently selected from O, S and N.

In this context, the prefixes 3-, 4-, 5-, 6-, 7-, 8-, 9- and 10-membered denote the number of ring atoms, or range of ring atoms, whether carbon atoms or heteroatoms. For example, the term "3-10 membered heterocylyl", as used herein, pertains to a heterocyclyl group having 3, 4, 5, 6, 7, 8, 9 or 10 ring atoms. Examples of heterocylyl groups include 5-6-membered monocyclic heterocyclyls and 9-10 membered fused bicyclic heterocyclyls.

Examples of monocyclic heterocyclyl groups include, but are not limited to, those containing one nitrogen atom such as aziridine (3-membered ring), azetidine (4-membered ring), pyrrolidine (tetrahydropyrrole), pyrroline (e.g., 3-pyrroline, 2,5-dihydropyrrole), 2H-pyrrole or 3H-pyrrole (isopyrrole, isoazole) or pyrrolidinone (5-membered rings), piperidine, dihydropyridine, tetrahydropyridine (6-membered rings), and azepine (7-membered ring); those containing two nitrogen atoms such as imidazoline, pyrazolidine (diazolidine), imidazoline, pyrazoline (dihydropyrazole) (5-membered rings), piperazine (6-membered ring); those containing one oxygen atom such as oxirane (3-membered ring), oxetane (4-membered ring), oxolane (tetrahydrofuran), oxole (dihydrofuran) (5-membered rings), oxane (tetrahydropyran), dihydropyran, pyran (6-membered rings), oxepin (7-membered ring); those containing two oxygen atoms such as dioxolane (5-membered ring), dioxane (6-membered ring), and dioxepane (7-membered ring); those containing three oxygen atoms such as trioxane (6-membered ring); those containing one sulfur atom such as thiirane (3-membered ring), thietane (4-membered ring), thiolane (tetrahydrothiophene) (5-membered ring), thiane (tetrahydrothiopyran) (6-membered ring), thiepane (7-membered ring); those containing one nitrogen and one oxygen atom such as tetrahydrooxazole, dihydrooxazole, tetrahydroisoxazole, dihydroisoxazole (5-membered rings), morpholine, tetrahydrooxazine, dihydrooxazine, oxazine (6-membered rings); those containing one nitrogen and one sulfur atom such as thiazoline, thiazolidine (5-membered rings), thiomorpholine (6-membered ring); those containing two nitrogen and one oxygen atom such as oxadiazine (6-membered ring); those containing one oxygen and one sulfur such as: oxathiole (5-membered ring) and oxathiane (thioxane) (6-membered ring); and those containing one nitrogen, one oxygen and one sulfur atom such as oxathiazine (6-membered ring).

Heterocyclyls also encompass aromatic heterocyclyls and non-aromatic heterocyclyls. Such groups may be substituted or unsubstituted.

The term "aromatic heterocyclyl" may be used interchangeably with the term "heteroaromatic" or the term "heteroaryl" or "hetaryl". The heteroatoms in the aromatic heterocyclyl group may be independently selected from N, S and O.

"Heteroaryl" is used herein to denote a heterocyclic group having aromatic character and embraces aromatic monocyclic ring systems and polycyclic (e.g. bicyclic) ring systems containing one or more aromatic rings. The term aromatic heterocyclyl also encompasses pseudoaromatic heterocyclyls. The term "pseudoaromatic" refers to a ring system which is not strictly aromatic, but which is stabilized by means of delocalization of electrons and behaves in a similar manner to aromatic rings. The term aromatic heterocyclyl therefore covers polycyclic ring systems in which all of the fused rings are aromatic as well as ring systems where one or more rings are non-aromatic, provided that at least one ring is aromatic. In polycyclic systems containing both aromatic and non-aromatic rings fused together, the group may be attached to another moiety by the aromatic ring or by a non-aromatic ring.

Examples of heteroaryl groups are monocyclic and bicyclic groups containing from five to ten ring members. The heteroaryl group can be, for example, a five membered or six membered monocyclic ring or a bicyclic structure formed from fused five and six membered rings or two fused six membered rings or two fused five membered rings. Each ring may contain up to about four heteroatoms typically selected from nitrogen, sulfur and oxygen. The heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Aromatic heterocyclyl groups may be 5-membered or 6-membered mono-cyclic aromatic ring systems.

Examples of 5-membered monocyclic heteroaryl groups include but are not limited to furanyl, thienyl, pyrrolyl, oxazolyl, oxadiazolyl (including 1,2,3 and 1,2,4 oxadiazolyls and furazanyl i.e. 1,2,5-oxadiazolyl), thiazolyl, isoxazolyl, isothiazolyl, pyrazolyl, imidazolyl, triazolyl (including 1,2,3, 1,2,4 and 1,3,4 triazolyls), oxatriazolyl, tetrazolyl, thiadiazolyl (including 1,2,3 and 1,3,4 thiadiazolyls) and the like.

Examples of 6-membered monocyclic heteroaryl groups include but are not limited to pyridinyl, pyrimidinyl, pyridazinyl, pyrazinyl, triazinyl, pyranyl, oxazinyl, dioxinyl, thiazinyl, thiadiazinyl and the like. Examples of 6-membered aromatic heterocyclyls containing nitrogen include pyridyl (1 nitrogen), pyrazinyl, pyrimidinyl and pyridazinyl (2 nitrogens).

Aromatic heterocyclyl groups may also be bicyclic or polycyclic heteroaromatic ring systems such as fused ring systems (including purine, pteridinyl, napthyridinyl, 1H thieno[2,3-c]pyrazolyl, thieno[2,3-b]furyl and the like) or linked ring systems (such as oligothiophene, polypyrrole and the like). Fused ring systems may also include aromatic 5-membered or 6-membered heterocyclyls fused to carbocyclic aromatic rings such as phenyl, naphthyl, indenyl, azulenyl, fluorenyl, anthracenyl and the like, such as 5-membered aromatic heterocyclyls containing nitrogen fused to phenyl rings, 5-membered aromatic heterocyclyls containing 1 or 2 nitrogens fused to phenyl ring.

A bicyclic heteroaryl group may be, for example, a group selected from: a) a benzene ring fused to a 5- or 6-membered ring containing 1, 2 or 3 ring heteroatoms; b) a pyridine ring fused to a 5- or 6-membered ring containing 1, 2 or 3 ring heteroatoms; c) a pyrimidine ring fused to a 5- or 6-membered ring containing 1 or 2 ring heteroatoms; d) a pyrrole ring fused to a 5- or 6-membered ring containing 1, 2 or 3 ring heteroatoms; e) a pyrazole ring fused to a 5- or 6-membered ring containing 1 or 2 ring heteroatoms; f) an imidazole ring fused to a 5- or 6-membered ring containing 1 or 2 ring heteroatoms; g) an oxazole ring fused to a 5- or 6-membered ring containing 1 or 2 ring heteroatoms; h) an isoxazole ring fused to a 5- or 6-membered ring containing 1 or 2 ring heteroatoms; i) a thiazole ring fused to a 5- or 6-membered ring containing 1 or 2 ring heteroatoms; j) an isothiazole ring fused to a 5- or 6-membered ring containing 1 or 2 ring heteroatoms; k) a thiophene ring fused to a 5- or 6-membered ring containing 1, 2 or 3 ring heteroatoms; l) a furan ring fused to a 5- or 6-membered ring containing 1, 2 or 3 ring heteroatoms; m) a cyclohexyl ring fused to a 5- or 6-membered ring containing 1, 2 or 3 ring heteroatoms; and n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), benzodioxole and pyrazolopyridine (e.g. pyrazolo[1,5-a]pyridine) groups. A further example of a six membered ring fused to a five membered ring is a pyrrolopyridine group such as a pyrrolo[2,3-b]pyridine group.

Particular examples of bicyclic heteroaryl groups containing two fused six membered rings include but are not limited to quinoline, isoquinoline, chroman, thiochroman, chromene, isochromene, isochroman, benzodioxan, quinolizine, benzoxazine, benzodiazine, pyridopyridine, quinoxaline, quinazoline, cinnoline, phthalazine, naphthyridine and pteridine groups.

Examples of heteroaryl groups containing an aromatic ring and a non-aromatic ring include tetrahydronaphthalene, tetrahydroisoquinoline, tetrahydroquinoline, dihydrobenzothiophene, dihydrobenzofuran, 2,3-dihydro-benzo[1,4]dioxine, benzo[1,3]dioxole, 4,5,6,7-tetrahydrobenzofuran, indoline, isoindoline and indane groups.

Examples of aromatic heterocyclyls fused to carbocyclic aromatic rings may therefore include but are not limited to benzothiophenyl, indolyl, isoindolyl, benzofuranyl, isobenzofuranyl, benzimidazolyl, indazolyl, benzoxazolyl, benzisoxazolyl, isobenzoxazoyl, benzothiazolyl, benzisothiazolyl, quinolinyl, isoquinolinyl, quinoxalinyl, quinazolinyl, cinnolinyl, benzotriazinyl, phthalazinyl, carbolinyl, naphthimidazolyl, anthracene imidazolyl, phenanthrene imidazolyl, and the like.

The term "non-aromatic heterocyclyl" encompasses optionally substituted saturated and unsaturated rings which contain at least one heteroatom selected from the group consisting of N, S and O.

Non-aromatic heterocyclyls may be 3-7 membered mono-cyclic rings.

Examples of 5-membered non-aromatic heterocyclyl rings include 2H-pyrrolyl, 1-pyrrolinyl, 2-pyrrolinyl, 3-pyrrolinyl, pyrrolidinyl, 1-pyrrolidinyl, 2-pyrrolidinyl, 3-pyrrolidinyl, tetrahydrofuranyl, tetrahydrothiophenyl, pyrazolinyl, 2-pyrazolinyl, 3-pyrazolinyl, pyrazolidinyl, 2-pyrazolidinyl, 3-pyrazolidinyl, imidazolidinyl, 3-dioxalanyl, thiazolidinyl, isoxazolidinyl, 2-imidazolinyl and the like.

Examples of 6-membered non-aromatic heterocyclyls include piperidinyl, piperidinonyl, pyranyl, dihyrdopyranyl, tetrahydropyranyl, 2H pyranyl, 4H pyranyl, thianyl, thianyl oxide, thianyl dioxide, piperazinyl, diozanyl, 1,4-dioxinyl, 1,4-dithianyl, 1,3,5-triozalanyl, 1,3,5-trithianyl, 1,4-morpholinyl, thiomorpholinyl, 1,4-oxathianyl, triazinyl, 1,4-thiazinyl and the like.

Examples of 7-membered non-aromatic heterocyclyls include azepanyl, oxepanyl, thiepanyl and the like.

Non-aromatic heterocyclyl rings may also be bicyclic heterocyclyl rings such as linked ring systems (for example uridinyl and the like) or fused ring systems. Fused ring systems include non-aromatic 5-membered, 6-membered or 7-membered heterocyclyls fused to carbocyclic aromatic rings such as phenyl, napthyl, indenyl, azulenyl, fluorenyl, anthracenyl and the like. Examples of non-aromatic 5-membered, 6-membered or 7-membered heterocyclyls fused to carbocyclic aromatic rings include indolinyl, benzodiazepinyl, benzazepinyl, dihydrobenzofuranyl and the like.

In one embodiment, the term "heterocyclyl" includes an optionally substituted aromatic or non-aromatic 3 to 10 membered mono-, bi- or tri-cyclic ring system, of which 1, 2, 3 or 4 ring atoms are independently selected from O, S and N. In one embodiment, the term "heterocyclyl" includes an optionally substituted aromatic or non-aromatic 5 or 6 membered mono-cyclic ring or a 9 or 10 membered bi-cyclic ring system, of which 1, 2, 3 or 4 ring atoms are independently selected from O, S and N; for example, an optionally substituted triazolyl, an optionally substituted morpholinyl, an optionally substituted pyrrolidinyl, an optionally substituted imidazolyl, an optionally substituted indolyl, an optionally substituted benzimidazolyl, an optionally substituted naphthimidazolyl, an optionally substituted anthracene imidazolyl, an optionally substituted phenanthrene imidazolyl, an optionally substituted pyridyl, an optionally substituted pyrimidinyl, an optionally substituted furanyl, an optionally substituted piperidinyl, an optionally substituted pyrazinyl and an optionally substituted oxazolyl. In one embodiment, the term "heterocyclyl" includes an optionally substituted aromatic 5 or 6 membered mono-cyclic ring comprising 1, 2 or 3 ring heteroatoms independently selected from O, S and N, preferably O and N, most preferably N; for example, an optionally substituted triazolyl, an optionally substituted pyrrolidinyl, an optionally substituted imidazolyl, an optionally substituted pyridyl, an optionally substituted furanyl, an optionally substituted pyrazinyl and an optionally substituted oxazolyl. In another embodiment, the term "heterocyclyl" includes an optionally substituted non-aromatic 5 or 6 membered mono-cyclic ring comprising 1, 2 or 3 ring heteroatoms independently selected from O, S and N, preferably 0 and N, most preferably N; for example, an optionally substituted morpholinyl and an optionally substituted piperidinyl.

The term "halo" refers to fluoro, chloro, bromo or iodo.

Unless otherwise defined, the term "optionally substituted" or "optional substituent" as used herein refers to a group which may or may not be further substituted with 1, 2, 3, 4 or more groups, preferably 1, 2 or 3, more preferably 1 or 2 groups selected from the group consisting of $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, aryl$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case of heterocycles containing N may also include but are not limited to $C_{1-6}$alkyl e.g. N—$C_{1-6}$alkyl, more preferably methyl particularly N-methyl. Optional substituents in the case of aryls preferably include, but are not limited to, halo, $C_{1-6}$alkyl, $C_{2-6}$alkenyl, $C_{2-6}$alkynyl, $C_{3-8}$cycloalkyl, $C_{1-6}$alkoxy, 6-membered aryloxy, $C_{1-6}$alkylhalo, carboxyl, $C_{1-6}$alkylester, 6-membered arylester, cyano, nitro, amino, substituted amino, disubstituted amino, acyl, substituted ketone, amide, aminoacyl, substituted amides, disubstituted amides, thiol, $C_{1-6}$alkylthio, 6-membered aryl$C_{1-6}$alkyl and 3-10-membered heterocyclyl, wherein each alkyl, alkenyl, alkynyl, cycloalkyl, aryl and heterocyclyl and groups containing them may be further optionally substituted.

In one embodiment, the term "optionally substituted" or "optional substituent" as used herein refers to a group which may be substituted with 0, 1, 2 or 3 groups (preferably 0, 1 or 2 groups) selected from $C_{1-20}$alkyl (preferably $C_{1-6}$alkyl, most preferably $C_{1-4}$alkyl), $C_{2-6}$alkenyl (preferably $C_{2-4}$alkenyl), $C_{2-6}$alkynyl (preferably $C_{1-4}$alkynyl), $C_{1-6}$alkoxy (preferably $C_{1-4}$alkoxy), halo, $C_{3-8}$cycloalkyl, hydroxyl, carboxy, $C_{1-6}$alkylester, 6-membered arylester, 6-membered aryl-$C_{1-6}$alkyl, thiol, oxo, thioxo, sulphonyl, sulphinyl, sulphonamide, $C_{1-6}$alkylsubphonamide, 6-membered arylsulphonamide 6-membered arylsulphonyl, 6-membered aryl sulfinyl, amino, amido, substituted amimo, disubstituted amino and substituted amido, wherein each each alkyl, alkenyl, alkynyl, cycloalkyl, aryl and heterocyclyl and groups containing them may be further optionally substituted with 0, 1, 2 or 3, preferably 1 or 2, further groups selected from $C_{1-20}$alkyl (preferably $C_{1-6}$alkyl, most preferably $C_{1-4}$alkyl), $C_{2-6}$alkenyl (preferably $C_{2-4}$alkenyl), $C_{2-6}$alkynyl (preferably $C_{1-4}$alkynyl), $C_{1-6}$alkoxy (preferably $C_{1-4}$alkoxy), halo, $C_{3-8}$cycloalkyl, hydroxyl, carboxy, $C_{1-6}$alkylester, 6-membered arylester, 6-membered aryl-$C_{1-6}$ alkyl, thiol, oxo, thioxo, sulphonyl, sulphinyl, sulphonamide, $C_{1-6}$alkylsubphonamide, 6-membered arylsulphonamide 6-membered arylsulphonyl, 6-membered aryl sulfinyl, amino, amido, substituted amimo, disubstituted amino and substituted amido.

It will be understood that suitable derivatives of aromatic heterocyclyls containing nitrogen include N-oxides thereof.

The compounds of the invention may also be prepared as salts, which may be useful as intermediates for the generation of a compound of the present invention, or may exhibit a similar absorption/emission profile as the non-salt form of the compound. Examples of salts include salts of cations such as sodium, potassium, lithium, calcium, magnesium, ammonium and alkylammonium; acid addition salts of inorganic acids such as hydrochloric, orthophosphoric, sulfuric, phosphoric, nitric, carbonic, boric, sulfamic and hydrobromic acids; or salts of organic acids such as acetic, propionic, butyric, tartaric, maleic, hydroxymaleic, fumaric, citric, lactic, mucic, gluconic, benzoic, succinic, oxalic, phenylacetic, methanesulfonic, trihalomethanesulfonic, toluenesulfonic, benzenesulfonic, isethionic, salicylic, sulfanilic, aspartic, glutamic, edetic, stearic, palmitic, oleic, lauric, pantothenic, tannic, ascorbic, valeric and orotic acids. Salts of amine groups may also comprise quaternary ammonium salts in which the amino nitrogen atom carries a suitable organic group such as an alkyl, alkenyl, alkynyl or aralkyl moiety.

The salts may be formed by conventional means, such as by reacting the free base form of the compound with one or more equivalents of the appropriate acid, or by reacting the free acid, or anhydride, form of the compound with one or more equivalents of the appropriate base.

It should be understood that a reference to a salt includes the solvent addition forms or crystal forms thereof, particularly solvates or polymorphs. Solvates contain either stoichiometric or non-stoichiometric amounts of a solvent, and may be formed during the process of crystallization with solvents such as water, alcohols such as methanol, ethanol or isopropyl alcohol, dimethylsulphoxide (DMSO), acetonitrile, dimethyl formamide (DMF) and the like with the solvate forming part of the crystal lattice by either non-covalent binding or by occupying a hole in the crystal lattice. Hydrates are formed when the solvent is water, alcoholates are formed when the solvent is alcohol. Solvates of the compounds of the present invention can be conveniently prepared or formed during the processes described herein. In general, the solvated forms are considered equivalent to the unsolvated forms for the purposes of the compounds and methods provided herein.

Additionally, the compounds of the present invention can exist in unsolvated as well as solvated forms with solvents such as water, ethanol, and the like. The solvated forms of the compounds of the present invention are also considered to be encompassed.

It will be understood that compounds described herein may possess a chiral centre and may therefore exist as an isomer such as a racemate or an R- or S-enantiomer. The compounds may therefore be used as a purified enantiomer or diastereomer, or as a mixture of any ratio thereof. The isomers may be separated conventionally by chromatographic methods or using a resolving agent. Alternatively the individual isomers may be prepared by asymmetric synthesis using chiral intermediates. Where the compound has a carbon-carbon double bond, it may occur in Z- or E-form and all isomeric forms of the compounds being included in the present invention.

It will be understood that compounds described herein may be present as a mixture of regioisomers. Typically, the regioisomers are formed under the same reaction conditions and possess substantially similar spectroscopic properties. For example, in a reaction, the compounds may therefore be used as a purified regioisomer or as a mixture of any ratio of regioisomers. The isomers may be separated conventionally, for example, by chromatographic methods or by selective crystalisation. For example, a regioisomeric mixture of a substituted perylene comprising two bay substitutents typically includes a mixture of 1,6 (cis), 12,7 (cis) and 1,7 (trans) regioisomeric substitution patterns; generally one of these regioisomers predominates, typically the 1,7 (trans) regioisomer. In the structures shown where a regioisomeric mixture is indicated, the dominant regioisomer is depicted.

It will also be understood that the compound of the invention may exist in rotomeric form, where, for example, rotation about an otherwise rotable bond is restricted. It is intended that all such rotomers are included within the scope of the present invention.

It will also be understood that compounds described herein may undergo tautomerisation. Typically, an equilibrium is established between two tautomers under certain conditions, for example, when in solution.

In one embodiment, the light harvesting array, compound of Formula I (e.g. a compound of Formula IA-IF) or oligomeric unit (including a compound of Formula II, e.g., a compound of Formula IIA to IIT) described herein includes a salt, stereoisomer, rotomer, tautomeric equilibrium, regioisomer or solvate thereof.

Methods for Preparing Oligomeric Units and Light Harvesting Arrays

In one aspect, there is provided a method for preparing a light harvesting array, comprising coupling an acceptor with one or more donors. In one embodiment, at least one donor is an oligomeric unit comprising an optionally substituted donor rylene core linked via a linker group to one or more optionally substituted peripheral donor rylenes. In one embodiment, at least one of the acceptor or the one or more donors is an oligomeric unit comprising a first optionally substituted rylene linked via a linker group to a second optionally substituted rylene, the first optionally substituted rylene is linked to the acceptor or the donor and the second optionally substituted rylene is capable of energy transfer to at least one of the first optionally substituted rylene, the acceptor or the donor. In one embodiment, the acceptor is an oligomeric unit comprising an optionally substituted rylene core linked via a linker group to one or more optionally substituted peripheral rylenes.

Any suitable coupling reaction known in the art may be used. It will be appreciated that the donor and acceptors will be substituted such that the selected coupling reaction may occur.

In one embodiment, the donor is coupled to the acceptor via nucleophilic aromatic substitution. In this embodiment, either the donor or the acceptor is substituted with a leaving group, such as halo or optionally substituted alkylsulfonyloxy, preferably chloro, bromo or triflate. The coupling partner, i.e. the donor or the acceptor, will be substituted with a nucleophilic group suitable for displacement of the leaving group. Suitable nucleophilic groups include optionally substituted aryloxy, optionally substituted heterocyclyloxy, for example optionally substituted phenol, optionally substituted pyridyloxy and so on.

As described above, in one embodiment, two or more rylenes are linked via an optionally substituted tyramine group. In one embodiment, an optionally substituted perylene is prepared by reacting tyramine with a 3,4-anhydride substituted perylene to form an optionally substituted monoimide perylene substituted by a 4-phenylethanol group at the imide position. Then reacting two equivalents of the 4-phenylethanol substituted perylene monoimide with an optionally substituted perylene halogenated at the bay positions to form an oligomeric unit, wherein the halogens are substituted to form a phenoxy linker group at the corresponding bay position of the optionally substituted perylene to the imide position of the monoimide perylene.

In one embodiment, the acceptor and the donor are coupled by formation of an ester or an amide. The ester or amide coupling may be catalysed with a coupling reagent as is known in the art, such as an acid. A reactive intermediate may be formed to assist progression of the coupling reaction, e.g. if the donor or the acceptor is substituted with a carboxylic acid moiety, an activated carboxyl group may be formed as an intermediate, for example, an acid chloride, an activated N-hydroxy succinimide (NHS) ester, a mixed anhydride or other suitable activated carboxyl as is known in the art. The activated carboxyl intermediate may be prepared using known methods.

In one embodiment, the acceptor is coupled to two or more donors simultaneously. In another embodiment, each donor is coupled sequentially. It will be appreciated that asymmetric light harvesting arrays may be prepared by sequential addition of donors.

In one embodiment, the acceptor and the donor are coupled by "click chemistry" (sometimes referred to as the Huisgen cycloaddition), i.e. the copper catalysed [3+2] cycloaddition of an alkyne with an azide (i.e. —$N_3$).

In another embodiment, the acceptor and the donor are coupled by metal mediated cross-coupling as is known in the art, for example palladium cross-coupling. For example, a donor and acceptor may be linked by a Suzuki or a Buchwald reaction. In this embodiment, it will be understood that the coupling partners will be substituted with suitable substituents to allow progression of the reaction, e.g. for a Suzuki cross coupling one coupling partner will be substituted with a boronic acid or ester (or equivalent) and the other coupling partner will be substituted with a halo substituent.

It will be appreciated that for embodiments where the acceptor is linked to the one or more donors via a linker group, that the linker group may be formed concomitantly with the coupling of the acceptor to the one or more donors. Therefore, part of the linker group may be a substituent of the acceptor or the donor.

In another embodiment, the method comprises forming the oligomeric unit in situ. For example, an optionally substituted donor rylene core is coupled with an acceptor. Then, one or more optionally substituted peripheral donor rylenes are coupled with the optionally substituted donor rylene core. In this embodiment, the linker group may be formed concomitantly with the coupling of the optionally substituted rylene core (preferably an optionally substituted perylene core) with the one or more optionally substituted peripheral donor rylenes (preferably optionally substituted peripheral donor perylenes).

In another embodiment, the method comprises forming the oligomeric unit in situ. For example, an optionally substituted donor peripheral rylene is coupled with an acceptor. Then, an optionally substituted donor rylene core (optionally linked to one or more further optionally substituted peripheral donor rylenes) is coupled with the optionally substituted peripheral donor rylene. Further optionally substituted peripheral donor rylenes may then be coupled to the optionally substituted donor rylene core. In this embodiment, the linker group may be formed concomitantly with the coupling of the optionally substituted peripheral donor rylene (preferably an optionally substituted peripheral donor perylene) with the optionally substituted rylene core (preferably an optionally substituted perylene core).

There is also provided a method for preparing an oligomeric unit, comprising coupling an optionally substituted perylene core with two or more optionally substituted donor perylenes. This coupling may include as a reaction step any of the reactions described above.

Suitable types of coupling reactions for the optionally substituted perylene and two or more optionally substituted donor perylenes are as described above for coupling the donor and acceptor of the light harvesting array. Preferably, the coupling is a reaction selected from the group consisting of neucleophilic aromatic substitution, ester formation, amide formation, Huisgen cycloaddition or a combination thereof.

In one embodiment, the two or more optionally substituted peripheral perylenes are coupled at the same time to the optionally substituted perylene core. In another embodiment, the optionally substituted perylene core is coupled to each optionally substituted peripheral donor perylene simultaneously. In further embodiments, each of the two or more optionally substituted peripheral perylenes is coupled in separate reactions. In still further embodiments, the optionally substituted perylene core is coupled to each optionally substituted peripheral donor perylene sequentially.

The linker group may be formed concomitantly with the coupling of the optionally substituted perylene core with the one or more optionally substituted peripheral donor perylenes. For example, where one coupling partner comprises a carboxyl group and the other coupling partner comprises an amino group, these two may couple to form an amido containing linker group. It will be appreciated that this linker group only forms during the coupling of the coupling partners together.

In one embodiment, there is provided a method for preparing a light harvesting array or compound of formula I as described above, comprising reacting a compound of formula A:

Formula A wherein A is an acceptor, and X' is a nucleophile or an electrophile (e.g. a leaving group);
with a compound of formula B:

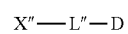

Formula B wherein D is an oligomeric unit comprising an optionally substituted donor rylene core and one or more optionally substituted peripheral donor rylenes;
L" is a pre-linker group; and
X" is a nucleophile or an electrophile (e.g. a leaving group); and wherein when X' is an electrophile, X" is a nucleophile, and when X' is a nucleophile, X" is an electrophile; and wherein following reaction of X' and X" a linker group linking A and D is formed.

In one embodiment, after the reaction, the group -L"-X'— or the group -L"-X"— is a linker group described above.

In one embodiment, there is provided a method for preparing a light harvesting array or compound of formula I as described above, comprising reacting a compound of formula C:

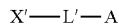

Formula C wherein A is an acceptor, and X' is a nucleophile or an electrophile (e.g. a leaving group);
with a compound of formula D:

Formula D wherein D is an oligomeric unit comprising an optionally substituted donor rylene core and one or more optionally substituted peripheral donor rylenes;
L" is a pre-linker group; and
X" is a nucleophile or an electrophile (e.g. a leaving group); and
wherein when X' is an electrophile, X" is a nucleophile, and when X' is a nucleophile, X" is an electrophile; and
wherein following reaction of X' and X" a linker group linking A and D is formed.

In one embodiment, there is provided a method for preparing a light harvesting array or compound of formula I as described above, comprising reacting a compound of formula E:

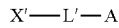

Formula E wherein A is an acceptor, L' is a first pre-linker group and X' is a nucleophile or an electrophile (e.g. a leaving group); with a compound of formula F:

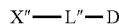

Formula F wherein D is an oligomeric unit comprising an optionally substituted donor rylene core and one or more optionally substituted peripheral donor rylenes;
L" is a second pre-linker group; and
X" is a nucleophile or an electrophile (e.g. a leaving group); and
wherein when X' is an electrophile, X" is a nucleaophile, and when X' is a nucleophile, X" is an electrophile; and
wherein following reaction of X' and X" a linker group linking A and D is formed.

In one embodiment, at least one of X' and X" is a leaving group. It will be appreciated that the leaving group will not form part of the linker group. The linker group may be any of the linker groups described above. Accordingly, in one embodiment, after reaction, the group -L'-X'-L"- is a linker group described above. In another embodiment, after reaction, the group -L-X"-L"- is a linker group described above.

In one embodiment, there is provided a method for preparing a light harvesting array or compound of formula I as described above, comprising reacting a compound of formula G:

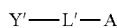

Formula G wherein A is an acceptor, L' is a first pre-linker group and Y' is an unsaturated moiety capable of participating in a cycloaddition reaction, preferably Y' is selected from an optionally substituted $C_2$alkynyl and an azide;
with a compound of formula H:

Formula H wherein D is an oligomeric unit comprising an optionally substituted donor rylene core and one or more optionally substituted peripheral donor rylenes;
L" is a second pre-linker group; and
Y" is a second unsaturated moiety capable of participating in a cycloaddition reaction with the first unsaturated moiety, preferably Y" is selected from a $C_2$alkynyl and an azide; and
wherein following reaction of Y' and Y" a linker group linking A and D is formed.

In one embodiment, Y' is an azide and Y" is an optionally substituted $C_2$alkynyl. In another embodiment, Y" is an azide and Y' is an optionally substituted $C_2$alkynyl.

In the compounds of Formula A to H, the acceptor may be any acceptor described above.

In the compounds of Formula A to H, the oligomeric unit may any oligomeric unit described above.

In the compounds of Formula A to H, the linker group may be any linker group described above.

The compound of Formula I may be any compound of Formula I described above, e.g. a compound of any one of formulas IA to IF, I-1, I-2 and I-3.

In one embodiment, there is provided a method for preparing a compound of formula III by reacting a compound of formula IIIa with a compound of formula IIIb according the following scheme:

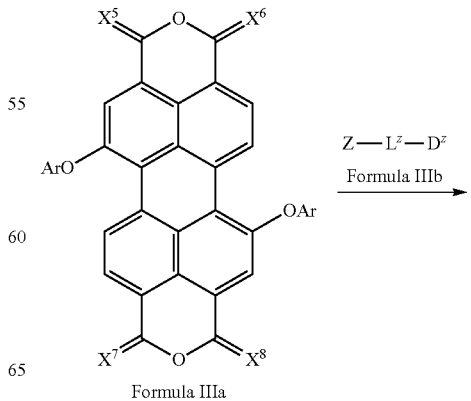

Formula IIIa

-continued

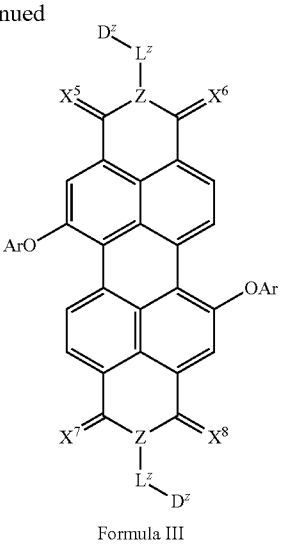

Formula III wherein:

X⁵, X⁶, X⁷ and X⁸ are selected from the group consisting of O or S;

Ar is an optionally substituted aryl;

Z is a nucleophile, preferably Z is amino;

L$^z$ is absent or a linker group selected from the linker groups described above; and D$^z$ is an optionally substituted donor perylene.

For example, a 0.1 M solution of perylene of formula IIIa and peripheral perylene of formula IIIb may be dissolved in a solvent, generally dimethylformamide, and heated to about 95° C. for at least 8 hours, typically overnight. The reaction is quenched with acid and the product may be isolated by either centrifuge or filtration, followed by purification by or in combination with, for example, chromatography (silica, alumina or size-exclusion), sohxlet extraction with an appropriate solvent or recrystallization.

In another embodiment, there is provided a method for preparing a compound of formula IV by reacting a compound of formula IVa with a compound of formula IVb according the following scheme:

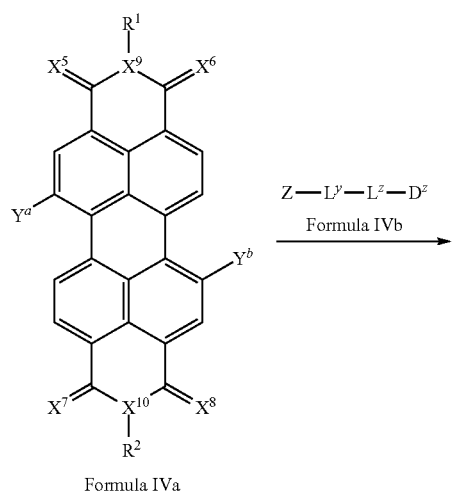

Formula IVa

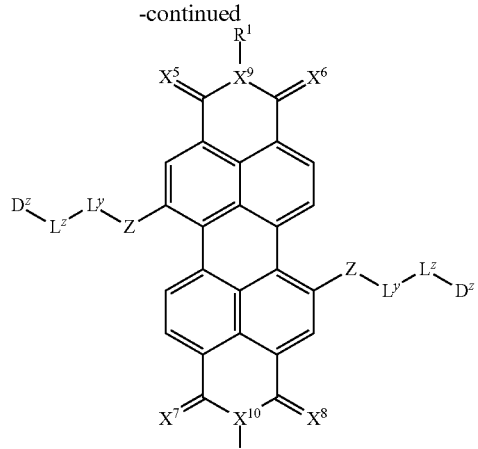

Formula IV wherein:

X⁵, X⁶, X⁷ and X⁸ are selected from the group consisting of O or S;

Y$^a$ and Y$^b$ are independently selected from the group consisting of halo and optionally substituted alkylsulfonyl, preferably independently selected from the group consisting of Br, Cl and OTf, wherein Tf is triflate (i.e. trifluoromethanesulfonate);

X⁹ and X¹⁰ are selected from the group consisting of N, S, O, CR³

R¹, R² and R³ are independently an optional substituent as defined above;

Z is a nucleophile, preferably Z is hydroxyl;

L$^y$ is absent or selected from the group selected from aryl, heterocyclyl or cycloalkyl, preferably L$^y$ is aryl or heteroaryl;

L$^z$ is absent or a linker group selected from the linker groups described above; and D$^z$ is an optionally substituted donor perylene.

For example, a 0.1 M solution of perylene of formula IVa and peripheral perylene of formula IVb may be dissolved in a solvent, generally dimethylformamide (DMF), and heated to about 95° C. for at least 8 hours, typically overnight, in the presence of a base, such as a carbonate (e.g. K₂CO₃, Na₂CO₃, CsCO₃, NaHCO₃ and so on) or a tertiary amine (e.g. triethylamine, diisopropylethylamine, and so on). The reaction is quenched with acid and the product may be isolated by techniques known in the art, such as recrystallisation, liquid-liquid extraction and so on.

In one embodiment, the compound of formula IVb is a compound of formula IVb'

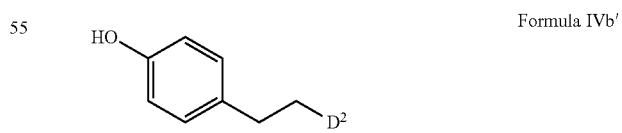

Formula IVb' wherein D$^z$ is as defined above.

Materials or Devices

The present invention provides a chromophoric material comprising a light harvesting array comprising an acceptor linked to one or more donors, wherein at least one donor is an oligomeric unit. In one embodiment, at least one donor is an oligomeric unit comprising an optionally substituted donor rylene core linked via a linker group to one or more optionally substituted peripheral donor rylenes. In one embodiment, at least one of the acceptor or the one or more donors is an oligomeric unit comprising a first optionally substituted rylene linked via a linker group to a second optionally substituted rylene, the first optionally substituted rylene is linked to the acceptor or the donor and the second optionally substituted rylene is capable of energy transfer to at least one of the first optionally substituted rylene, the acceptor or the donor. In one embodiment, the acceptor is an oligomeric unit comprising an optionally substituted rylene core linked via a linker group to one or more optionally substituted peripheral rylenes. In one embodiment, the chromophoric material is a luminescent material, preferably a fluorescent material or a phosphorescent material.

The chromophoric material may additionally comprise a substrate. The substrate may comprise a dielectric material. The dielectric material may comprise a polymer, glass, or quartz. In one embodiment, the polymer comprises acrylate or polycarbonate. In one embodiment, the polymer is polymethyl methacrylate or polycarbonate. In one embodiment, the polymer is polymethyl methacrylate.

In one embodiment, the chromophoric material comprises the light harvesting array described above and a polymer, preferably the light harvesting array is dispersed in a matrix of the polymer. In one embodiment, the light harvesting array is evenly dispersed in the polymer. In another embodiment, the light harvesting array is not evenly dispersed in the polymer, for example, the concentration of light harvesting array may taper through the polymer or may form localised regions of higher relative concentration relative to other regions of polymer which may contain a lower relative concentration of light harvesting array or no detectable amount of light harvesting array. In another embodiment, the chromophoric material may comprise a coating of light harvesting array on a polymer substrate.

In the chromophoric material, the polymer may comprise: an acrylic, a urethane; an ester; a methacrylate; a thiophene; a co-polymer of any bond conjugated polymer; a light transparent polymer; a low ultra violet absorbent polymer; a heat conducting polymer; or an electrically conducting polymer. In another embodiment, the polymer may be: aniline based; pyrrole based; acetylene based; or furan based.

In another embodiment, the polymer may comprise polyurethane, polyester, polyamide, polyurea, polycarbonate and polymethyl methacrylate. The constituent monomers in the polymers of the present disclosure may be methacrylate-based, carbonate-based, acrylamide-based, methacrylamide-based, or styrene-based monomers.

Constituent monomers of the vinyl polymers that may be used include acrylic esters, specifically, e.g., methyl acrylate, ethyl acrylate, n-propyl acrylate, isopropyl acrylate, n-butyl acrylate, isobutyl acrylate, sec-butyl acrylate, tert-butyl acrylate, amyl acrylate, hexyl acrylate, 2-ethylhexyl acrylate, octyl acrylate, tert-octyl acrylate, 2-chloroethyl acrylate, 2-bromoethyl acrylate, 4-chlorobutyl acrylate, cyanoethyl acrylate, 2-acetoxyethyl acrylate, dimethylaminoethyl acrylate, benzyl acrylate, methoxybenzyl acrylate, 2-chlorocyclohexyl acrylate, cyclohexyl acrylate, furfuryl acrylate, tetrahydrofurfuryl acrylate, phenyl acrylate, 5-hydroxypentyl acrylate, 2-methoxyethyl acrylate, 3-methoxybutyl acrylate, 2-ethoxybutyl acrylate, 2-ethoxyethyl acrylate, 2-isopropoxy acrylate, 2-butoxyethyl acrylate, 2-(2-methoxyethoxy)ethyl acrylate, 2-(2-methoxyethoxy)ethyl acrylate, 2-(2-butoxyethoxy) ethyl acrylate, ω-methoxypolyethylene glycol acrylate (addition mol number: 9), 1-bromo-2-methoxyethyl acrylate, and 1,1-dichloro-2-ethoxyethyl acrylate.

In addition, the following monomers can be used. Methacrylic esters, specifically, e.g., methyl methacrylate, ethyl methacrylate, n-propyl methacrylate, isopropyl methacrylate, n-butyl methacrylate, isobutyl methacrylate, sec-butylmethacrylate, tert-butylmethacrylate, amylmethacrylate, hexylmethacrylate, cyclohexylmethacrylate, benzyl methacrylate, chlorobenzyl methacrylate, octyl methacrylate, stearylmethacrylate, sulfopropylmethacrylate, N-ethyl-N-phenylaminoethyl methacrylate, 2-(3-phenylpropyloxy) ethyl methacrylate, dimethylaminophenoxyethyl methacrylate, furfuryl methacrylate, tetrahydrofurfuryl methacrylate, phenyl methacrylate, cresyl methacrylate, naphthyl methacrylate, 2-hydroxyethyl methacrylate, 4-hydroxybutyl methacrylate, triethylene glycol monomethacrylate, dipropylene glycol monomethacrylate, 2-methoxyethyl methacrylate, 3-methoxybutyl methacrylate, 2-acetoxyethyl methacrylate, 2-acetoacetoxyethyl methacrylate, 2-ethoxyethyl methacrylate, 2-isopropoxyethyl methacrylate, 2-butoxyethyl methacrylate, 2-(2-methoxyethoxy)ethyl methacrylate, 2-(2-ethoxyethoxy)ethyl methacrylate, 2-(2-butoxyethoxy)ethyl methacrylate, ω-methoxypolyethylene glycol methacrylate (addition mol number: 6), acryl methacrylate, and methacrylic acid dimethylaminoethylmethyl chloride salt can be exemplified.

Vinylesters, specifically, e.g., vinylacetate, vinyl propionate, vinyl butyrate, vinyl isobutyrate, vinyl caproate, vinyl chloroacetate, vinylmethoxy acetate, vinylphenyl acetate, vinyl benzoate and vinyl salicylate can be exemplified.

Acrylamides, e.g., acrylamide, methylacrylamide, ethylacrylamide, propylacrylamide, isopropylacrylamide, n-butylacrylamide, sec-butylacrylamide, tert-butylacrylamide, cyclohexylacrylamide, benzylacrylamide, hydroxymethylacrylamide, methoxyethylacrylamide, dimethylaminoethylacrylamide, phenylacrylamide, dimethylacrylamide, diethylacrylamide, β-cyanoethylacrylamide, N-(2-acetoacetoxyethyl)acrylamide, and diacetoneacrylamide can be exemplified.

Methacrylamides, e.g., methacrylamide, methylmethacrylamide, ethylmethacrylamide, propylmethacrylamide, isopropylmethacrylamide, n-butylmethacrylamide, sec-butylmethacrylamide, tert-butyl methacrylamide, cyclohexylmethacrylamide, benzylmethacrylamide, hydroxymethacrylamide, chlorobenzylmethacrylamide, octylmethacrylamide, stearylmethacrylamide, sulfopropylmethacrylamide, N-ethyl-N-phenylaminoethylmethacrylamide, 2-(3-phenylpropyloxy)ethylmethacrylamide, dimethylaminophenoxyethylmethacrylamide, furfurylmethacrylamide, tetrahydrofurfurylmethacrylamide, phenylmethacrylamide, cresylmethacrylamide, naphthylmethacrylamide, 2-hydroxyethyl methacrylamide, 4-hydroxybutylmethacrylamide, triethylene glycol monomethacrylamide, dipropylene glycol monomethacrylamide, 2-methoxyethylmethacrylamide, 3-methoxybutylmethacrylamide, 2-acetoxyethylmethacrylamide, 2-acetoacetoxyethylmethacrylamide, 2-ethoxyethylmethacrylamide, 2-isopropoxyethylmethacrylamide, 2-butoxyethylmethacrylamide, 2-(2-methoxyethoxy) ethylmethacrylamide, 2-(2-ethoxyethoxy) ethylmethacrylamide, 2-(2-butoxyethoxy) ethylmethacrylamide, ω-methoxypolyethylene glycol methacrylamide (addition mol number: 6), acrylmethacrylamide, dimethylaminomethacrylamide, diethylaminomethacrylamide, B-cyanoethylmethacrylamide, and N-(2-acetoacetoxyethyl)methacrylamide can be exemplified.

Olefins, e.g., dicyclopentadiene, ethylene, propylene, 1-butene, 1-pentene, vinyl chloride, vinylidene chloride, isoprene, chloroprene, butadiene, and 2,3-dimethylbutadiene can be exemplified.

Styrenes, e.g., styrene, methylstyrene, dimethylstyrene, trimethylstyrene, ethylstyrene, isopropylstyrene, chloromethylstyrene, methoxystyrene, acetoxystyrene, chlorostyrene, dichlorostyrene, bromostyrene, and vinylbenzoic acid methyl ester can be exemplified.

Vinyl ethers, e.g., methylvinyl ether, butylvinyl ether, hexylvinyl ether, methoxyethylvinyl ether and dimethylaminoethylvinyl ether can be exemplified.

As other examples, e.g., butyl crotonate, hexyl crotonate, dibutyl itaconate, dimethyl maleate, dibutyl maleate, dimethyl fumarate, dibutyl fumarate, methyl vinyl ketone, phenyl vinyl ketone, methoxyethyl vinyl ketone, glycidyl acrylate, glycidyl methacrylate, N-vinyloxazolidone, N-vinylpyrrolidone, acrylonitrile, methacrylonitrile, methylene moronnitrile, and vinylidene can be exemplified.

Two or more monomers may be used as co-monomers with each other according to purposes (e.g., improvement of hardness, flexibility, tensile strength and light fastness), thereby producing co-polymers.

In another embodiment, the chromophoric material may comprise a light harvesting array as described above and one or more additional dyes. The one or more additional dyes may be a chromophoric dye. The dyes may be of any type described above or any type of dye that is currently used in the industry, which may or may not luminescent, and which may act to shift the transmittance spectrum of the total dye mixture, to a desired perceived colour, without having any absorbance capability in the range of the final acceptor fluorescence to avoid interfering with the light harvesting and emission of the array. For example, the one or more additional dyes may be selected from an optionally substituted rylene (e.g. an optionally substituted perylene or an optionally substituted terylene), an optionally substituted porphyrin or an optionally substituted benzocoronene. In one embodiment, the one or more additional dyes may be any dye that may be used as a sensitizer in a photovoltaic cell, such as transition metal (e.g. ruthenium) complexes or a metal-free organic dye, such as cyanine, oxazine, thiazine, acridine, naphthalene diimide, and the like.

Embodiments of the light harvesting array described above comprising an acceptor that emits photons outside the visible range may advantageously be transparent to the human eye. Accordingly, in one embodiment, the chromophoric material comprises a light harvesting array comprising an acceptor that emits light outside the visible range. This chromophoric material may further comprise a substrate. The substrate may be any of the substrates described above. Preferably, this chromophoric material will be transparent or translucent, more preferably transparent.

It will be appreciated that the light harvesting array may be present in the chromophoric material at a concentration sufficient to harvest and emit light. In one embodiment, the chromophoric material comprises the light harvesting array in an amount of less than about 1 wt % of the total mass of the material, preferably the light harvesting array is present in an amount of about 0.001 wt % to about 0.2 wt %, preferably about 0.01 wt % to about 0.1 wt %, of the material.

It will also be appreciated that the light harvesting array may be present in the chromophoric material at a concentration insufficient to disrupt or prevent energy collection (e.g. absorbance), transfer or luminescence by the light harvesting array described herein or a compound of Formula (I) described herein in the chromophoric material, for example, by forming aggregates of two or more molecules of the light harvesting array or compound of Formula (I). In one embodiment, the light harvesting array does not form aggregates when dispersed in a chromophoric material. In another embodiment, the light harvesting array forms aggregates of less than twice the molecular mass of the light harvesting array, preferably less than about 110% of the molecular mass of the light harvesting array, more preferably of no more than the molecular mass of the light harvesting array. Average particle mass may be determined by techniques known in the art.

In one embodiment, the light harvesting array is present in the chromophoric material at a concentration sufficient to harvest and emit light and insufficient to disrupt or prevent energy collection, transfer or luminescence by the light harvesting array in the chromophoric material.

The methods of adding and mixing the components with a polymer are not restricted. For example, methods of thoroughly mixing the powders, flakes or pellets of translucent polymers with the above components and then melt-mixing by an extruder may be used. In translucent thermoplastic polymers, methods of adding the above components to unhardened liquid state starting materials and thoroughly mixing and dispersing may be used. At this time, generally used additives, e.g., a thermal stabiliser, an antioxidant, a mould releasing agent, an antistatic agent, and a flame retarder may be added. Moulding may be performed according to ordinary methods. That is, in the case of thermoplastic polymers, covered pipes can be produced by a melt-extrusion method, shrink tubes can be produced by stretching and quenching of the pipes obtained by melt-extrusion, and covers can be produced by injection moulding, extrusion moulding and, if necessary, vacuum moulding. In the case of thermo-setting polymers, cast moulding is advantageous.

The present invention also provides a device comprising the chromophoric material described above. In one embodiment, the chromophoric material is a luminescent material, preferably a fluorescent material or a phosphorescent material.

In one embodiment, the device is selected from a light guide, a photobioreactor, a photoluminescent algae system, a luminescent/fluorescent solar concentrator, a photodetector and a photovoltaic device.

Examples of light guides able to incorporate the luminescent material described above have been described in Australian patent application nos. 2011218633 and 2011211390, which are incorporated herein entirely by reference. These applications also describe the use of light guides in photoluminescent algae systems. The light guides may also be used as Fluorescence probes and labels useful as tools for clinical diagnostics, high-throughput screening, and other biomedical applications, such as, for example, an endoscopic light source.

The light harvesting arrays may be capable of harvesting light in one region of the usable spectrum of solar radiation and channelling the absorbed energy into the optimal wavelengths for photosynthesis. By incorporating such light harvesting arrays into a device, such as a photoluminescent algae system, the efficiency of a photosynthetic system may be improved, for example, by increasing the growth rate of the organism.

Figure 8:
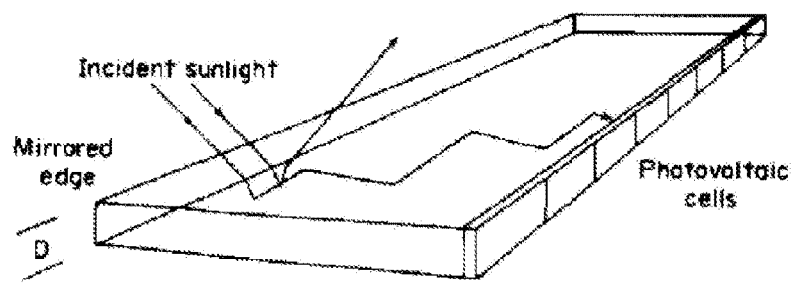
FIG. 8 is a schematic of a Luminescent Solar Concentrator (LSC) which may incorporate a chromophoric material comprising a light harvesting array of the first, third or fourth aspects or compound of the second or fifth aspects.

A luminescent solar concentrator ("LSC") (also known as a luminescent solar collector, or fluorescent solar concentrator) functions in the following manner. Incident sunlight upon a transparent (for certain wavelengths) material of a high refractive index is retained within the plane of the material by internal reflection. In conjunction with this a dye, often impregnated within the LSC material or as a thin film coating, absorbs part of that light, and fluoresces it at a longer wavelength, lower energy. This emitted light is also confined within the plane of the LSC material. Finally, the internally reflected light is directed outwards from the edges of the LSC material. Typically, LSCs direct the internally reflected light to one or more photovoltaic cells, as depicted in FIG. 8.

One method used to improve existing photovoltaic technologies is through the use of luminescent solar concentrators. These firstly aim to improve the ratio between the areas of light collection and photovoltaic material used. Secondly they can also be tuned to particular wavelengths so as to absorb higher wavelength energies followed by emission at lower energy wavelengths. These fluoresced wavelengths are better absorbed by the photovoltaic material, and hence improve the efficiency per photon. Luminescent solar concentrators however still possess a number of hurdles to be overcome before they can effectively contribute to current solar technologies. These hurdles include: low dye quantum yield, reabsorption losses and low dye photo-stability.

In one embodiment, the device is an LSC. Advantageously, the incorporation of a light harvesting array described above into an LSC may overcome the hurdles associated with LSC use. At least preferred embodiments of the light harvesting arrays possess a high quantum yield, are extremely photostable and have a wide range of absorptions and emissions enabling a high degree of flexibility with respect to fine tuning absorption and emission profiles depending on their desired end use. Also, through using oligomeric units such as a trimer and pentamer as described above, the ratio of donor rylenes to acceptors is significantly increased while maintaining short distances between the acceptor and donor moieties. Consequently, in at least these preferred embodiments, this approach significantly reduces reabsorption loss by strongly reducing the amount of final acceptors and maximises the efficiency of FRET by decreasing the distance between donors and acceptor.

In one embodiment, the device is a photodetector. Advantageously, the incorporation of a light harvesting array described above into a photodetector may enhance the sensitivity of the photodetector as a greater amount of light from across the spectrum may be harvested by the light harvesting array relative to conventional dyes.

Accordingly, in one aspect, there is provided a use of a light harvesting array described above or compound described above as a light harvesting dye. In one embodiment, the light harvesting array or compound is used as a photosensitiser in a photovoltaic cell. In another embodiment, the light harvesting array or compound is used in a device selected from a light guide, a photobioreactor, a photoluminescent algae system, a luminescent/fluorescent solar concentrator, a photodetector and a photovoltaic device.

In one aspect, there is provided a method for selecting an optionally substituted rylene for incorporation into a light harvesting array as described above or a compound as described above. The method comprising comparing a UV-vis spectrum for the optionally substituted rylene with UV-visible spectra for two or more further optionally substituted rylenes, and selecting the optionally substituted rylene such that its UV-vis spectrum contains at least one of:
a fluorescence emission maxima of a wavelength at least partially overlapping an absorption maxima of at least one of the two or more further optionally substituted rylenes; and
an absorption maxima of a wavelength at least partially overlapping a fluorescence emission maxima of at least one of the two or more further optionally substituted rylenes.

As described above, in order to achieve efficient FRET, the FRET donor fluorescence emission maxima should overlap with the absorption maxima of the FRET acceptor; the better the overlap, the more efficient the FRET. Poorly overlapping absorption and emission maxima result in "leaky" FRET and a loss of efficiency due to, for example, some energy absorbed by the donor being partially emitted as donor fluorescence which may then be subject to large reabsorption losses. Therefore, the ability to "tune" the absorbance/emission profile of the donor and/or the acceptor may increase the overlap of the donor emission maxima with the acceptor absorption maxima which may increase the FRET efficiency. Advantageously, as described above the absorption/emission profile of an optionally substituted rylene may be "tuned" in order to match the absorption/emission profiles of a FRET pair to increase FRET efficiency.

In one embodiment, the method further comprises incorporating the selected optionally substituted rylene into a light harvesting array described above or into a compound of Formula I (e.g. a compound of any one of formulas IA to IF).

The invention will be further described, by way of example only, in the following examples. It will be appreciated that variations may be made to any of the embodiments exemplified as would be known to a person skilled in the art.

EXAMPLES

Example 1—In Silico Modeling of Light Harvesting Arrays

Two components of a basic perylene-based donor and acceptor system are diester perylene monoimide as an energy donor, and tetraphenoxy diimide as an energy acceptor. The diester perylene monoimide donor possesses an absorption maxima at 506 nm (log(ε)=4.6) and emission maxima at 526 nm. The tetraphenoxy perylene diimide acceptor with an absorption maxima at 578 nm (Log(ε)=4.7) and emission at 607 nm.

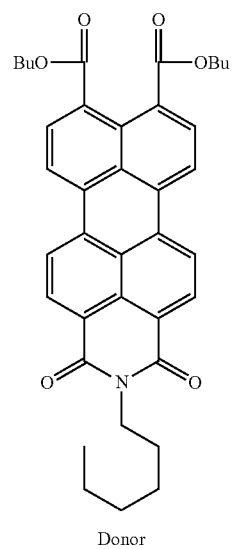

Donor

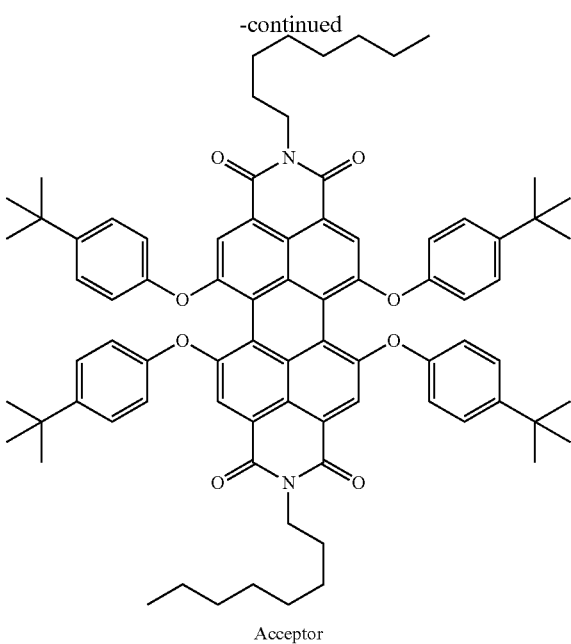

Acceptor

Figure 3:
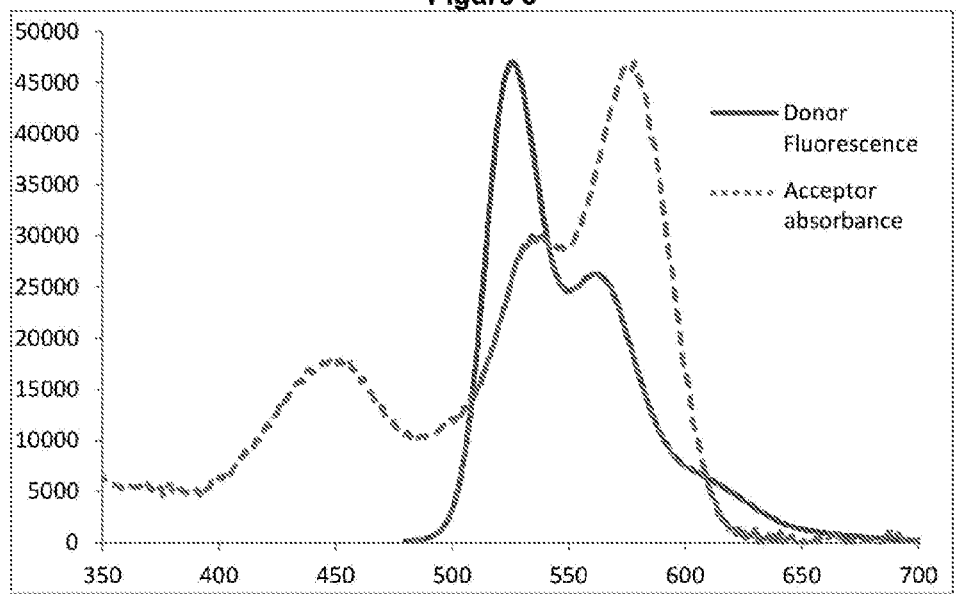
FIG. 3 is spectra showing the overlap region of the donor fluorescence and the acceptor absorbance for a diester perylene monoimide and tetraphenoxy diimide.

These two substituted perylenes possess overlapping fluorescence and absorbance profiles, leading to a large overlap region indicating a potentially very good FRET pair. The absorption of tetraphenoxy diimide and emission of diester perylene monoimide and their overlap region is illustrated in FIG. 3.

FRET can be understood via quantum electrodynamics, however a simple approximation is described by equation 1.

$$R_o = \sqrt[6]{8.79 \times 10^{-5}\left(\frac{k^2 Q_o}{n^4}\right) J(\lambda)} \quad \text{Equation 1}$$

wherein
- $R_o$ is the Førster Radius (the point at which the rate of decay by FRET processes is equal to the rate of energy loss through other radiative and non radiative means).
- $k^2$ is the average orientation factor of the dipole moments of the interacting donor and acceptor. For random molecular motion (generally assumed to be the case) this is equal to ⅔. However in cases where the dipole moments of the donor and acceptor are orthogonal, precluding energy transfer, other normally minor interactions between the quadrupolar moments of the donor and acceptor systems can become the predominant mode of energy transfer, sometimes in quite high efficiency.[2]
- $Q_o$ is the quantum efficiency of the donor in the absence of the acceptor.
- n is the refractive index of the medium to the $4^{th}$ power.
- $J(\lambda)$ is the overlap integral and is a measure of the degree that the fluorescence of the donor overlaps with the absorbance of the acceptor.

Equation 1 is a function of both the extinction coefficient of the acceptor and the normalised fluorescence of the donor and photon wavelength which may be described by equation 2.

$$J(\lambda) = \int \varepsilon_a(\lambda) \times F_d(\lambda) \times \lambda^4 d\lambda \quad \text{Equation 2}$$

$\varepsilon_a(\lambda)$ is the extinction coefficient of the acceptor at $\lambda$.

$F_d(\lambda)$ is the fluorescence of the donor at $\lambda$ normalised to an area of 1.

$\lambda$ is the wavelength in nm

Given the $4^{th}$ power to which the wavelength (in nm) is raised, the overlap integral can be quite large, generally of the order of $10^{12}$ to $10^{17}$.

The efficiency of FRET with respect to distance, may be described by equation 3.

$$E = \frac{R_o^6}{R_o^6 + R^6} \quad \text{Equation 3}$$

Where E is the efficiency of FRET,
$R_o$ is the Førster radius, and
R is the actual donor-acceptor distance through space.

The relationship described by equations 1, 2 and 3 gives the FRET efficiency response as a function of the distance between acceptor and donor in terms of $R_o$. For a model FRET pair this relationship is shown graphically in FIG. 2.

FIG. 2 shows the efficiency of energy transfer from the overlap region of the fluorescence spectrum of the donor and the absorbance of the acceptor. The efficiency is inversely proportional to the sixth power of the distance between the donor and acceptor. As such there is a rapid decay in FRET efficiency past 0.8 Førster radii.

As can be seen from these calculations, a donor and acceptor pair separated by 60 of the Førster radius corresponds to an energy transfer efficiency of 95%. Increasing that distance to 70% only decreases the fret efficiency to 89%. However past this there is a rapid decrease in fret efficiency. Through using this understanding of the relationship between energy transfer and the physical distances between donors and acceptors we can identify how many oligomeric units we can include, before the energy transfer from the donor to acceptor becomes inefficient.

Equations 1, 2 and 3 approximating Førster distances for FRET pairs, approximates a Førster radius of 56.3 Å. Comparing this theoretical Førster distance to a simple model optimised by UFF, reasonable donor-acceptor distances can be suggested for a final oligomeric dye.

Basic level modelling (UFF) given a linear array with a simple and reasonable linking system suggests approximately a 22.6 Å distance between each oligomeric unit. This is approximately 0.42 of the theoretical $R_o$ value, corresponding to a FRET efficiency of 99.6%. If we assume that there is no significant difference in distance from the donors to the acceptor within each individual trimeric and pentameric unit, we can treat the FRET between the trimeric and pentameric oligomers and the acceptor in the same manner as a monomeric array. With this information we can place diester monoimide donors (monomeric, trimeric and pentameric) at regular intervals to look at how efficiently the FRET proceeds corresponding to $1^{st}$ to $4^{th}$ generation oligomers. Given a spacing of 22.6 Å between donors, a linear chain of the form A-D-D-D will drop off in efficiency as illustrated in FIG. 4.

From the graph shown in FIG. 4 the efficiency of each of the perylenes is depicted. Each system shows a significant decrease in efficiency of the perylenes as they are removed further from the acceptor core. The most significant drop occurs between the $2^{nd}$ and $3^{rd}$ generation of oligomers. This illustrates that after a 2:1 linear monomer (the $2^{nd}$ generation, DD-A) there does not appear to be a significant improvement gained through extending a linear monomeric system, but that can be overcome if the oligomeric array is made up of trimers or pentamer units in a manner that the additional donors are incorporated orthogonally to the linking method.

Additionally, in order to improve donor to acceptor distances, the use of trimeric or pentameric units within the oligomeric array improves losses due to reabsorption by decreasing the absorption and fluorescence overlap region of an oligomeric dye. This is best exampled through a linear addition of the individual chromophores. In this case a D-A-D array will be used as it most effectively describes the proposed final system, and given the distances involved (less than Førster radius of 53 Å) the best case assumption of 100% FRET is made.

TABLE 3

| Oligomeric unit | Donor chromophores | $1^{st}$ degree (D-A-D) array overlap (%), ratio (D:A) | $2^{nd}$ degree (DD-A-DD) array overlap (%), ratio (D:A) |
|---|---|---|---|
| Core (tetraphen) | 0 | 27% (0:1) | n/a |
| Monomer (bisphendiimide) | 1 | 13% (2:1) | 9% (4:1) |
| Trimer | 3 | 7% (6:1) | 5% (12:1) |
| Pentamer | 5 | 5% (10:1) | 4% (20:1) |

As can be seen from Table 3, the use of either monomeric, trimeric or pentameric units significantly increase the local density of chromophores, which acts to both maximise FRET processes and minimise reabsorption. The chosen donor for this example is close in energy to the acceptor and therefore has a tailing absorbance band that will overlap slightly with the acceptor fluorescence. It is expected that a higher energy donor would achieve a greater reduction in overlap. In the next section a more precise description of the target system will be made that exploits oligomeric arrays of trimer and tetramer units.

Example 2—Synthesis

Monomer Preparation

Preparation of a Tetraester Perylene from a Dianhydrido Perylene

Dianhydridoperylene (25 mmol) was suspended in butanol (44 mL, 480 mmol) and tetrabutylammonium hydroxide (50-60%, 31 mL, 65 mmol) and stirred until all dissolved. To this was then added bromobutane (40 mL, 370 mmol) and $K_2CO_3$ (10 g, 70 mmol) and the reaction placed in an oil bath at 120° C. After 3 hours the reaction was poured onto chloroform (200 mL), washed with water (3×100 mL), sat. $NaHCO_3$ (2×100 mL), and water once more (100 mL). The solvent was removed and the oily residue taken up in hexane with precipitation induced by trituration in the presence of a small amount of ethylacetate. The precipitate was then purified by column chromatography and/or recrystallization.

The compounds of Table 4 may be prepared according to this method. The yield shown in this table is representative of the yield obtained when that compound is produced by this method.

TABLE 4

| Compound No. | Short Name | Structure | Yield | Characterisation |
|---|---|---|---|---|
| 100 | Tetrabutylester perylene | (structure) | 97% | $^1$H NMR (300 MHz CDCl$_3$, ppm (integration, splitting, J(Hz), assignment)): 8.26 (4H, d, 8.0 Hz, perylene-H$_{ar}$), 8.02 (4H, d, 8.0 Hz, perylene-H$_{ar}$), 4.35 (8H, t, 6.8 Hz, COO—[CH$_2$]—CH$_2$), 1.78 (8H, quin, 7.2 Hz, COOCH$_2$—[CH$_2$]—CH$_2$), 1.48 (8H, sext, 7.5 Hz, COOCH$_2$CH$_2$—[CH$_2$]—CH$_3$), 0.99 (12H, t, 7.4 Hz, COOCH$_2$CH$_2$CH$_2$—[CH$_3$]). |
| 101 | Dibromo tetra(butylester) perylene | (structure, regioisomers) | 90% | $^1$H NMR (300 MHz, CDCl$_3$, ppm (integration, splitting, J(Hz), assignment)): 8.98 (2H, d, perylene-H$_{ar}$ (1,6 isomer), 7.9 Hz), 8.95 (2H, d, perylene-H$_{ar}$ (1,7 isomer), 7.9 Hz), 8.31 (2H, s, perylene-H$_{ar}$ (1,6 isomer)), 8.29 (2H, s, perylene-H$_{ar}$ (1,7 isomer)), 8.14-8.06 (2H, d, perylene-H$_{ar}$ (1,6 and 1,7 isomers)), 4.34 (8H, m, COO—[CH$_2$]—CH$_2$ (1,6 and 1,7 isomers)), 1.78 (8H, m, OCH$_2$—[CH$_2$]—CH$_2$ (1,6 and 1,7 isomers)), 1.49 (8H, m, CH$_2$—[CH$_2$]—CH$_3$ (1,6 and 1,7 isomers)), 1.00 (12H, m, CH$_2$—[CH$_3$] (1,6 and 1,7 isomers)). |

TABLE 4-continued

| Compound No. | Short Name | Structure | Yield | Characterisation |
|---|---|---|---|---|
| 102 | Di(p-tBu-phenoxy) tetra(butylester) perylene | 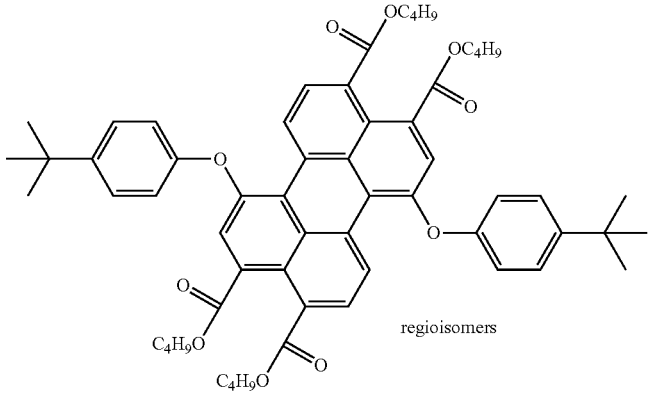 regioisomers | 83% | $^1$H NMR (300 MHz, CDCl$_3$, ppm (integration, splitting, J(Hz), assignment)): 9.09 (2H, d, 8.2 Hz, perylene-H), 7.98 (2H. d, 8.2 Hz, perylene-H$_{ar}$), 7.74 (2H, s, perylene-H$_{ar}$), 7.39 (4H, d, 8.9 Hz, p-tBu-phenoxy-H$_{ar}$), 7.02 (4H, d, 8.9 Hz, p-tBu-phenoxy-H$_{ar}$), 4.29 (4H, t, 6.8 Hz, COO—[CH$_2$]—CH$_2$), 4.23 (4H, t, 6.8 Hz, COO—[CH$_2$]'—CH$_2$), 1.74 (4H, quin, 7.2 Hz, COOCH$_2$—[CH$_2$]—CH$_2$), 1.67 (4H, quin, 7.1 Hz, COOCH$_2$—[CH$_2$]'—CH$_2$), 1.46 (4H, sext, 7.5 Hz, COOCH$_2$CH$_2$—[CH$_2$]—CH$_3$), 1.35 (4H, sext, 7.5 Hz, COOCH$_2$CH$_2$_[CH$_2$]'—CH$_3$), 1.34 (18H, s, [p-tBu]-phenoxy), 0.97 (6H, t, 7.4 Hz, CH$_2$—[CH$_3$]), 0.90 (6H, t, 7.4 Hz, CH$_2$—[CH$_3$]'). |

Preparation of a Monoanhydrido Perylene Via Acid Catalysed Ester Clevage

Tetraester perylene (1.5 mmol) with p-toluene sulfonic acid hydrate (290 mg, 1.5 mmol) was combined in toluene (5 ml) in a well stirred sealed flask. This was then heated to 120° C. under nitrogen until the precipitate had completely formed and the reaction solution was mostly colourless. The reaction material was then poured on to hexane, filtered to remove the precipitate, and extracted with a methanol and 2% (vol) aqueous potassium hydroxide (2M). The methanolic extract was then acidified with aqueous hydrochloric acid and heated until the solution became clear. The precipitate was then filtered off purified by column chromatography and/or recrystallization to yield the dibromomonoanhydride perylene.

The compounds of Table 5 may be prepared according to this method. The yield shown in this table is representative of the yield obtained when that compound is produced by this method.

TABLE 5

| Compound No. | Short Name | Structure | Yield | Characterisation |
|---|---|---|---|---|
| 103 | Monoanhydride di(butylester) perylene | 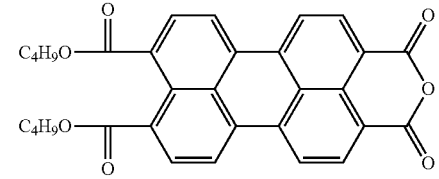 | 91% | $^1$H NMR (300 MHz CDCl$_3$, ppm (integration, splitting, J(Hz), assignment)): 8.66 (2H, d, 8.1 Hz, perylene-H$_{ar}$), 8.54 (2H, d, 8.0 Hz, perylene-Har), 8.52 (2H, d, 8.1 Hz, perylene-Har), 8.14 (2H, d, 8.0 Hz, perylene-Har), 4.36 (4H, t, 6.8 Hz, COO—[CH2]—CH2), 1.80 (4H, quin, 7.2 Hz, COOCH2—[CH2]—CH2), 1.50 (4H, sext, 7.5 Hz, COOCH2CH2—[CH2]—CH3), 1.00 (6H, t, 7.4 Hz, COOCH2CH2CH2—[CH3]). |
| 104 | Dibromomonoanhydride dibutylester | 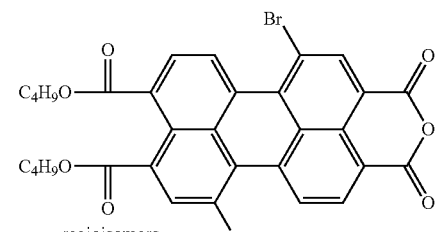 regioisomers | 60% | $^1$H NMR (300 MHz CDCl$_3$, ppm (integration, splitting, J(Hz), assignment)): 9.30 (0.6H, d, 8.1 Hz, (7,12) isomer perylene-H$_{ar}$), 9.29 (1H, d, 8.2 Hz, (1,7) isomer perylene-H$_{ar}$), 9.26 (1H, d, 8.0 Hz, (1,7) isomer perylene-H$_{ar}$), 8.91 (1H, s, (1,7) isomer perylene-H$_{ar}$), 8.70 (0.6H, d, 8.1 Hz, (7,12) isomer perylene-H$_{ar}$), 8.69 (1H, d, 8.2 Hz, (1,7) isomer perylene-H$_{ar}$), 8.38 (0.6H, |

TABLE 5-continued

| Compound No. | Short Name | Structure | Yield | Characterisation |
|---|---|---|---|---|
| | | | | s, (7,12) isomer perylene-$H_{ar}$), 8.36 (1H, s, (1,7) isomer perylene-$H_{ar}$), 8.17 (1H, d, 8.0 Hz, (1,7) isomer perylene-$H_{ar}$), 4.36 (2H, t, 6.9 Hz, (1,7) isomer COO—[CH$_2$]—CH$_2$), 4.36 (2H, t, 6.8 Hz, (1,7) isomer COO—[CH$_2$]'—CH$_2$), 4.35 (1.2H, t, 6.8 Hz, (7,12) isomer COO—[CH$_2$]—CH$_2$), 1.86-1.74 (5.2H, (1,7) and (7,12) isomers COOCH$_2$—[CH$_2$]—CH$_2$), 1.56-1.42 (5.2H, (1,7) and (7,12) isomers COOCH$_2$CH$_2$—[CH$_2$]—CH$_3$), 1.05-0.97 (7.8H, (1,7) and (7,12) isomers COOCH$_2$CH$_2$CH$_2$—[CH$_3$]). |
| 105 | MonoSwallowtail imide monoanhydride perylene | (structure with C$_6$H$_{13}$ swallowtail) | 80% | $^1$H NMR (300 MHz CDCl$_3$, ppm (integration, splitting, J(Hz), assignment)): 8.76-8.65 (8H, Perylene-$H_{ar}$), 5.18 (1H, m, N—[CH]—(CH$_2$)$_2$), 2.24 (2H, m, NCH—[CH$_2$]—CH$_2$), 1.87 (2H, m, NCH—[CH$_2$]'—CH$_2$), 1.39-1.15 (16H, Alkyl), 0.83 (6H, t, 6.7 Hz, CH$_2$—[CH$_3$]). |

Preparation of a Dibromo-Monoimido Perylene from a Primary Amine and an Anhydrido Perylene Dibromo-monoanhydrido perylene (150 μmol) was combined with a primary amine (390 μmol) in a 1% acetic acid solution in ethanol (E95, 15 mL) and refluxed until thin layer chromatography (TLC) indicated reaction completion. The reaction was then precipitated by the addition of a solution of hydrochloric acid (2M) and then the precipitate filtered off, washed with water and methanol, then subjected to purification via column chromatography and/or recrystallization to yield the imide adduct.

The compounds of Table 6 may be prepared according to this method. The yield shown in this table is representative of the yield obtained when that compound is produced by this method.

TABLE 6

| Compound No. | Short Name | Structure | Yield | Characterisation |
|---|---|---|---|---|
| 106 | Dibromo mono-propanolimide di(butylester) | (structure, regioisomers, with C$_4$H$_9$O— groups and Br) | 83% | $^1$H NMR (300 MHz, CDCl$_3$, ppm (integration, splitting, J(Hz), assignment)): 9.27 (0.2H, d, 8.1 Hz, (7,12) isomer), 9.25 (0.8H, d, 8.0 Hz, (1,7) isomer), 9.22 (0.8H, d, 8.0 Hz, (1,7) isomer), 8.88 (0.8H, s, (1,7) isomer), 8.67 (0.2H, d, 8.1 Hz, (7,12) isomer), 8.66 (0.8H, d, 8.0 Hz, (1,7) isomer), 8.52 (0.9H, s, NH from both (1,7) and (7,12) isomers), 8.37 (0.2H, s, (7,12) isomer), 8.35 (0.8H, s, (1,7) isomer), 8.15 (0.8H, d, 8.0 Hz, (1,7) isomer), 4.36 (1.6H, t, 6.9 Hz, (1,7) isomer), 4.35 (1.6H, t, 6.8 Hz, (1,7) isomer), 4.35 (0.4H, t, 6.8 Hz, (7,12) isomer), 1.86-1.74 (3.8H, m, β-CH$_2$ in butyl (1,7) and (7,12) isomers), 1.54-1.43 (3.8H, m, γ-CH$_2$ in butyl (1,7) and (7,12) isomers), 1.01 (2.4H, t, 7.4 Hz, CH$_2$—CH$_3$ |

TABLE 6-continued

| Compound No. | Short Name | Structure | Yield | Characterisation |
|---|---|---|---|---|
| | | | | (1,7) isomer), 1.00 (2.4H, t, 7.4 Hz, CH$_2$—CH$_3$' (1,7) isomer), 0.99 (0.6H, CH$_2$—CH$_3$ (7,12) isomer). |
| 107 | Dibromo mono-ethanolimide di(butylester) perylene | 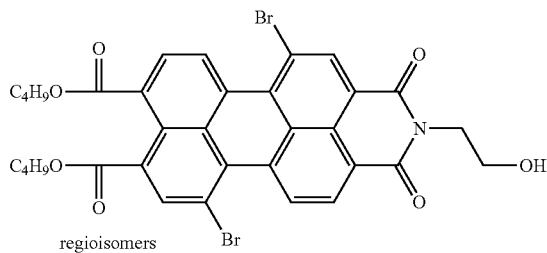 regioisomers | 42% | $^1$H NMR (300 MHz, CDCl$_3$, ppm (integration, splitting, J(Hz), assignment)): 9.26 (0.5H, d, 8.0 Hz, H$_{ar}$ 7,12-isomer), 9.24 (0.75H, d, 7.9 Hz, H$_{ar}$ 1,7-isomer), 9.21 (0.75H, d, 7.8 Hz, H$_{ar}$ 1,7-isomer), 8.88 (0.75H, s, H$_{ar}$ 1,7-isomer), 8.68 (0.5H, d, 8.1 Hz, H$_{ar}$ 7,12-isomer), 8.66 (0.75H, d, 8.1 Hz, H$_{ar}$ 1,7-isomer), 8.36 (0.5H, s, H$_{ar}$ 7,12-isomer), 8.33 (0.75H, s, H$_{ar}$ 1,7-isomer), 8.13 (0.75H, d, 8.0 Hz, H$_{ar}$ 1,7-isomer), 4.49 (2H, t, N—[CH$_2$]—CH$_2$), 4.35 (4H, m, COO—[CH$_2$]—CH$_2$), 4.01 (2H, t, 5.3 Hz, N CH$_2$—[CH$_2$]—OH), 1.86-1.73 (4H, m, OCH$_2$—[CH$_2$]—CH$_2$), 1.57-1.41 (4H, m, CH$_2$—[CH$_2$]—CH$_3$), 1.00 (6H, t, 7.4 Hz, CH$_2$—[CH$_3$]) |
| 108 | Dibromo mono-propanolimide di(butylester) perylene | 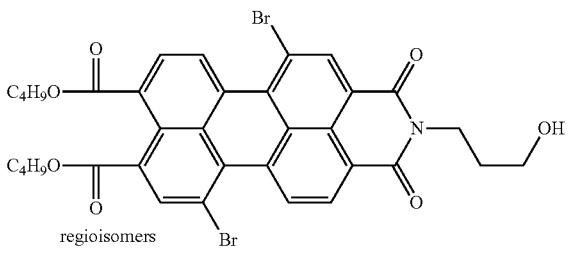 regioisomers | 98% | $^1$H NMR (300 MHz, CDCl$_3$, ppm (integration, splitting, J(Hz), assignment)): 9.27 (0.3H, d, 8.1 Hz, (7,12) isomer), 9.25 (0.6H, d, 8.1 Hz, (1,7) isomer), 9.22 (0.6H, d, 8.0 Hz, (1,7) isomer), 8.89 (0.6H, s, (1,7) isomer), 8.69 (0.3H, d, 8.1 Hz, (7,12) isomer), 8.67 (0.6H, d, 8.1 Hz, (1,7) isomer), 8.37 (0.3H, s, (7,12) isomer), 8.34 (0.6H, 1H, s, (1,7) isomer), 8.14 (0.6H, d, 8.0 Hz, (1,7) isomer), 4.44-4.30 (4.5H, m, NCH$_2$CH$_2$—[CH$_2$]—OH of (1,7) & (7,12) isomers), 3.62 (1.5H, t, 5.6 Hz, NCH2CH2—[CH2]—OH of (1,7) & (7,12) isomers), 2.04 (1.5H, m, NCH2—[CH2]—CH2OH of (1,7) & (7,12) isomers), 1.78 (3H, β-CH$_2$ butyl of (1,7) & (7,12) isomers), 1.50 (3H, γ-CH$_2$ butyl of (1,7) & (7,12) isomers), 1.01 (1.8H, t, 7.4 Hz, —CH$_3$ butyl of (1,7) isomer), 1.00 (0.9H, t, —CH$_3$ butyl of (7,12) isomer), 1.00 (1.8H, t, 7.4 Hz, —CH$_3$' butyl of (1,7) isomer). |
| 109 | Dibromo monobutyric acid imide di-(butylester) perylene | 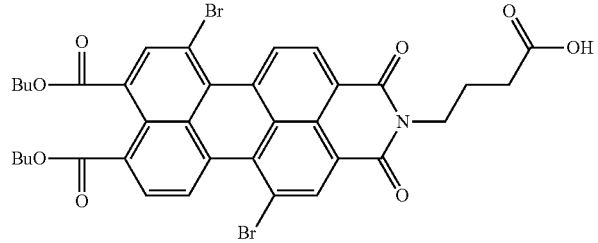 | 86% | $^1$H NMR (300 MHz, CDCl$_3$, ppm (integration, splitting, J(Hz), assignment)): 9.24 (1H, d, 8.1 Hz, perylene-H$_{ar}$), 9.21 (1H, d, 8.0 Hz, perylene-H$_{ar}$), 8.87 (1H, s, perylene-H$_{ar}$), 8.66 (1H, d, 8.1 Hz, perylene-H$_{ar}$), 8.33 (1H, s, perylene-H$_{ar}$), 8.14 (1H, d, 8.0 Hz, perylene-H$_{ar}$), 4.35 (2H, t, 6.9 Hz, COO—[CH$_2$]—CH$_2$), 4.35 (2H, t, 6.9 Hz, COO—[CH$_2$]'—CH$_2$), 4.29 (2H, t, |

TABLE 6-continued

| Compound No. | Short Name | Structure | Yield | Characterisation |
|---|---|---|---|---|
| | | | | 6.9 Hz, N—[CH$_2$]—CH$_2$), 2.50 (2H, t, 7.3 Hz, NCH$_2$CH$_2$—[CH$_2$]—COOH), 2.12 (2H, quin, 7.1 Hz, NCH$_2$—[CH$_2$]—CH$_2$COOH), 1.79 (2H, quin, 7.3 Hz, COOCH$_2$—[CH$_2$]—CH$_2$), 1.79 (2H, quin, 7.2 Hz, COOCH$_2$—[CH$_2$]'—CH$_2$), 1.50 (2H, sext, 7.5 Hz, COOCH$_2$CH$_2$—[CH$_2$]—CH$_3$), 1.49 (2H, sext, 7.4 Hz, COOCH$_2$CH$_2$—[CH$_2$]'—CH$_3$), 1.00 (3H, t, 7.4 Hz, CH$_2$—[CH$_3$]). |
| 110 | Dibromo monotyrimide dibutylester | 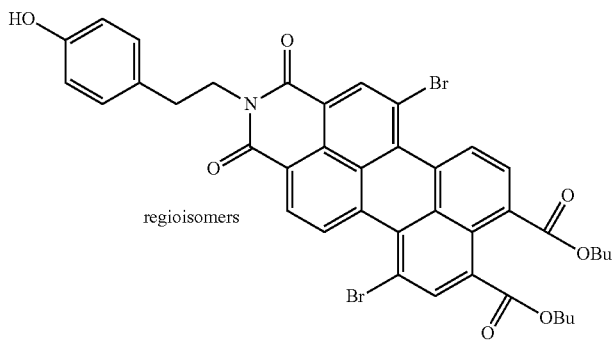 regioisomers | 85% | $^1$H NMR (300 MHz CDCl$_3$, ppm (integration, splitting, J(Hz), assignment)): 9.25 (1H, d, 8.1 Hz, perylene-H$_{ar}$), 9.22 (1H, d, 8.0 Hz, perylene-H$_{ar}$), 8.88 (1H, s, perylene-H$_{ar}$), 8.66 (1H, d, 8.1 Hz, perylene-H$_{ar}$), 8.34 (1H, s, perylene-H$_{ar}$), 8.14 (1H, d, 3.0 Hz, perylene-H$_{ar}$), 7.23 (2H, d, 8.5 Hz, Tyr-H$_{ar}$), 6.79 (2H, d, 8.5 Hz, Tyr-H$_{ar}$), 4.39 (2H, m, N—[CH$_2$]—CH$_2$Tyr), 4.36 (2H, t, 6.8 Hz, COO—[CH$_2$]—CH$_2$), 4.35 (2H, t, 6.8 Hz, COO—[CH$_2$]'—CH$_2$), 1.80 (2H, quin, 7.2 Hz, COOCH$_2$—[CH$_2$]—CH$_2$), 1.80 (2H, quin, 7.1 Hz, COOCH$_2$—[CH$_2$]'—CH$_2$), 1.50 (4H, sext, COOCH$_2$CH$_2$—[CH$_2$]—CH$_3$), 1.01 (3H, t, 7.4 Hz, COOCH$_2$CH$_2$CH$_2$—[CH$_3$]), 1.00 (3H, t, 7.4 Hz, COOCH$_2$CH$_2$CH$_2$—[CH$_3$]'). |

Preparation of a Bisphenoxy Bay Substituted Perylene from a Dibromo-Monoimido Perylene Into dimethylformamide (0.5 mL) was combined dibromo monoimide perylene (25 µmol), p-tBu-phenol (16 mg, 100 µmol) and potassium carbonate (15 mg, 110 µmol). The reaction was then placed under nitrogen and heated at 95° C. until complete by TLC. Subsequent purification by column chromatography and/or recrystallization yielded the bisphenoxy adduct.

The compounds of Table 7 may be prepared according to this method. The yield shown in this table is representative of the yield obtained when that compound is produced by this method.

TABLE 7

| Compound No. | Short Name | Structure | Yield | Characterisation |
|---|---|---|---|---|
| 111 | Di-1,7-(p-tBu-phenoxy) monopropanolimide di(butylester)perylene | 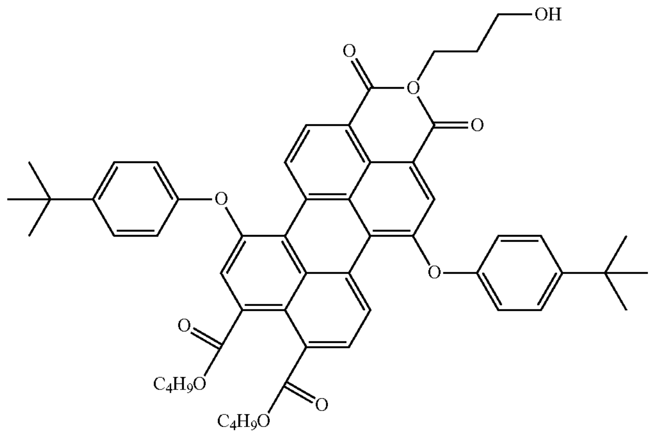 | 60% | ¹H NMR (300 MHz, CDCl₃, ppm (integration, splitting, J(Hz), assignment)): 9.37 (1H, d, 8.4 Hz, perylene-H$_{ar}$), 9.37 (1H, d, 8.2 Hz, perylene-H$_{ar}$), 8.55 (1H, d, 8.4 Hz, perylene-H$_{ar}$), 8.33 (1H, s, perylene-H$_{ar}$), 8.03 (1H, d, 8.2 Hz, perylene-H$_{ar}$), 7.44 (2H, d, 8.8 Hz, p-tBu-phenoxy-H$_{ar}$), 7.42 (2H, d, 8.8 Hz, p-tBu-phenoxy-H$_{ar}$), 7.08 (2H, d, 8.8 Hz, p-tBu-phenoxy-H$_{ar}$), 7.03 (2H, d, 8.8 Hz, p-tBu-phenoxy-H$_{ar}$), 4.32 (2H, t, 6.0 Hz, N—[CH₂]—CH₂), 4.31 (2H, t, 6.7 Hz, COO—[CH₂]—CH₂), 4.24 (2H, t, 6.7 Hz, COO—[CH₂]'—CH₂), 1.97 (2H, quin, 5.8 Hz, NCH₂—[CH₂]—CH₂), 1.76 (2H, quin, 7.2 Hz, COOCH₂—[CH₂]—CH₂), 1.67 (2H, quin, 7.6 Hz, COOCH₂—[CH₂]'—CH₂), 1.49 (2H, sext, 6.9 Hz, COOCH₂CH₂—[CH₂]—CH₃), 1.47 (2H, sext, 7.6 Hz, COOCH₂CH₂—[CH₂]'—CH₃), 1.36 (9H, s, [p-tBu]-phenoxy), 1.35 (9H, s, [p-tBu]'-phenoxy), 0.97 (3H, t, 7.3 Hz, COOCH₂CH₂CH₂—[CH₃]'), 0.90 (3H, t, 7.4 Hz, COOCH₂CH₂CH₂—[CH₃]). |
| 112 | Di-7,12-(p-tBu-phenoxy) monopropanolimide di(butylester)perylene | 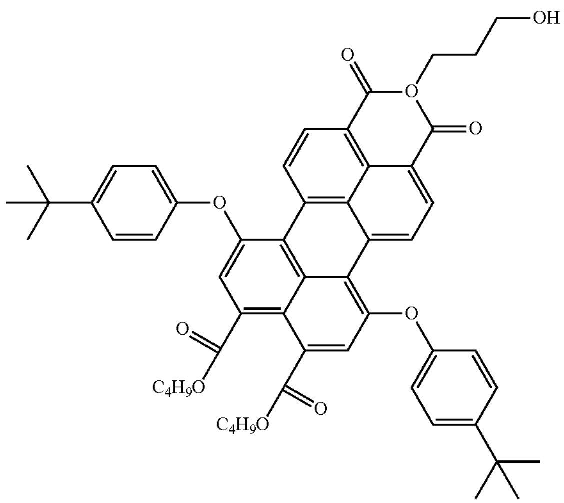 | 10% | ¹H NMR (300 MHz, CDCl₃, ppm (integration, splitting, J(Hz), assignment)): 9.36 (2H, d, 8.4 Hz, perylene-H$_{ar}$), 9.14 (2H, d, 8.4 Hz, perylene-H$_{ar}$), 7.70 (2H, s, perylene-H$_{ar}$), 7.45 (4H, d, 8.8 Hz, p-tBu-phenoxy-H$_{ar}$), 7.09 (4H, d, 8.8 Hz, p-tBu-phenoxy-H$_{ar}$), 4.37 (2H, t, 6.1 Hz, N—[CH₂]—CH₂), 4.23 (4H, t, 6.7 Hz, COO—[CH₂]—CH₂), 3.58 (2H, t, 5.5 Hz, NCH₂CH₂—[CH₂]—OH), 2.00 (2H, quin, 5.6 Hz, NCH₂CH₂—[CH₂]—OH), 2.00 (2H, quin, 5.6 Hz, NCH₂—[CH₂]—CH₂OH), 1.77-1.58 (4H, m, COOCH₂—[CH₂]—CH₂), 1.36 (18H, s, [p-tBu]-phenoxy), 1.35 (4H, sext, 7.5 Hz, COOCH₂CH₂—[CH₂]—CH₃), 0.90 (6H, t, 7.4 Hz, COOCH₂CH₂CH₂—[CH₃]). |

TABLE 7-continued

| Compound No. | Short Name | Structure | Yield | Characterisation |
|---|---|---|---|---|
| 113 | Dibromo di(propanolimide)perylene | [structure of dibromo perylene diimide with two 3-hydroxypropyl N-substituents] | 82% | $^1$H NMR (300 MHz, CDCl$_3$, ppm (integration, splitting, J(Hz), assignment)): 9.53 (2H, d, 8.2 Hz, perylene-H$_{ar}$), 8.96 (2H, s, perylene-H$_{ar}$), 8.75 (2H, d, 8.2 Hz, perylene-H$_{ar}$), 4.40 (4H, t, 6.3 Hz, N—[CH$_2$]—CH2), 3.65 (4H, m, HO—[CH$_2$]—CH$_2$), 2.03 (4H, quin, 6.2 Hz, NCH$_2$—[CH$_2$]—CH$_2$). |

Imide Formation from Anhydrido Perylene

Anhydrido perylene (0.15 mmol) was combined with primary amine (0.40 mmol) in dimethylformamide (15 ml) and heated to 110° C. under nitrogen. Once TLC indicated completion, the product was then precipitated out with acidic methanol (10 drops 2M aq. HCl in 10 ml methanol) then the precipate isolated by filtration and subjected to column chromatography on a gradient of methanol in chloroform and/or recrystallization yielding the imide perylene.

The compounds of Table 8 may be prepared according to this method. The yield shown in this table is representative of the yield obtained when that compound is produced by this method.

TABLE 8

| Compound No. | Short Name | Structure | Yield | Characterisation |
|---|---|---|---|---|
| 114 | Monotyrimide di(butylester) perylene | 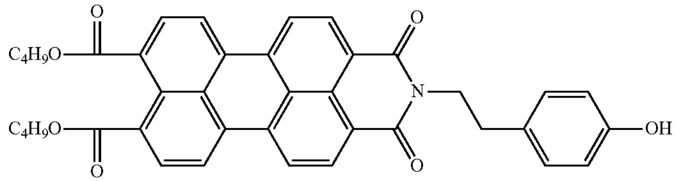 | 92% | $^1$H NMR (300 MHz, CDCl$_3$, ppm (integration, splitting, J(Hz), assignment): 8.59 (2H, d, 8.1 Hz, perylene-H$_{ar}$), 8.43 (2H, d, 8.1 Hz, perylene-H$_{ar}$), 8.41 (2H, d, 8.0 Hz, perylene-H$_{ar}$), 8.09 (2H, d, 8.0 Hz, perylene-H$_{ar}$), 7.24 (2H, d, 8.5 Hz, Tyr-H$_{ar}$), 6.79 (2H, d, 8.5 Hz, Tyr-H$_{ar}$), 4.38 (2H, m, N—[CH$_2$]—CH$_2$Tyr), 4.36 (4H, t, 6.8 Hz, COO—[CH$_2$]—CH$_2$), 2.99 (2H, m, NCH$_2$—[CH$_2$]-Tyr), 1.80 (4H, quin, 7.2 Hz, COOCH$_2$—[CH$_2$]—CH$_2$), 1.50 (4H, sext, 7.5 Hz, COOCH$_2$CH$_2$—[CH$_2$]—CH$_3$), 1.00 (6H, t, 7.4 Hz, COOCH$_2$CH$_2$CH$_2$—[CH$_3$]). |
| 115 | di(p-tBu-phenoxy) monotyrimide di(butylester) perylene | 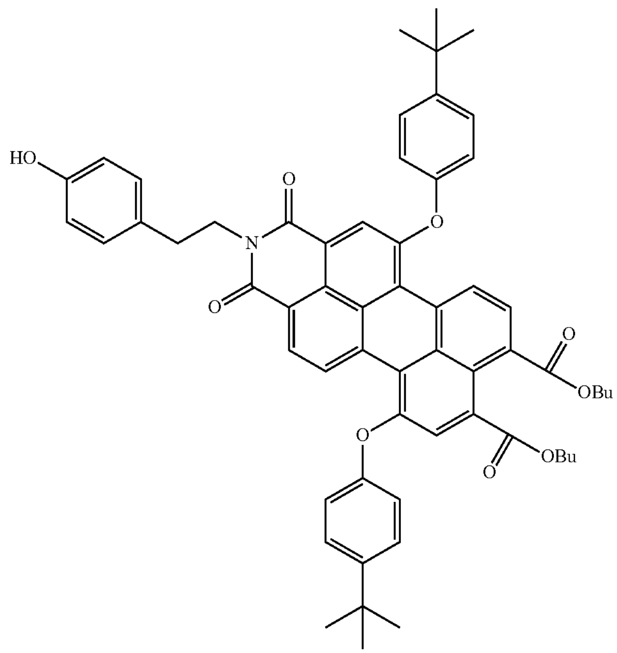 | 78% | $^1$H NMR (300 MHz, CDCl$_3$, ppm (integration, splitting, J(Hz), assignment): 9.39 (1H, d, 8.3 Hz, perylene-H$_{ar}$), 9.38 (1H, d, 8.2 Hz, perylene-H$_{ar}$), 8.56 (1H, s, 8.3 Hz, perylene-H$_{ar}$), 8.35 (1H, s, perylene-H$_{ar}$), 8.04 (1H, d, 8.2 Hz, perylene-H$_{ar}$), 7.76 (1H, s, perylene-H$_{ar}$), 7.48-7.40 (4H, m, p-tBu-phenoxy-H$_{ar}$), 7.20 (2H, d, 8.5 Hz, Tyr-H$_{ar}$), 7.11-7.01 (4H, m, p-tBu-phenoxy-H$_{ar}$), 6.77 (2H, d, 8.5 Hz, Tyr-H$_{ar}$), 4.33 (2H, m, N—[CH$_2$]—CH$_2$Tyr), 4.31 (2H, t, 6.7 Hz, COO—[CH$_2$]—CH$_2$), 4.24 (2H, t, 6.8 Hz, COO—[CH$_2$]—CH$_2$), 2.39 (2H, m, NCH$_2$—[CH$_2$]Tyr), 1.76 (2H, quin, 7.2 Hz, COOCH$_2$—[CH$_2$]—CH$_2$), 1.67 (2H, quin, 7.2 Hz, COOCH$_2$—[CH$_2$]—CH$_2$), 1.47 (2H, sext, 7.5 Hz, COOCH$_2$CH$_2$—[CH$_2$]—CH$_3$), 1.40-1.30 (20H, m, COOCH$_2$CH$_2$—[CH$_2$]'—CH$_3$ and [p-tBu]-phenoxy), 0.97 (3H, t, 7.3 Hz, CH$_2$—[CH$_3$]), 0.90 (3H, t, 7.4 Hz, CH$_2$—[CH$_3$]). |

TABLE 8-continued

| Compound No. | Short Name | Structure | Yield | Characterisation |
|---|---|---|---|---|
| 116 | Mono-imidobutyric acid di(butylester) perylene | 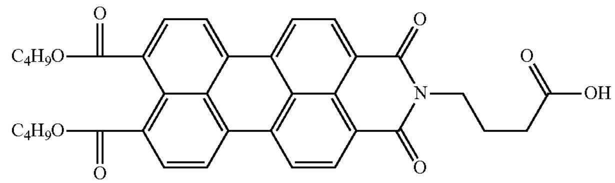 | 95% | $^1$H NMR (300 MHz, CDCl$_3$, ppm (integration, splitting, J(Hz), assignment)): 8.67 (2H, d, perylene-H$_{ar}$, 7.8 Hz), 8.65 (2H, d, perylene-H$_{ar}$, 8.0 Hz), 8.41 (2H, d, H$_{ar}$, 8.0 Hz), 8.03 (2H, d, H$_{ar}$, 7.8 Hz), 4.26 (4H, t, COO—[CH$_2$]—CH$_2$, 6.8 Hz), 4.08 (2H, t, N—[CH$_2$]—CH$_2$, 6.9 Hz), 2.31 (2H, t, HOOC—[CH$_2$]—CH$_2$, 7.5 Hz), 1.91 (2H, m, HOOCCH$_2$—[CH$_2$]—CH$_2$), 1.73 (4H, m, OCH$_2$—[CH$_2$]—CH$_2$), 1.44 (4H, m, CH$_2$—[CH$_2$]—CH$_3$), 0.95 (6H, t, CH$_2$—[CH$_3$], 7.3 Hz). |
| 117 | Mono-Swallowtail imide monotyrimide perylene | 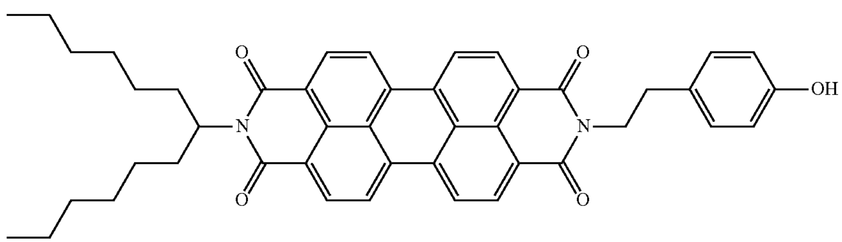 [SMILES: CCCCCCC(CCCCCC)N1C(=O)c2ccc3c4ccc5c6c(ccc(c7ccc(c2c37)C1=O)c64)C(=O)N(CCc1ccc(O)cc1)C5=O] | 65% | $^1$H NMR (300 MHz, CDCl$_3$, ppm (integration, splitting, J(Hz), assignment)): 8.71-8.57 (8H, perylene-H$_{ar}$), 7.25 (4H, d, 8.5 Hz, Tyr-H$_{ar}$), 6.80 (4H, d, 8.5 Hz, Tyr-H$_{ar}$), 5.19 (1H, m, Sw-[CH]), 4.39 (2H, m, TyrCH$_2$—[CH$_2$]—N), 2.99 (2H, m, Tyr-[CH$_2$]—CH$_2$N), 2.22 (2H, m, SwCH-α[CH$_2$]—), 1.88 (2H, m, SwCH-α'[CH$_2$]—), 1.42-1.15 (16H, Sw-β,γ,δ,ε,—[CH$_2$]), 0.83 (6H, t, 6.9 Hz, CH$_2$—[CH$_3$]). |

TABLE 8-continued

| Compound No. | Short Name | Structure | Yield | Characterisation |
|---|---|---|---|---|
| 118 | Tetra(p-tBu-phenoxy)di(imido-isophthalic acid)perylene | 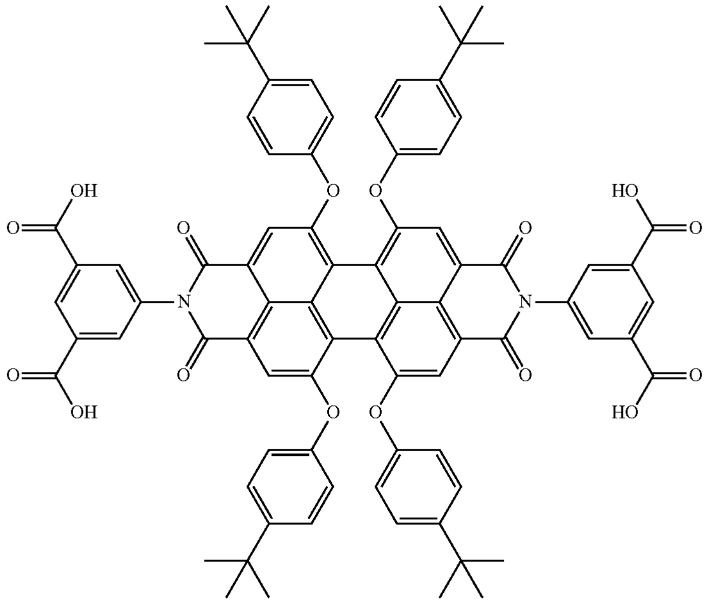 [SMILES: CC(C)(C)c1ccc(Oc2cc3c4c(cc(Oc5ccc(C(C)(C)C)cc5)c5c6c(Oc7ccc(C(C)(C)C)cc7)cc7c8c(cc(Oc9ccc(C(C)(C)C)cc9)c(c2c45)c86)C(=O)N(c2cc(C(=O)O)cc(C(=O)O)c2)C7=O)C(=O)N(c2cc(C(=O)O)cc(C(=O)O)c2)C3=O)cc1] | 75% | $^1$H NMR (300 MHz, D$_6$-DMSO, ppm (integration, splitting, J(Hz), assignment)): 13.42 (4H, COOH), 8.51 (2H, t, 1.6 Hz, para benzamide-H$_{ar}$), 8.19 (4H, d, 1.6 Hz, ortho benzimide-H$_{ar}$), 7.92 (4H, s, perylene-H$_{ar}$), 7.28 (8H, d, 8.5 Hz, p-tBu-phenoxy-H$_{ar}$), 6.87 (8H, d, 8.5 Hz, p-tBu-phenoxy-H$_{ar}$), 1.22 (36H, s, [p-tBu]-phenoxy-H$_{ar}$). |
| 119 | Mono-ethanolimide di(butylester) perylene | 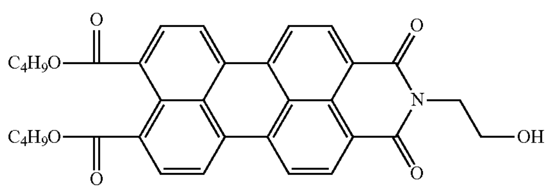 | 85% | $^1$H NMR (300 MHz, CDCl$_3$, ppm (integration, splitting, J(Hz), assignment)): 8.58 (2H, d, 8.0 Hz, perylene-H$_{ar}$), 8.42-8.37 (4H, perylene-H$_{ar}$), 8.09 (2H, d, 7.9 Hz, perylene-H$_{ar}$), 4.50 (2H, t, 5.2 Hz, N—[CH$_2$]—CH$_2$OH), 4.36 (4H, t, 6.9 Hz, COO—[CH$_2$]—CH$_2$), 4.03 (2H, t, 5.2 Hz, NCH$_2$—[CH$_2$]—OH), 1.81 (4H, quin, 7.2 Hz, COOCH$_2$—[CH$_2$]—CH$_2$), 1.50 (4H, sext, 7.1 Hz, COOCH$_2$CH$_2$—[CH$_2$]—CH$_3$), 1.01 (6H, t, 7.4 Hz, COOCH$_2$CH$_2$CH$_2$—[CH$_3$]). |

Dimer Preparation

Preparation of Perylene Dimer from Di-Bromoperylene

Monotyrimide perylene (155 μmol) was dissolved in DMF (1 mL) with potassium carbonate (25 mg, 180 μmol), to this was added a solution of dibromo perylene (70 μmol)) in DMF (1.5 mL). The reaction was then placed in an oil bath at 70° C. After 4 hours the reaction was worked up by precipitated by addition of water, isolation of the ppt and washed with ethanol (E95). The crude material was then purified by chromatographic separation and/or recrystallization.

The compounds of Table 9 may be prepared according to this method. The yield shown in this table is representative of the yield obtained when that compound is produced by this method.

TABLE 9

| # | Short Name | Structure | Yield | Characterisation |
|---|---|---|---|---|
| 120 | Dimer-Bay-mono(tyrimide di(butylester)perylene) core (monobromo monophenoxy ethanolimide di(butylester)perylene) | regioisomers | 80% | ¹H NMR (300 MHz, CDCl₃, ppm (integration, splitting, J(Hz), assignment)): 9.30 (1H, d, 8.1 Hz, Core-H$_{ar}$), 9.15 (1H, d, 8.3 Hz, Core-H$_{ar}$), 8.86 (1H, s, Core-H$_{ar}$), 8.59 (2H, d, 8.1 Hz, App-H$_{ar}$), 8.56 (1H, d, 8.3, Core-H$_{ar}$), 8.43 (2H, d, 8.1 Hz, App-H$_{ar}$), 8.42 (2H, d, 8.1 Hz, App-H$_{ar}$), 8.09 (2H, d, 8.1 Hz, App-H$_{ar}$), 8.07 (1H, d, 80 Hz, Core-H$_{ar}$), 7.73 (1H, s, Core-H$_{ar}$), 7.45 (2H, d, 8.6 Hz, Tyr-H$_{ar}$), 7.10 (2H, d, 8.6 Hz, Tyr-H$_{ar}$), 4.45 (4H, m, N—[CH₂]—CH₂C and N—[CH₂]—CH₂O), 4.36 (4H, t, 6.8 Hz, App-COO—[CH₂]—CH₂), 4.35 (2H, t, 6.9 Hz, Core(carbon 10)-COO—[CH₂]—CH₂), 4.27 (2H, t, 6.9 Hz, Core(carbon 9)-COO—[CH₂]—CH₂), 2.99 (2H, t, 5.2 Hz, NCH₂—[CH₂]—O), 3.10 (2H, m, NCH₂—[CH₂]—C), 1.87-1.65 (8H, m, butyl chains), 1.55-1.41 (8H, m, butyl chains), 1.00 (6H, t, 7.4 Hz, App-0.92 (3H, t, Core(carbon 10)-OCH₂CH₂CH₂—[CH₃]), 0.88 (3H, t, 6.7 Hz, Core(carbon 9)-OCH₂CH₂CH₂[CH₃]). |

TABLE 9-continued

| # | Short Name | Structure | Yield | Characterisation |
|---|---|---|---|---|
| 121 | Dimer-Bay-mono(tyrimide di(butylester)perylene) core (bisphneoxy monoimidobutyric acid di(butylester)perylene) | 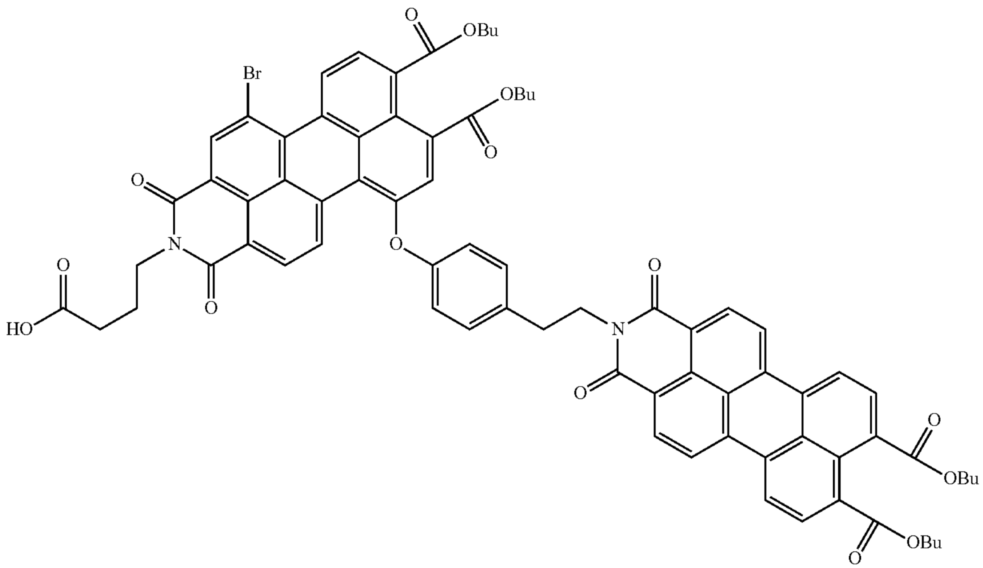 | 45% | $^1$H NMR (300 MHz, CDCl$_3$, ppm (integration, splitting, J(Hz), assignment)): 9.30 (1H, d, 8.1 Hz, Core-H$_{ar}$), 9.14 (1H, d, 8.3 Hz, Core-H$_{ar}$), 8.86 (1H, s, Core-H$_{ar}$), 8.60-8.51 (3H, App-H$_{ar}$ and Core H$_{ar}$), 8.45-8.36 (4H, m, App-H$_{ar}$), 8.12-8.03 (3H, App-H$_{ar}$ and Core-H$_{ar}$), 7.73 (1H, s, Core-H$_{ar}$), 7.43 (2H, d, 8.4 Hz, Tyr-H$_{ar}$), 7.08 (2H, d, 8.4 Hz, Tyr-H$_{ar}$), 4.44 (2H, m, N—[CH$_2$]—CH$_2$C$_{ar}$), 4.36 (4H, t, 6.8 Hz, App-COO[CH$_2$]—CH$_2$CH$_3$), 4.34 (2H, t, 6.8 Hz, Core-COO[CH$_2$]—CH$_2$CH$_3$), 4.27 (2H, t, 6.9 Hz, N—[CH$_2$]—CH$_2$CH$_2$COOH), 4.26 (2H, t, 6.7 Hz, Core-COO[CH$_2$]'—CH$_2$CH$_2$CH$_3$), 3.09 (2H, m, NCH$_2$—[CH$_2$]—C$_{ar}$), 2.49 (2H, t, 7.3 Hz, NCH$_2$CH$_2$—[CH$_2$]—COOH), 2.11 (2H, quin, 6.9 Hz, NCH$_2$—[CH$_2$]—CH$_2$COOH), 1.86-1.63 (8H), 1.58-1.29 (8H), 1.05-0.96 (9H), 0.92 (3H, 7.4 Hz, CH$_2$—[CH$_3$]). |

Trimer Preparation

Preparation of Trimer from Dibromo-Substituted Perylene

Dibromo substituted perylene (120 μmol) was combined with "tyrimide" perylene (400 μmol) and potassium carbonate (700 mg, 5.1 mmol) in DMF (4 mL). This was then stirred and heated to 90° C. for 6 hours. The reaction was then acidified by addition of hydrochloric acid (2M) until the precipitate had completely formed. The ppt was then isolated and washed via centrifuge (1×H2O, 2×MeOH) and then purified by column chromatography and/or recrystallization yielding the trimeric species.

The compounds of Table 10 may be prepared according to this method. The yield shown in this table is representative of the yield obtained when that compound is produced by this method.

TABLE 10

| # | Short Name | Structure | Yield | Characterisation |
|---|---|---|---|---|
| II-15 | Tetra ester perylene di (swallow-tail tyrimide) | regioisomers | 95% | $^1$H NMR (300 MHz, CDCl$_3$, ppm (integration, splitting, J(Hz), assignment)): 9.06 (2H, d, 8.3 Hz, TC-H$_{ar}$), 8.71-8.61 (16H, m, App-H$_{ar}$), 8.00 (2H, d, 8.3 Hz, TC-H$_{ar}$), 7.74 (2H, s, TC-H$_{ar}$), 7.34 (4H, d, 8.7 Hz, tyrimide-H$_{ar}$), 7.01 (4H, d, 8.7 Hz, tyrimide-H$_{ar}$), 5.19 (2H, m, App-Swallowtail-CH), 4.44 (4H, t, 7.8 Hz, N—[CH$_2$]—CH$_2$—C$_{ar}$), 2.24 (4H, m, App Swallowtail αCH$_2$), 1.87 (4H, m, App Swallowtail α'CH$_2$), 1.80-1.64 (8H, m, App Swallowtail and TC butyl), 1.51-1.26 (40H, m, App Swallowtail and TC butyl), 0.97 (6H, t, 7.3 Hz, TC-CH$_3$), 0.90 (6H, t, 7.4 Hz, TC-CH$_3$), 0.82 (12H, t, 6.8 Hz, App-CH$_3$). |
| II-17 | Bay-di(tyrimide cyclohexyl perylene) core (bis-phenoxy tetra (butylester) perylene) | regioisomers | 25% | |

TABLE 10-continued

| # | Short Name | Structure | Yield Characterisation |
|---|---|---|---|
| II-10 | Trimer Bay-di(di(p-tBu-phenoxy) mono-tyrimide di(butyl-ester) core (bis-phenoxy dipropanolimide perylene) | 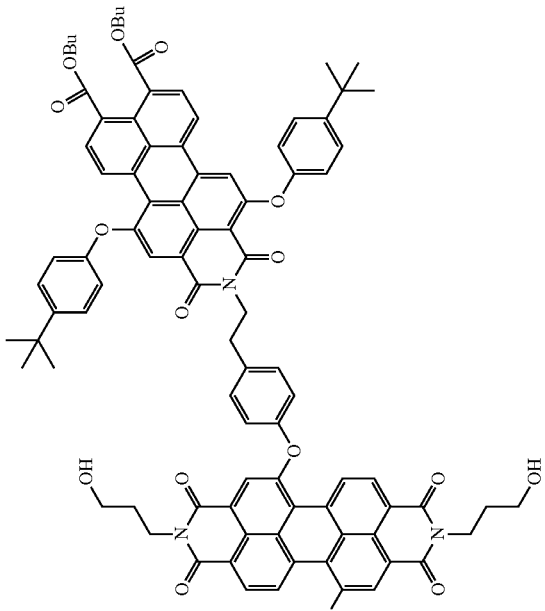 | 85% $^1$H NMR (300 MHz, CDCl$_3$, ppm (integration, splitting, J(Hz), assignment)): 9.58 (2H, d, 8.4 Hz, Core-H$_{ar}$), 9.39 (2H, d, 8.3 Hz, App-H$_{ar}$), 9.37 (2H, d, 8.2 Hz, App-H$_{ar}$), 8.60 (2H, d, 8.3 Hz, App-H$_{ar}$), 8.36 (2H, s, Core-H$_{ar}$), 8.31 (2H, s, App-H$_{ar}$), 8.03 (2H, d, 8.2 Hz, App-H$_{ar}$), 7.76 (2H, s, app-H$_{ar}$), 7.50–7.40 (12H, p-tBu-phenoxy-H$_{ar}$ and Tyr-H$_{ar}$), 7.16–7.02 (p-tBu-phenoxy-H$_{ar}$ and Tyr-H$_{ar}$), 4.41 (4H, m, N—[CH$_2$]—CH$_2$Tyr), 4.31 (4H, t, 6.8 Hz, COO—[CH$_2$]—CH$_2$), 4.30 (4H, m, N—[CH$_2$]—CH$_2$CH$_2$OH), 4.24 (4H, t, 6.7 Hz, COO—[CH$_2$]'—CH$_2$), 3.57 (4H, t, 5.5 Hz, NCH$_2$CH$_2$—[CH$_2$]—OH), 3.06 (4H, m, NCH$_2$—[CH$_2$]-Tyr), 1.96 (4H, quin, 5.7 Hz, NCH$_2$—[CH$_2$]—CH$_2$OH), 1.76 (4H, quin, 7.0 Hz, COOCH$_2$—[CH$_2$]—CH$_2$), 1.67 (4H, quin, 7.2 Hz, COOCH$_2$—[CH$_2$]'—CH$_2$), 1.48 (4H, sext, 7.5 Hz, COOCH$_2$CH$_2$—[CH$_2$]—CH$_3$), 1.32 (4H, sext, 7.7 Hz, COOCH$_2$CH$_2$—[CH$_2$]'—CH3), 1.36 (9H, s, [p-tBu]-phenoxy), 1.35 (9H, [p-tBu]'-phenoxy), 0.98 (6H, |

TABLE 10-continued

| # | Short Name | Structure | Yield | Characterisation |
|---|---|---|---|---|
| II-9 | Trimer-Bay-di(tyrimide swallowtail perylene) core (bis-phenoxy mono-cyclohexylimide di(butyl-lester) perylene) | 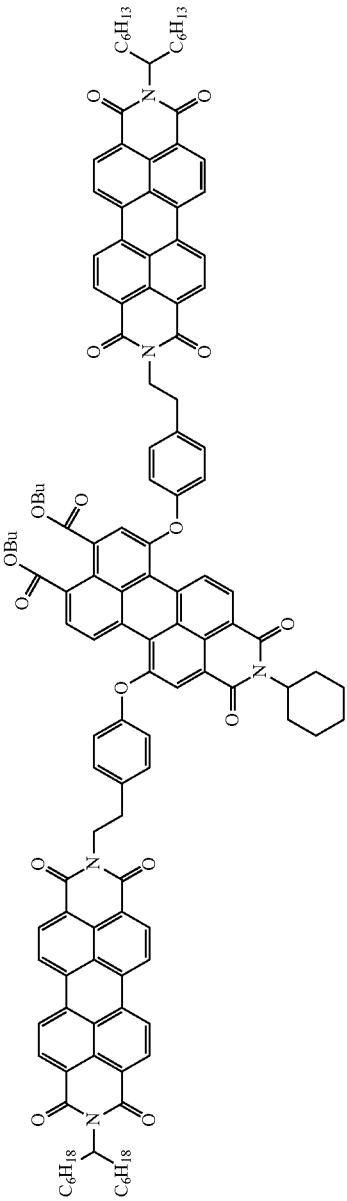 | 77% | t, 7.4 Hz, CH₂—[CH₃]), 0.90 (6H, t, 7.4 Hz, CH₂—[CH₃]'). ¹H NMR (300 MHz, CDCl₃, ppm (integration, splitting, J(Hz), assignment)): 9.35-9.25 (1.5H, m, Core-H$_{ar}$), 9.09 (0.25H, d, 8.2 Hz, Core-H$_{ar}$), 8.77-8.55 (17H, m, H$_{ar}$), 8.56, 1H, d, 8.4 Hz, H$_{ar}$), 8.25-8.03 (3H, m, H$_{ar}$), 7.76 (0.6H, s, Core-H$_{ar}$), 7.48-7.38 (4H, m, Tyr-H$_{ar}$), 7.17-7.01 (4H, m, Tyr-H$_{ar}$), 5.19 (2H, m, swallowtail CH), 5.00 (1H, m, cyclohexyl CH), 4.47 (4H, m, N—[CH₂]—CH₂C$_{ar}$), 4.33 (2.7H, m, O—[CH₂]—CH₂), 4.26 (1.3H, t, 6.8 Hz O—[CH₂]—CH2), 3.08 (4H, t, 7.9 Hz, NCH₂—[CH₂]—C$_{ar}$), 2.50 (2H, m, cyclohexyl CH₂), 2.24 (4H, m, α-CH₂ swallowtail), 1.88 (4H, m, α'-CH₂ swallowtail), 1.81-1.64 (4H, m, β-CH₂ butyl chain), 1.52-1.15 (12H, m, Butyl and swallowtail chains), 1.02-0.79 (18H, —CH₃ Butyl and swallowtail chains). |

TABLE 10-continued

| # | Short Name | Structure | Yield Characterisation |
|---|---|---|---|
| II-Trimer-18 | Bay-di (tyrimide di (butyl-ester) perylene) core (bis-phenoxy mono-imide di (butyl-ester) perylene) | | 37% ¹H NMR (300 MHz, CDCl₃, ppm (integration, splitting, JHz), assignment)): 9.21 (2H), 7.74-7.35 (20H), 7.40 (4H, tyrimide-H$_{ar}$), 7.17 (4H, tyrimide-H$_{ar}$), 4.35 (16H, all O—[CH₂]— and N—[CH₂]—), 1.92-1.74 (12H, βCH₂ butyl chain), 1.57-1.43 (12H, γCH₂ butyl chain), 1.13-0.83 (18H, CH₂—[CH₃]). |
| II-Trimer-6 | Bay-di (tyrimide di (butyl-ester) perylene) core (bis-phenoxy mono-imido-butyric acid di (butyl-ester) perylene) | | 50% ¹H NMR (300 MHz, CDCl₃, ppm (integration, splitting, JHz), assignment)): 9.37-9.03 (2H, TC-H$_{ar}$), 8.65-7.64 (18H, TC-H$_{ar}$ and App-H$_{ar}$), 7.50-7.35 (4H, tyrimide-H$_{ar}$), 7.17-6.92 (4H, tyrimide-H$_{ar}$), 4.30-4.10 (18H, O—[CH₂]— and N—[CH₂]—), 3.24-2.76 (6H, NCH₂CH₂—[CH₂]— and NCH₂CH₂[CH₂]—COOH), 1.75 (12H, β-CH₂ butyl chain), 1.44 (12H, γ-CH₂ butyl chain), 0.95 (15H, App—CH₃ and TC-CH₃), 0.83 (3H, TC-CH₃'). |

TABLE 10-continued

| # | Short Name | Structure | Yield | Characterisation |
|---|---|---|---|---|
| II-19 | Trimer-Bay-di (Swallow-tail Tyrimide perylene) core (bis-phenoxy monopropanolimide di (butyl-ester) perylene) | 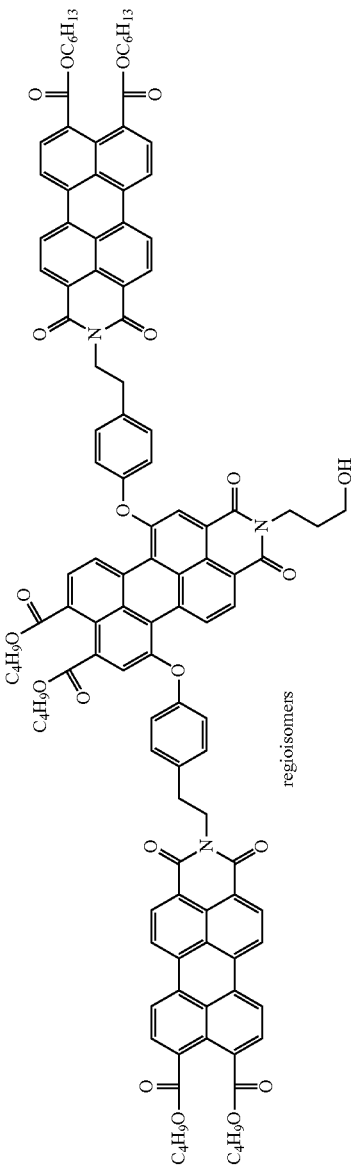 regioisomers | 75% | $^1$H NMR (300 MHz, CDCl$_3$, ppm (integration, J(Hz), splitting, J(Hz), assignment)): 9.18 (2H, Core-H$_{ar}$), 8.55-7.35 (24H, Core-H$_{ar}$, App-H$_{ar}$, and Tyr-H$_{ar}$), 7.06 (4H, d, 7.8 Hz, Tyr-H$_{ar}$), 4.50-4.13 (18H, COO—[CH$_2$]—CH$_2$, N—[CH$_2$]—CH$_2$C$_{ar}$, and N—[CH$_2$]—CH$_2$CH$_2$), 3.44 (2H, NCH$_2$CH$_2$—[CH$_2$]—OH), 3.26 (2H, NCH$_2$—[CH$_2$]—CH$_2$OH), 3.16 (4H, NCH$_2$—[CH$_2$]—C$_{ar}$), 1.84 (12H, COOCH$_2$—[CH$_2$]—CH$_2$), 1.54 (12H, COOCH$_2$CH$_2$—[CH$_2$]—CH$_3$), 1.05 (6H, t, 7.0 Hz, App-COOCH$_2$CH$_2$CH$_2$—[CH$_3$]), 0.98 (3H, t, 7.21 Hz, Core-COOCH$_2$CH$_2$CH$_2$—[CH$_3$]), 0.92 (3H, t, 7.3 Hz, Core-COOCH$_2$CH$_2$CH$_2$—[CH$_3$]). |

TABLE 10-continued

| # | Short Name | Structure | Yield Characterisation |
|---|---|---|---|
| II-8 | Trimer-Bay-di(tyrimide di(butyl-ester)perylene)core(bis-phenoxy monoethanolimide di(butyl-ester)perylene) | 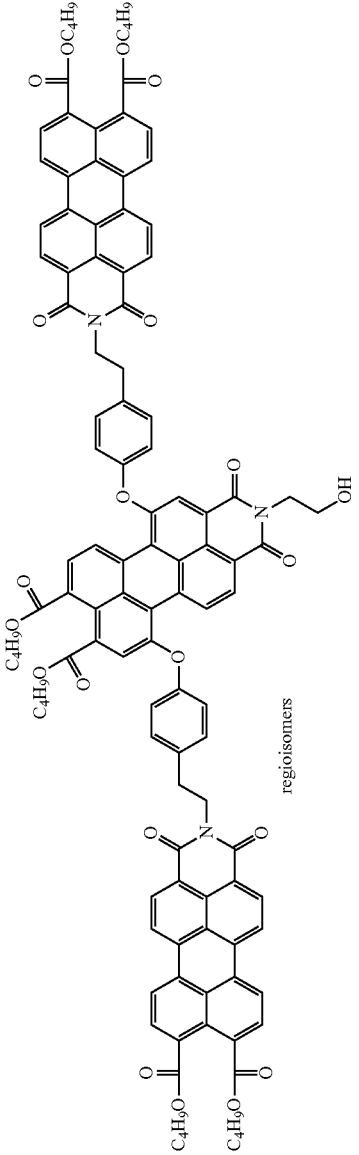 regioisomers | 16% ¹H NMR (300 MHz, CDCl₃, ppm (integration, splitting, J(Hz), assignment)): 9.11-8.57 (2H, TC-H$_{ar}$), 9.36-7.31 28H, TC-H$_{ar}$ and Tyr-H$_{ar}$), 7.21-7.02 (4H, Tyr-H$_{ar}$) 4.53-4.08 (18H, all N—[CH₂]—CH₂ and O—[CH₂]—CH₂), 3.92 (2H, NCH₂—[CH₂]—OH), 3.13 (4H, NCH₂—[CH₂]—C$_{ar}$), 1.95-1.77 (12H, OCH₂—[CH₂]—CH₂CH₃), 1.61-1.46 (12H, OCH₂CH₂—[CH₂]—CH₃), 1.11-1.01 (15H, App-OCH₂CH₂CH₂—[CH₃] and Core-OCH₂CH₂CH₂—[CH₃]), 0.93 (3H, t, 7.4 Hz, Core-OCH₂CH₂CH₂—[CH₃]'). |

TABLE 10-continued

| # | Short Name | Structure | Yield Characterisation |
|---|---|---|---|
| II-Trimer-20 | Bay-di(Swallowtail)Tyrimide perylene core (bisphenoxy monopropanol-imide di(butylester)perylene) regioisomers | 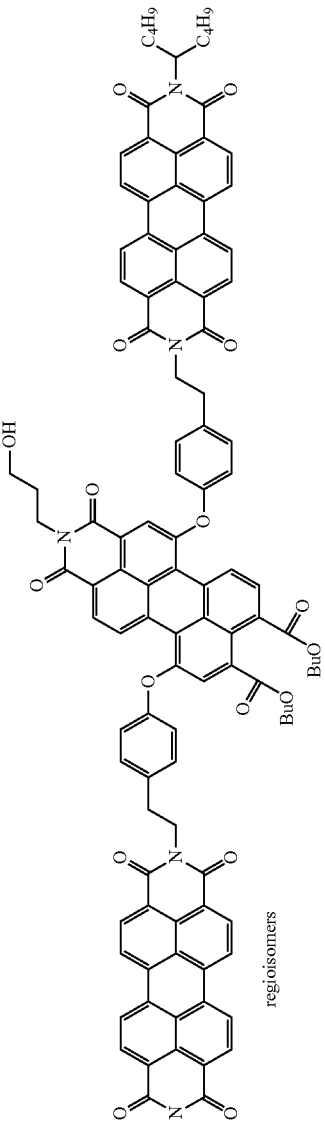 | 60% ¹H NMR (300 MHz, CDCl₃, ppm (integration, splitting, J(Hz), assignment)): 9.20 (1H, d, 8.4 Hz, Core-H$_{ar}$), 9.15 (1H, d, 8.0 Hz, Core-H$_{ar}$), 8.68-7.99 (18H, App-H$_{ar}$, and Core-H$_{ar}$), 7.95 (1H, d, 8.4 Hz, Core-H$_{ar}$), 7.68 (1H, s, Core-H$_{ar}$), 7.47 (2H, d, 7.4 Hz, Tyr-H$_{ar}$), 7.38 (2H, d, 6.8 Hz, Tyr-H$_{ar}$), 7.06-6.99 (4H, Tyr-H$_{ar}$), 5.09 (2H, m, N—[CH]—), 4.38 (4H, m, N—[CH$_2$]—CH$_2$Tyr), 4.27 (2H, t, 6.8 Hz, COO—[CH$_2$]—CH$_2$), 4.22 (2H, t, 6.8 Hz, COO—[CH$_2$]'—CH$_2$), 3.93 (2H), 3.48 (2H), 3.12 (4H, m, NCH$_2$—[CH$_2$]-Tyr), 2.18 (4H, m, NCH—[CH$_2$]—CH$_2$), 1.88 (4H, m, NCH—[CH$_2$]'—CH$_2$), 1.79-1.59 (4H, COOCH$_2$—[CH$_2$]—CH$_2$ and COOCH$_2$—[CH$_2$]'—CH$_2$), 1.45 (2H, sext, 7.5 Hz, COOCH$_2$CH$_2$—[CH$_2$]—CH3), 1.39-1.17 (18H, |

TABLE 10-continued

| # | Short Name | Structure | Yield | Characterisation |
|---|---|---|---|---|
| | | | | COOCH2CH2-[CH2]'-CH3 and Sw—CH2's), 0.94 (3H, t, 7.4 Hz, COOCH2CH2CH2-[CH3]), 0.88 (3H, t, 7.4 Hz, COOCH2CH2CH2-[CH3]'), 0.81 (12H, t, 6.5 Hz, Sw-[CH3]). |
| II-1 | Trimer-Bay-di (tyrimide di (butyl-ester) perylene) mono (bis-phenoxy dicyclo-hexyl-imide) | 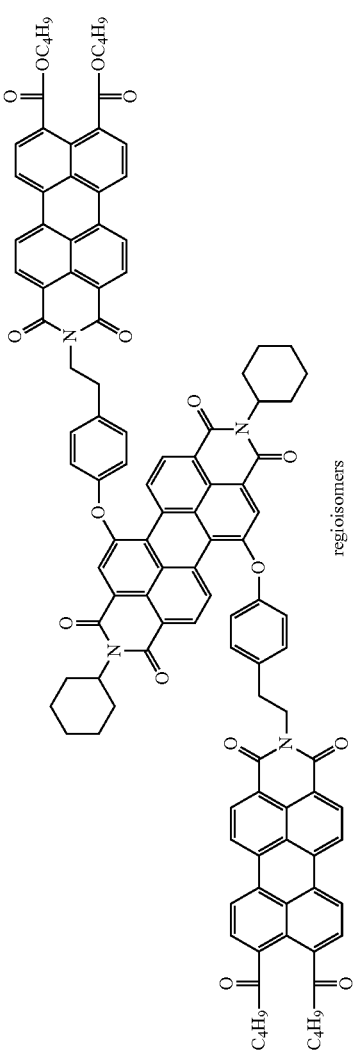 regioisomers | 75% | $^{1}$H NMR (300 MHz, CDCl$_3$, ppm (integration, splitting, J(Hz), assignment)): 9.54 (2H, d, 8.7 Hz, Core-H$_{ar}$), 8.65 (4H, d, 8.0 Hz, App-H$_{ar}$), 8.55 (2H, d, 8.7 Hz, Core-H$_{ar}$), 8.49 (4H, d, 8.0 Hz, App-H$_{ar}$), 8.46 (4H, d, 7.8 Hz, App-H$_{ar}$), 8.27 (2H, s, Core-H$_{ar}$), 8.11 (4H, d, 7.8 Hz, App-H$_{ar}$), 7.47 (4H, d, 8.5 Hz, Tyr-H$_{ar}$), 7.12 (4H, d, 8.5 Hz, Tyr-H$_{ar}$), 5.00 (2H, m, N—[CH]—), 4.47 (4H, t, 7.8 Hz, N—[CH$_2$]—CH$_2$), 2.52 (4H, m, cyclohexyl CH$_2$—[CH$_2$]—CH$_2$), 1.90-1.35 (6H, m, cyclohexyl), 1.78 (8H, m, OCH$_2$—[CH$_2$]—CH$_2$), 1.49 (8H, m, —[CH$_2$]—CH$_3$), 1.01 (12H, t, 7.4 Hz, CH$_2$—[CH$_3$]). |

Preparation of Trimer from Carboxy-Substituted Perylene

Diimidobutyric acid perylene (50 µmol) was reacted with thionyl chloride (2 mL) in dichloromethane (3 mL) and refluxed until complete by TLC. The solvent and residual thionyl chloride were removed in vacuo. The residue was then taken up in dichloromethane (1 ml) and added dropwise into a stirred solution of alkylalcohol-imide perylene (210 µmol) with triethylamine (210 µmol) in dichloromethane (4 ml) and stirred under nitrogen at room temperature until TLC indicated completion. The reaction mixture was subsequently poured onto aqueous hydrochloric acid (0.5M, 50 mL) and extracted with chloroform (2×100 mL), then saturated aqueous sodium bicarbonate solution (50 mL), water (50 mL), dried over sodium sulphate, filtered and solvent removed. The residue was then purified by column chromatography and/or recrystallization.

The compounds of Table 11 may be prepared according to this method. The yield shown in this table is representative of the yield obtained when that compound is produced by this method.

TABLE 11

| # Short Name | Structure | Yield Characterisation |
|---|---|---|
| II-3 Trimer-Linear-di(butylester) monoethylimide perylene core (tetra(p-tBu-phenoxy) dibutylimide perylene) | (structure shown) | 40% $^1$H NMR (300 MHz, CDCl$_3$, ppm (integration, splitting, J(Hz), assignment): 8.47 (4H, d, 8.1 Hz, App-H$_{ar}$), 8.29-8.24 (8H, App-H$_{ar}$), 8.09 (4H, s, Core-H$_{ar}$), 7.94 (4H, d, 7.9 Hz, App-H$_{ar}$), 7.18 (8H, d, 8.9 Hz, p-tBu-phenoxy-H$_{ar}$), 6.75 (8H, d, 8.9 Hz, p-tBu-phenoxy-H$_{ar}$), 4.43 (8H, all N—[CH$_2$]—CH$_2$), 4.28 (8H, t, 6.9 Hz, COO—[CH$_2$]—CH$_2$), 4.06 (4H, t, 7.1 Hz, NCH$_2$—[CH$_2$]—O), 2.39 (4H, t, 7.2 Hz, OOC—[CH$_2$]—CH$_2$), 1.97 (4H, quin, 7.1 Hz, NCH$_2$—[CH$_2$]—CH$_2$), 1.76 (8H, quin, 7.1 Hz, OCH$_2$—[CH$_2$]—CH$_2$), 1.47 (8H, sext, 7.4 Hz, OCH$_2$CH$_2$—[CH$_2$]—CH$_3$), 1.26 (36H, s, [p-tBu]-phenoxy). |

Preparation of Trimer Via NH Alkylation

To stirred dimethylformamide (2 mL) was added mono-imide perylene (70 µmol), caesium carbonate (50 mg, 150 µmol) and di(bromoalkylimide) perylene (33 µmol). This was then placed under nitrogen and heated at 80° C. for 90 minutes. The reaction was then precipitated with methanol, washed repeatedly and then purified by column chromatography and/or recrystallization.

The compounds of Table 12 may be prepared according to this method. The yield shown in this table is representative of the yield obtained when that compound is produced by this method.

TABLE 12

| # Short Name | Structure | Yield Characterisation |
|---|---|---|
| II-4 Trimer-Linear-diester di(di-do(p-tBu-phenoxy) monoimide) linear core tetra(p-tBu-phenoxy) di(propylimide) | 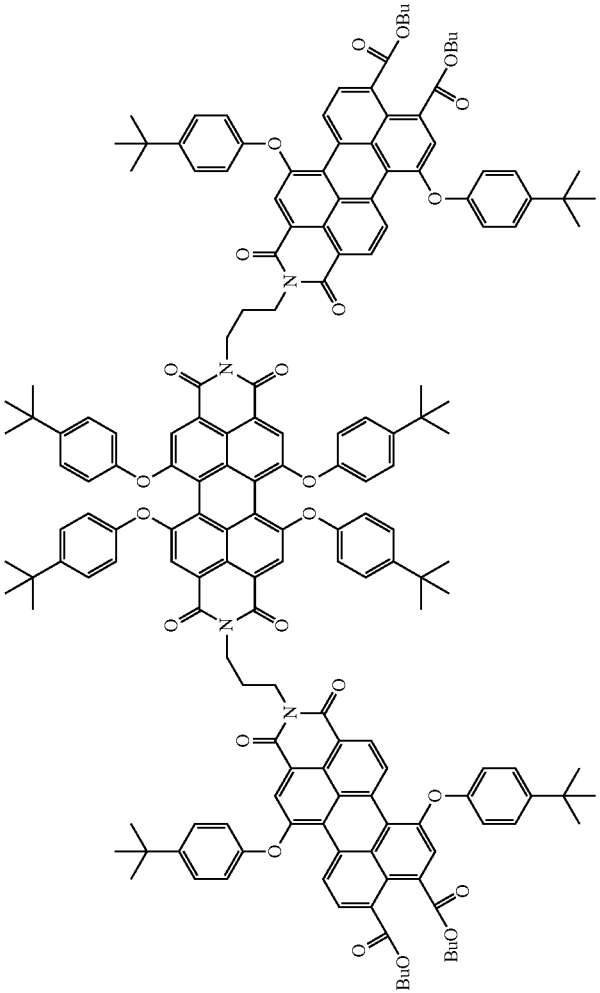 | 92% $^1$H NMR (300 MHz, CDCl$_3$, ppm (integration, splitting, J(Hz), assignment): 9.35 (2H, d, 8.3 Hz, App-H$_{ar}$), 9.34 (2H, d, 8.3 Hz, App-H$_{ar}$), 8.49 (2H, d, 8.3 Hz, App-H$_{ar}$), 8.28 (2H, s, App-H$_{ar}$), 8.17 (4H, s, Core-H$_{ar}$), 8.01 (2H, d, 8.3 Hz, App-H$_{ar}$), 7.74 (2H, d, App-H$_{ar}$), 7.42 (4H, d, 8.8 Hz, App-p-tBu-Phenoxy-H$_{ar}$), 7.39 (4H, d, 8.8 Hz, App-p-tBu-Phenoxy-H$_{ar}$), 7.19 (8H, d, 8.8 Hz, Core-p-tBu-Phenoxy-H$_{ar}$), 7.05 (4H, d, 8.8 Hz, App-p-tBu-Phenoxy-H$_{ar}$), 7.01 (4H, d, 8.8 Hz, App-p-tBu-Phenoxy-H$_{ar}$), 6.79 (8H, d, 8.8 Hz, Core-p-tBu-Phenoxy-H$_{ar}$), 4.35-4.19 (16H, all COO—[CH$_2$]—CH$_2$ and N—[CH$_2$]—CH$_2$—[CH$_2$]—N), 2.15 (4H, NCH$_2$—[CH$_2$]—CH$_2$N), 1.75 (4H, quin, 7.1 Hz, COOCH$_2$—[CH$_2$]—CH$_2$), 1.66 (4H, quin, 7.1 Hz, COOCH$_2$—[CH$_2$]'—CH$_2$), 1.53-1.27 (8H, COOCH$_2$CH$_2$—[CH$_2$]—CH$_3$ and COOCH$_2$CH$_2$—[CH$_2$]'—CH$_3$), 1.34 (18H, s, App-[p-tBu]-Phenoxy), 1.33 (18H, s, App-[p-tBu]'-Phenoxy), 1.26 (36H, s, Core-[p-tBu]-Phenoxy), 0.97 (6H, t, 7.4 Hz, CH$_2$—[CH$_3$]), 0.89 (6H, t, 7.4 Hz, CH$_2$—[CH$_3$]'). |

Preparation of Trimer Via Ether Formation

Di(bromoalkylimide) perylene (10 μmol) was combined with monotyrimide perylene (60 μmol) and potassium carbonate (50 mg, 360 μmol) in dimethylformamide (5 mL) under nitrogen and heated at 130° C. over 4 hours. The product was then precipitated by addition of aqueous HCl (2M, 20 mL), filtered then purified by column chromatography and/or recrystallization.

The compounds of Table 13 may be prepared according to this method. The yield shown in this table is representative of the yield obtained when that compound is produced by this method.

TABLE 13

| # | Short Name | Structure | Yield | Characterisation |
|---|---|---|---|---|
| II-13 | Trimer-Linear-di(tyrimide cyclohexylimide) core (tetra(p-tBu-phenoxy) dipropylimide perylene) | 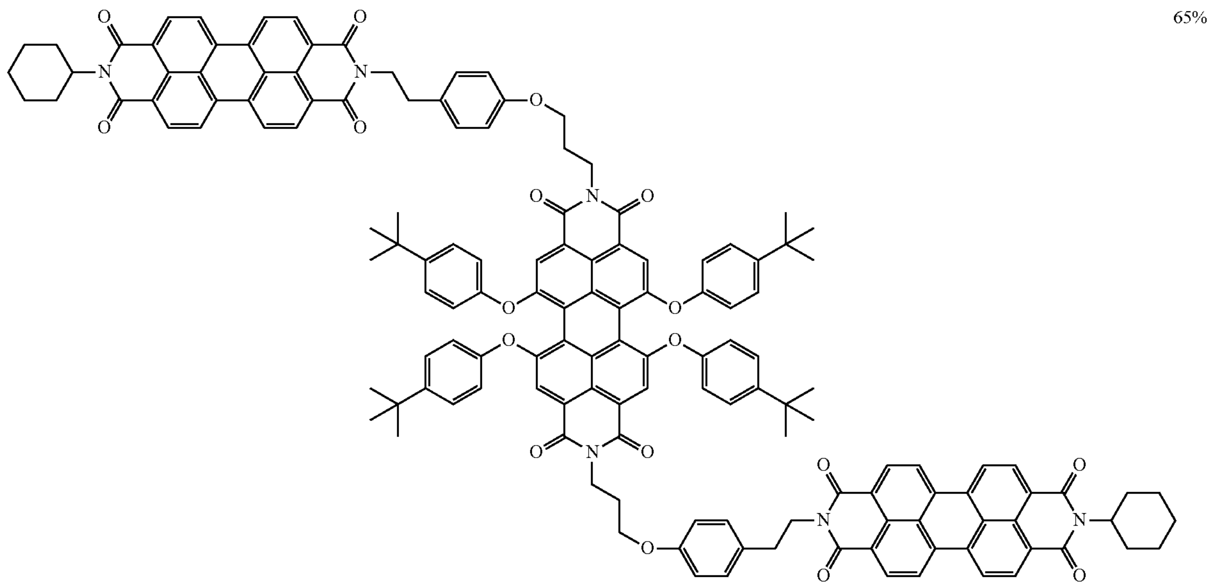 | 65% | ¹H NMR (300 MHz, CDCl₃, ppm (integration, splitting, J(Hz), assignment): 8.70-8.60 (4H, m, App-H$_{ar}$), 8.56-8.44 (8H, App-H$_{ar}$), 8.40-8.37 (4H, m, App-H$_{ar}$), 8.18 (4H, s, Core-H$_{ar}$), 7.23 (8H, d, 8.8 Hz, p-tBu-phenoxy-H$_{ar}$), 7.16 (4H, d, 8.6 Hz, Tyr-H$_{ar}$), 6.82 (8H, d, 8.8 Hz, p-tBu-phenoxy-H$_{ar}$), 6.60 (4H, d, 8.6 Hz, Tyr-H$_{ar}$), 5.02 (2H, m, N—CH—), 4.44-4.21 (8H), 4.03 (4H, m, CO—[CH₂]—CH₂), 2.93 (4H, C—[CH₂]—CH₂N), 2.67-2.47 (8H), 2.02-1.68 (16H, cyclohexyl). |

Preparation of N-alkyl Trimer

Trimer monoimide (15 µmol) was combined with sodium hydride (60% wt. mineral oil, 200 µmol) and stirred in tetrahhydrofuran (2 mL) at 70° C. To this was then added potassium iodide (5 mg, 30 µmol) and 1,3-dibromopropane (20 µL, 200 µmol). This was then stirred under nitrogen until completion as indicated by TLC. The reaction was then quenched, solvent removed in vacuo and residue subjected to column chromatography and/or recrystallization to yield the alkylated trimer.

The compounds of Table 14 may be prepared according to this method. The yield shown in this table is representative of the yield obtained when that compound is produced by this method.

TABLE 14

| # | Short Name | Structure | Yield Characterisation |
|---|---|---|---|
| II-7 | Trimer-Bay-di(Swallowtail Tyrimide perylene) core (bisphenoxy monobromo propylimide di(butylester) perylene) | 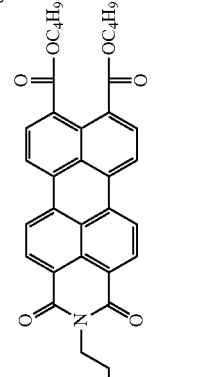 regioisomers | 80% $^1$H NMR (300 MHz, CDCl$_3$, ppm (integration, splitting, J(Hz), assignment)): 9.39 (1H, d, 8.4 Hz, Core-H$_{ar}$), 8.70-8.36 (18H, Core-H$_{ar}$ + App-H$_{ar}$), 8.17-8.02 (2H, App-H$_{ar}$), 7.46 (4H, d, 8.3 Hz, Tyr-H$_{ar}$), 7.44 (4H, d, 7.8 Hz, Tyr-H$_{ar}$), 7.16-7.06 (8H, Tyr-H$_{ar}$), 4.51-4.19 (18H), 3.52 (2H, NCH$_2$CH$_2$—[CH$_2$]—Br), 3.10 (4H, NCH$_2$—[CH$_2$]-Tyr), 2.36 (2H, NCH$_2$—[CH$_2$]—CH$_2$Br), 1.97-1.63 (12H, Butyl chain), 1.54-1.30 (12H, Butyl chain), 1.05-0.85 (15H, CH$_2$—[CH$_3$]). |

Preparation of Trimer Dianhydridoperylene Via Acid Catalysed Hydrolysis

To toluene (5 ml) was added the tetraester core trimer (88 µmol) and p-toluene sulfonic acid hydrate (320 mg, 1.9 mmol). This was refluxed until the toluene became clear and no more precipitate formed. This was then isolated by centrifuge and washed by centrifuge (2×10 ml acetone, 2×10 ml dichloromethane) to yield the dianhydride as an insoluble purple solid.

The compounds of Table 15 may be prepared according to this method. The yield shown in this table is representative of the yield obtained when that compound is produced by this method.

TABLE 15

| # | Short Name | Structure | Yield | Characterisation |
|---|---|---|---|---|
| II-14 | Trimer-Bay-di(tyrimide swallowtail perylene) core (bisphenoxy dianhydride perylene) | 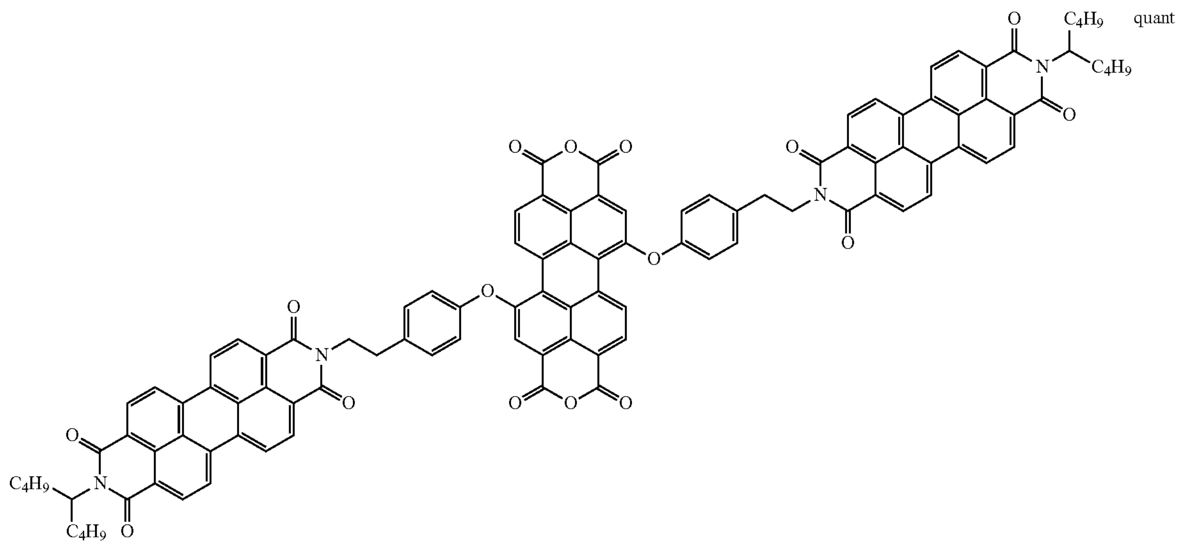 | quant | ATR-IR (cm$^{-1}$): 2940 m, 2917 m, 2865 m, 2850 m, 1777 m, 1762 m, 1735 m, 1695 s, 1647 s, 1591 s, 1576 m, 1501 m, 1438 m, 1401 s, 1341 s, 1311 w, 1293 s, 1263 s, 1248 s, 1222 w, 1199 m, 1166 m, 1091 m, 1017 s, 857 m. |

Preparation of Trimer Diimide Via Ammonium Acetate Condensation

Trimer dianhydride (21 μmol) was combined with ammonium acetate (320 mg, 2.1 mmol) in dimethylformamide (3 mL) in a sealed vial then placed into an oil bath at 150° C. for 2 hours. The reaction mixture was then added to methanol (10 mL) and isolated by centrifuge. This solid was then centrifuge washed (2×10 ml methanol, 2×10 mL dichloromethane) to yield the diimide perelene trimer typically as an insoluble purple solid.

The compounds of Table 16 may be prepared according to this method. The yield shown in this table is representative of the yield obtained when that compound is produced by this method.

TABLE 16

| # | Short Name | Structure | Yield | Characterisation |
|---|---|---|---|---|
| II-11 | Trimer-Bay-di(tyrimide swallowtail perylene) core (bisphenoxy diimide perylene) | 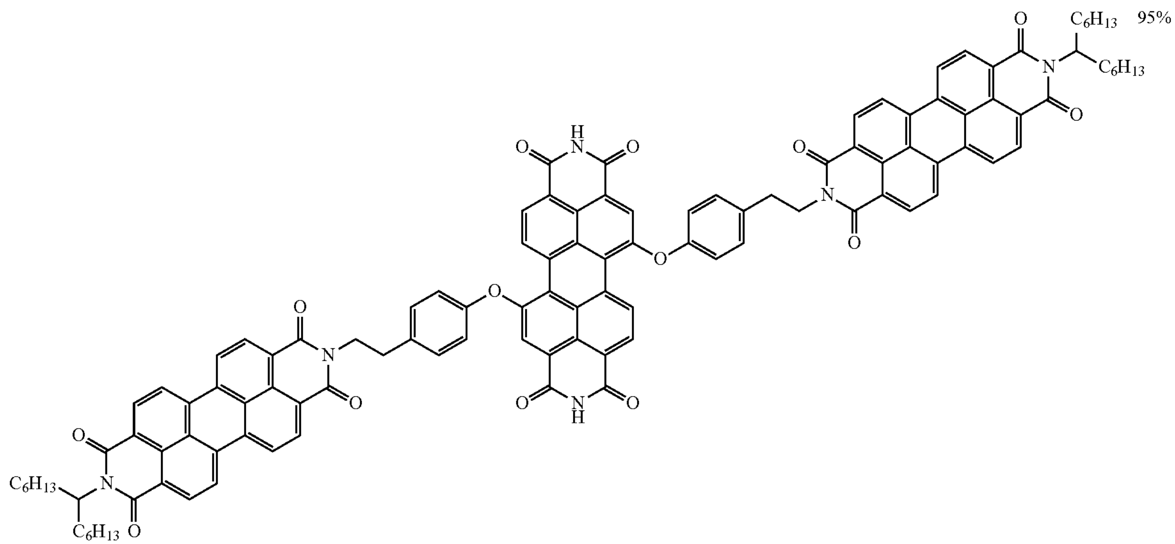 | 95% | ATR-IR (cm$^{-1}$): 3159 m, 3115 w, 3040 m, 2955 m, 2921 m, 2846 m, 1691 s, 1680 s, 1505 m, 1434 m, 1423 m, 1404 m, 1334 s, 1224 m, 1196 m, 1162 m, 1121 w, 1103 w, 1035 w, 1017 w, 998 w, 950 w, 890 w, 850 m, 808 m. |

Preparation of Trimer Diimide Via Quinoline Condensation

Dianhydride trimer (3 μmol) was added to quinoline (0.5 ml) and amine (0.6 mmol) the reaction sealed and placed in an oil bath at 130° C. for 2.5 hours. The reaction was then precipitated with acidified methanol and precipitate isolated by centrifuge. The precipitate was then washed by centrifuge (2×acidified methanol 10 ml, 2×methanol 10 ml) to yield a purple solid with limited solubility.

The compounds of Table 17 may be prepared according to this method. The yield shown in this table is representative of the yield obtained when that compound is produced by this method.

TABLE 17

| # | Short Name | Structure | Yield | Characterisation |
|---|---|---|---|---|
| II-5 | Trimer-Bay-di(tyrimide swallowtail perylene) core (bisphenoxy di(n-dodecyl)imide perylene) | *regioisomers | quant | ¹H NMR (300 MHz, CDCl₃, ppm (integration, splitting, J(Hz), assignment): 9.49 (2H, d, 8.3 Hz, Core-H$_{ar}$), 8.77-8.10 (20H, App-H$_{ar}$ and Core-H$_{ar}$), 7.51 (4H, d, 7.7 Hz, Tyr-H$_{ar}$), 7.18 (4H, d, 7.7 Hz, Tyr-H$_{ar}$), 5.14 (2H, m, N—[CH]—), 4.48 (4H, m, N—[CH$_2$]—CH$_2$Tyr), 3.97 (4H, m, N—[CH$_2$]—CH$_2$CH$_2$), 3.21 (4H, m, NCH$_2$—[CH$_2$]-Tyr), 2.23 (4H, m, Swaaltowtail-αCH2), 1.92 (4H, m, Swallowtail-αCH2), 1.45-1.09 (72H, alkyl chain), 0.95-0.81 (18H, swallowtail-CH3 and dodecyl-CH3), H |
| II-12 | Trimer-Bay-di(tyrimide swallowtail perylene) core (bisphenoxy dipropanolimide perylene) | regioisomers | quant | ATR-IR (cm-1): 2943 m, 2917 m, 2846 m, 1691 s, 1647 s, 1591 s, 1576 sh, 1501 m, 1434 m, 1401 s, 1330 s, 1259 sh, 1244s, 1214 s, 1196 s, 1162 s, 1121 m, 1103 m, 1032 m, 1013 m, 935 w, 849 s, 808 s. |

TABLE 17-continued
| # | Short Name | Structure | Yield Characterisation |
|---|---|---|---|
| II-16 | Trimer-Bay-di(tyrimide swallowtail perylene) core (bisphenoxy) dityrimide perylene) | 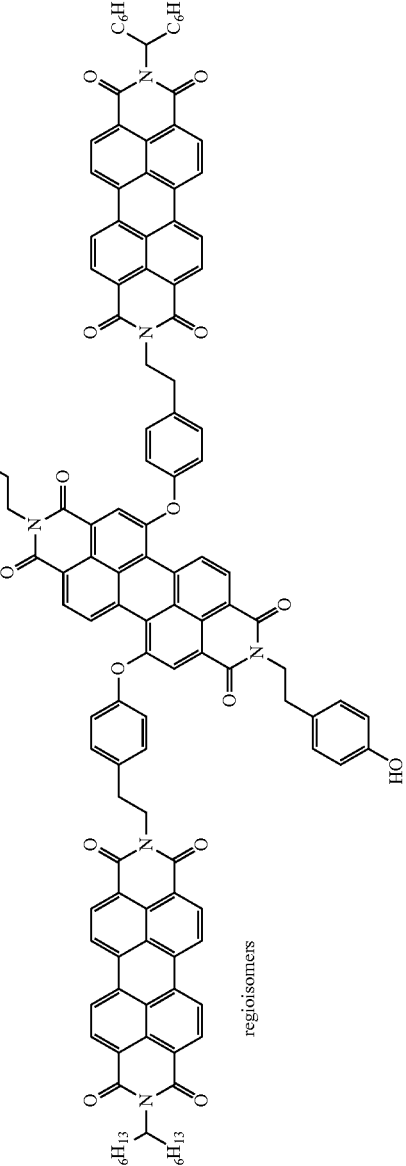 regioisomers | 96% ATR-IR (cm-1): 2954 m, 2928 m, 2857 m, 1694 s, 1650 s, 1616 w, 1952 s, 1580 s, 1515 m, 1503 m, 1438 m, 1401 s, 1335 s, 1256 s, 1248 s, 1218 m, 1198 m, 1166 s, 1125 m, 1105 m, 1016 w, 99 w, 853 m, 828 m, 809 s. |

Pentamer Preparation

Preparation of Pentamer Via Acid Chloride Formation

Di(3,4-dicarboxylic acid benzimide) perylene (90 µmol) was refluxed with thionyl chloride (4 mL) in dichloromethane (20 mL). Once complete by TLC, the solvent and residual thionyl chloride was removed by distillation. The acid chloride then taken up in dichloromethane (10 ml) and added drop-wise into a stirred solution of monoalkylalcoholimide perylene (850 µmol) with triethylamine (120 µL, 860 µmol) in dichloromethane (100 ml). Stirred under nitrogen at room temperature, the reaction was worked up when TLC indicated completion. The solvent was then removed and the residue then purified by sonicating the solid in dichloromethane (100 mL), then addition of methanol (20 mL) and isolating the resultant solid material affording the pentamer as a dark crystalline solid.

The compounds of Table 18 may be prepared according to this method. The yield shown in this table is representative of the yield obtained when that compound is produced by this method.

TABLE 18

| # | Short Name | Structure | Yield | Characterisation |
|---|---|---|---|---|
| II-2 | Pentamer-tetra(monoethanolimide diester perylene) mono(tetra(p-tBu-phenoxy) di(isophthalate benzimide) perylene) | 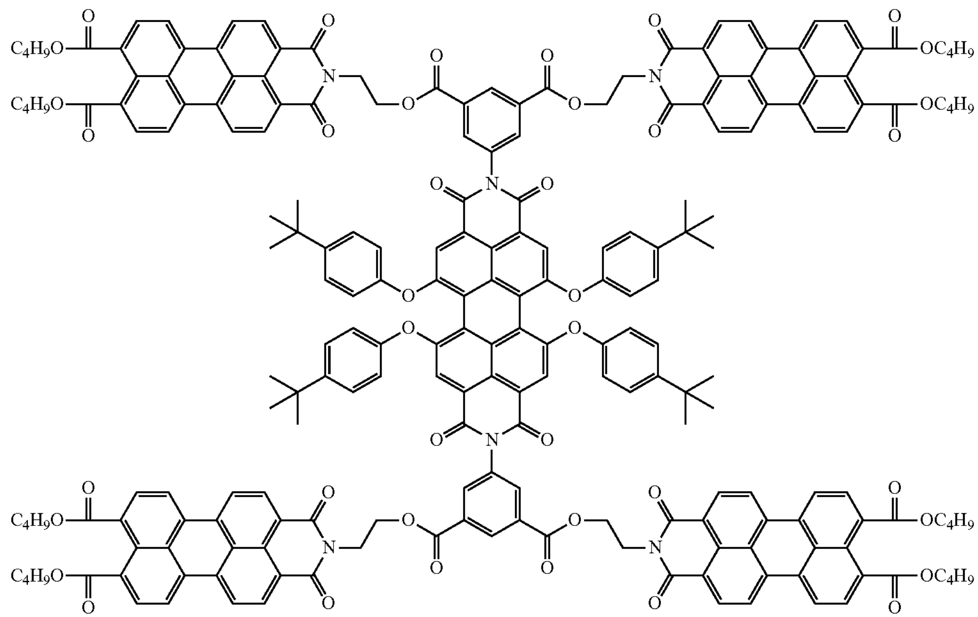 | 60% | $^1$H NMR (300 MHz, CDCl$_3$, ppm (integration, splitting, J(Hz), assignment): 8.67 (2H, s, benzimide-para-H$_{ar}$), 8.26 (4H, s, Core-H$_{ar}$), 8.23-7.84 (36H, App-H$_{ar}$ and Benzimide-ortho-H$_{ar}$), 7.19 (8H, d, 8.8 Hz, p-tBu-phenoxy-H$_{ar}$), 6.81 (8H, d, 8.8 Hz, p-tBu-phenoxy-H$_{ar}$), 4.72 (8H, m, N—[CH$_2$]—CH$_2$O), 4.53 (8H, m, NCH$_2$—[CH$_2$]—O), 4.33 (16H, t, 6.7 Hz, COO—[CH$_2$]—CH$_2$CH$_2$CH$_3$), 1.79 (16H, quin, 7.1 Hz, COOCH$_2$—[CH$_2$]—CH$_2$CH$_3$), 1.48 (6H, sext, 7.4 Hz, COOCH$_2$CH$_2$—[CH$_2$]—CH$_3$), 1.20 (36H, s, [p-tBu]-phenoxy), 0.99 (24H, t, 7.4 Hz, COOCH$_2$CH$_2$CH$_2$—[CH$_3$]).H |

Optical Properties

Optical properties of the compounds II-1 to II-20 may be assessed by the following general techniques.

UV-Vis spectroscopy. UV-Vis spectroscopy is performed by taking 1 mg of dye, dissolving it in 10 mL of solvent, generally chloroform, then diluting 1 mL of that solution up to 10 mL, making a final solution of approximately 0.01 mg mL$^{-1}$. After a background scan of the blank solvent in a quartz fluorescence cuvette (1 cm path length) was taken, the blank solvent was replaced with approximately 3 mL of the solution containing the sample and the absorbance measured between 250 and 900 nm.

Fluorescence spectroscopy. Fluorescence spectroscopy may be performed using the same solution used for UV-Vis measurements. Generally emitter and detector slit widths were kept to 2.5 nm, however this was reduced in some cases to compensate for bright samples.

Ultra-fast transient grating photoluminescence spectrometry. FRET lifetime measurements were performed on a custom built ultra-fast transient grating photoluminescence spectrometer. A solution with approximately an absorbance of 0.1 for a 1 mm path length was made, then after calibration and tuning of the laser, optical Kerr gate and detector, the change in the fluorescence lifetimes of the monomeric dyes, array dyes and the individual components directly corresponds back to the FRET efficiency.

Table 19 sets out the absorbance maximum (Abs Max) and the fluorescence maximum (Em max) for compounds described herein.

TABLE 19

| Compound No. | Abs Max (nm) | Em Max (nm) |
|---|---|---|
| II-1 | 509 | 572 |
| II-2 | 508 | 620 |

TABLE 19-continued

| Compound No. | Abs Max (nm) | Em Max (nm) |
|---|---|---|
| II-3 | 506 | 611 |
| II-4 | 508 | 620 |
| II-5 | 527 | 575 |
| II-6 | 508 | 562 |
| II-7 | 510 | 561 |
| II-8 | 508 | 571 |
| II-9 | 526 | 571 |
| II-10 | 519 | 577 |
| II-13 | 526 | 620 |
| II-15 | 527 | 539 |
| II-18 | 508 | 565 |
| II-19 | 508 | 571 |
| II-20 | 527 | 574 |

Example 3—Synthesis of Light Harvesting Arrays

The compounds I-1, I-2 and I-3 may be prepared by the following general procedures.

Preparation of an Array Via Imide N-Alkylation

Into a flask containing DMF (5 mL) was combined NH imide trimer (33 µmol) with haloalkylimide tetra(p-tBu-phenoxy) perylene (16 µmol) and caesium carbonate (30 mg, 92 µmol). This was then stirred at room temperature over 2 days, then at 70° C. for 1 hour. The reaction was then precipitated with methanol, centrifuge washed with methanol (2×) and water (1×) then again with methanol (1×). The resulting material was then purified by chromatography and/or recrystallization yielding the heptameric adduct.

For example, compound I-3 may be produced in a yield of 6% according to this method.

Characterisation Data for Compound I-3

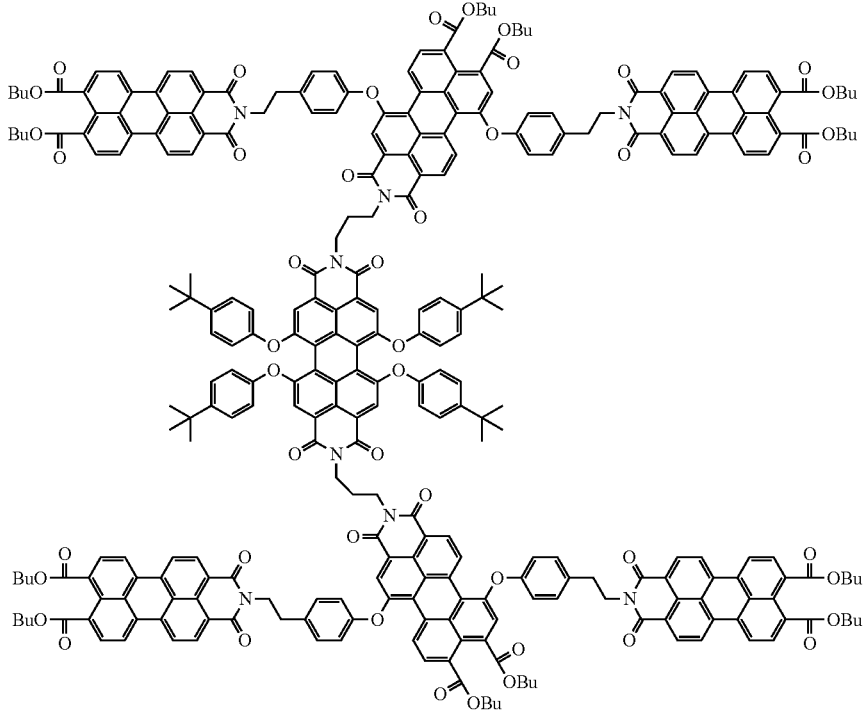

Compound I-3

¹H NMR (300 MHz, CDCl₃, ppm (integration, splitting, J (Hz), assignment)): 9.27 (2H, d, 8.6 Hz, TC H$_{ar}$), 9.16 (2H, d, 8.4 Hz, TC H$_{ar}$), 8.45 (4H, d, 8.1 Hz, App H$_{ar}$), 8.39 (4H, d, 8.1 Hz, App H$_{ar}$), 8.35-8.14 (6H, m, H$_{ar}$), 8.12 (4H, s, Core H$_{ar}$), 8.07-7.93 (8H, m, H$_{ar}$), 7.72 (2H, s, TC H$_{ar}$), 7.43 (4H, d, 8.5 Hz, Tyrimide-H$_{ar}$), 7.40 (4H, d, 8.3 Hz, Tyrimide-H$_{ar}$), 6.73 (8H, d, 8.7 Hz, Core phenoxy), 4.56-4.02 (40H, m, all N—[CH₂]— and O—[CH₂]—), 3.06 (8H, m, NCH₂—[CH₂]—C$_{ar}$), 2.19 (4H, m, NCH₂—[CH₂]—CH₂N), 1.91-1.66 (24H, β-CH₂ butyl chain), 1.54-1.43 (24H, γ-CH₂ butyl chain), 1.02 (12H, t, 7.4 Hz, App CH₂—[CH₃]), 1.01 (12H, t, 7.4 Hz, App CH₂—[CH₃]), 1.00 (6H, t, 7.1 Hz, TC CH₂—[CH₃]), 0.91 (6H, t, 7.4 Hz, TC CH₂—[CH₃]).

Absorbance max.: 507 nm. Emission max.: 614 nm.

Figure 9:
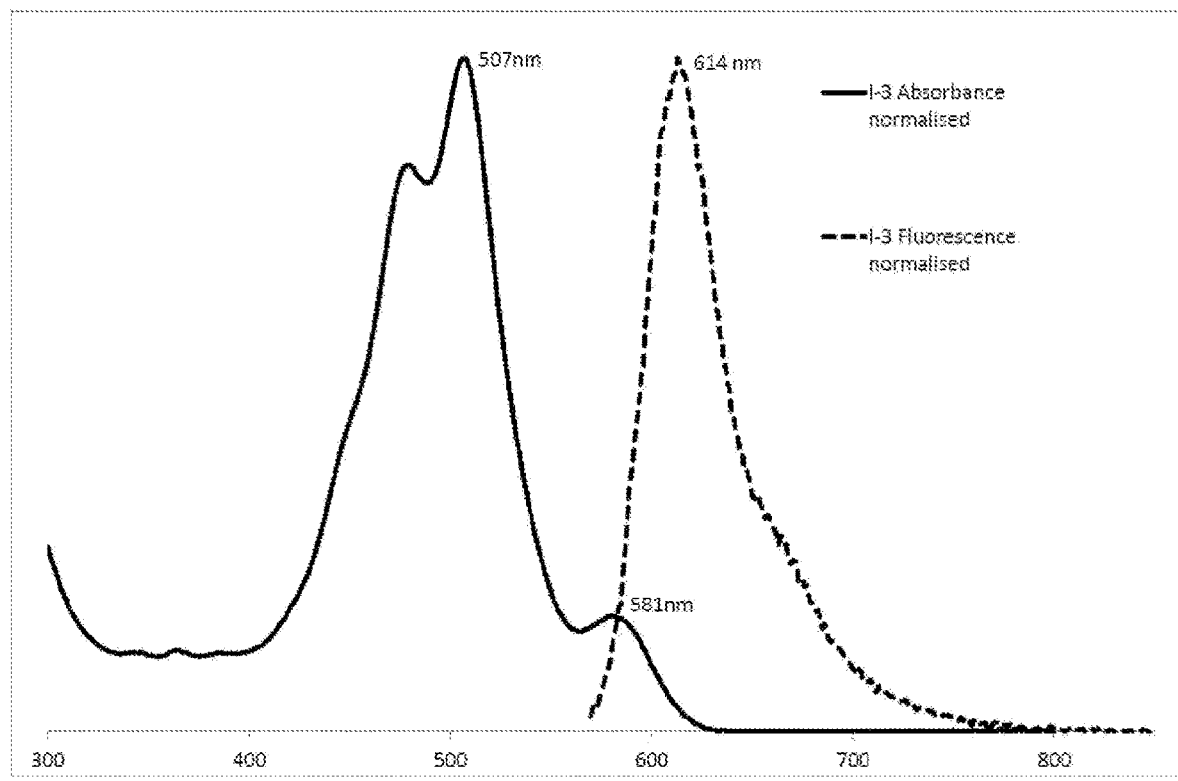
FIG. 9 is the UV-visible absorbance spectrum and fluorescence emission spectrum for Compound I-3 shown on the same set of axes.

The UV-vis absorbance and fluorescence emission spectra for Compound I-3 are shown in FIG. 9. The absorbance maximum shown in FIG. 9 for Compound I-3 is at 507 nm. The oligomeric units of Compound I-3 contribute this absorption band. The small band at 581 nm is the absorbance maxima for the tetra-phenoxy substituted perylene moiety (the acceptor) of Compound I-3. The band at 581 nm is dwarfed by the large combined donor absorbance band contributed by the two oligomeric units. The fluorescence emission maxima in FIG. 9 is at 614 nm, which represents the fluorescence emission contributed by the acceptor portion of the Compound I-3. FIG. 9 shows that the majority of the absorbance is largely decoupled from the fluorescence emission with its peak at 614 nm.

Preparation of a Light Harvesting Array Via Ester Formation

To thionyl chloride (5 ml) was added the carboxylic acid substituted perylene (6 µmol) and refluxed until all dissolved and acid chloride formation complete by TLC as indicated by quenching with methanol. Thionyl chloride was then removed in vacuo and the resultant material placed under high vacuum. The acid chloride adduct was then dissolved in dry dichloromethane and added drop-wise to a stirred solution of alkyl-alcohol trimer (21 µmol). This was stirred until complete by TLC. Chromatographic separation and/or recrystallization yields the light harvesting array (tetramer).

For example, compound I-1 may be produced in a yield of 55% according to this method and compound I-2 may be produced in a yield of 60% according to this method.

Characterisation Data for Compound I-1

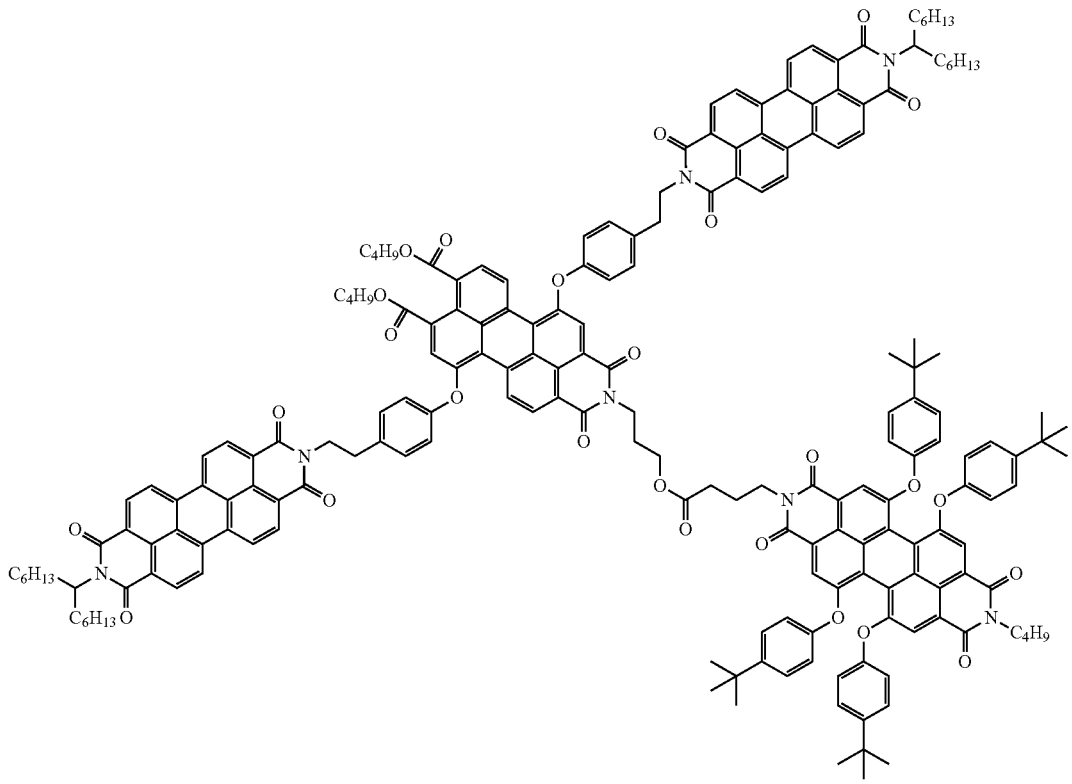

Compount I-1

¹H NMR (300 MHz, CDCl₃, ppm (integration, splitting, J (Hz), assignment)): 9.32 (1H, d, 8.4 Hz, TC-H$_{ar}$), 9.29 (1H, d, 8.3 Hz, TC-H$_{ar}$), 8.73-8.47 (17H, m, TC-H$_{ar}$ and App-H$_{ar}$), 8.27 (1H, s, TC-H$_{ar}$), 8.22 (2H, s, Core-H$_{ar}$), 8.05 (1H, d, 8.3 Hz, TC-H$_{ar}$) 8.00 (2H, s, Core-H$_{ar}$), 7.74 (1H, s, TC-H$_{ar}$), 7.40 (2H, d, 8.5 Hz, Tyr-H$_{ar}$), 7.32 (2H, d, 8.4 Hz, Tyr-H$_{ar}$), 7.23 (4H, d, 8.7 Hz, p-tBu-phenoxy-H$_{ar}$), 7.20 (4H, d, 8.7 Hz, p-tBu-phenoxy-H$_{ar}$), 6.85 (4H, d, 8.7 Hz, p-tBu-phenoxy-H$_{ar}$), 6.78 (4H, d, 8.7 Hz, p-tBu-phenoxy-H$_{ar}$), 5.18 (2H, m, N—[CH]—), 4.48-3.93 (14H), 4.00 (2H, m, N—[CH₂]—), 3.61 (2H, m), 3.03 (2H, m), 2.86 (2H, m), 2.38-2.16 (6H, m), 1.91 (4H, m), 1.78-1.39 (60H), 1.29 (18H, s, [p-tBu]-phenoxy), 1.26 (18H, s, [p-tBu]'-phenoxy), 0.97 (3H, t, 7.4 Hz, COOCH₂CH₂CH₂—[CH₃]), 0.90 (3H, t, 7.4 Hz, COOCH₂CH₂CH₂—[CH₃]'), 0.83 (3H, t, 7.2 Hz, NCH₂CH₂CH₂—[CH₃]), 0.82 (12H, t, 6.8 Hz, Sw-[CH₃]).

Absorbance max. 528 nm. Emission max.: 616 nm.

Characterisation Data for Compound I-2

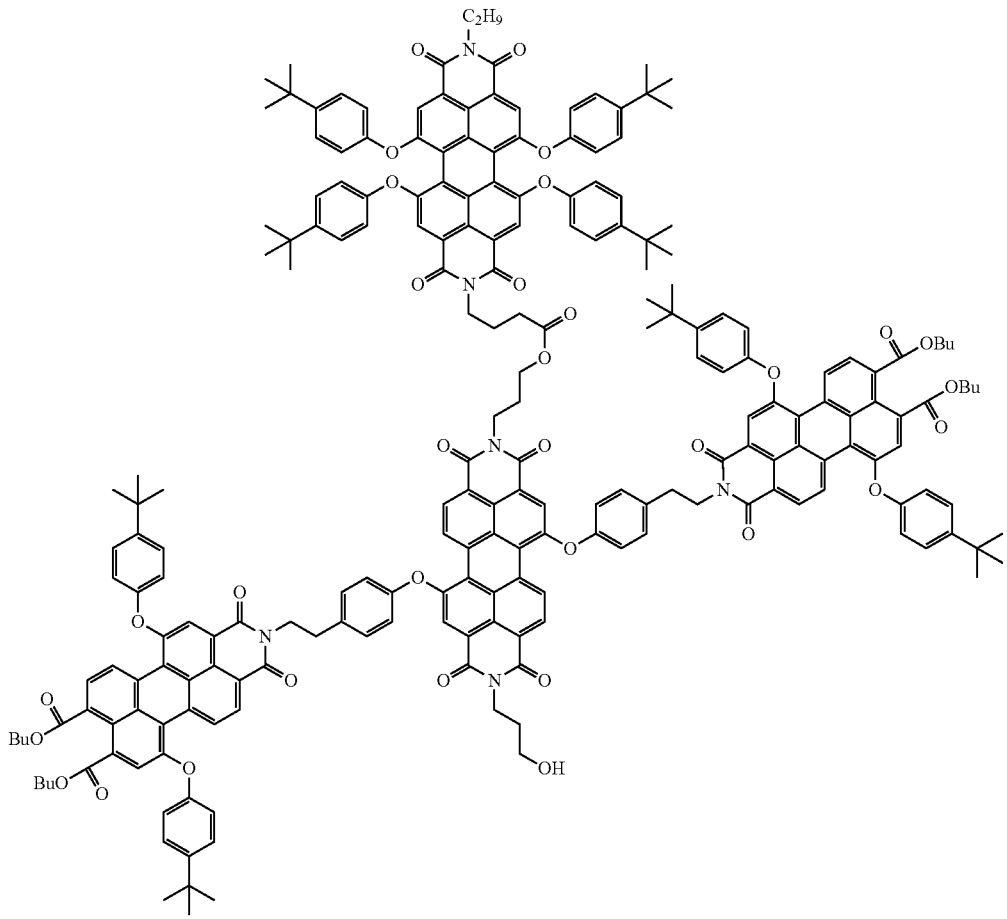

Compound I-2

¹H NMR (300 MHz, CDCl₃, ppm (integration, splitting, J (Hz), assignment)): 9.57 (1H, d, 8.4 Hz, TC-H$_{ar}$), 9.56 (1H, d, 8.4 Hz, TC-H$_{ar}$), 9.41 (1H, d, 7.6 Hz, App-H$_{ar}$), 9.39 (1H, d, 8.2 Hz, App-H$_{ar}$), 9.39 (1H, d, 8.2 Hz, App-H$_{ar}$), 9.38 (1H, d, 6.9 Hz, App-H$_{ar}$), 8.66-8.50 (4H, App-H$_{ar}$), 8.38 (1H, s, TC-H$_{ar}$), 8.36 (1H, s, TC-H$_{ar}$), 8.30 (2H, S, App-H$_{ar}$), 8.13 (2H, s, Core-H$_{ar}$), 8.12 (2H, s, Core-H$_{ar}$), 8.04 (1H, d, 8.2 Hz, App-H$_{ar}$), 8.03 (1H, d, 8.3 Hz, App-H$_{ar}$), 7.76 (1H, s, TC-H$_{ar}$), 7.76 (1H, s, TC-H$_{ar}$), 7.50-7.36 (12H, m, App-p-tBu-phenoxy-H$_{ar}$ and Tyr-H$_{ar}$), 7.21 (4H, d, 8.8 Hz, Core-p-tBu-phenoxy-H$_{ar}$), 7.19 (4H, d, 8.7 Hz, Core-p-tBu-phenoxy-H$_{ar}$), 7.16-7.02 (12H, m, App-p-tBu-phenoxy-H$_{ar}$ and Tyr-H$_{ar}$), 6.82 (4H, d, 8.8 Hz, Core-p-tBu-phenoxy-H$_{ar}$), 6.78 (4H, d, 8.7 Hz, Core-p-tBu-phenoxy-H$_{ar}$), 4.49-4.19 (22H), 4.13 (2H), 3.97 (2H), 3.88 (2H), 3.54 (2H), 3.02 (2H), 2.94 (2H), 2.28 (2H), 2.03 (2H), 1.91 (4H), 1.80-1.31 (14H), 1.36 (18H, s, [p-tBu]-phenoxy), 1.35 (18H, s, [p-tBu]-phenoxy), 1.28 (18H, s, [p-tBu]-phenoxy), 1.26 (18H, s, [p-tBu]-phenoxy), 0.98 (6H, t, 7.4 Hz, COOCH₂CH₂CH₂—[CH₃], 0.90 (6H, t, 7.4 Hz, COOCH₂CH₂CH₂—[CH₃]'), 0.89 (3H, t, 7.2 Hz, NCH₂CH₂CH₂—[CH₃]).

Absorbance max.: 518 nm. Emission max.: 606 nm.

Example 4—Synthesis of Dimer 7

The dimer 7 is one example of an oligomeric unit, comprising an optionally substituted donor rylene core linked via a linker group to one or more optionally substituted peripheral donor rylenes.

Tetrabutyl perylene-3,4-9,10-tetracarboxylate (2)

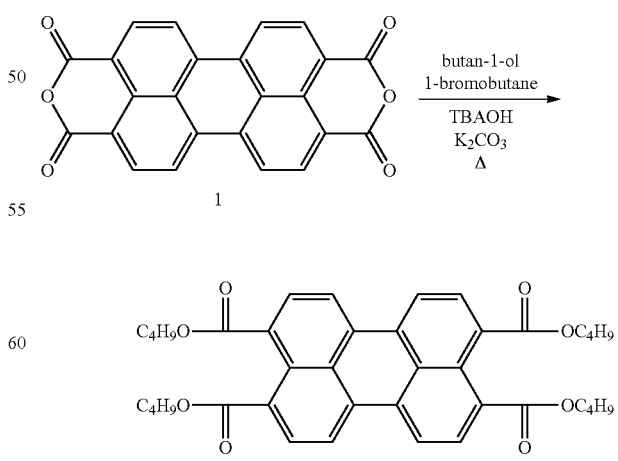

Into a stirred mixture of butan-1-ol (40 ml, 0.44 mol) and an aqueous solution of tetrabutyl ammonium hydroxide (30 mL, 50-60% w/v, 56 mmol) was added perylene-3,4,9,10-tetracarboxylic dianhydride (10.0 g, 25.5 mmol). This was then stirred under nitrogen until completely dissolved. After this 1-bromobutane (40 mL, 0.37 mol) and potassium carbonate (10.0 g, 72 mmol) was added with stirring and the reaction placed into an oil bath at 120° C. under nitrogen for 2 hours. The reaction mixture was then taken up in dichloromethane (500 ml) and washed with water (3×100 mL). The organic layer then dried over sodium sulfate, filtered, subjected to a silica plug and evaporated to dryness to yield the tetraester as a fine yellow crystalline material (16.16 g, 24.8 mmol, 97%)$^1$H NMR (300 MHz, CDCl$_3$, ppm (assignment, J (Hz))): 8.26 (4H, d, Har, 8.2 Hz), 8.02 (4H, d, Har, 8.2 Hz), 4.33 (8H, t, O—[CH$_2$]—CH$_2$—, 6.8 Hz), 1.76 (8H, m, OCH$_2$—[CH$_2$]—CH$_2$), 1.48 (8H, m, CH$_2$CH$_2$—[CH$_2$]—CH$_3$), 0.98 (12H, t, CH$_2$—[CH$_3$], 7.3 Hz).

9,10-bis(butoxycarbonyl)perylene-3,4-dicarboxylic anhydride (3)

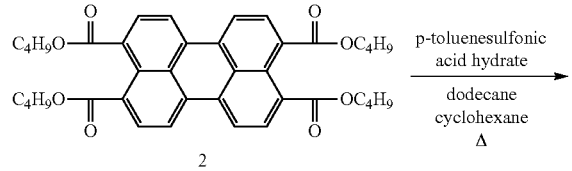

Tetrabutyl-3,4,9,10-perylene tetracarboxylate (2.0 g, 3.1 mmol) and p-toluene sulfonic acid (580 mg, 3.0 mmol) were combined in cyclohexane (2 mL) and dodecane (10 mL). This mixture was then placed in an oil bath under nitrogen at 120° C. for 100 minutes. The resultant material was then filtered hot, washed with hot cyclohexane, then acetonitrile to yield the 9,10-bis(butoxycarbonyl)perylene-3,4-dicarboxylic anhydride as a red solid (1.46 g, 2.8 mmol, 91% yield)$^1$H NMR (300 MHz, CDCl$_3$, ppm (assignment, J (Hz))): 8.67 (2H, d, Har, 8.1 Hz), 8.54 (2H, d, Har, 7.3 Hz), 8.52 (2H, d, Har, 7.3 Hz), 8.15 (2H, d, Har, 8.1 Hz), 4.36 (4H, t, COO—[CH$_2$]—CH$_2$, 6.8 Hz), 1.80 (4H, m, OCH$_2$—[CH$_2$]—CH$_2$), 1.51 (4H, m, CH$_2$—[CH$_2$]—CH$_3$), 1.00 (6H, t, CH$_2$—[CH$_3$], 7.4 Hz).

9,10-bis(butoxycarbonyl)perylene-3,4-dicarboxylic (6-aminohexyl)imide (4)

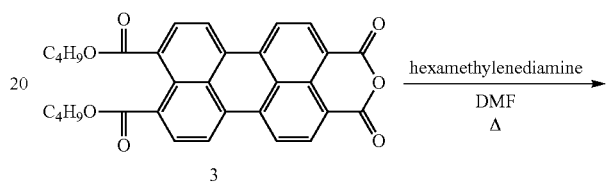

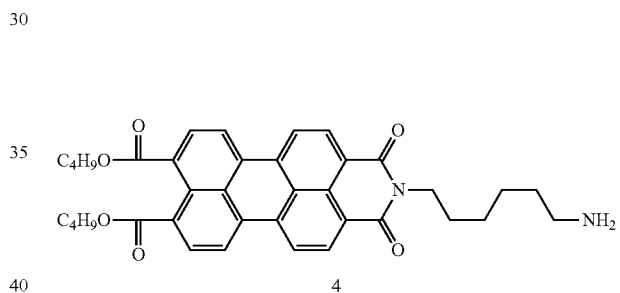

Hexamethylenediamine (600 mg, 5.2 mmol) was stirred in dimethylformamide (5 mL) at 120° C., to this was added 9,10-bis(butoxycarbonyl)perylene-3,4-dicarboxylic anhydride (150 mg, 0.3 mmol). This was then stirred under nitrogen for 2 hours. The reaction mixture was then precipitated by addition to water (40 mL) and washed by repeated centrifuge cycles (2 40 mL). The residual solid after the water was decanted was transferred with dichloromethane and absolute ethanol, solvent removal yielded the 9,10-bis(butoxycarbonyl)perylene-3,4-dicarboxylic (6-aminohexyl)imide as a red solid (173 mg, 0.3 mmol, 96%)$^1$H NMR (300 MHz, D$_6$-DMSO, ppm (assignment, J (Hz))): 8.61 (2H, d, Har (perylene), unresolved), 8.59 (2H, d, Har (perylene), unresolved), 8.37 (2H, d, Har (perylene), 8.1 Hz), 8.02 (2H, d, Har (perylene), 8.0 Hz), 4.27 (4H, t, COO—[CH$_2$]—CH$_2$, 6.7 Hz), 4.01 (2H, t, imide N—[CH$_2$]—CH$_2$, 7.3 Hz), 1.80-1.30 (18H, m, alkyl), 0.96 (6H, t, CH$_2$—[CH$_3$], 7.4 Hz).

1,7-bis(4-tert-butylphenoxy)perylene-3,4,9,10-tetracarboxylic dianhydride (as Mixture of Regioisomers 6)

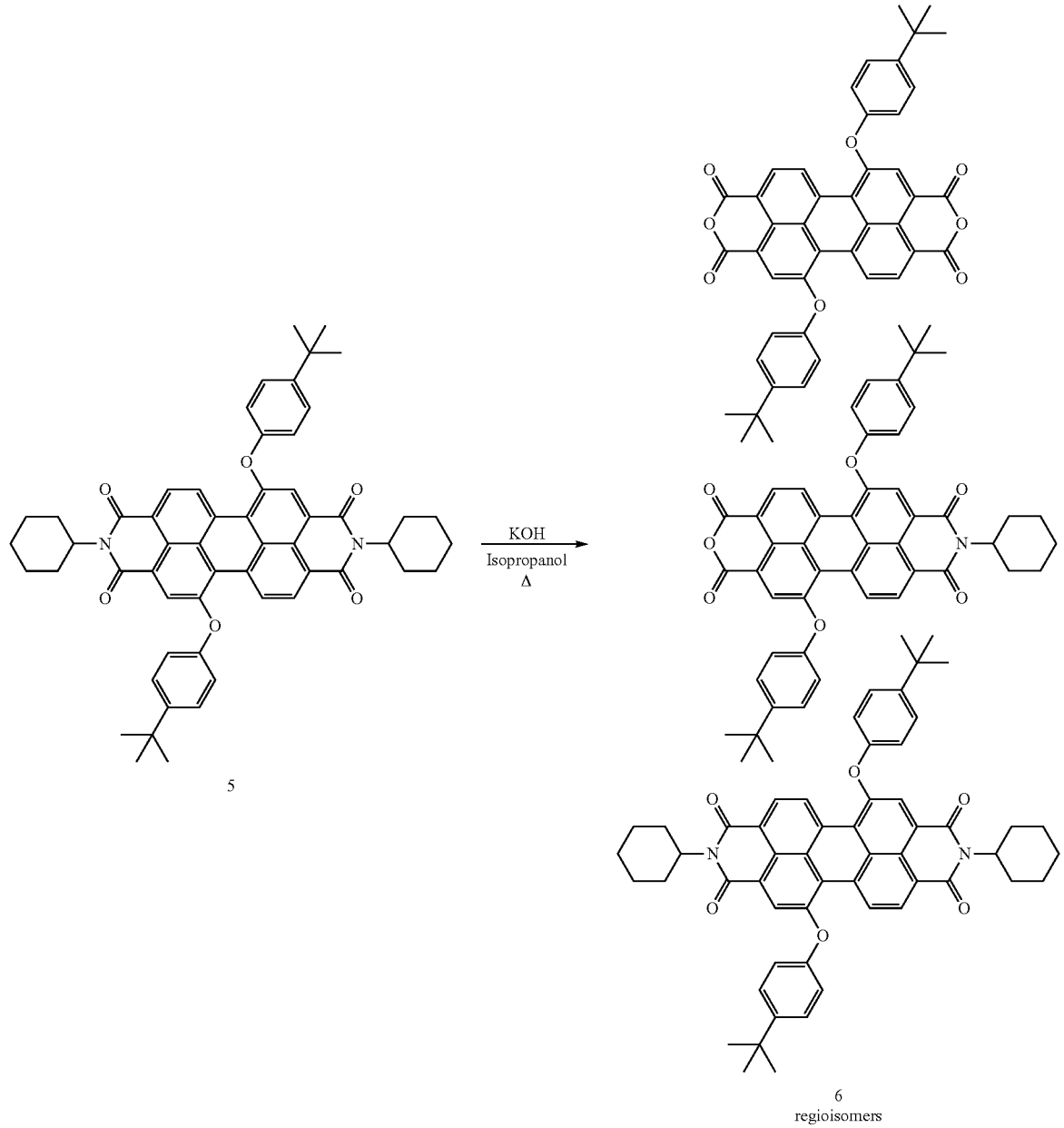

6
regioisomers

Dimer (7)

Into a stirred mixture of potassium hydroxide (1.3 g, 23.2 mmol) in isopropanol (30 mL) was added 1,7 and 1,6-bis(p-tert-butylphenoxy)perylene-3,4,9,10-tetracarboxylic di(cyclohexylimide) (2.0 g, 2.3 mmol) which was refluxed under nitrogen. The reaction mixture was then poured on to 5 M hydrochloric acid (150 mL) and stirred for 1 hour. The precipitate was then isolated, and subjected to reflux in toluene with a Dean-Stark setup. The precipitate was then filtered, yielding a mixture of partially cleaved material containing 1,7 and 1,6 regioisomers of bis(4-tert-butylphenoxy)perylene-3,4,9,10-tetracarboxylic dianhydride, monoanhydride mono cyclohexylimide and unreacted dicyclohexylimide as a fine purple solid (1.5 g).

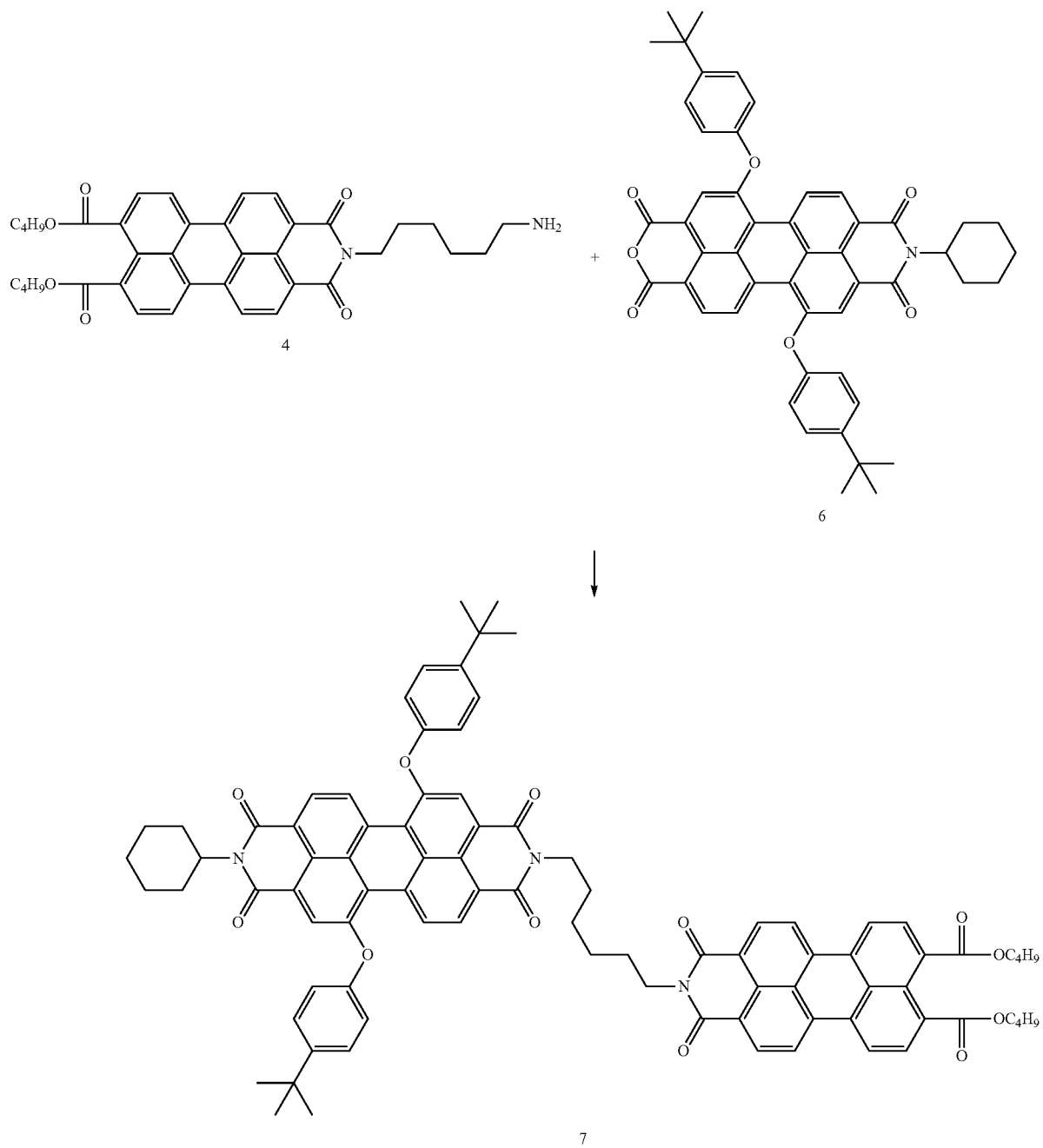

Into a vial was added the 9,10-bis(butoxycarbonyl) perylene-3,4-dicarboxylic (6-aminohexyl)imide (50 mg, 0.08 mmol) along with the partially cleaved material containing the 1,6 and 1,7-bis(4-tert-butylphenoxy)perylene-3,4,9,10-tetracarboxylic monoanhydride monocyclohexylimide (22 mg) and N-methylpyrrolidone (0.75 mL). This was then sparged with nitrogen and sealed, then placed in an oil bath at 95° C. and stirred magnetically overnight. The reaction material was then added to 2.5 M hydrochloric acid (5 mL) and the precipitate washed repeatedly by centrifuge with 2.5 M hydrochloric acid (2 5 mL) and water (2 5 mL). The solid material was then transferred with dichloromethane and absolute ethanol, solvent removed and subjected to purification via column chromatography. An impure fraction eluted at 2.5% methanol in dichloromethane contained the linear dimer 7. This fraction was then purified on biobeads S-X1 in toluene with the linear dimer 7 as the front running fraction. Evaporation yielded the dimer 7 as a dark red solid (2.7 mg, 0.001 mmol, 6%) $^1$H NMR (300 MHz, CDCl$_3$, ppm (assignment, J (Hz))): 9.56 (2H, d, Har-perylene 8.9 Hz), 8.58-8.51 (4H, Har-perylene), 8.45-8.36 (4H, Har-perylene), 8.31 (2H, d, Har-perylene, 5.6 Hz), 8.08 (2H, d, Har-perylene, 8.1 Hz), 7.48-7.43 (4H, Har-phenoxy), 7.11-7.05 (4H, Har-phenoxy), 4.98 (1H, N-Cyclohexyl[CH]), 4.35 (4H, t, COO—[CH$_2$]—CH$_2$, 7.0 Hz), 4.17 (4H, m, [CH$_2$]-cyclohexyl), 2.51 (2H, m, Cyclohexyl-[CH$_2$]), 1.82-1.75

(16H, alkyl+cyclohexyl), 1.55-1.44 (16H, alkyl+cyclohexyl), 1.37 (9H, s, tBu), 1.35 (9H, s, tBu), 1.00 (6H, t, CH$_2$—[CH$_3$] 7.4 Hz).

Example 5—Synthesis and Optical Properties of Trimer (10)

Synthesis of Trimer (10)

9,10-Bis(butoxycarbonyl)perylene-3,4-dicarboxylic (2-[4-hydroxyphenethyl])imide (8)

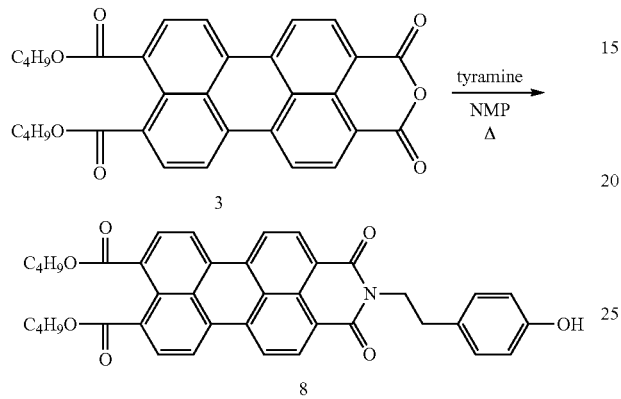

Tyramine (200 mg, 1.46 mmol) and 9,10-bis(butoxycarbonyl)perylene-3,4-dicarboxylic anhydride (200 mg, 0.38 mmol) were combined in N-methylpyrrolidone (2.5 mL) then placed in an oil bath at 140° C. under nitrogen with stirring for 30 minutes. The reaction mixture was then added to a 2.5 M hydrochloric acid solution (50 mL), the precipitate isolated washed with 2.5 M hydrochloric acid (50 mL) and water (50 mL) then dissolved with dichloromethane and absolute ethanol, then evaporated to dryness to yield 9,10-bis(butoxycarbonyl)perylene-3,4-(2-[4-hydroxyphenethyl]) imide as a red powdery solid (225 mg, 0.35 mmol, 92%): $^1$H NMR (300 MHz, CDCl$_3$, ppm (assignment, J (Hz))): 8.59 (2H, d, Har, 8.1 Hz), 8.43 (2H, d, Har, 6.5 Hz), 8.40 (2H, d, Har, 6.5 Hz), 8.09 (2H, d, Har, 8.1 Hz), 7.24 (2H, d, Har (tyr), 8.8 Hz), 6.79 (2H, d, Har (tyr), 8.8 Hz), 4.38 (2H, t, N—[CH$_2$]—CH$_2$, 5.3 Hz) MS-MALDI [C$_{40}$H$_{35}$NO$_7$+H$^+$] calc. 642.25, found 642.22.

Dibutyl 2-(4-((12-(4-(2-(8,9-bis(butoxycarbonyl)-1,3-dioxo-1H-benzo[5,10]anthra[2,1,9-def]isoquinolin-2(3H,5bH,9H)-yl)ethyl)phenoxy)-2,9-dicyclohexyl-1,3,8,10-tetraoxo-1,2,3,5a,8,9,10,14a-octahydroanthra[2,1,9-def:6,5,10-d'e'f']diisoquinolin-5-yl)oxy)phenethyl)-1,3-dioxo-2,3,3a,11b-tetrahydro-1H-benzo[5,10]anthra[2,1,9-def]isoquinoline-8,9-dicarboxylate (as Mixture of Regioisomers 10)

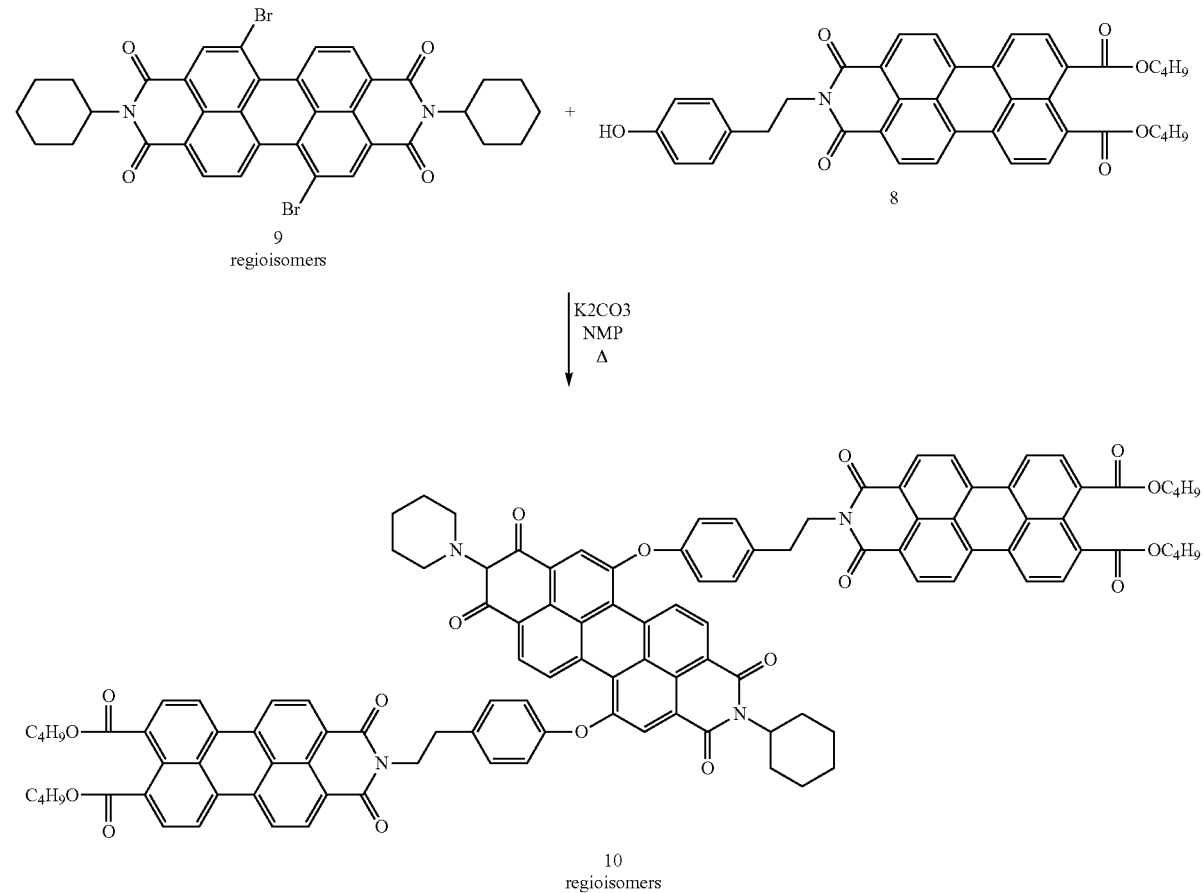

Into N-methylpyrrolidone (1 mL) was added 9,10-di(butoxycarbonyl)perylene-3,4-dicarboxylic (2-[4-hydroxyphenethyl])imide (75 mg, 0.12 mmol) and 1,7-bisbromoperylene-3,4,9,10-carboxylic di(cyclohexylimide) (22 mg, 0.03 mmol) along with potassium carbonate (17 mg, 0.12 mmol). The mixture was then purged of oxygen via nitrogen/vacuum cycles until the N-methylpyrrolidone ceased to bubble. After the final introduction of nitrogen, the reaction was then placed in an oil bath at 120° C. and stirred magnetically for 3 hours. The crude product was the precipitated out by addition to 1M hydrochloric acid (10 mL) and the precipitate filtered then washed with 1M hydrochloric acid (10 mL), water (20 mL), methanol (25 mL) and a methanol/dichloromethane mixture (7:3, 200 mL) until the eluent ran clear. The remaining solid was then washed through with chloroform to yield the bay trimer as a dark red solid (43 mg, 0.02 mmol, 75%): $^1$H NMR (300 MHz, CDCl$_3$, ppm (assignment, J (Hz))): 9.54 (2H, d, Har (core perylene), 8.7 Hz), 8.65 (4H, d, Har (peripheral perylene), 8.0 Hz), 8.55 (2H, d, Har (core perylene), 8.7 Hz), 8.49 (4H, d, Har (peripheral perylene), 8.0 Hz), 8.46 (4H, d, Har (peripheral perylene), 7.8 Hz), 8.27 (2H, s, Har (core perylene)), 8.11 (4H, d, Har (peripheral perylene), 7.8 Hz), 7.47 (4H, d, Har (tyr), 8.5 Hz), 7.12 (4H, d, Har (tyr), 8.5 Hz), 5.00 (2H, m, N—[CH]—), 4.47 (4H, t, N—[CH$_2$]—CH$_2$, 7.8 Hz), 2.52 (4H, m, cyclohexyl CH$_2$—[CH$_2$]—CH$_2$), 1.90-1.35 (16H, m, cyclohexyl), 1.78 (8H, m, OCH$_2$—[CH$_2$]—CH$_2$), 1.49 (8H, m, —[CH$_2$]—CH$_3$), 1.01 (12H, t, CH$_2$—[CH$_3$], 7.4 Hz) MS-MALDI [C$_{116}$H$_{96}$N$_4$O$_{18}$+Na$^+$] calc. 1856.67, found 1855.93.

Synthesis of Pentamer (15)

The simple core unit depicted illustrates the incorporation of dendritic qualities into the core structure, further improving the donor to acceptor ratio. This example demonstrates a simple dendritic core utilising ester linkages.

1,6,7,12-tetra(4-tert-butylphenoxy)perylene-3,4,9,10-tetracarboxylic dianhydride (12)

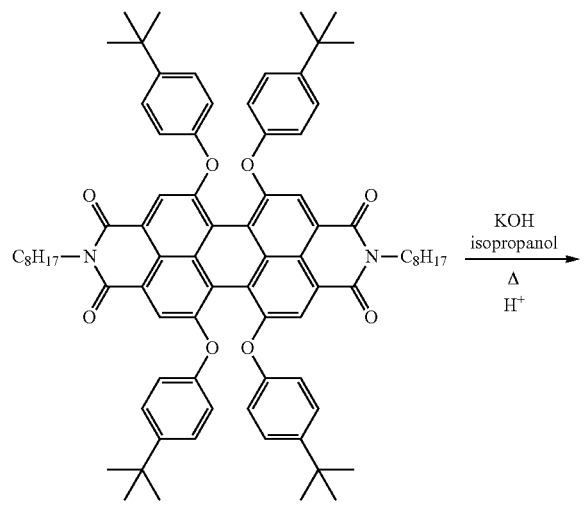

11

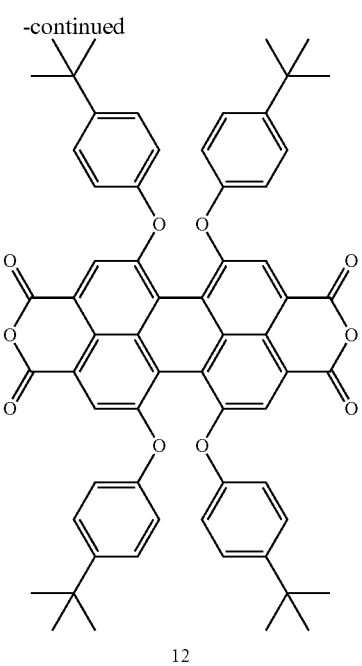

12

Potassium hydroxide (1.0 g, 17.8 mmol) was stirred in isopropanol (20 mL) to which was added 1,6,7,12-tetra(4-tert-butylphenoxy)perylene-3,4,9,10-tetracarboxylic di(octylimide) (2.0 g, 1.6 mmol) and set to reflux overnight. The reaction material was then added to 5 M hydrochloric acid (60 mL) then centrifuged. The resultant solid was then washed by centrifuge with 5 M hydrochloric acid (2 80 mL) then water (2 80 mL). The crude material was then dried and recrystalised from dichloromethane and hot hexane to yield the 1,6,7,12-tetra(4-tert-butylphenoxy) perylene-3,4,9,10-tetracarboxylic dianhydride as a fine purple solid (1.49 g, 1.5 mmol, 90% yield). 1H NMR (300 MHz, CDCl3, ppm (assignment, J (Hz))): 8.21 (4H, s, Har), 7,27 (8H, d, Har (phenoxy), 6.7 Hz), 6.83 (8H, d, Har (phenoxy), 6.7 Hz), 1.30 (H36, s, tBu).

Tetra-acid perylene (13)

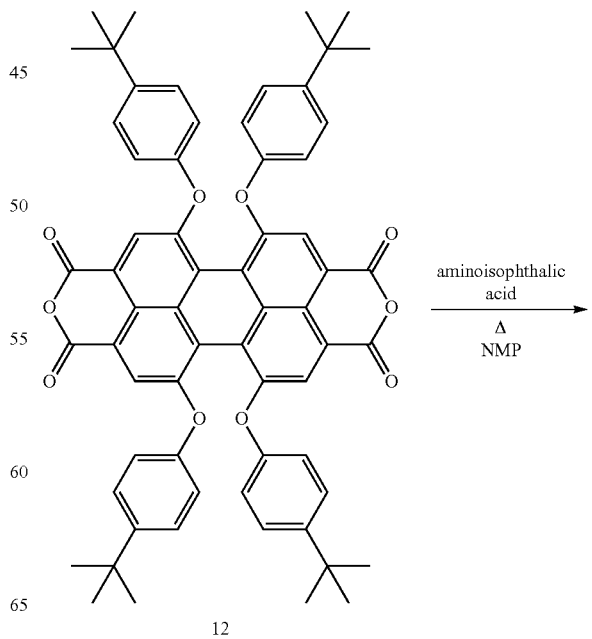

12

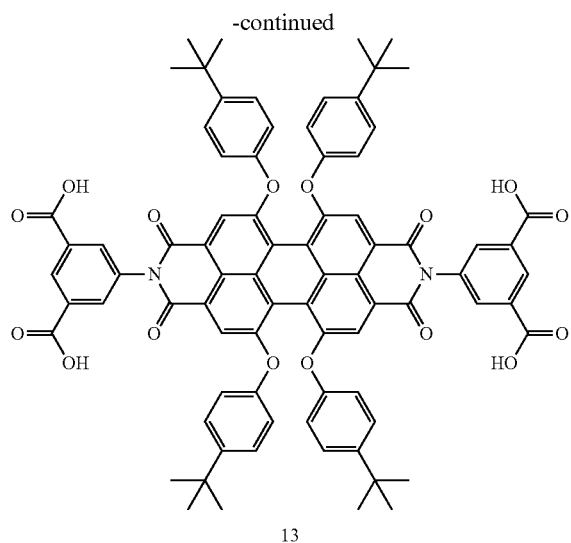

13

Tetraphenoxy perylene dianhydride (400 mg, 0.4 mmol) was combined with 5-aminoisophthalic acid (400 mg, 2.2 mmol) in N-4-methyl 2-pyrrolidone (NMP) (3 mL) was subjected to degassing by vacuum/$N_2$ cycles until the NMP ceased to bubble while under vacuum. This was then placed under nitrogen and into a hot oil bath at 120° C. and stirred for 2 hours. The reaction was then precipitated by addition to 2.5 M hydrochloric acid and filtered. After washing with 2.5 M hydrochloric acid solution, then water, the reaction material was extracted with chloroform, and then evaporated to dryness to yield the tetra-acid as a dark purple solid (396 mg, 75%) $^1$H NMR (300 MHz, $CDCl_3$, ppm (assignment, J (Hz))): 13.42 (4H, s, [H]OOC), 8.51 (2H, t, Har (para), 3.2 Hz), 8.19 (4H, d, Har (ortho), 3.2 Hz), 7.92 (4H, s, Har (perylene)), 7.28 (8H, d, Har (tBu-phenoxy), 8.2 Hz), 6.87 (8H, d, Har (tBu-phenoxy), 8.2 Hz), 1.22 (36H, s, tBu).

Perylene Ethanolimide Diester (14)

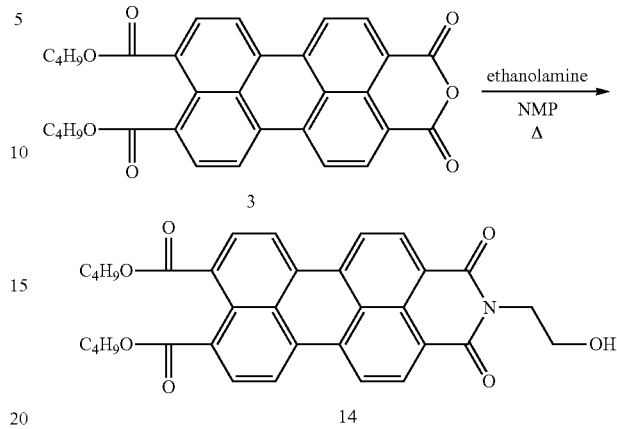

Perylene monoanhydride diester (200 mg, 0.38 mmol) was combined with ethanolamine (230 μL, 3.82 mmol) in DMF (2 mL). This was placed under nitrogen and stirred for 20 minutes, then placed in an oil bath at 120° C. with stirring for another 20 minutes. The reaction was then allowed to cool, added to water then filtered with the precipitate washed with water and dried. This afforded the perylene ethanolimide diester as an orange-red solid (208 mg, 97%): $^1$H NMR (300 MHz, $CDCl_3$, ppm (assignment, J (Hz))): 8.59 (2H, d, Har (perylene), 7.6 Hz), 8.41 (2H, d, Har (perylene), unresolved), 8.40 (2H, d, Har (perylene), unresolved), 8.09 (2H, d, Har (perylene), 7.8 Hz), 4.49 (2H, t, HO—[$CH_2$]—$CH_2$, 5.3 Hz), 4.36 (4H, t, COO—[$CH_2$]—$CH_2$, 6.9 Hz), 4.03 (2H, t, N—[$CH_2$]—$CH_2$, 5.3 Hz), 1.79 (4H, m, $OCH_2$—[$CH_2$]—$CH_2$), 1.50 (4H, m, $CH_2$—[$CH_2$]—$CH_3$), 1.00 (6H, t, $CH_2$—[$CH_3$], 7.4 Hz).

Pentamer (15)

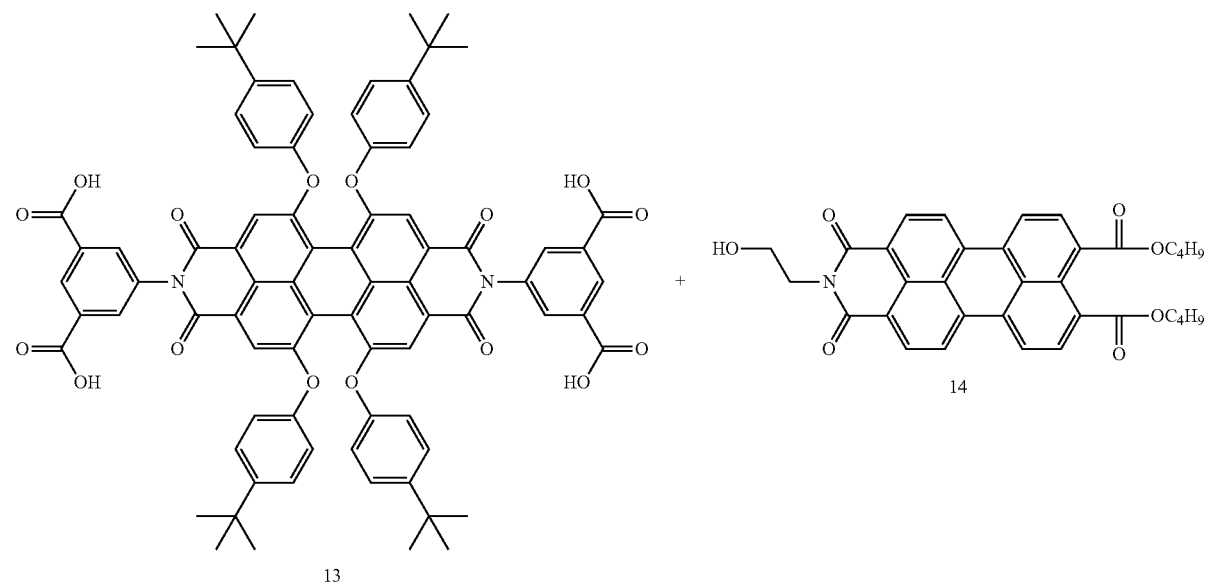

1. $SOCl_2$, $CHCl_3$
2. TEA, DCM

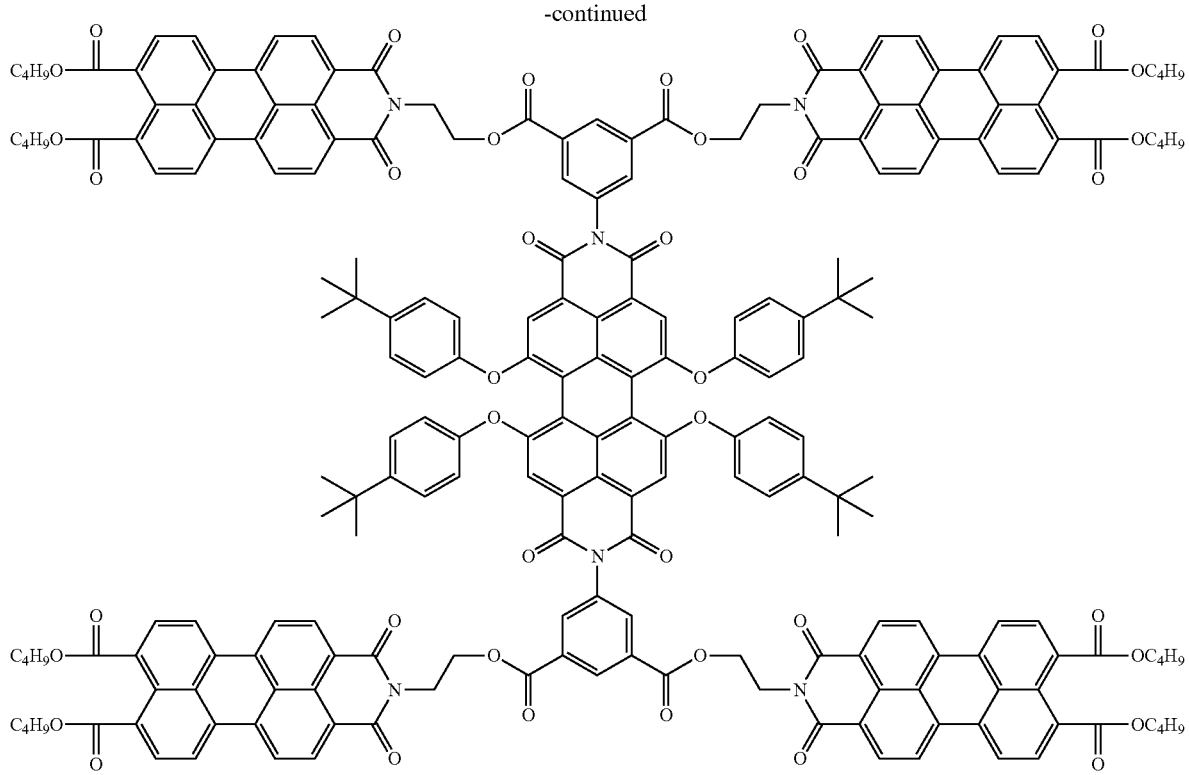

15

Thionyl chloride (4 mL) was added to a stirred solution of tetraphenoxy tetraacid 13 (120 mg, $9.2\times10^{-5}$ mol) in dry distilled chloroform (20 mL) and refluxed under nitrogen until all the solid material had dissolved. The residual thionyl chloride and chloroform was then removed under reduced pressure and residual volatiles removed from the purple residue by high vacuum. The acid chloride was then taken up in chloroform (10 mL) and added dropwise over 10 minutes to a stirred solution of ethanolimide perylene dibutyl ester 14 (500 mg, $8.84\times10^{-4}$ mol) and dry distilled triethylamine (120 µL, $8.60\times10^{-4}$ mol) in dry dichloromethane (100 mL). After 90 minutes hexane (100 ml) was added to the reaction, the ppt filtered off using celite, then washed with a 20% methanol in dichloromethane mix (till the eluent ran clear) then the product isolated from the celite with chloroform, which after removal of the solvent yielded a dark purple maroon crystalline powder (192 mg, 60% yield). $^1$H NMR (300 MHz, $CDCl_3+D_3COD$, ppm (assignment, J (Hz))): 8.67 (2H, s, Har (para protons from arylimide)), 8.26 (4H, 2, Har (core perylene)), 8.24-7.83 (40H, Har (appended perylene), Har (ortho protons from arylimide)), 7.19 (8H, d, Har (tBu-phenoxy), 8.8 Hz), 6.80 (8H, d, Har (tBu-phenoxy), 8.8 Hz), 4.72 (8H, m, O—[$CH_2$]—$CH_2$N), 4.53 (8H, m, $CH_2$—[$CH_2$]—N), 4.33 (16H, t, COO—[$CH_2$]—$CH_2$, 6.7 Hz), 1.78 (16H, m, $OCH_2$—[$CH_2$]—$CH_2$), 1.49 (16H, m, $CH_2$—[$CH_2$]—$CH_3$), 1.20 (36H, s, tBu), 0.99 (24H, t, $CH_2$—[$CH_3$], 7.4 Hz).

Optical Properties of Trimer 10

The optical properties of the trimer 10 were explored through UV-Vis and Fluorescence spectroscopy and compared with the monomeric counterparts. Through this a number of main points arise. Firstly, that the simple trimer can be modelled as a linear sum of the monomeric perylenes it incorporates, supporting the in silico prediction described in Example 1 above concerning reabsorption losses, and secondly that the energy transfer due to FRET processes is highly efficient, supporting the inference that the donor and acceptor are well within the Førster radius for this FRET pair.

Figure 6:
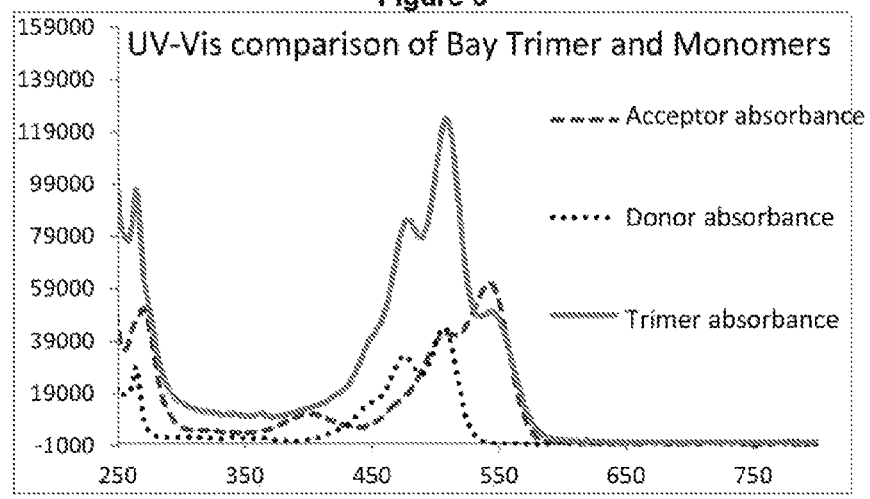
FIG. 6 is the UV-vis spectra comparing the absorption profiles of trimer 10 and its constituent donors and acceptor

As shown in FIG. 6, the main absorption bands of the bay trimer correspond directly to those of the constituent donor and acceptor components. This is illustrated through the projected extinction values arrived at by a simple additive approach compared with the actual spectrum of trimer 10.

As can be seen from the spectra shown in FIG. 6 the maxima for linear combination of donors and acceptors coincide with the observed maxima of the trimer 10. This supports the use of a predictive model developed on an additive basis for later generation perylene-based arrays.

Figure 7:
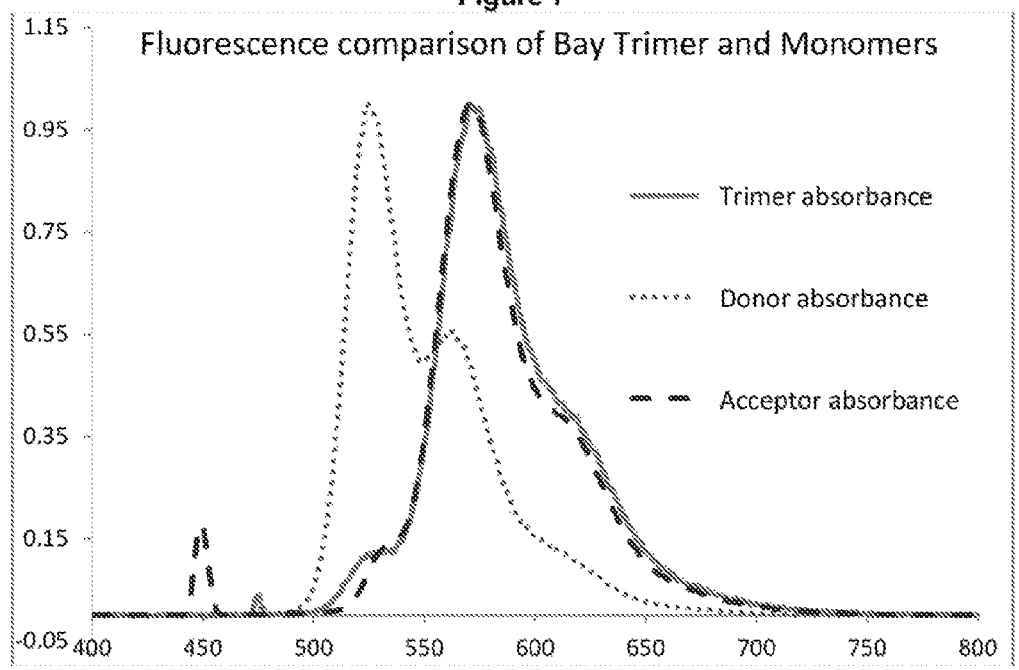
FIG. 7 is the fluorescence emission spectra of trimer 10 and its constituent donors and acceptor.

Comparison of the fluorescence spectra highlights the efficient FRET-based transfer of energy along the 'optical wire'. FIG. 7 shows the fluorescence emission of the constituent donor and acceptor of trimer 10 compared to the fluorescence emission of trimer 10. As can be seen in FIG. 7, the fluorescence emission maxima of trimer 10 are almost identical to that of the acceptor bisphenoxy perylene.

In the spectra shown in FIG. 7 of trimer 10 there is no clear sign of fluorescence of the donor component of trimer 10 other than the presence of the shoulder at about 520 nm. This may be due to a minor impurity, such as the mono bromination product, or a regioisomer produced during the bromination of the core perylene unit as seen following.

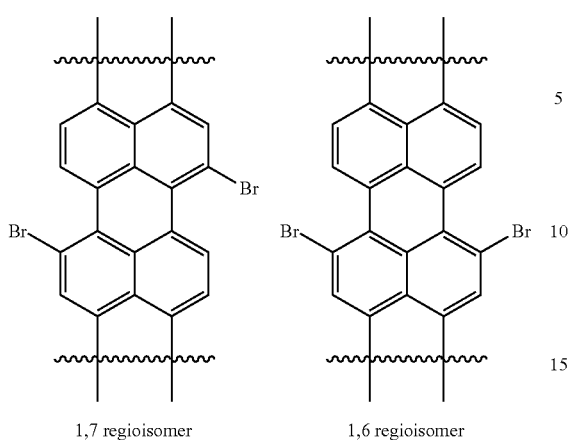

1,7 regioisomer   1,6 regioisomer

The bay-position bromination of perylenes has been shown to be regioselective for the 1 and the 7 positions over the 1 and 6 positions, due to the deactivating nature of the bromine towards electrophilic aromatic substitution. The bulk of the product formed in this reaction is therefore the 1,7 derivative, with approximately between a 10-15% yield of the 1,6 derivative.

Example 6—Components and Arrays

Rylene Core

Two rylene cores that may be obtained following a similar synthetic route as described above for pentamer 15 are depicted as follows.

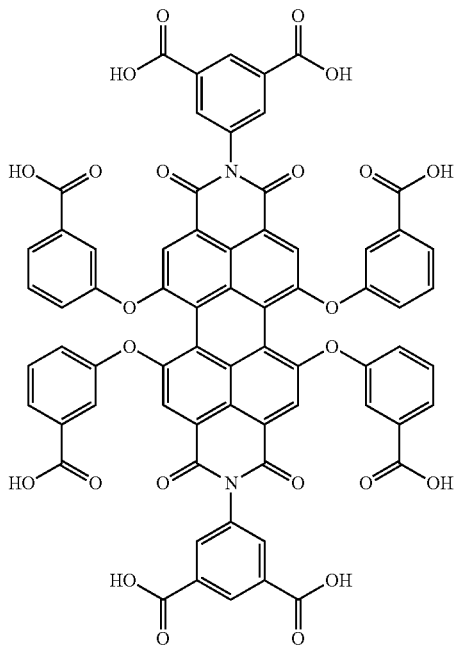

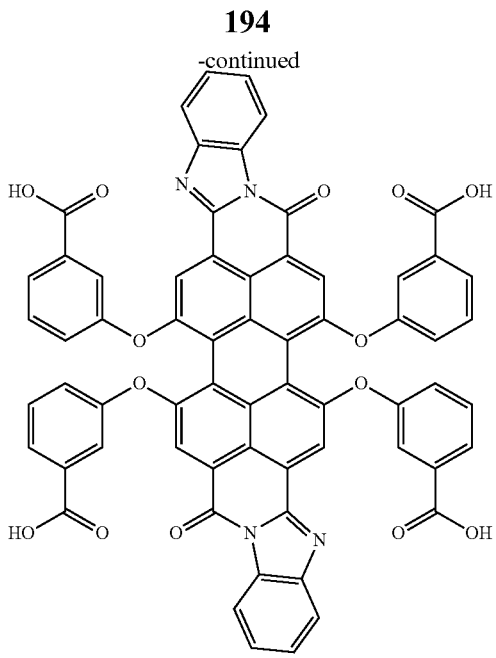

Both these rylene cores are functionalised such that at least four donors may be appended. Rylene core 1 (left hand side) may be advantageous as it would be possible to address either the imide or bay positions separately, thus could be more effectively tuned to particular absorbance wavelengths. Rylene core 2 (right hand side), focuses on the red-shifting of the emission fluorescence so as to match better the requirements of a device into which a light harvesting array may be incorporated, such as, for example, a photovoltaic device and photocurrent generation device.

Acceptors

The following acceptors are of the class of substituted benzocoronene acceptors.

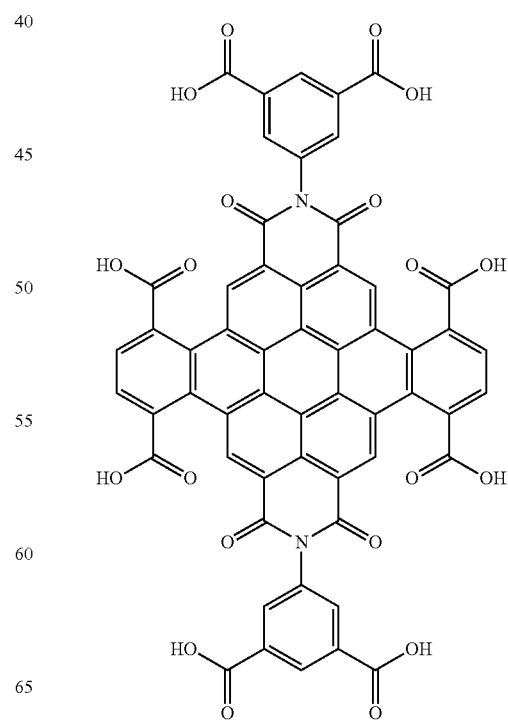

-continued
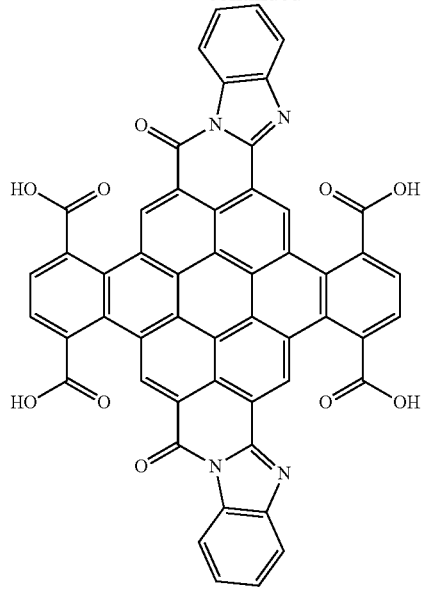
Example 7—Synthesis of Light Harvesting Arrays
The following retrosynthesis of a light harvesting array demonstrates a potential synthetic route to access such systems.

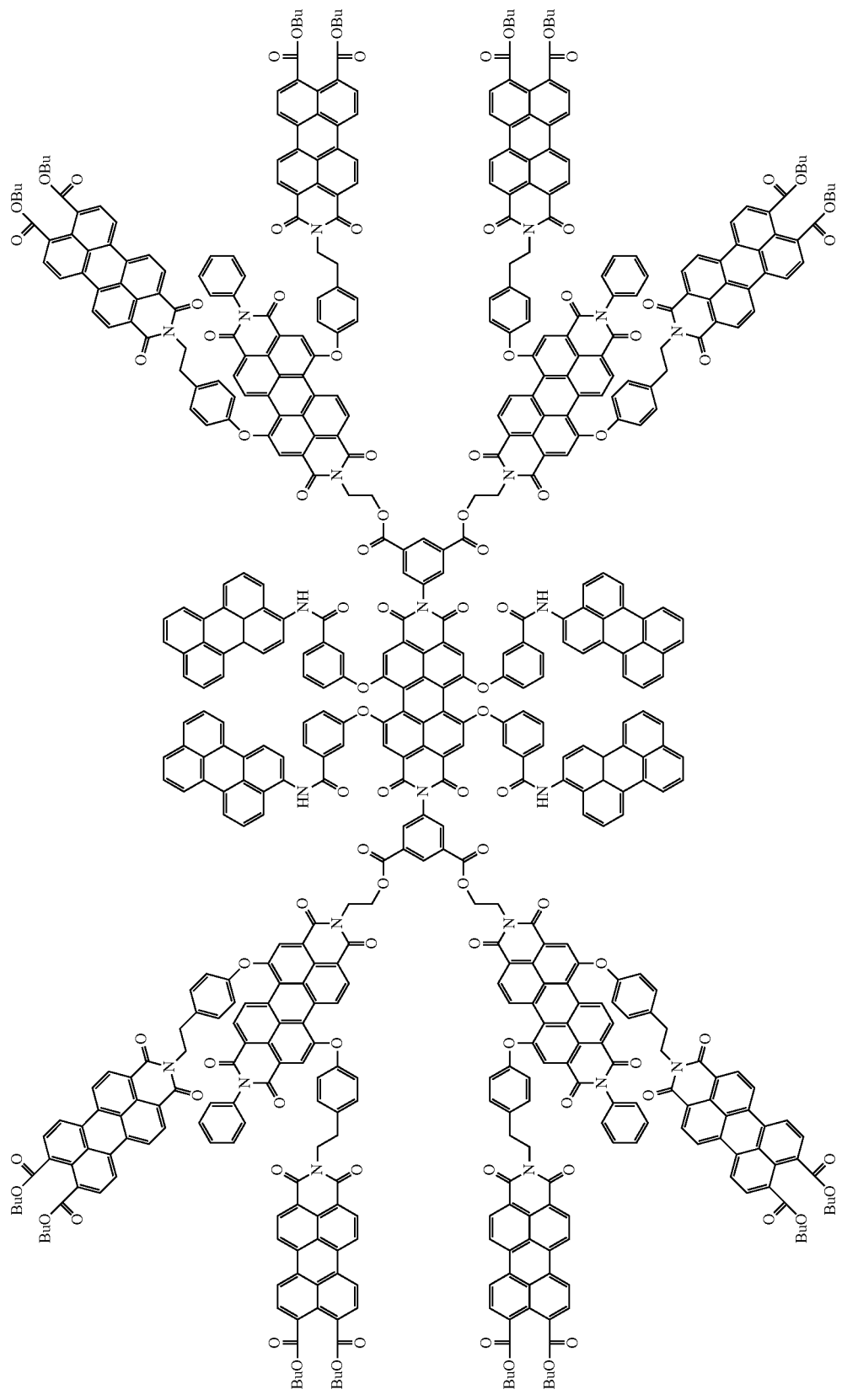

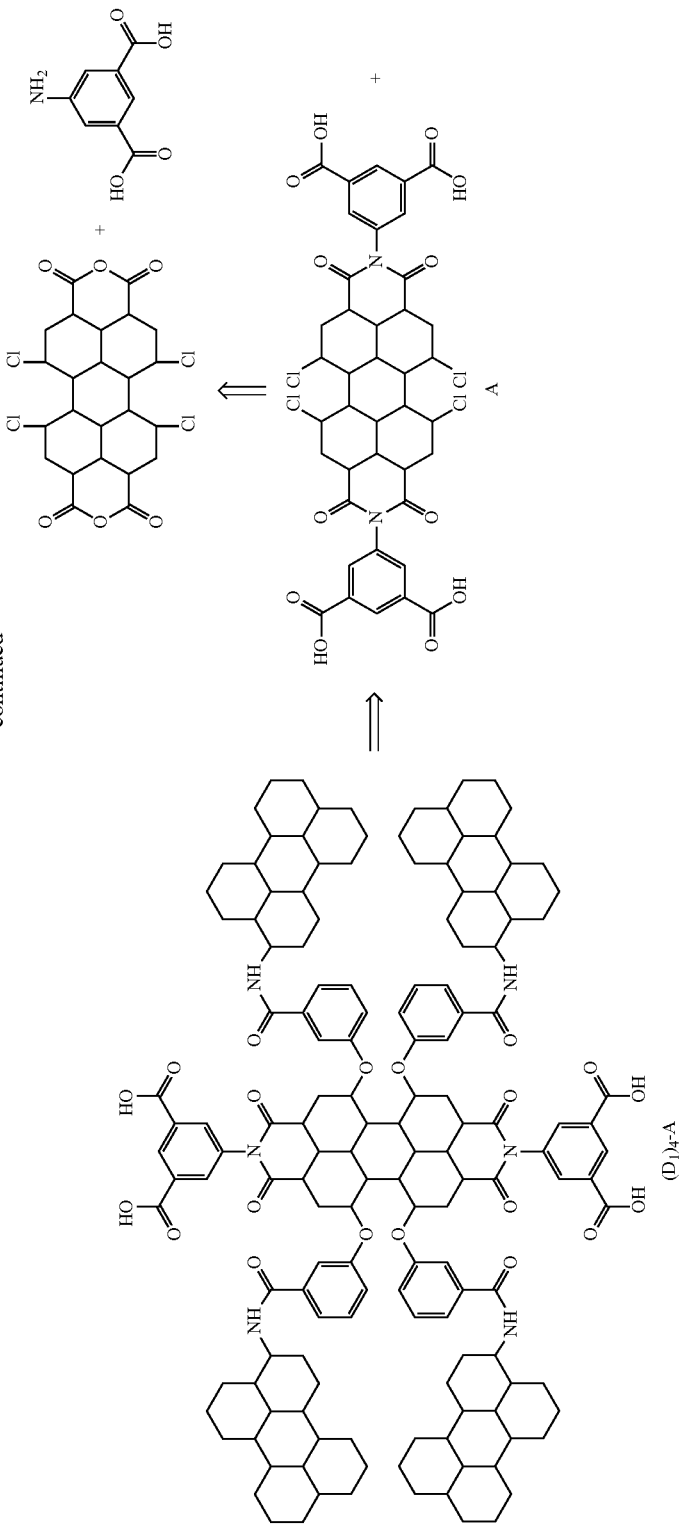
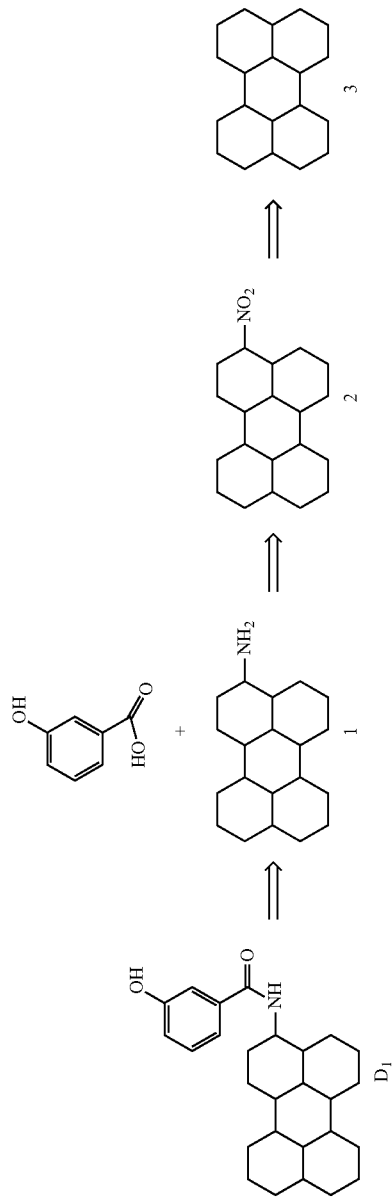

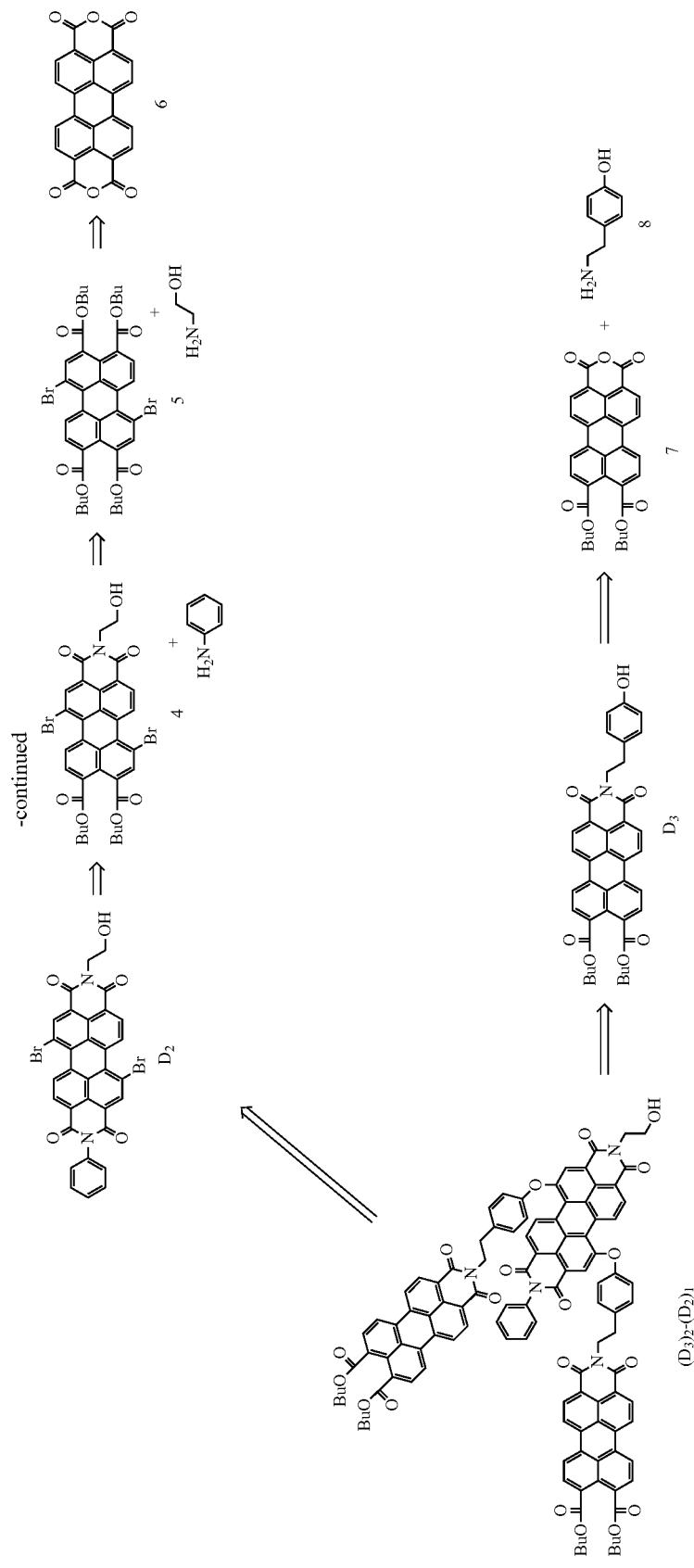

Example 8—Optical Measurements

Additional tests on the arrays include exploring the changes in FRET and total quantum efficiencies in response to dye array solvation, for example dye arrays in the solid state, varying solvent and how the lifetimes change when in an effectively frozen state in various plastics including polycarbonate, polyvinyl butyral or any other material described above. These tests are typically similar to those carried out for the compounds described above.

Also, further analysis of the surface patterning and how it can influence the extraction of light from the plastic, this will be performed through comparison of the transmission, reflectance and emission from the plastic using a Lambda 1050 UV-Vis spectrophotomer with reflectance and integrating sphere accessories.

In addition, re-absorption losses of the FRET arrays compared to the final acceptor weighted against the total light energy absorbed may be quantified by the optical measurements described above.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication, or information derived from it, or to any matter which is known, is not, and should not be taken as an acknowledgement or admission or any form of suggestion that prior publication, or information derived from it, or known matter forms part of the common general knowledge in the field of endeavour to which this specification relates.

The invention claimed is:

1. A compound of Formula X:

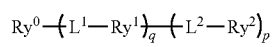

Formula X wherein $Ry^0$ is an optionally substituted acceptor rylene selected from an optionally substituted perylene, an optionally substituted terrylene and an optionally substituted quaterrylene;

$Ry^1$ is a first optionally substituted rylene selected from an optionally substituted perylene, an optionally substituted terrylene and an optionally substituted quaterrylene;

$Ry^2$ is a second optionally substituted rylene selected from an optionally substituted perylene, an optionally substituted terrylene and an optionally substituted quaterrylene, the second optionally substituted rylene is capable of transferring energy to $Ry^0$, $Ry^1$ or both;

wherein $Ry^0$ contains more substituents than each of $Ry^1$ and $Ry^2$;

$L^1$ is a linker group having a chain length of 1 to 20 atoms;

$L^2$ is a linker group having a chain length of 1 to 20 atoms;

q is an integer of 1 to 10; and p is an integer of 2 to 20.

2. A light harvesting array comprising an acceptor selected from the group consisting of an optionally substituted rylene, an optionally substituted porphyrin, an optionally substituted benzocoronene and an oligomeric unit comprising two or more optionally substituted rylenes; and two or more donors selected from an optionally substituted rylene, an optionally substituted naphthylene, an optionally substituted tetra pyrrole, an optionally substituted benzopyrones, an optionally substituted fluorescein, an optionally substituted rhodamine, an optionally substituted cyanine, an optionally substituted indocarbocyanine, an optionally substituted pyridyloxazole, an optionally substituted nitrobenzoxadiazole, an optionally substituted benzoxadiazole, an optionally substituted pyrene, Nile red, Nile blue, cresyl violet, an optionally substituted proflavine, an optionally substituted acridine orange, and optionally substituted acridine yellow, an optionally substituted aromatic hydrocarbon, an optionally substituted thiophene, an optionally substituted polyhtiophenes, or a combination thereof, or an oligomeric unit comprising an optionally substituted donor rylene core linked via a linker group having a chain length of 1 to 20 atoms to one or more optionally substituted peripheral donor rylenes, wherein at least one donor is the oligomeric unit and the acceptor is linked to the two or more donors by a linker group having a chain length of 1 to 20 atoms, with the proviso that the two or more donors are selected from a different compound, and further wherein the acceptor contains a larger number of substituents than each of the two or more donors.

3. The light harvesting array of claim 2, wherein the acceptor is linked to two or more donors and at least two of the donors are oligomeric units.

4. The light harvesting array of claim 2, wherein each oligomeric unit comprises an optionally substituted donor rylene core linked via a linker group to two or more optionally substituted peripheral donor rylenes.

5. The light harvesting array of claim 2, wherein the optionally substituted donor rylene core is linked to the acceptor.

6. The light harvesting array of claim 2, wherein the optionally substituted donor rylene core is an optionally substituted donor perylene core.

7. The light harvesting array of claim 2, wherein each optionally substituted peripheral donor rylene is an optionally substituted donor perylene.

8. The light harvesting array of claim 2, wherein the acceptor is an optionally substituted perylene.

9. The light harvesting array of claim 2, which is a compound of formula I:

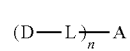

Formula I wherein:

A is an acceptor;

n is an integer of 1 to 10;

D is an oligomeric unit comprising an optionally substituted donor rylene core and one or more optionally substituted peripheral donor rylenes; and L is a linker group having a chain length of 1 to 20 atoms.

10. The light harvesting array of claim 9, which is a compound selected from formula IA, IB, IC, ID, IG and IH:

Formula IA wherein:
A is the acceptor;
n is an integer of 1 to 10;
$L^1$ is a linker group having a chain length of 1 to 20 atoms;
$L^2$ is a linker group having a chain length of 1 to 20 atoms;
$D^1$ is an optionally substituted donor rylene core;
$D^2$ is an optionally substituted peripheral donor rylene; and
m is an integer of 1 to 10;

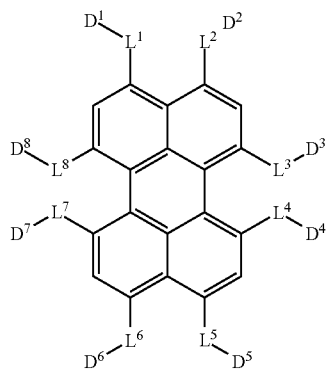

Formula IB wherein:
$L^1, L^2, L^3, L^4, L^5, L^6, L^7$ and $L^8$ are independently absent or a linker group having a chain length of 1 to 20 atoms; or
$L^1$ and $L^2$, $L^3$ and $L^4$, $L^5$ and $L^6$, and $L^7$ and $L^8$ together with the perylene scaffold to which they are attached form an optionally substituted $C_{5-8}$cycloalkyl, an optionally substituted heterocyclyl or an optionally substituted aryl group; and
$D^1, D^2, D^3, D^4, D^5, D^6, D^7$ and $D^8$ are independently H or a donor,
wherein at least one of $D^1, D^2, D^3, D^4, D^5, D^6, D^7$ and $D^8$ is an oligomeric unit comprising an optionally substituted donor rylene core and one or more optionally substituted peripheral donor rylenes;

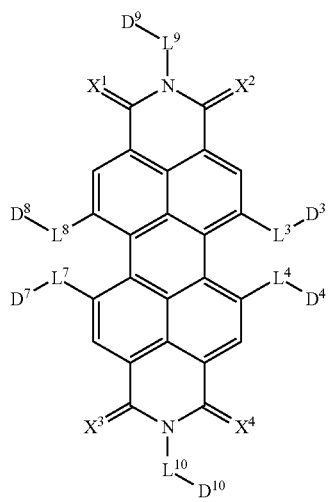

Formula IC wherein:
$X^1, X^2, X^3$ and $X^4$ are independently selected from O, S, $NR^1$ and $CR^1R^2$;

$R^1$ and $R^2$ are each independently selected from H, optionally substituted $C_{1-6}$alkyl, optionally substituted $C_{2-6}$alkenyl, optionally substituted $C_{2-6}$alkynyl, optionally substituted $C_{3-8}$cycloalkyl, hydroxyl, optionally substituted $C_{1-6}$alkoxy, optionally substituted aryloxy, optionally substituted $C_{1-6}$alkoxyaryl, optionally substituted $C_{1-6}$alkylhalo, optionally substituted $C_{1-6}$alkoxyhalo, carboxyl, optionally substituted esters, optionally substituted ketones, optionally substituted amides, optionally substituted aminoketones, thiol, optionally substituted alkylthio, optionally substituted sulfates, optionally substituted sulfonates, optionally substituted sulfinyl, optionally substituted sulfonyl, optionally substituted aryl, optionally substituted aryl$C_{1-6}$alkyl, and optionally substituted heterocyclyl;
$L^3, L^4, L^7$ and $L^8$ are independently absent or a linker group having a chain length of 1 to 20 atoms; and/or $L^3$ and $L^4$ together with the perylene scaffold to which they are attached form an optionally substituted $C_{5-8}$cycloalkyl, an optionally substituted heterocyclyl or an optionally substituted aryl group; and/or $L^7$ and $L^8$ together with the perylene scaffold to which they are attached form an optionally substituted $C_{5-8}$cycloalkyl, an optionally substituted heterocyclyl or an optionally substituted aryl group; and
$L^9$ and $L^{10}$ are independently absent or a linker group having a chain length of 1 to 20 atoms; and/or $L^9$ and $X^1$ or $X^2$ together with the heterocyclic scaffold to which they are attached form an optionally substituted heterocyclyl group; and/or $L^{10}$ and $X^3$ or $X^4$ together with the heterocyclic scaffold to which they are attached form an optionally substituted heterocyclyl group; and
$D^3, D^4, D^7, D^8, D^9$ and $D^{10}$ are each independently H or a donor,
wherein at least one of $D^3, D^4, D^7, D^8, D^9$ and $D^{10}$ is an oligomeric unit comprising an optionally substituted donor rylene core and one or more optionally substituted peripheral donor rylenes;

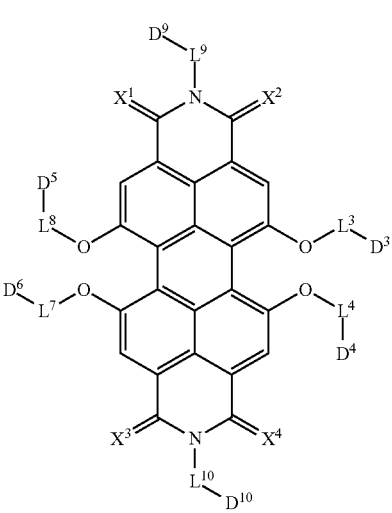

Formula ID wherein:
$X^1, X^2, X^3$ and $X^4$ are independently selected from O, S, $NR^1$ and $CR^1R^2$;
$R^1$ and $R^2$ are independently selected from H, optionally substituted $C_{1-6}$alkyl, optionally substituted $C_{2-6}$alkenyl, optionally substituted $C_{2-6}$alkynyl, optionally substituted $C_{3-8}$cycloalkyl, hydroxyl, optionally substituted $C_{1-6}$alkoxy, optionally substituted aryloxy, optionally substituted $C_{1-6}$alkoxyaryl, optionally substituted $C_{1-6}$alkylhalo, optionally substituted $C_{1-6}$alkoxyhalo, carboxyl, optionally substituted esters, optionally substituted ketones, optionally substituted amides, optionally substituted aminoketones, thiol, optionally substituted alkylthio, optionally substituted sulfates, optionally substituted sulfonates, optionally substituted sulfinyl, optionally substituted sulfonyl, optionally substituted aryl, optionally substituted aryl$C_{1-8}$alkyl, and optionally substituted heterocyclyl;

$L^3$, $L^4$, $L^7$, $L^8$, $L^9$ and $L^{10}$ are independently absent or a linker group having a chain length of 1 to 20 atoms; or $L^3$ and $L^4$ and $L^7$ and $L^8$ together with the perylene scaffold to which they are attached form an optionally substituted $C_{5-8}$cycloalkyl, an optionally substituted heterocyclyl or an optionally substituted aryl group; and $L^9$ and $X^1$ or $X^2$ together with the heterocyclic scaffold to which they are attached form an optionally substituted heterocyclyl group; and $L^{10}$ and $X^3$ or $X^4$ together with the heterocyclic scaffold to which they are attached form an optionally substituted heterocyclyl group; and $D^3$, $D^4$, $D^5$, $D^6$, $D^9$ and $D^{10}$ are independently H or a donor, wherein at least one of $D^3$, $D^4$, $D^5$, $D^6$, $D^9$ and $D^{10}$ is an oligomeric unit comprising an optionally substituted donor rylene core and one or more optionally substituted peripheral donor rylenes;

Formula IG

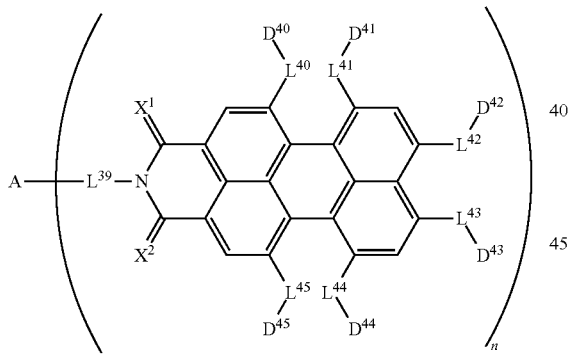

wherein:

A is the acceptor;

n is an integer of 1 to 10;

$X^1$ and $X^2$ are independently selected from O, S, $NR^1$ and $CR^1R^2$;

$R^1$ and $R^2$ are independently selected from H, optionally substituted $C_{1-6}$alkyl, optionally substituted $C_{2-6}$alkenyl, optionally substituted $C_{2-6}$alkynyl, optionally substituted $C_{3-8}$cycloalkyl, hydroxyl, optionally substituted $C_{1-6}$alkoxy, optionally substituted aryloxy, optionally substituted $C_{1-6}$alkoxyaryl, optionally substituted $C_{1-6}$alkylhalo, optionally substituted $C_{1-6}$alkoxyhalo, carboxyl, optionally substituted esters, optionally substituted ketones, optionally substituted amides, optionally substituted aminoketones, thiol, optionally substituted alkylthio, optionally substituted sulfates, optionally substituted sulfonates, optionally substituted sulfinyl, optionally substituted sulfonyl, optionally substituted aryl, optionally substituted aryl$C_{1-6}$alkyl, and optionally substituted heterocyclyl;

$D^{40}$, $D^{41}$, $D^{42}$, $D^{43}$, $D^{44}$ and $D^{45}$ are independently H or an optionally substituted peripheral donor perylene;

$L^{39}$ is a linker group having a chain length of 1 to 20 atoms;

$L^{40}$, $L^{41}$, $L^{42}$, $L^{43}$, $L^{44}$ and $L^{45}$ are independently absent or a linker group having a chain length of 1 to 20 atoms; or $L^{40}$ and $L^{41}$, $L^{42}$ and $L^{43}$ and $L^{44}$ and $L^{45}$ together with the perylene scaffold to which they are attached form an optionally substituted $C_{5-8}$cycloalkyl, an optionally substituted heterocyclyl or an optionally substituted aryl group;

wherein at least one of $D^{40}$, $D^{41}$, $D^{42}$, $D^{43}$, $D^{44}$ and $D^{45}$ is an optionally substituted peripheral donor perylene;

Formula 1H

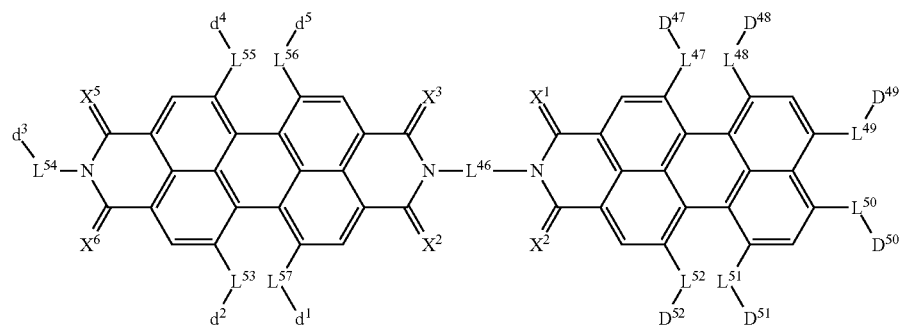

wherein:

$X^1$, $X^2$, $X^3$, $X^4$, $X^5$ and $X^6$ are independently selected from O, S, $NR^1$ and $CR^1R^2$;

$R^1$ and $R^2$ are independently selected from H, optionally substituted $C_{1-6}$alkyl, optionally substituted $C_{2-6}$alkenyl, optionally substituted $C_{2-6}$alkynyl, optionally substituted $C_{3-8}$cycloalkyl, hydroxyl, optionally substituted $C_{1-6}$alkoxy, optionally substituted aryloxy, optionally substituted $C_{1-6}$alkoxyaryl, optionally substituted $C_{1-6}$alkylhalo, optionally substituted $C_{1-6}$alkoxyhalo, carboxyl, optionally substituted esters, optionally substituted ketones, optionally substituted amides, optionally substituted aminoketones, thiol, optionally substituted alkylthio, optionally substituted sulfates, optionally substituted sulfonates, optionally substituted sulfinyl, optionally substituted sulfonyl, optionally substituted aryl, optionally substituted aryl$C_{1-6}$alkyl, and optionally substituted heterocyclyl;

$D^{47}$, $D^{48}$, $D^{49}$, $D^{50}$, $D^{51}$ and $D^{52}$ are independently H or an optionally substituted peripheral donor perylene;

$d^1$, $d^2$, $d^3$, $d^4$ and $d^5$ are independently H or a donor;

$L^{46}$ is a linker group having a chain length of 1 to 20 atoms;

$L^{47}$, $L^{48}$, $L^{49}$, $L^{50}$, $L^{51}$, $L^{52}$, $L^{53}$, $L^{54}$, $L^{55}$, $L^{56}$ and $L^{57}$ are independently absent or a linker group having a chain length of 1 to 20 atoms; or $L^{47}$ and $L^{48}$, $L^{49}$ and $L^{50}$, $L^{51}$ and $L^{52}$, $L^{57}$ and $L^{53}$, $L^{55}$ and $L^{56}$ together with the perylene scaffold to which they are attached form an optionally substituted $C_{5-8}$cycloalkyl, an optionally substituted heterocyclyl or an optionally substituted aryl group;

wherein at least one of $D^{47}$, $D^{48}$, $D^{49}$, $D^{50}$, $D^{51}$ and $D^{52}$ is an optionally substituted peripheral donor perylene.

11. The light harvesting array of claim 2, wherein the oligomeric unit comprises two or more optionally substituted peripheral donor rylenes.

12. The light harvesting array of claim 11, wherein the optionally substituted donor rylene core is an optionally substituted donor perylene core and/or each optionally substituted peripheral donor rylene is an optionally substituted donor perylene.

13. The light harvesting array of claim 2, wherein the acceptor is an optionally substituted rylene selected from an optionally substituted perylene, an optionally substituted terrylene and an optionally substituted quaterrylene or the acceptor is an oligomeric unit comprising two or more optionally substituted rylenes selected from optionally substituted perylenes, optionally substituted terrylenes, optionally substituted quaterrylenes and a combination thereof.

* * * * *